US009175076B2

(12) United States Patent
Lerner et al.

(10) Patent No.: US 9,175,076 B2
(45) Date of Patent: Nov. 3, 2015

(54) ANTI-GDF15 ANTIBODIES

(71) Applicant: AVEO Pharmaceuticals, Inc., Cambridge, MA (US)

(72) Inventors: Lorena Lerner, Newton Centre, MA (US); Sandra Abbott, Boston, MA (US); Ailin Bai, Newton, MA (US); Ting Chen, Acton, MA (US); Maria Isabel Chiu, Newton Centre, MA (US); Qing Liu, Acton, MA (US); Laura Poling, Boston, MA (US); Nianjun Tao, Brighton, MA (US); Solly Weiler, Newton, MA (US); Zhigang Weng, Brookline, MA (US); William M. Winston, Jr., Marlborough, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/137,415

(22) Filed: Dec. 20, 2013

(65) Prior Publication Data

US 2014/0193427 A1 Jul. 10, 2014

Related U.S. Application Data

(60) Provisional application No. 61/827,325, filed on May 24, 2013, provisional application No. 61/745,508, filed on Dec. 21, 2012.

(51) Int. Cl.
| | | |
|---|---|---|
| C07K 16/00 | (2006.01) | |
| C07K 16/18 | (2006.01) | |
| C07K 16/22 | (2006.01) | |
| C12N 1/21 | (2006.01) | |
| C12N 5/10 | (2006.01) | |
| C12N 5/12 | (2006.01) | |
| C12N 15/09 | (2006.01) | |
| C12N 15/13 | (2006.01) | |
| C12N 15/63 | (2006.01) | |
| C12N 15/64 | (2006.01) | |
| A61K 39/00 | (2006.01) | |

(52) U.S. Cl.
CPC ........... *C07K 16/22* (2013.01); *A61K 2039/505* (2013.01); *C07K 2317/24* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,994,102 A | 11/1999 | Hudson et al. | |
| 6,051,424 A | 4/2000 | Kato et al. | |
| 6,180,602 B1 | 1/2001 | Kato et al. | |
| 6,420,543 B1 | 7/2002 | Lee et al. | |
| 6,465,181 B2 | 10/2002 | Billing-Medel et al. | |
| 6,500,638 B2 | 12/2002 | Hudson et al. | |
| 6,521,227 B1 | 2/2003 | Hudson et al. | |
| 7,157,235 B2 | 1/2007 | Breit et al. | |
| 7,282,351 B2 | 10/2007 | Hudson et al. | |
| 7,514,221 B2 | 4/2009 | Breit et al. | |
| 7,741,055 B2 | 6/2010 | Hudson et al. | |
| 7,919,084 B2 | 4/2011 | Breit et al. | |
| 7,968,303 B2 | 6/2011 | Breit et al. | |
| 8,173,434 B2 | 5/2012 | Fan et al. | |
| 8,192,735 B2 | 6/2012 | Breit et al. | |
| 2007/0207462 A1 | 9/2007 | Ichinose et al. | |
| 2009/0021293 A1 | 1/2009 | Hebert et al. | |
| 2011/0033886 A1 | 2/2011 | Hess et al. | |
| 2011/0065204 A1 | 3/2011 | Wollert et al. | |
| 2011/0262444 A1 | 10/2011 | Kim | |
| 2011/0300548 A1* | 12/2011 | Lambrecht et al. | 435/6.12 |
| 2012/0083420 A1 | 4/2012 | Clark et al. | |

FOREIGN PATENT DOCUMENTS

| | | |
|---|---|---|
| CA | 2534871 A1 | 8/2007 |
| EP | 2103943 A1 | 9/2009 |
| WO | WO-94/03599 | 2/1994 |
| WO | WO-96/18730 | 6/1996 |
| WO | WO-97/00958 | 1/1997 |
| WO | WO-99/06445 | 2/1999 |
| WO | WO-00/20449 | 4/2000 |
| WO | WO-00/56352 | 9/2000 |
| WO | WO-00/70051 | 11/2000 |
| WO | WO-02/20759 | 3/2002 |
| WO | WO-2004/043385 | 5/2004 |
| WO | WO-2005/044990 | 5/2005 |
| WO | WO-2009/021293 | 2/2009 |
| WO | WO-2009/046495 | 4/2009 |
| WO | WO-2011/117254 | 9/2011 |
| WO | WO-2012/113103 | 8/2012 |

OTHER PUBLICATIONS

Allan et al., "A selective androgen receptor modulator that reduces prostate tumor size and prevents orchidectomy-induced bone loss in rats." J Steroid Biochem Mol Biol. Jan. 2007;103(1):76-83.

Argilés et al., "Anti-inflammatory therapies in cancer cachexia." Eur J Pharmacol. Sep. 2011;668 Suppl 1:S81-6.

Bauerlein et al., "Efficacy of REGN1033, a fully human anti-myostatin antagonist antibody, in rodent muscle function." J. Cachexia Sarcopenia Muscle 2013;4:295-343 Abstract 4-06 from 7th Cachexia Conference, Kobe/Osaka, Japan, Dec. 9-11, 2013.

Baumgartner et al., "Epidemiology of sarcopenia among the elderly in New Mexico." Am J Epidemiol. Apr. 15, 1998;147(8):755-63.

Bauskin et al., "Role of macrophage inhibitory cytokine-1 in tumorigenesis and diagnosis of cancer." Cancer Res. May 15, 2006;66(10):4983-6.

Bialek et al., "A myostatin and activin decoy receptor enhances bone formation in mice." Bone. Mar. 2014; 60:162-171.

(Continued)

*Primary Examiner* — Elizabeth C Kemmerer
(74) *Attorney, Agent, or Firm* — Goodwin Procter LLP

(57) ABSTRACT

Monoclonal antibodies that bind and inhibit the activity of human GDF15 are disclosed. The antibodies can be used to treat body weight loss, including cachexia, associated with the over-expression of human GDF15.

11 Claims, 36 Drawing Sheets

(56) References Cited

OTHER PUBLICATIONS

Bovee et al., "SERMs and SARMs: detection of their activities with yeast based bioassays." J. Steroid Biochem. Mol. Biol. 2010;118:85-92.
Breit et al. "The TGF-β superfamily cytokine, MIC-1/GDF15: a pleotrophic cytokine with roles in inflammation, cancer and metabolism" *Growth Factors*. Oct. 2011;29(5):187-95.
Chen et al., "Discovery and Therpeutic Promise of Selective Androgen Receptor Modulators." Mol. Interv. Jun. 2005; 5(3):173-188.
Dalton et al., "The selective androgen receptor modulator GTx-024 (enobosarm) improves lean body mass and physical function in healthy elderly men and postmenopausal women: results of a double-blind, placebo-controlled phase II trial." J Cachexia Sarcopenia Muscle. Sep. 2011;2(3):153-161.
Davenport and Wright, "Treating Obesity: is it all in the gut?" Drug Discov Today (2013), <http://dx.doi.org/10.1016/j.drudis.2013.10.025>.
DeBoer and Marks, "Cachexia: lessons from melanocortin antagonism." Trends Endocrinol Metab. Jul. 2006;17(5):199-204.
Enomoto et al., "Suppression of cancer cachexia by 20S,21-epoxy-resibufogenin-3-acetate-a novel nonpeptide IL-6, receptor antagonist." Biochem Biophys Res Commun. Oct. 22, 2004;323(3):1096-102.
Evans et al., "Cachexia: a new definition." Clin Nutr. Dec. 2008;27(6):793-9.
Fairlie et al., "Expression of a TGF-beta superfamily protein, macrophage inhibitory cytokine-1, in the yeast *Pichia pastoris*." Gene. Aug. 22, 2000;254(1-2):67-76.
Fearon et al., "Cancer cachexia: mediators, signaling, and metabolic pathways." Cell Metab. Aug. 8, 2012;16(2):153-66.
Fearon et al., "Definition and classification of cancer cachexia: an international consensus." Lancet Oncol. May 2011;12(5):489-95.
Fong et al. "Cachectin/TNF or IL-1 alpha induces cachexia with redistribution of body proteins." Am J Physiol. Mar. 1989;256(3 Pt 2):R659-65.
Glass, "Signaling pathways perturbing muscle mass." Curr Opin Clin Nutr Metab Care. May 2010;13(3):225-9.
Guillory et al., "Chapter 3: The Role of Ghrelin in Anorexia-Cachexia Syndromes." Vitamins and Hormones. 2013; 92:61-106.
Hinoi et al. "Positive regulation of osteoclastic differentiation by growth differentiation factor 15 upregulated in osteocytic cells under hypoxia" *J Bone Miner Res*. Apr. 2012;27(4):938-49.
Hryniewicz et al., Partial reversal of cachexia by beta-adrenergic receptor blocker therapy in patients with chronic heart failure. J Card Fail. Dec. 2003;9(6):464-8.
International Search Report and Written Opinion for International Application No. PCT/US2013/077139, mailed May 22, 2014, 20 pages.
Inui, "Cancer anorexia-cachexia syndrome: current issues in research and management." Cancer J Clin. Mar.-Apr. 2002;52(2):72-91.
Johnen et al., "Tumor-induced anorexia and weight loss are mediated by the TGF-beta superfamily cytokine MIC-1." Nat Med. Nov. 2007;13(11):1333-40.
Joppa et al., "Central infusion of the melanocortin receptor antagonist agouti-related peptide (AgRP(83-132)) prevents cachexia-related symptoms induced by radiation and colon-26 tumors in mice." Peptides. Mar. 2007;28(3):636-42.
Lokireddy et al., "Myostatin is a novel tumoral factor that induces cancer cachexia." Biochem J. Aug. 15, 2012;446(1):23-36.
Marino et al., "The therapeutic potential of blocking the activin signalling pathway." Cytokine Growth Factor Rev. Oct. 2013;24(5):477-84.
Matthys and Billiau, "Cytokines and cachexia." Nutrition. Sep. 1997;13(9):763-70.
Mohler et al., "Nonsteroidal Selective Androgen Receptor Modulators (SARMs): Dissociating the Anabolic and Androgenic Activities of the Androgen Receptor for Therapeutic Benfit." J. Med. Chem. 2008;52(12):3597-3617.
Muscaritoli et al., "Consensus definition of sarcopenia, cachexia and pre-cachexia: joint document elaborated by Special Interest Groups (SIG) 'cachexia-anorexia in chronic wasting diseases' and 'nutrition in geriatrics.'" Clin Nutr. Apr. 2010;29(2):154-9.
Nagata et al., "Design and synthesis of tricyclic tetrahydroquinolines as a new series of nonsteroidal selective androgen receptor modulators (SARMs)." Bioorg. Med. Chem. Lett. 2011;21:1744-1747.
Ng et al., Synthesis of potent and tissue-selective androgen receptor modulators (SARMs): 2-(2,2,2)-Trifluoroethyl-benzimidazole scaffold. Bioorg Med Chem Lett. Mar. 15, 2007;17(6):1784-7.
Prado et al., "Skeletal muscle anabolism is a side effect of therapy with the MEK inhibitor: selumetinib in patients with cholangiocarcinoma." Br J Cancer. May 8, 2012;106(10):1583-6.
Roth et al. "GDF-15 contributes to proliferation and immune escape of malignant gliomas" *Clin Cancer Res*. Aug. 1, 2010;16(15):3851-9.
Rüegg and Glass, "Molecular mechanisms and treatment options for muscle wasting diseases." Annu Rev Pharmacol Toxicol. 2011;51:373-95.
Sharma et al., "Molecular targets of cancer cachexia: opportunities for pharmanutritional approaches." PharmaNutrition. 2013, <http://dx.doi.org/10.1016/j.phanu.2013.07.002>.
Steinman and DeBoer, "Chapter 8: Treatment of Cachexia: Melanocortin and Ghrelin Interventions." Vitamins and Hormones. 2013; 92:197-240.
Stewart-Coats et al., "The ACT-ONE trial, a multicentre, randomised, double-blind, placebo-controlled, dose-finding study of the anabolic/catabolic transforming agent, MT-102 in subjects with cachexia related to stage III and IV non-small cell lung cancer and colorectal cancer:study design." J Cachexia Sarcopenia Muscle. Dec. 2011;2(4):201-207.
Strassmann et al., Mechanisms of experimental cancer cachexia. Local involvement of IL-1 in colon-26 tumor. J Immunol. Mar. 15, 1993;150(6):2341-5.
Temel et al., "Efficacy and safety results from a phase II study of anamorelin HCl, a ghrelin receptor agonist, in NSCLC patients." J. Cachexia Sarcopenia Muscle 2013;4:295-343 Abstract 5-01 from 7th Cachexia Conference, Kobe/Osaka, Japan, Dec. 9-11, 2013.
Thomas, "Loss of skeletal muscle mass in aging: examining the relationship of starvation, sarcopenia and cachexia." Clin Nutr. Aug. 2007;26(4):389-99.
Tisdale, "Cachexia in cancer patients." Nat Rev Cancer. Nov. 2002;2(11):862-71.
Tsai et al., "Anorexia/cachexia of chronic diseases: a role for the TGF-β family cytokine MIC-1/GDF15." J Cachexia Sarcopenia Muscle. Dec. 2012;3(4):239-43.
Tuca et al., "Clinical evaluation and optimal management of cancer cachexia." Crit Rev Oncol Hematol. Dec. 2013;88(3):625-36.
Zhang et al., "Serendipitous discovery of novel imidazolopyrazole scaffold as selective androgen receptor modulators." Bioorg Med Chem Lett. Jan. 15, 2007;17(2):439-43.
Zhang et al., "Synthesis and SAR of novel hydantoin derivatives as selective androgen receptor modulators." Bioorg Med Chem Lett. Nov. 15, 2006;16(22):5763-6.
Zhou et al., "Reversal of cancer cachexia and muscle wasting by ActRIIB antagonism leads to prolonged survival." Cell. Aug. 20, 2010;142(4):531-43.

\* cited by examiner

Complete Mouse Heavy Chain Variable Region Amino Acid Alignments

Heavy Variable

```
                  1          2          3          4        5 55       6         7
                  0          0          0          0        0 22       0         0
                                         AB                    A
01G06  EVLLQQSGPELVKPGASVKIPCKASGYTFT DYNMD--WVKQSHGKSLEWIG QINPNNGGIFFNQKFKG KATLT
03G05  QVQLQQPGAELVKPGASVKLSCKASGYTFT SYWIH--WVNQRPGQGLEWIG DINPSNGRSKYNEKFKN KATMT
04F08  QVTLKESGPGILQPSQTLSLTCSFSGFSLS TYGMGVTWIRQPSGKGLEWLA HIY-WDDDKRYNPSLKS RLTIS
06C11  QVTLKESGPGILQPSQTLSLTCSFSGFSLN TYGMGVSWIRQPSGKGLEWLA HIY-WDDDKRYNPSLKS RLTIS
08G01  EVLLQQSGPEVVKPGASVKIPCKASGYTFT DYNMD--WVKQSHGKSLEWIG EINPNNGGTFYNQKFKG KATLT
14F11  QVTLKESGPGILQPSQTLSLTCSFSGFSLS TYGMGVGWIRQPSGKGLEWLA DIW-WDDDKYYNPSLKS RLTIS
17B11  QVTLKESGPGILQPSQTLSLTCSFSGFSLS TSGMGVSWIRQPSGKGLEWLA HND-WDDDKRYKSSLKS RLTIS
                                   CDR1                    CDR2
```

CDR3

```
         7     8 888                     9         1111           1
         1     0 222                     0         0000           1
                 ABC                                ABC           0
01G06  VDKSSNTAFMEVRSLTSEDTAVYYCAR EAITTVGAMDY WGQGTSVTVSS   (SEQ ID NO:40)
03G05  ADKSSNTAYMQLSSLTSEDSAVYYCAR EVLDGAM--DY WGQGTSVTVSS   (SEQ ID NO:42)
04F08  KDTSNNQVFLKITSVDTADTATYYCAQ TGYSNLF--AY WGQGTLVTVSA   (SEQ ID NO:44)
06C11  KDASNNRVFLKITSVDTADTATYYCAQ RGYDDYW--GY WGQGTLVTISA   (SEQ ID NO:46)
08G01  VDKSSSTAYMELRSLTSEDTAVYYCAR EAITTVGAMDY WGQGTSVTVSS   (SEQ ID NO:48)
14F11  KDTSSNEVFLKIAIVDTADTATYYCAR RGHYSAM--DY WGQGTSVTVSS   (SEQ ID NO:50)
17B11  KDTSRNQVFLKITSVDTADTATYYCAR RVGGLEGYFDY WGQGTTLTVSS   (SEQ ID NO:52)
```

FIG. 10

Mouse Heavy Chain CDR Amino Acid Alignments

Heavy Variable

| | CDR1 | | CDR2 | |
|---|---|---|---|---|
| 01G06 | DYNMD-- | (SEQ ID NO:1) | QINPNNGGIFFNQKFKG | (SEQ ID NO:7) |
| 03G05 | SYWIH-- | (SEQ ID NO:2) | DINPSNGRSKYNEKFKN | (SEQ ID NO:8) |
| 04F08 | TYGMGVT | (SEQ ID NO:3) | HIY-WDDDKRYNPSLKS | (SEQ ID NO:9) |
| 06C11 | TYGMGVS | (SEQ ID NO:4) | HIY-WDDDKRYNPSLKS | (SEQ ID NO:9) |
| 08G01 | DYNMD-- | (SEQ ID NO:1) | EINPNNGGTFYNQKFKG | (SEQ ID NO:10) |
| 14F11 | TYGMGVG | (SEQ ID NO:5) | DIW-WDDDKYNPSLKS | (SEQ ID NO:11) |
| 17B11 | TSGMGVS | (SEQ ID NO:6) | HND-WDDDKRYKSSLKS | (SEQ ID NO:12) |

Heavy Variable

| | CDR3 | |
|---|---|---|
| 01G06 | EAITTVGAMDY | (SEQ ID NO:15) |
| 03G05 | EVLDGAM--DY | (SEQ ID NO:16) |
| 04F08 | TGYSNLF--AY | (SEQ ID NO:17) |
| 06C11 | RGYDDYW--GY | (SEQ ID NO:18) |
| 08G01 | EAITTVGAMDY | (SEQ ID NO:15) |
| 14F11 | RGHYSAM--DY | (SEQ ID NO:19) |
| 17B11 | RVGGLEGYFDY | (SEQ ID NO:20) |

FIG. 11

Complete Mouse Light (Kappa) Chain Variable Region Amino Acid Alignments

Light (Kappa) Variable

```
                    1         2          3   CDR1                4          5   CDR2          6          7
                    0         0      22222   0                   0      0       0          0          0
                                     77777
                                      ABCD
01G06  DIQMTQSPASLSASVGETVTITC RTSE----NLHNYLA WYQQKQGKSPQLLVY DAKTLAD GVPSRFSGSGSGTQ
03G05  DIVLTQSPASLAVSLGQRATISC RASESVDNYGISFMN WFQQKPGQPPKLLIY AASNQGS GVPARFSGSGSGTD
04F08  DIVMTQSQKFMSTSVGDRVSVTC KASQ----NVGTNVA WYQQKLGQSPKTLIY SASYRYS GVPDRFTGSGSGTD
06C11  DIVMTQSQKFMSTSVGDRVSVTC KASQ----NVGTNVA WFQQKPGQSPKALIY SASYRYS GVPDRFTGSGSGTD
08G01  DIQMTQSPASLSASVGETVTITC RASG----NLHNYLA WYQQKQGKSPQLLVY NAKTLAD GVPSRFSGSGSGTQ
14F11  DIVMTQSQKFMSTSVGDRVSVTC KASQ----NVGTNVA WYQQKPGQSPKALIY SPSYRYS GVPDRFTGSGSGTD
17B11  DIVLTQSPASLAVSLGQRATISC RASQSVSTSRFSYMH WFQQKPGQAPKLLIK YASNLES GVPARFSGSGSGTD
```

```
             7     8                    9          1
             0     0                    0          0
                                                   0
                                 CDR3
01G06  YSLKINSLQPEDFGSYYC QHFWSSPYT FGGGTKLEIK   (SEQ ID NO:76)
03G05  FSLNIHPMEEDDTAMYFC QQSKEVPWT FGGGSKLEIK   (SEQ ID NO:78)
04F08  FTLTISNVQSEDLAEYFC QQYNSYPYT FGGGTKLEIK   (SEQ ID NO:80)
06C11  FILTISNVQSEDLAEYFC QQYNNYPLT FGAGTKLEIK   (SEQ ID NO:82)
08G01  YSLKINSLQPEDFGSYYC QHFWSSPYT FGGGTKLEIK   (SEQ ID NO:84)
14F11  FTLTISNVQSEDLAEYFC QQYNSYPHT FGGGTKLEMK   (SEQ ID NO:86)
17B11  FTLNIHPVEGEDTATYYC QHSWEIPYT FGGGTKLEIK   (SEQ ID NO:88)
```

FIG. 12

Mouse Light (Kappa) Chain CDR Amino Acid Alignments

Light (Kappa) Variable

| | CDR1 | | CDR2 | |
|---|---|---|---|---|
| 01G06 | RTSE----NLHNYLA | (SEQ ID NO:21) | DAKTLAD | (SEQ ID NO:26) |
| 03G05 | RASESVDNYGISFMN | (SEQ ID NO:22) | AASNQGS | (SEQ ID NO:27) |
| 04F08 | KASQ----NVGTNVA | (SEQ ID NO:23) | SASYRYS | (SEQ ID NO:28) |
| 06C11 | KASQ----NVGTNVA | (SEQ ID NO:23) | SASYRYS | (SEQ ID NO:28) |
| 08G01 | RASG----NIHNYLA | (SEQ ID NO:24) | NAKTLAD | (SEQ ID NO:29) |
| 14F11 | KASQ----NVGTNVA | (SEQ ID NO:23) | SPSYRYS | (SEQ ID NO:30) |
| 17B11 | RASQSVSTSRFSYMH | (SEQ ID NO:25) | YASNLES | (SEQ ID NO:31) |

Light (Kappa) Variable

| | CDR3 | |
|---|---|---|
| 01G06 | QHFWSSPYT | (SEQ ID NO:32) |
| 03G05 | QQSKEVPWT | (SEQ ID NO:33) |
| 04F08 | QQYNSYPYT | (SEQ ID NO:34) |
| 06C11 | QQYNNYPLT | (SEQ ID NO:35) |
| 08G01 | QHFWSSPYT | (SEQ ID NO:32) |
| 14F11 | QQYNSYPHT | (SEQ ID NO:36) |
| 17B11 | QHSWEIPYT | (SEQ ID NO:37) |

FIG. 13

Complete Humanized Heavy Chain Variable Region Amino Acid Alignments

Heavy Variable

```
                                    1          2          3          4          5 55    6          7
                           1        0          0          0   333    0          0 22     0          0
                                                              555                A
                                                              AB                 CDR1                                CDR2
Ch01G06 Chimeric           EVLLQQSGPELVKPGASVKIPCKASGYTFT DYNMD-- WVKQSHGKSLEWIG QINPNNGGIFFNQKFKG KATLT
Hu01G06 IGHV1-18           QVQLVQSGAEVKKPGASVKVSCKASGYTFT DYNMD-- WVRQAPGKSLEWIG QINPNNGGIFFNQKFKG RATLT
Hu01G06 IGHV1-69           QVQLVQSGAEVKKPGSSVKVSCKASGYTFT DYNMD-- WVRQAPGKSLEWIG QINPNNGGIFFNQKFKG RATLT
Sh01G06 IGHV1-18 M69L      QVQLVQSGAEVKKPGASVKVSCKASGYTFT DYNMD-- WVRQAPGQGLEWMG QINPNNGGIFFNQKFKG RVTLT
Sh01G06 IGHV1-18 M69L G44S QVQLVQSGAEVKKPGASVKVSCKASGYTFT DYNMD-- WVRQAPGQSLEWMG QINPNNGGIFFNQKFKG RVTLT
Sh01G06 IGHV1-18 M69L K64Q QVQLVQSGAEVKKPGASVKVSCKASGYTFT DYNMD-- WVRQAPGQGLEWMG QINPNNGGIFFNQKFQG RVTLT
Sh01G06 IGHV1-69 T30S I69L QVQLVQSGAEVKKPGSSVKVSCKASGYTFS DYNMD-- WVRQAPGQGLEWMG QINPNNGGIFFNQKFKG RVTLT
Sh01G06 IGHV1-69 T30S K64Q I69L QVQLVQSGAEVKKPGSSVKVSCKASGYTFS DYNMD-- WVRQAPGQGLEWMG QINPNNGGIFFNQKFQG RVTLT
Hu01G06 IGHV1-18 F1        QVQLVQSGAEVKKPGASVKVSCKASGYTFT DYNMD-- WVRQAPGQSLEWMG QINPNNGLIFFNQKFQG RVTLT
Hu01G06 IGHV1-18 F2        QVQLVQSGAEVKKPGASVKVSCKASGYTFT DYNMD-- WVRQAPGQGLEWMG QINPNNGLIFFNQKFQG RVTLT
Hu01G06 IGHV1-69 F1        QVQLVQSGAEVKKPGSSVKVSCKASGYTFS DYNMD-- WVRQAPGQGLEWMG QINPYNHLIFFNQKFKG RVTLT
Hu01G06 IGHV1-69 F2        QVQLVQSGAEVKKPGSSVKVSCKASGYTFS DYNMD-- WVRQAPGQGLEWMG QINPYNHLIFFNQKFKG RVTLT
Ch06C11 Chimeric           QVTLKESGPGILQPSQTLSLTCSFSGFSLN TYGMGVS WIRQPSGKGLEWLA HIY-WDDDKRYNPSLKS RLTIS
HE LM 06C11 IGHV2-70       QVTLKESGPALVKPTQTLTLTCTFSGFSLN TYGMGVS WIRQPPGKALEWLA HIY-WDDDKRYNPSLKT RLTIS
Hu06C11 IGHV2-5            QVTLKESGPTLVKPTQTLTLTCTFSGFSLN TYGMGVS WIRQPPGKGLEWLA HIY-WDDDKRYNPSLKS RLTIS
Ch14F11 Chimeric           QVTLKESGPGILQPSQTLSLTCSFSGFSLS TYGMGVG WIRQPSGKGLEWLA DIW-WDDDKYYNPSLKS RLTIS
Sh14F11 IGHV2-5            QITLKESGPTLVKPTQTLTLTCTFSGFSLS TYGMGVG WIRQPPGKALEWLA DIW-WDDDKYYNPSLKS RLTIT
Sh14F11 IGHV2-70           QVTLKESGPALVKPTQTLTLTCTFSGFSLS TYGMGVG WIRQPPGKALEWLA DIW-WDDDKYYNPSLKS RLTIS
```

FIG. 19

Complete Humanized Heavy Chain Variable Region Amino Acid Alignments

Heavy Variable

```
                                           7   8    9            CDR3
                                           1   8    0          1111       1
                                               888             0000       1
                                               222             0000       0
                                               ABC              ABC
Ch01G06 Chimeric             VDKSSNTAFMEVRSLTSEDTAVYYCAREAITTVGAMDYWGQGTSVTVSS  (SEQ ID NO:40)
Hu01G06 IGHV1-18             VDTSTNTAYMELRSLRSDTAVYYCAREAITTVGAMDYWGQGTLVTVSS  (SEQ ID NO:54)
Hu01G06 IGHV1-69             VDKSTNTAYMELSSLRSEDTAVYYCAREAITTVGAMDYWGQGTLVTVSS (SEQ ID NO:56)
Sh01G06 IGHV1-18 M69L        TDTSTSTAYMELRSLRSDDTAVYYCAREAITTVGAMDYWGQGTLVTVSS (SEQ ID NO:58)
Sh01G06 IGHV1-18 M69L K64Q G44S TDTSTSTAYMELRSLRSDDTAVYYCAREAITTVGAMDYWGQGTLVTVSS (SEQ ID NO:60)
Sh01G06 IGHV1-18 M69L K64Q   TDTSTSTAYMELRSLRSDDTAVYYCAREAITTVGAMDYWGQGTLVTVSS (SEQ ID NO:62)
Sh01G06 IGHV1-69 T30S I69L   ADKSTSTAYMELSSLRSEDTAVYYCAREAITTVGAMDYWGQGTLVTVSS (SEQ ID NO:64)
Sh01G06 IGHV1-69 T30S K64Q I69L ADKSTSTAYMELSSLRSEDTAVYYCAREAITTVGAMDYWGQGTLVTVSS (SEQ ID NO:66)
Hu01G06 IGHV1-18 F1          TDTSTSTAYMELRSLRSDDTAVYYCAREAITTVGAMDYWGQGTLVTVSS (SEQ ID NO:246)
Hu01G06 IGHV1-18 F2          TDTSTSTAYMELRSLRSDDTAVYYCAREAITTVGAMDYWGQGTLVTVSS (SEQ ID NO:248)
Hu01G06 IGHV1-69 F1          ADKSTSTAYMELSSLRSEDTAVYYCAREAITTVGAMDYWGQGTLVTVSS (SEQ ID NO:250)
Hu01G06 IGHV1-69 F2          ADKSTSTAYMELSSLRSEDTAVYYCAREAITTVGAMDYWGQGTLVTVSS (SEQ ID NO:252)
Ch06C11 Chimeric             KDASNNRVFLKITSVDTADTATYYCAQRGYDDYW--GYWGQGTLVTISA (SEQ ID NO:46)
HE_LM_06C11 IGHV2-70         KDTSKNQVVLTITNVDPVDTAVYYCAQRGYDDYW--GYWGQGTLVTISS (SEQ ID NO:68)
Hu06C11 IGHV2-5              KDTSKNQVVLTITNMDPVDTATYYCAQRGYDDYW--GYWGQGTLVTVSS (SEQ ID NO:70)
Ch14F11 Chimeric             KDTSSNEVFLKIAIVDTADTATYYCARRGHYSAM--DYWGQGTSVTVSS (SEQ ID NO:50)
Sh14F11 IGHV2-5              KDTSKNQVVLTMTNMDPVDTATYYCARRGHYSAM--DYWGQGTLVTVSS (SEQ ID NO:72)
Sh14F11 IGHV2-70             KDTSKNQVVLTMTNMDPVDTAVYYCARRGHYSAM--DYWGQGTLVTVSS (SEQ ID NO:74)
```

FIG. 19 Continued

Humanized Heavy Chain CDR Amino Acid Alignments

| Heavy Variable | CDR1 | | CDR2 | |
|---|---|---|---|---|
| Ch01G06 Chimeric | DYNMD-- | (SEQ ID NO:1) | QINPNNGGIFFNQKFKG | (SEQ ID NO:7) |
| Hu01G06 IGHV1-18 | DYNMD-- | (SEQ ID NO:1) | QINPNNGGIFFNQKFKG | (SEQ ID NO:7) |
| Hu01G06 IGHV1-69 | DYNMD-- | (SEQ ID NO:1) | QINPNNGGIFFNQKFKG | (SEQ ID NO:7) |
| Sh01G06 IGHV1-18 M69L | DYNMD-- | (SEQ ID NO:1) | QINPNNGGIFFNQKFKG | (SEQ ID NO:7) |
| Sh01G06 IGHV1-18 M69L K64Q | DYNMD-- | (SEQ ID NO:1) | QINPNNGGIFFNQKFQG | (SEQ ID NO:13) |
| Sh01G06 IGHV1-18 M69L K64Q G44S | DYNMD-- | (SEQ ID NO:1) | QINPNNGGIFFNQKFQG | (SEQ ID NO:13) |
| Sh01G06 IGHV1-69 I69L | DYNMD-- | (SEQ ID NO:1) | QINPNNGGIFFNQKFKG | (SEQ ID NO:7) |
| Sh01G06 IGHV1-69 T30S | DYNMD-- | (SEQ ID NO:1) | QINPNNGGIFFNQKFQG | (SEQ ID NO:13) |
| Sh01G06 IGHV1-69 T30S K64Q I69L | DYNMD-- | (SEQ ID NO:1) | QINPNNGGIFFNQKFQG | (SEQ ID NO:13) |
| Hu01G06 IGHV1-18 F1 | DYNMD-- | (SEQ ID NO:1) | QINPYNHLIFFNQKFQG | (SEQ ID NO:236) |
| Hu01G06 IGHV1-18 F2 | DYNMD-- | (SEQ ID NO:1) | QINPNNGLIFFNQKFQG | (SEQ ID NO:237) |
| Hu01G06 IGHV1-69 F1 | DYNMD-- | (SEQ ID NO:1) | QINPNNGLIFFNQKFKG | (SEQ ID NO:238) |
| Hu01G06 IGHV1-69 F2 | DYNMD-- | (SEQ ID NO:1) | QINPYNHLIFFNQKFKG | (SEQ ID NO:239) |
| Ch06C11 Chimeric | TYGMGVS | (SEQ ID NO:4) | HIY-WDDDKRYNPSLKS | (SEQ ID NO:9) |
| HE LM 06C11 IGHV2-70 | TYGMGVS | (SEQ ID NO:4) | HIY-WDDDKRYNPSLKT | (SEQ ID NO:14) |
| Hu06C11 IGHV2-5 | TYGMGVS | (SEQ ID NO:4) | HIY-WDDDKRYNPSLKS | (SEQ ID NO:9) |
| Ch14F11 Chimeric | TYGMGVG | (SEQ ID NO:5) | DIW-WDDDKYYNPSLKS | (SEQ ID NO:11) |
| Sh14F11 IGHV2-5 | TYGMGVG | (SEQ ID NO:5) | DIW-WDDDKYYNPSLKS | (SEQ ID NO:11) |
| Sh14F11 IGHV2-70 | TYGMGVG | (SEQ ID NO:5) | DIW-WDDDKYYNPSLKS | (SEQ ID NO:11) |

FIG. 20

Humanized Heavy Chain CDR Amino Acid Alignments

| Heavy Variable | | | CDR3 | |
|---|---|---|---|---|
| Ch01G06 Chimeric | | | EAITTVGAMDY | (SEQ ID NO:15) |
| Hu01G06 IGHV1-18 | | | EAITTVGAMDY | (SEQ ID NO:15) |
| Hu01G06 IGHV1-69 | | | EAITTVGAMDY | (SEQ ID NO:15) |
| Sh01G06 IGHV1-18 M69L | | | EAITTVGAMDY | (SEQ ID NO:15) |
| Sh01G06 IGHV1-18 M69L K64Q | | | EAITTVGAMDY | (SEQ ID NO:15) |
| Sh01G06 IGHV1-18 M69L K64Q G44S | | | EAITTVGAMDY | (SEQ ID NO:15) |
| Sh01G06 IGHV1-69 T30S I69L | | | EAITTVGAMDY | (SEQ ID NO:15) |
| Sh01G06 IGHV1-69 T30S K64Q I69L | | | EAITTVGAMDY | (SEQ ID NO:15) |
| Hu01G06 IGHV1-18 F1 | | | EAITTVGAMDY | (SEQ ID NO:15) |
| Hu01G06 IGHV1-18 F2 | | | EAITTVGAMDY | (SEQ ID NO:15) |
| Hu01G06 IGHV1-69 F1 | | | EAITTVGAMDY | (SEQ ID NO:15) |
| Hu01G06 IGHV1-69 F2 | | | EAITTVGAMDY | (SEQ ID NO:15) |
| Ch06C11 Chimeric | | | RGYDDYW--GY | (SEQ ID NO:18) |
| HE_LM_06C11 IGHV2-70 | | | RGYDDYW--GY | (SEQ ID NO:18) |
| Hu06C11 IGHV2-5 | | | RGYDDYW--GY | (SEQ ID NO:18) |
| Ch14F11 Chimeric | | | RGHYSAM--DY | (SEQ ID NO:19) |
| Sh14F11 IGHV2-5 | | | RGHYSAM--DY | (SEQ ID NO:19) |
| Sh14F11 IGHV2-70 | | | RGHYSAM--DY | (SEQ ID NO:19) |

FIG. 20 Continued

Complete Humanized Light (Kappa) Chain Variable Region Amino Acid Alignments

Light (Kappa) Variable

```
                              1         2         3         4         5         6         7
                              0         0         0         0         0         0         0
                                                  CDR1                     CDR2
Ch01G06 Chimeric        DIQMTQSPASLSASVGETVTITCRTSENLHNYLAWYQQKQGKSPQLLVYDAKTLADGVPSRFSGSGSGTQ
Hu01G06 IGKV1-39        DIQMTQSPSSLSASVGDRVTITCRTSENLHNYLAWYQQKPGKSPKLLVYDAKTLADGVPSRFSGSGSGTD
Hu01G06 IGKV1-39 S43A V48I DIQMTQSPSSLSASVGDRVTITCRTSENLHNYLAWYQQKPGKAPKLLIYDAKTLADGVPSRFSGSGSGTD
Hu01G06 IGKV1-39 V48I   DIQMTQSPSSLSASVGDRVTITCRTSENLHNYLAWYQQKPGKSPKLLIYDAKTLADGVPSRFSGSGSGTD
Hu01G06 IGKV1-39 F1     DIQMTQSPSSLSASVGDRVTITCRTSENLHNYLAWYQQKPGKAPKLLIYDAKTLADGVPSRFSGSGSGTD
Hu01G06 IGKV1-39 F2     DIQMTQSPSSLSASVGDRVTITCRTSENLHNYLAWYQQKPGKSPKLLIYDAKTLADGVPSRFSGSGSGTD
Ch06C11 Chimeric        DIVMTQSQKFMSTSVGDRVSVTCKASQNVGTNVAWFQQKPGQSPKALIYSASYRYSGVPDRFTGSGSGTD
Sh06C11 IGKV1-16        DIQMTQSPSSLSASVGDRVTITCKASQNVGTNVAWFQQKPGKAPKSLIYSASYRYSGVPSRFSGSGSGTD
Ch14F11 Chimeric        DIVMTQSQKFMSTSVGDRVSVTCKASQNVGTNVAWYQQKPGQSPKALIYSPSYRYSGVPDRFTGSGSGTD
Hu14F11 IGKV1-16        DIQMTQSPSSLSASVGDRVTITCKASQNVGTNVAWFQQKPGKSPKALIYSPSYRYSGVPSRFSGSGSGTD
```

Light (Kappa) Variable

```
                              7         8         9         1
                              1         0         0         0         0
                                              CDR3
Ch01G06 Chimeric        YSLKINSLQPEDFGSYYCQHFWSSPYTFGGGTKLEIK    (SEQ ID NO:76)
Hu01G06 IGKV1-39        YTLTISSLQPEDFATYYCQHFWSSPYTFGQGTKLEIK    (SEQ ID NO:90)
Hu01G06 IGKV1-39 S43A V48I YTLTISSLQPEDFATYYCQHFWSSPYTFGQGTKLEIK (SEQ ID NO:92)
Hu01G06 IGKV1-39 V48I   YTLTISSLQPEDFATYYCQHFWSSPYTFGQGTKLEIK    (SEQ ID NO:94)
Hu01G06 IGKV1-39 F1     YTLTISSLQPEDFATYYCQHFWSDPYTFGQGTKLEIK    (SEQ ID NO:254)
Hu01G06 IGKV1-39 F2     YTLTISSLQPEDFATYYCQHFWSDPYTFGQGTKLEIK    (SEQ ID NO:92)
Ch06C11 Chimeric        FILTISNVQSEDLAEYFCQQYNNYPLTFGAGTKLELK    (SEQ ID NO:82)
Sh06C11 IGKV1-16        FTLTISSLQPEDFATYFCQQYNNYPLTFGQGTKLEIK    (SEQ ID NO:96)
Ch14F11 Chimeric        FTLTISNVQSEDLAEYFCQQYNSYPHTFGGGTKLEMK    (SEQ ID NO:86)
Hu14F11 IGKV1-16        FTLTISSLQPEDFATYFCQQYNSYPHTFGQGTKLEIK    (SEQ ID NO:98)
```

FIG. 21

Humanized Light (Kappa) Chain CDR Amino Acid Alignments

Light (Kappa) Variable | CDR1 | CDR2
---|---|---
Ch01G06 Chimeric | RTSENLHNYLA (SEQ ID NO:21) | DAKTLAD (SEQ ID NO:26)
Hu01G06 IGKV1-39 | RTSENLHNYLA (SEQ ID NO:21) | DAKTLAD (SEQ ID NO:26)
Hu01G06 IGKV1-39 S43A V48I | RTSENLHNYLA (SEQ ID NO:21) | DAKTLAD (SEQ ID NO:26)
Hu01G06 IGKV1-39 V48I | RTSENLHNYLA (SEQ ID NO:21) | DAKTLAD (SEQ ID NO:26)
Hu01G06 IGKV1-39 F1 | RTSENLHNYLA (SEQ ID NO:21) | DAKTLAD (SEQ ID NO:26)
Hu01G06 IGKV1-39 F2 | RTSENLHNYLA (SEQ ID NO:21) | DAKTLAD (SEQ ID NO:26)
Ch06C11 Chimeric | KASQNVGTNVA (SEQ ID NO:23) | SASYRYS (SEQ ID NO:28)
Sh06C11 IGKV1-16 | KASQNVGTNVA (SEQ ID NO:23) | SASYRYS (SEQ ID NO:28)
Ch14F11 Chimeric | KASQNVGTNVA (SEQ ID NO:23) | SPSYRYS (SEQ ID NO:30)
Hu14F11 IGKV1-16 | KASQNVGTNVA (SEQ ID NO:23) | SPSYRYS (SEQ ID NO:30)

Light (Kappa) Variable | CDR3
---|---
Ch01G06 Chimeric | QHFWSSPYT (SEQ ID NO:32)
Hu01G06 IGKV1-39 | QHFWSSPYT (SEQ ID NO:32)
Hu01G06 IGKV1-39 S43A V48I | QHFWSSPYT (SEQ ID NO:32)
Hu01G06 IGKV1-39 V48I | QHFWSSPYT (SEQ ID NO:32)
Hu01G06 IGKV1-39 F1 | QHFWSSPYT (SEQ ID NO:32)
Hu01G06 IGKV1-39 F2 | QHFWSDPYT (SEQ ID NO:244)
Ch06C11 Chimeric | QQYNNYPLT (SEQ ID NO:35)
Sh06C11 IGKV1-16 | QQYNNYPLT (SEQ ID NO:35)
Ch14F11 Chimeric | QQYNSYPHT (SEQ ID NO:36)
Hu14F11 IGKV1-16 | QQYNSYPHT (SEQ ID NO:36)

FIG. 22

ANTI-GDF15 ANTIBODIES

CROSS-REFERENCE TO RELATED APPLICATIONS

This application claims the benefit of and priority to U.S. Provisional Patent Application No. 61/827,325, filed May 24, 2013, and U.S. Provisional Patent Application No. 61/745,508, filed Dec. 21, 2012, the entire disclosure of each of which is incorporated by reference herein in its entirety.

FIELD OF THE INVENTION

The field of the invention is molecular biology, immunology, cachexia and cachexia-like disorders, and oncology. More particularly, the field is therapeutic antibodies.

BACKGROUND

Involuntary weight loss can be categorized into three primary etiologies that include, cachexia, sarcopenia and starvation. Cachexia is a debilitating metabolic syndrome associated with numerous diseases, including cancer, AIDS, chronic heart failure (also known as congestive heart failure), chronic obstructive pulmonary disease (COPD), chronic kidney disease, tuberculosis, sepsis and other forms of systemic inflammation. Cachexia varies in its manifestations, but generally involves involuntary loss of skeletal muscle mass and some form of underlying illness (Evans et al. (2008) CLIN. NUTR. 27:793-799). Cachexia is a wasting disorder involving involuntary weight loss and may be associated with systemic inflammation and/or an acute inflammatory response. Thomas (2007) CLIN. NUTRITION 26:389-399. Loss of fat mass as well as fat-free mass, such as muscle mass, often is a prominent clinical feature of cachexia. In many but not all cases, cachexia progresses through stages that have been designated precachexia, cachexia and refractory cachexia (Fearon et al. (2011) LANCET ONC. 12:489-495). Two different, but sometimes overlapping, processes appear to drive the development and progression of cachexia: (a) metabolic processes that act directly on muscle, reducing its mass and function; and (b) reduced food intake, which leads to loss of both fat and Muscle (Tsai et al. (2012) J. CACHEXIA SARCOPENIA MUSCLE 3:239-243).

Although cachexia is a complex and incompletely understood syndrome, it is clear that GDF15 (also known as MIC-1, PLAB, PDF and NAG-1), a member of the TGF-β superfamily, is an important mediator of cachexia in various diseases (Tsai et al., supra). At least some tumors over-express and secrete GDF15, and elevated serum GDF15 levels have been associated with various cancers (Johnen et al. (2007) NAT. MED. 13:1333-1340; Bauskin et al. (2006) CANCER RES. 66:4983-4986). Monoclonal antibodies against GDF15 have been recognized as potential anti-cachexia therapeutic agents. See, e.g., U.S. Pat. No. 8,192,735.

Weight loss resulting from cachexia is associated with poor prognosis in various diseases (Evans et al., supra), and cachexia and its consequences are considered to be the direct cause of death in about 20% of cancer deaths (Tisdale (2002) NAT. REV. CANCER 2:862-871). Cachexia is infrequently reversed by nutritional intervention, and currently this syndrome is seldom treated with drug therapy (Evans et al., supra).

Sarcopenia is a clinical condition related to cachexia that is characterized by loss of skeletal muscle mass and muscle strength. The decrease in muscle mass can lead to functional impairment, with loss of strength, increased likelihood of falls, and loss of autonomy. Respiratory function may also be impaired with a reduced vital capacity. During metabolic stress, muscle protein is rapidly mobilized in order to provide the immune system, liver and gut with amino acids, particularly glutamine. Sarcopenia often is a disease of the elderly; however, its development may also be associated with muscle disuse and malnutrition, and may coincide with cachexia. Sarcopenia can be diagnosed based upon functional observations such as low muscle weight and low gait speed. See, e.g., Muscaritoli et al. (2010) CLIN. NUTRITION 29:154-159.

Starvation typically results in a loss of body fat and non-fat mass due to inadequate diet and/or nutritional uptake (Thomas (2007) supra). The effects of starvation often are reversed by improving diet and nutritional, for example, protein, uptake.

Naturally occurring antibodies are multimeric proteins that contain four polypeptide chains (FIG. 1). Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($C_{H1}$, $C_{H2}$ and $C_{H3}$ in FIG. 1). The variable regions determine the specificity of the antibody. Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

There is a significant unmet need for effective therapeutic agents for treating cachexia and sarcopenia, including monoclonal antibodies targeting GDF15. Such therapeutic agents have the potential to play an important role in the treatment of various cancers and other life-threatening diseases.

SUMMARY

The invention is based, in part, upon the discovery of a family of antibodies that specifically bind human GDF15 (hGDF15). The antibodies contain hGDF15 binding sites based on the CDRs of the antibodies. The antibodies can be used as therapeutic agents. When used as therapeutic agents, the antibodies are engineered, e.g., humanized, to reduce or eliminate an immune response when administered to a human patient.

The disclosed antibodies prevent or inhibit the activity of (i.e., neutralize) hGDF15. When administered to a mammal, the antibodies can inhibit the loss of muscle mass, for example, the loss of muscle mass associated with an underlying disease. The underlying disease may be selected from the group consisting of cancer, chronic heart failure, chronic kidney disease, COPD, AIDS, multiple sclerosis, rheumatoid arthritis, sepsis, and tuberculosis. In some embodiments, the loss of muscle mass may be accompanied by a loss of fat mass. The disclosed antibodies can also be used to inhibit involuntary weight loss in a mammal. In some embodiments, the disclosed antibodies may also be used to inhibit the loss of organ mass. Further, a method of treating cachexia and/or sarcopenia in a mammal comprising administering an effective amount of one of at least one of the disclosed antibodies to a mammal in need thereof is disclosed.

Also disclosed is a method for establishing a steady-state level of mature recombinant human GDF15 (rhGDF15) in plasma or serum in a mammal comprising administering a rhGDF15-immunoglobulin Fc (Fc-rhGDF15) fusion protein to the mammal. The Fc-rhGDF15 can be a mouse Fc mature recombinant human GDF15 (mFc-rhGDF15). In some embodiments, the mammal is a rodent, e.g., a mouse.

In another aspect, a method of treating obesity in a mammal, for example, a human, comprising administering a therapeutically effective amount of Fc-rhGDF15, e.g., a human Fc mature recombinant human GDF 15 (hFc-rhGDF15), to the mammal in need thereof, is disclosed. Pharmaceutical compositions comprising an Fc-rhGDF15 fusion protein and a pharmaceutically acceptable carrier are also disclosed.

These and other aspects and advantages of the invention will become apparent upon consideration of the following figures, detailed description, and claims. As used herein, "including" means without limitation, and examples cited are non-limiting. As used herein, "antibody 01G06, 03G05, 04F08, 06C11, 08G01, 14F11, or 17B11" means antibody 01G06, 03G05, 04F08, 06C11, 08G01, 14F11, or 17B11, or humanized variants thereof.

DESCRIPTION OF THE DRAWINGS

The invention can be more completely understood with reference to the following drawings.

FIG. 10 is a sequence alignment showing the amino acid sequence of the complete immunoglobulin heavy chain variable region of antibodies 01G06, 03G05, 04F08, 06C11, 08G01, 14F11, and 17B11. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 11 is a sequence alignment showing the $CDR_1$, $CDR_2$, and $CDR_3$ sequences for each of the immunoglobulin heavy chain variable region sequences in FIG. 10.

FIG. 12 is a sequence alignment showing the amino acid sequence of the complete immunoglobulin light chain variable region of antibodies 01G06, 03G05, 04F08, 06C11, 08G01, 14F11, and 17B11. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 13 is a sequence alignment showing the $CDR_1$, $CDR_2$, and $CDR_3$ sequences for each of the immunoglobulin light chain variable region sequences in FIG. 12.

In FIG. 16A, the arrow indicates intra-peritoneal injection of antibody.

FIG. 19 is a sequence alignment showing the amino acid sequence of the complete immunoglobulin heavy chain variable region of chimeric 01G06 variable region denoted as Ch01G06 Chimeric; humanized 01G06 heavy chain variable regions denoted as Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, and Hu01G06 IGHV1-69 F2; chimeric 06C11 denoted as Ch06C11 Chimeric; humanized 06C11 heavy chain variable regions denoted as HE LM 06C11 IGHV2-70, and Hu06C11 IGHV2-5; chimeric 14F11 denoted as Ch14F11 Chimeric; and humanized 14F11 heavy chain variable regions denoted as Sh14F11 IGHV2-5 and Sh14F11 IGHV2-70. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 20 is a sequence alignment showing the $CDR_1$, $CDR_2$, and $CDR_3$ sequences for each of the immunoglobulin heavy chain variable region sequences in FIG. 19.

FIG. 21 is a sequence alignment showing the amino acid sequence of the complete immunoglobulin light chain variable region of chimeric 01G06 denoted as Ch01G06 Chimeric; humanized 01G06 light chain variable regions denoted as Hu01G06 IGKV1-39, Hu01G06 IGKV1-39 S43A V48I, Hu01G06 IGKV1-39 V48I, Hu01G06 IGKV1-39 F1, and Hu01G06 IGKV1-39 F2; chimeric 06C11 denoted as Ch06C11 Chimeric; humanized 06C11 light chain variable region denoted as Sh06C11 IGKV1-16; chimeric 14F11 denoted as Ch14F11 Chimeric; and humanized 14F11 light chain variable region denoted as Hu14F11 IGKV1-16. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 22 is a sequence alignment showing the $CDR_1$, $CDR_2$, and $CDR_3$ sequences for each of the immunoglobulin light chain variable region sequences in FIG. 21.

FIG. 29A) similar to levels found in non tumor bearing mice (SHAM (▲); FIG. 29A). The arrows in FIG. 29A indicate intra-peritoneal injection of antibody.

DETAILED DESCRIPTION

Figure 1:
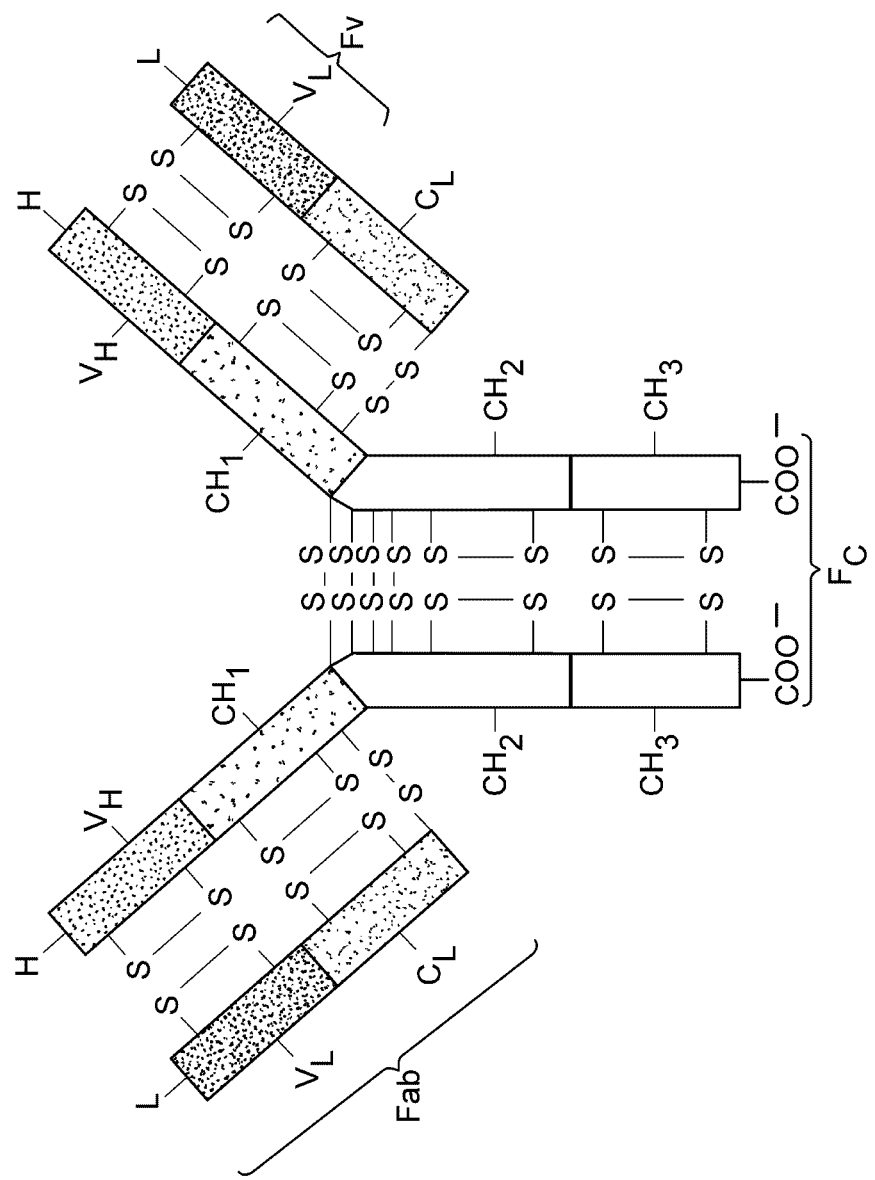
FIG. 1 (prior art) is a schematic representation of a typical naturally-occurring antibody.

The anti-GDF15 antibodies disclosed herein are based on the antigen binding sites of certain monoclonal antibodies that have been selected on the basis of binding and neutralization of human GDF15 (hGDF15). The antibodies contain immunoglobulin variable region CDR sequences that define a binding site for hGDF15.

By virtue of the neutralizing activity of these antibodies, they are useful for treating cachexia and/or sarcopenia. For use as therapeutic agents, the antibodies can be engineered to minimize or eliminate an immune response when administered to a human patient. Various features and aspects of the invention are discussed in more detail below.

As used herein, "cachexia" means a metabolic syndrome associated with underlying disease and characterized by involuntary loss of muscle mass. Cachexia is often accompanied by involuntary weight loss, loss of fat mass, anorexia, inflammation, insulin resistance, fatigue, weakness, significant loss of appetite, and/or increased muscle protein breakdown. Cachexia is distinct from starvation, age-related loss of muscle mass, malabsorption, and hyperthyroidism. Underlying diseases associated with cachexia include cancer, chronic heart failure, chronic kidney disease, COPD, AIDS, multiple sclerosis, rheumatoid arthritis, sepsis, and tuberculosis.

As used herein, "sarcopenia" is understood to be a condition characterized primarily by loss of skeletal muscle mass and muscle strength. Sarcopenia is frequently associated with aging. See, Ruegg and Glass (2011) ANNUAL REV. PHARMACOL. TOXICOL. 51:373-395. In one approach, sarcopenia can be identified in a subject if a value of the appendicular skeletal muscle mass of a subject divided by the height of the subject in meters is more than two standard deviations below the young normal mean. (Thomas (2007) supra; see also Baumgartner et al. (1999) MECH. AGEING DEV. 147:755-763).

As used herein, unless otherwise indicated, "antibody" means an intact antibody (e.g., an intact monoclonal antibody) or antigen-binding fragment of an antibody, including an intact antibody or antigen-binding fragment that has been modified or engineered, or that is a human antibody. Examples of antibodies that have been modified or engineered are chimeric antibodies, humanized antibodies, and multispecific antibodies (e.g., bispecific antibodies). Examples of antigen-binding fragments include Fab, Fab', F(ab')$_2$, Fv, single chain antibodies (e.g., scFv), minibodies and diabodies.

I. Antibodies that Bind GDF15

The antibodies disclosed herein comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding hGDF15 protein.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding hGDF15. A $CDR_{H1}$ comprises an amino acid sequence selected from the group consisting of SEQ ID NO:1 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:2 (03G05), SEQ ID NO:3 (04F08), SEQ ID NO:4 (06C11, Ch06C11 Chimeric, HE LM 06C11 IGHV2-70, Hu06C11 IGHV2-5), SEQ ID NO:5 (14F11, Ch14F11 Chimeric, Sh14F11 IGHV2-5, Sh14F11 IGHV2-70), and SEQ ID NO:6 (17B11); a $CDR_{H2}$ comprises an amino acid sequence selected from the group consisting of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), SEQ ID NO:8 (03G05), SEQ ID NO:9 (04F08, 06C11, Ch06C11 Chimeric, Hu06C11 IGHV2-5), SEQ ID NO:10 (08G01), SEQ ID NO:11 (14F11, Ch14F11 Chimeric, Sh14F11 IGHV2-5, Sh14F11 IGHV2-70), SEQ ID NO:12 (17B11), SEQ ID NO:13 (Sh01G06 IGHV1-18 M69L K64Q G44S, Sh01G06 IGHV1-18 M69L K64Q, Sh01G06 IGHV1-69 T30S K64Q I69L), SEQ ID NO:236 (Hu01G06 IGHV1-18 F1), SEQ ID NO:237 (Hu01G06 IGHV1-18 F2), SEQ ID NO:238 (Hu01G06 IGHV1-69 F1), SEQ ID NO:239 (Hu01G06 IGHV1-69 F2), and SEQ ID NO:14 (HE LM 06C11 IGHV2-70); and a $CDR_{H3}$ comprises an amino acid sequence selected from the group consisting of SEQ ID NO:15 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:16 (03G05), SEQ ID NO:17 (04F08), SEQ ID NO:18 (06C11, Ch06C11 Chimeric, HE LM 06C11 IGHV2-70, Hu06C11 IGHV2-5), SEQ ID NO:19 (14F11, Ch14F11 Chimeric, Sh14F11 IGHV2-5, Sh14F11 IGHV2-70), and SEQ ID NO:20 (17B11). Throughout this specification, a particular SEQ ID NO. is followed in parentheses by the antibody that was the origin of that sequence. For example, "SEQ ID NO:2 (03G05)" means that SEQ ID NO:2 comes from antibody 03G05.

In some embodiments, the antibody comprises an immunoglobulin heavy chain variable region comprising a $CDR_{H1}$ comprising the amino acid sequence of SEQ ID NO:1 (01G06, Ch01G06 Chimeric, Hu01G06 IGHV1-18, Hu01G06 IGHV1-69, Sh01G06 IGHV1-69 T30S I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:7 (01G06, Ch01G06 Chimeric, Hu01G06 IGHV1-18, Hu01G06 IGHV1-69, Sh01G06 IGHV1-69 T30S I69L), and a $CDR_{H3}$ comprising the amino acid sequence of SEQ ID NO:15 (01G06, Ch01G06 Chimeric, Hu01G06 IGHV1-18, Hu01G06 IGHV1-69, Sh01G06 IGHV1-69 T30S I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:2 (03G05), a $CDR_{H2}$ comprising the amino acid sequence of SEQ ID NO:8 (03G05), and a $CDR_{H3}$ comprising the amino acid sequence of SEQ ID NO:16 (03G05).

In some embodiments, the antibody comprises an immunoglobulin heavy chain variable region comprising a $CDR_{H1}$ comprising the amino acid sequence of SEQ ID NO:3 (04F08), a $CDR_{H2}$ comprising the amino acid sequence of SEQ ID NO:9 (04F08), and a $CDR_{H3}$ comprising the amino acid sequence of SEQ ID NO:17 (04F08).

In some embodiments, the antibody comprises an immunoglobulin heavy chain variable region comprising a $CDR_{H1}$ comprising the amino acid sequence of SEQ ID NO:4 (06C11, Ch06C11 Chimeric, Hu06C11 IGHV2-5), a $CDR_{H2}$ comprising the amino acid sequence of SEQ ID NO:9 (06C11, Ch06C11 Chimeric, Hu06C11 IGHV2-5), and a $CDR_{H3}$ comprising the amino acid sequence of SEQ ID NO:18 (06C11, Ch06C11 Chimeric, Hu06C11 IGHV2-5).

In some embodiments, the antibody comprises an immunoglobulin heavy chain variable region comprising a $CDR_{H1}$ comprising the amino acid sequence of SEQ ID NO:1

(08G01), a CDR$_{H2}$ comprising the amino acid sequence of SEQ ID NO:10 (08G01), and a CDR$_{H3}$ comprising the amino acid sequence of SEQ ID NO:15 (08G01).

In some embodiments, the antibody comprises an immunoglobulin heavy chain variable region comprising a CDR$_{H1}$ comprising the amino acid sequence of SEQ ID NO:5 (14F11, Ch14F11 Chimeric, Sh14F11 IGHV2-5, Sh14F11 IGHV2-70), a CDR$_{H2}$ comprising the amino acid sequence of SEQ ID NO:11 (14F11, Ch14F11 Chimeric, Sh14F11 IGHV2-5, Sh14F11 IGHV2-70), and a CDR$_{H3}$ comprising the amino acid sequence of SEQ ID NO:19 (14F11, Ch14F11 Chimeric, Sh14F11 IGHV2-5, Sh14F11 IGHV2-70).

In some embodiments, the antibody comprises an immunoglobulin heavy chain variable region comprising a CDR$_{H1}$ comprising the amino acid sequence of SEQ ID NO:6 (17B11), a CDR$_{H2}$ comprising the amino acid sequence of SEQ ID NO:12 (17B11), and a CDR$_{H3}$ comprising the amino acid sequence of SEQ ID NO:20 (17B11).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:13 (Sh01G06 IGHV1-18 M69L K64Q G44S, Sh01G06 IGHV1-18 M69L K64Q, Sh01G06 IGHV1-69 T30S K64Q I69L), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:236 (Hu01G06 IGHV1-18 F1), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:237 (Hu01G06 IGHV1-18 F2), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:238 (Hu01G06 IGHV1-69 F1), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:239 (Hu01G06 IGHV1-69 F2), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:4 (HE LM 06C11 IGHV2-70), a CDR$_{H2}$ comprising the amino acid sequence of SEQ ID NO:14 (HE LM 06C11 IGHV2-70), and a CDR$_{H3}$ comprising the amino acid sequence of SEQ ID NO:18 (HE LM 06C11 IGHV2-70).

Preferably, the CDR$_{H1}$, CDR$_{H2}$, and CDR$_{H3}$ sequences are interposed between fully human or humanized immunoglobulin FR sequences.

In some embodiments, the antibody comprises (a) an immunoglobulin light chain variable region comprising the structure CDR$_{L1}$-CDR$_{L2}$-CDR$_{L3}$, and (b) an immunoglobulin heavy chain variable region, wherein the immunoglobulin light chain variable region and the immunoglobulin heavy chain variable region together define a single binding site for binding hGDF15. A CDR$_{L1}$ comprises an amino acid sequence selected from the group consisting of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:22 (03G05), SEQ ID NO:23 (04F08, 06C11, Ch06C11 Chimeric, Sh06C11 IGKV1-16, 14F11, Ch14F11 Chimeric, Hu14F11 IGKV1-16), SEQ ID NO:24 (08G01), and SEQ ID NO:25 (17B11); a CDR$_{L2}$ comprises an amino acid sequence selected from the group consisting of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:27 (03G05), SEQ ID NO:28 (04F08, 06C11, Ch06C11 Chimeric, Sh06C11 IGKV1-16), SEQ ID NO:29 (08G01), SEQ ID NO:30 (14F11, Ch14F11 Chimeric, Hu14F11 IGKV1-16), and SEQ ID NO:31 (17B11); and a CDR$_{L3}$ comprises an amino acid sequence selected from the group consisting of SEQ ID NO:32 (01G06, Ch01G06 Chimeric, Hu01G06 IGKV1-39, Hu01G06 IGKV1-39 S43A V48I, Hu01G06 IGKV1-39 V48I, 08G01, Hu01G06 IGKV1-39 F1), SEQ ID NO:244 (Hu01G06 IGKV1-39 F2), SEQ ID NO:33 (03G05), SEQ ID NO:34 (04F08), SEQ ID NO:35 (06C11, Ch06C11 Chimeric, Sh06C11 IGKV1-16), SEQ ID NO:36 (14F11, Ch14F11 Chimeric, Hu14F11 IGKV1-16), and SEQ ID NO:37 (17B11).

In some embodiments, the antibody comprises an immunoglobulin light chain variable region comprising a CDR$_{L1}$ comprising the amino acid sequence of SEQ ID NO:21

(01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), a $CDR_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), and a $CDR_{L3}$ comprising the amino acid sequence of SEQ ID NO:32 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1).

In some embodiments, the antibody comprises an immunoglobulin light chain variable region comprising a $CDR_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), a $CDR_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), and a $CDR_{L3}$ comprising the amino acid sequence of SEQ ID NO:244 (Hu01G06 IGKV1-39 F2).

In some embodiments, the antibody comprises an immunoglobulin light chain variable region comprising a $CDR_{L1}$ comprising the amino acid sequence of SEQ ID NO:22 (03G05), a $CDR_{L2}$ comprising the amino acid sequence of SEQ ID NO:27 (03G05), and a $CDR_{L3}$ comprising the amino acid sequence of SEQ ID NO:33 (03G05).

In some embodiments, the antibody comprises an immunoglobulin light chain variable region comprising a $CDR_{L1}$ comprising the amino acid sequence of SEQ ID NO:23 (04F08), a $CDR_{L2}$ comprising the amino acid sequence of SEQ ID NO:28 (04F08), and a $CDR_{L3}$ comprising the amino acid sequence of SEQ ID NO:34 (04F08).

In some embodiments, the antibody comprises an immunoglobulin light chain variable region comprising a $CDR_{L1}$ comprising the amino acid sequence of SEQ ID NO:23 (06C11, Ch06C11 Chimeric, Sh06C11 IGKV1-16), a $CDR_{L2}$ comprising the amino acid sequence of SEQ ID NO:28 (06C11, Ch06C11 Chimeric, Sh06C11 IGKV1-16), and a $CDR_{L3}$ comprising the amino acid sequence of SEQ ID NO:35 (06C11, Ch06C11 Chimeric, Sh06C11 IGKV1-16).

In some embodiments, the antibody comprises an immunoglobulin light chain variable region comprising a $CDR_{L1}$ comprising the amino acid sequence of SEQ ID NO:24 (08G01), a $CDR_{L2}$ comprising the amino acid sequence of SEQ ID NO:29 (08G01), and a $CDR_{L3}$ comprising the amino acid sequence of SEQ ID NO:32 (08G01).

In some embodiments, the antibody comprises an immunoglobulin light chain variable region comprising a $CDR_{L1}$ comprising the amino acid sequence of SEQ ID NO:23 (14F11, Ch14F11 Chimeric, Hu14F11 IGKV1-16), a $CDR_{L2}$ comprising the amino acid sequence of SEQ ID NO:30 (14F11, Ch14F11 Chimeric, Hu14F11 IGKV1-16), and a $CDR_{L3}$ comprising the amino acid sequence of SEQ ID NO:36 (14F11, Ch14F11 Chimeric, Hu14F11 IGKV1-16).

In some embodiments, the antibody comprises an immunoglobulin light chain variable region comprising a $CDR_{L1}$ comprising the amino acid sequence of SEQ ID NO:25 (17B11), a $CDR_{L2}$ comprising the amino acid sequence of SEQ ID NO:31 (17B11), and a $CDR_{L3}$ comprising the amino acid sequence of SEQ ID NO:37 (17B11).

Preferably, the $CDR_{L1}$, $CDR_{L2}$, and $CDR_{L3}$ sequences are interposed between fully human or humanized immunoglobulin FR sequences.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding hGDF15. The $CDR_{H1}$ is an amino acid sequence selected from the group consisting of SEQ ID NO:1 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:2 (03G05), SEQ ID NO:3 (04F08), SEQ ID NO:4 (06C11, Ch06C11 Chimeric, HE LM 06C11 IGHV2-70, Hu06C11 IGHV2-5), SEQ ID NO:5 (14F11, Ch14F11 Chimeric, Sh14F11 IGHV2-5, Sh14F11 IGHV2-70), and SEQ ID NO:6 (17B11); the $CDR_{H2}$ is an amino acid sequence selected from the group consisting of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), SEQ ID NO:8 (03G05), SEQ ID NO:9 (04F08, 06C11, Ch06C11 Chimeric, Hu06C11 IGHV2-5), SEQ ID NO:10 (08G01), SEQ ID NO:11 (14F11, Ch14F11 Chimeric, Sh14F11 IGHV2-5, Sh14F11 IGHV2-70), SEQ ID NO:12 (17B11), SEQ ID NO:13 (Sh01G06 IGHV1-18 M69L K64Q G44S, Sh01G06 IGHV1-18 M69L K64Q, Sh01G06 IGHV1-69 T30S K64Q I69L), SEQ ID NO:236 (Hu01G06 IGHV1-18 F1), SEQ ID NO:237 (Hu01G06 IGHV1-18 F2), SEQ ID NO:238 (Hu01G06 IGHV1-69 F1), SEQ ID NO:239 (Hu01G06 IGHV1-69 F2), and SEQ ID NO:14 (HE LM 06C11 IGHV2-70); and the $CDR_{H3}$ is an amino acid sequence selected from the group consisting of SEQ ID NO:15 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:16 (03G05), SEQ ID NO:17 (04F08), SEQ ID NO:18 (06C11, Ch06C11 Chimeric, HE LM 06C11 IGHV2-70, Hu06C11 IGHV2-5), SEQ ID NO:19 (14F11, Ch14F11 Chimeric, Sh14F11 IGHV2-5, Sh14F11 IGHV2-70), and SEQ ID NO:20 (17B11). The $CDR_{L1}$ is an amino acid sequence selected from the group consisting of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:22 (03G05), SEQ ID NO:23 (04F08, 06C11, Ch06C11 Chimeric, Sh06C11 IGKV1-16, 14F11, Ch14F11 Chimeric, Hu14F11 IGKV1-16), SEQ ID NO:24 (08G01), and SEQ ID NO:25 (17B11); the $CDR_{L2}$ is an amino acid sequence selected from the group consisting of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:27 (03G05), SEQ ID NO:28 (04F08, 06C11, Ch06C11 Chimeric, Sh06C11 IGKV1-16), SEQ ID NO:29 (08G01), SEQ ID NO:30 (14F11, Ch14F11 Chimeric, Hu14F11 IGKV1-16), and SEQ ID NO:31 (17B11); and the $CDR_{L3}$ is an amino acid sequence selected from the group consisting of SEQ ID NO:32 (01G06, Ch01G06 Chimeric, Hu01G06 IGKV1-39, Hu01G06 IGKV1-39 S43A V48I, Hu01G06 IGKV1-39 V48I, 08G01, Hu01G06 IGKV1-39 F1), SEQ ID NO:244 (Hu01G06 IGKV1-39 F2), SEQ ID NO:33 (03G05), SEQ ID NO:34 (04F08), SEQ ID NO:35 (06C11, Ch06C11 Chimeric, Sh06C11 IGKV1-16), SEQ ID NO:36 (14F11, Ch14F11 Chimeric, Hu14F11 IGKV1-16), and SEQ ID NO:37 (17B11).

In some embodiments, the antibody comprises an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F1), a $CDR_{H2}$ comprising an amino acid sequence selected from the group consisting of SEQ ID NO:236 and SEQ ID NO:240 (Hu01G06 IGHV1-18 F1), and a $CDR_{H3}$ comprising the amino acid sequence of SEQ ID NO:15 (Hu01G06 IGHV1-18 F1); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F2), a $CDR_{H2}$ comprising an amino acid sequence selected from the group consisting of SEQ ID NO:237 and SEQ ID NO:241 (Hu01G06 IGHV1-18 F2), and a $CDR_{H3}$ comprising the amino acid sequence of SEQ ID NO:15 (Hu01G06 IGHV1-18 F2); and an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F1), a $CDR_{H2}$ comprising an amino acid sequence selected from the group consisting of SEQ ID NO:238 and SEQ ID NO:241 (Hu01G06 IGHV1-69 F1), and a $CDR_{H3}$ comprising the amino acid sequence of SEQ ID NO:15 (Hu01G06 IGHV1-69 F1); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F2), a $CDR_{H2}$ comprising an amino acid sequence selected from the group consisting of SEQ ID NO:239 and SEQ ID NO:240 (Hu01G06 IGHV1-69 F2), and a $CDR_{H3}$ comprising the amino acid sequence of SEQ ID NO:15 (Hu01G06 IGHV1-69 F2); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F2), a $CDR_{H2}$ comprising an amino acid sequence selected from the group consisting of SEQ ID NO:239 and SEQ ID NO:240 (Hu01G06 IGHV1-69 F2), and a $CDR_{H3}$ comprising the amino acid sequence of SEQ ID NO:15 (Hu01G06 IGHV1-69 F2); and an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2).

The antibodies disclosed herein comprise an immunoglobulin heavy chain variable region and an immunoglobulin light chain variable region. In some embodiments, the antibody comprises an immunoglobulin heavy chain variable region selected from the group consisting of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70); and an immunoglobulin light chain variable region.

In other embodiments, the antibody comprises an immunoglobulin light chain variable region selected from the group consisting of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:96 (Sh06C11 IGKV1-16), SEQ ID NO:254 (Hu01G06 IGKV1-39 F2), and SEQ ID NO:98 (Hu14F11 IGKV1-16), and an immunoglobulin heavy chain variable region.

In some embodiments, the antibody comprises an immunoglobulin heavy chain variable region selected from the group consisting of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70), and an immunoglobulin light chain variable region selected from the group consisting of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:96 (Sh06C11 IGKV1-16), SEQ ID NO:254 (Hu01G06 IGKV1-39 F2), and SEQ ID NO:98 (Hu14F11 IGKV1-16).

In some embodiments, the antibody comprises an immunoglobulin heavy chain variable region comprising the amino acid sequence of SEQ ID NO:40 (01G06, Ch01G06 Chimeric), and an immunoglobulin light chain variable region comprising the amino acid sequence of SEQ ID NO:76 (01G06, Ch01G06 Chimeric).

In some embodiments, the antibody comprises an immunoglobulin heavy chain variable region comprising the amino acid sequence of SEQ ID NO:42 (03G05), and an immunoglobulin light chain variable region comprising the amino acid sequence of SEQ ID NO:78 (03G05).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:46 (06C11), and an immunoglobulin light chain variable region comprising the amino acid sequence of SEQ ID NO:82 (06C11).

In some embodiments, the antibody comprises an immunoglobulin heavy chain variable region comprising the amino acid sequence of SEQ ID NO:48 (08G01), and an immunoglobulin light chain variable region comprising the amino acid sequence of SEQ ID NO:84 (08G01).

In some embodiments, the antibody comprises an immunoglobulin heavy chain variable region comprising the amino acid sequence of SEQ ID NO:50 (14F11), and an immunoglobulin light chain variable region comprising the amino acid sequence of SEQ ID NO:86 (14F11).

In some embodiments, the antibody comprises an immunoglobulin heavy chain variable region comprising the amino acid sequence of SEQ ID NO:52 (17B11), and an immunoglobulin light chain variable region comprising the amino acid sequence of SEQ ID NO:88 (17B11).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:90 (Hu01G06 IGKV1-39).

In some embodiments, the antibody comprises an immuoglobulin heavy chain variable region comprising the amino acid sequence of SEQ ID NO:40 (Ch01G06 Chimeric), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:246 (Hu01G06 IGHV1-18 F1), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:248 (Hu01G06 IGHV1-18 F2), and an immunoglobulin light chain variable region comprising the amino acid sequence of SEQ ID NO:254 (Hu01G06 IGKV1-39 F2).

In some embodiments, the antibody comprises an immunoglobulin heavy chain variable region comprising the amino acid sequence of SEQ ID NO:250 (Hu01G06 IGHV1-69 F1), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:254 (Hu01G06 IGKV1-39 F2).

In some embodiments, the antibody comprises an immunoglobulin heavy chain variable region comprising the amino acid sequence of SEQ ID NO:68 (HELM 06C11 IGHV2-70), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:68 (HE LM 06C11 IGHV2-70), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:48 (08G01), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:84 (08G01).

In certain embodiments, the antibodies disclosed herein comprise an immunoglobulin heavy chain and an immunoglobulin light chain. In some embodiments, the antibody comprises an immunoglobulin heavy chain selected from the group consisting of SEQ ID NO:100 (01G06), SEQ ID NO:104 (03G05), SEQ ID NO:108 (04F08), SEQ ID NO:112 (06C11), SEQ ID NO:116 (08G01), SEQ ID NO:120 (14F11), SEQ ID NO:124 (17B11), SEQ ID NO:176 (Ch01G06 Chimeric), SEQ ID NO:178 (Hu01G06 IGHV1-18), SEQ ID NO:180 (Hu01G06 IGHV1-69), SEQ ID NO:182 (Sh01G06 IGHV1-18 M69L), SEQ ID NO:184 (Sh01G06 IGHV1-18 M69L K64Q G44S), SEQ ID NO:186 (Sh01G06 IGHV1-18 M69L K64Q), SEQ ID NO:188 (Sh01G06 IGHV1-69 T30S I69L), SEQ ID NO:190 (Sh01G06 IGHV1-69 T30S K64Q I69L), SEQ ID NO:256 (Hu01G06 IGHV1-18 F1), SEQ ID NO:258 (Hu01G06 IGHV1-18 F2), SEQ ID NO:260 (Hu01G06 IGHV1-69 F1), SEQ ID NO:262 (Hu01G06 IGHV1-69 F2), SEQ ID NO:192 (Ch06C11 Chimeric), SEQ ID NO:194 (HE LM 06C11 IGHV2-70), SEQ ID NO:196 (Hu06C11 IGHV2-5), SEQ ID NO:198 (Ch14F11 Chimeric), SEQ ID NO:200 (Sh14F11 IGHV2-5), and SEQ ID NO:202 (Sh14F11 IGHV2-70); and an immunoglobulin light chain.

In other embodiments, the antibody comprises an immunoglobulin light chain selected from the group consisting of SEQ ID NO:102 (01G06), SEQ ID NO:106 (03G05), SEQ ID NO:110 (04F08), SEQ ID NO:114 (06C11), SEQ ID NO:118 (08G01), SEQ ID NO:122 (14F11), SEQ ID NO:126 (17B11), SEQ ID NO:204 (Ch01G06 Chimeric), SEQ ID NO:206 (Hu01G06 IGKV1-39), SEQ ID NO:208 (Hu01G06 IGKV1-39 S43A V48I or Hu01G06 IGKV1-39 F1), SEQ ID NO:210 (Hu01G06 IGKV1-39 V48I), SEQ ID NO:264 (Hu01G06 IGKV1-39 F2), SEQ ID NO:212 (Ch06C11 Chimeric), SEQ ID NO:214 (Sh06C11 IGKV1-16), SEQ ID NO:216 (Ch14F11 Chimeric), and SEQ ID NO:218 (Hu14F11 IGKV1-16), and an immunoglobulin heavy chain.

In some embodiments, the antibody comprises (i) an immunoglobulin heavy chain selected from the group consisting of SEQ ID NO:100 (01G06), SEQ ID NO:104 (03G05), SEQ ID NO:108 (04F08), SEQ ID NO:112 (06C11), SEQ ID NO:116 (08G01), SEQ ID NO:120 (14F11), SEQ ID NO:124 (17B11), SEQ ID NO:176 (Ch01G06 Chimeric), SEQ ID NO:178 (Hu01G06 IGHV1-18), SEQ ID NO:180 (Hu01G06 IGHV1-69), SEQ ID NO:182 (Sh01G06 IGHV1-18 M69L), SEQ ID NO:184 (Sh01G06 IGHV1-18 M69L K64Q G44S), SEQ ID NO:186 (Sh01G06 IGHV1-18 M69L K64Q), SEQ ID NO:188 (Sh01G06 IGHV1-69 T30S I69L), SEQ ID NO:190 (Sh01G06 IGHV1-69 T30S K64Q I69L), SEQ ID NO:256 (Hu01G06 IGHV1-18 F1), SEQ ID NO:258 (Hu01G06 IGHV1-18 F2), SEQ ID NO:260 (Hu01G06 IGHV1-69 F1), SEQ ID NO:262 (Hu01G06 IGHV1-69 F2), SEQ ID NO:192 (Ch06C11 Chimeric), SEQ ID NO:194 (HE LM 06C11 IGHV2-70), SEQ ID NO:196 (Hu06C11 IGHV2-5), SEQ ID NO:198 (Ch14F11 Chimeric), SEQ ID NO:200 (Sh14F11 IGHV2-5), and SEQ ID NO:202 (Sh14F11 IGHV2-70), and (ii) an immunoglobulin light chain selected from the group consisting of SEQ ID NO:102 (01G06), SEQ ID NO:106 (03G05), SEQ ID NO:110 (04F08), SEQ ID NO:114 (06C11), SEQ ID NO:118 (08G01), SEQ ID NO:122 (14F11), SEQ ID NO:126 (17B11), SEQ ID NO:204 (Ch01G06 Chimeric), SEQ ID NO:206 (Hu01G06 IGKV1-39), SEQ ID NO:208 (Hu01G06 IGKV1-39 S43A V48I or Hu01G06 IGKV1-39 F1), SEQ ID NO:210 (Hu01G06 IGKV1-39 V48I), SEQ ID NO:264 (Hu01G06 IGKV1-39 F2), SEQ ID NO:212 (Ch06C11 Chimeric), SEQ ID NO:214 (Sh06C11 IGKV1-16), SEQ ID NO:216 (Ch14F11 Chimeric), and SEQ ID NO:218 (Hu14F11 IGKV1-16).

In some embodiments, the antibody comprises an immunoglobulin heavy chain comprising the amino acid sequence of SEQ ID NO:176 (Ch01G06 Chimeric), and an immunoglobulin light chain comprising the amino acid sequence of SEQ ID NO:204 (Ch01G06 Chimeric).

In some embodiments, the antibody comprises an immunoglobulin heavy chain comprising the amino acid sequence of SEQ ID NO:192 (Ch06C11 Chimeric), and an immunoglobulin light chain comprising the amino acid sequence of SEQ ID NO:212 (Ch06C11 Chimeric).

In some embodiments, the antibody comprises an immunoglobulin heavy chain comprising the amino acid sequence of SEQ ID NO:198 (Ch14F11 Chimeric), and an immunoglobulin light chain comprising the amino acid sequence of SEQ ID NO:216 (Ch14F11 Chimeric).

In some embodiments, the antibody comprises an immunoglobulin heavy chain comprising the amino acid sequence of SEQ ID NO:178 (Hu01G06 IGHV1-18), and an immunoglobulin light chain comprising the amino acid sequence of SEQ ID NO:206 (Hu01G06 IGKV1-39).

In some embodiments, the antibody comprises an immunoglobulin heavy chain comprising the amino acid sequence of SEQ ID NO:180 (Hu01G06 IGHV1-69), and an immunoglobulin light chain comprising the amino acid sequence of SEQ ID NO:206 (Hu01G06 IGKV1-39).

In some embodiments, the antibody comprises an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:210 (Hu01G06 IGKV1-39 V48I).

In some embodiments, the antibody comprises an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:210 (Hu01G06 IGKV1-39 V48I).

In some embodiments, the antibody comprises an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:208 (Hu01G06 IGKV1-39 S43A V48I).

In some embodiments, the antibody comprises an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:208 (Hu01G06 IGKV1-39 S43A V48I).

In some embodiments, the antibody comprises an immunoglobulin heavy chain comprising the amino acid sequence of SEQ ID NO:256 (Hu01G06 IGHV1-18 F1), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:258 (Hu01G06 IGHV1-18 F2), and an immunoglobulin light chain comprising the amino acid sequence of SEQ ID NO:264 (Hu01G06 IGKV1-39 F2).

In some embodiments, the antibody comprises an immunoglobulin heavy chain comprising the amino acid sequence of SEQ ID NO:260 (Hu01G06 IGHV1-69 F1), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:262 (Hu01G06 IGHV1-69 F2), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:262 (Hu01G06 IGHV1-69 F2), and an immunoglobulin light chain comprising the amino acid sequence of SEQ ID NO:264 (Hu01G06 IGKV1-39 F2).

In some embodiments, the antibody comprises an immunoglobulin heavy chain comprising the amino acid sequence of SEQ ID NO:194 (HE LM 06C11 IGHV2-70), and an immunoglobulin light chain comprising the amino acid sequence of SEQ ID NO:214 (Sh06C11 IGKV1-16).

In some embodiments, the antibody comprises an immunoglobulin heavy chain comprising the amino acid sequence of SEQ ID NO:196 (Hu06C11 IGHV2-5), and an immunoglobulin light chain comprising the amino acid sequence of SEQ ID NO:214 (Sh06C11 IGKV1-16).

In some embodiments, the antibody comprises an immunoglobulin heavy chain comprising the amino acid sequence of SEQ ID NO:200 (Sh14F11 IGHV2-5), and an immunoglobulin light chain comprising the amino acid sequence of SEQ ID NO:218 (Hu14F11 IGKV1-16)

In some embodiments, the antibody comprises an immunoglobulin heavy chain comprising the amino acid sequence of SEQ ID NO:202 (Sh14F11 IGHV2-70), and an immunoglobulin light chain comprising the amino acid sequence of SEQ ID NO:218 (Hu14F11 IGKV1-16).

In certain embodiments, an isolated antibody that binds hGDF15 comprises an immunoglobulin heavy chain variable region comprising an amino acid sequence that is at least 70%, 75%, 80%, 85%, 90%, 95%, 98%, or 99% identical to the entire variable region or the FR sequence of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70).

In certain embodiments, an isolated antibody that binds hGDF15 comprises an immunoglobulin light chain variable region comprising an amino acid sequence that is at least 70%, 75%, 80%, 85%, 90%, 95%, 98%, or 99% identical to the entire variable region or the FR sequence of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:254 (Hu01G06 IGKV1-39 F2), SEQ ID NO:96 (Sh06C11 IGKV1-16), and SEQ ID NO:98 (Hu14F11 IGKV1-16).

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36:290-300; Altschul et al., (1997) NUCLEIC ACIDS RES. 25:3389-3402, incorporated by reference herein) are tailored for sequence similarity searching. For a discussion of basic issues in searching sequence databases see Altschul et al., (1994) NATURE GENETICS 6:119-129, which is fully incorporated by reference herein. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference herein). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty). The equivalent settings in Bestfit protein comparisons are GAP=8 and LEN=2.

In each of the foregoing embodiments, it is contemplated herein that immunoglobulin heavy chain variable region sequences and/or light chain variable region sequences that together bind human GDF15 may contain amino acid alterations (e.g., at least 1, 2, 3, 4, 5, or 10 amino acid substitutions, deletions, or additions) in the framework regions of the heavy and/or light chain variable regions.

In some embodiments, the antibody binds hGDF15 with a $K_D$ of about 300 pM, 250 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, or 10 pM, or lower. Unless otherwise specified, $K_D$ values are determined by surface plasmon resonance methods or biolayer interferometry under the conditions described in Examples 8, 14, and 15.

In some embodiments, a monoclonal antibody binds to the same epitope on hGDF15 (e.g., mature hGDF15 or cleaved rhGDF15) bound by one or more of the antibodies disclosed herein (e.g., antibodies 01G06, 03G05, 04F08, 06C11, 08G01, 14F11, or 17B11). In some embodiments, a monoclonal antibody competes for binding to hGDF15 with one or more of the antibodies disclosed herein (e.g., antibody 01G06, 03G05, 04F08, 06C11, 08G01, 14F11, or 17B11).

Competition assays for determining whether an antibody binds to the same epitope as, or competes for binding with, an anti-GDF15 antibody disclosed herein are known in the art. Exemplary competition assays include immunoassays (e.g., ELISA assays, RIA assays), surface plasmon resonance analysis (e.g., using a BIAcore™ instrument), biolayer interferometry and flow cytometry.

Typically, a competition assay involves the use of an antigen (e.g., a hGDF15 protein or fragment thereof) bound to a solid surface or expressed on a cell surface, a test anti-GDF15-binding antibody and a reference antibody (e.g., antibody 01G06, 03G05, 04F08, 06C11, 08G01, 14F11, or 17B11). The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (i.e., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

In an exemplary competition assay, a reference anti-GDF15 antibody (e.g., antibody 01G06, 03G05, 04F08, 06C11, 08G01, 14F11, or 17B11) is biotinylated using commercially available reagents. The biotinylated reference antibody is mixed with serial dilutions of the test antibody or unlabeled reference antibody (self-competition control) resulting in a mixture of various molar ratios (e.g., 1×, 5×, 10×, 20× or 100×) of test antibody (or unlabeled reference antibody) to labeled reference antibody. The antibody mixture is added to a hGDF15 polypeptide coated-ELISA plate. The plate is then washed, and horseradish peroxidase (HRP)-strepavidin is added to the plate as the detection reagent. The amount of labeled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are measured using a SpectraMax® M2 spectrometer (Molecular Devices). OD units corresponding to zero percent inhibition are determined from wells without any competing antibody. OD units corresponding to 100% inhibition, i.e., the assay background are determined from wells without any labeled reference antibody or test antibody. Percent inhibition of labeled reference antibody to GDF15 by the test antibody (or the unlabeled reference antibody) at each concentration is calculated as follows: % inhibition=(1−(OD units−100% inhibition)/(0% inhibition−100% inhibition))*100. Persons skilled in the art will appreciate that the competition assay can be performed using various detection systems known in the art.

A competition assay may be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled.

A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99%, as measured in a competitive binding assay.

Two antibodies bind to the same epitope if essentially all amino acid mutations in the antigen that reduce or eliminate binding of one antibody reduce or eliminate binding of the other. Two antibodies bind to overlapping epitopes if only a subset of the amino acid mutations that reduce or eliminate binding of one antibody reduce or eliminate binding of the other.

II. Production of Antibodies

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukayotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In some embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as glutathione-S-transferase (GST) or histidine tags.

A monoclonal antibody that binds hGDF15, or an antigen-binding fragment of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

III. Antibody Modifications

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-GDF15 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) Nature 321: 522-525; Riechmann et al. (1988) Nature 332: 323-327; Verhoeyen et al. (1988) Science 239: 1534-1536; and Winter (1998) Febs Lett 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. Immunol. 169:1119-1125.

Other methods to reduce immunogenicity include "reshaping," "hyperchimerization," and "veneering/resurfacing." See, e.g., Vaswami et al., 1998, Annals of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., Nature 368:856-859, 1994; Fishwild et al., Nature Biotechnology 14:845-851, 1996; and Mendez et al., Nature Genetics 15:146-156, 1997. Fully human mAbs can also be prepared and optimized from phage display libraries by techniques referenced in, e.g., Knappik et al., J. Mol. Biol. 296: 57-86, 2000; and Krebs et al., J. Immunol. Meth. 254:67-84 2001).

IV. Therapeutic Uses

The antibodies disclosed herein can be used to treat a variety of disorders, for example, cachexia and/or sarcopenia. In some embodiments, the antibodies disclosed herein (e.g., 01G06, 03G05, 04F08, 06C11, 08G01, 14F11, or 17B11) are used to inhibit the loss of muscle mass, for example, the loss of muscle mass associated with an underlying disease. Underlying diseases associated with cachexia include, but are not limited to, cancer, chronic heart failure, chronic kidney disease, COPD, AIDS, multiple sclerosis, rheumatoid arthritis, sepsis, and tuberculosis. In some embodiments, the disclosed antibodies inhibit loss of muscle mass by at least 40%, 50%, 60%, 70%, 80%, 90%, 95%, 98%, 99%, or 100%.

In some embodiments, a loss of muscle mass is accompanied by a loss of fat mass. The antibodies disclosed herein (e.g., 01G06, 03G05, 04F08, 06C11, 08G01, 14F11, or 17B11) may inhibit loss of fat mass by at least 40%, 50%, 60%, 70%, 80%, 90%, 95%, 98%, 99%, or 100%.

In other embodiments, the antibodies disclosed herein (e.g., 01G06, 03G05, 04F08, 06C11, 08G01, 14F11, or 17B11) are used to treat one or more features accompanying cachexia and/or sarcopenia, e.g., involuntary body weight loss. In some embodiments, the antibodies revert involuntary body weight loss by at least 2%, 5%, 10%, 15%, 20%, 25%, 30% or 35%.

In another embodiment, the antibodies disclosed herein (e.g., 01G06, 03G05, 04F08, 06C11, 08G01, 14F11, or 17B11) are used to inhibit loss of organ mass, for example, loss of organ mass associated with an underlying disease. Underlying diseases associated with cachexia include, but are not limited to, cancer, chronic heart failure, chronic kidney disease, COPD, AIDS, multiple sclerosis, rheumatoid arthritis, sepsis, and tuberculosis. In some embodiments, the disclosed antibodies inhibit loss of organ mass by at least 40%, 50%, 60%, 70%, 80%, 90%, 95%, 98%, 99%, or 100%. In some embodiments, loss of organ mass is observed in heart, liver, kidney, and/or spleen. In some embodiments, the loss of organ mass in accompanied by a loss of muscle mass, a loss of fat mass and/or involuntary weight loss.

Antibody 01G06, 03G05, 04F08, 06C11, 08G01, 14F11, or 17B11 can be used in therapy. For example, antibody 01G06, 03G05, 04F08, 06C11, 08G01, 14F11, or 17B11 can be used to treat cachexia and/or sarcopenia. Use of antibody 01G06, 03G05, 04F08, 06C11, 08G01, 14F11, or 17B11 to treat cachexia and/or sarcopenia in a mammal comprises administering to the mammal a therapeutically effective amount of the antibody.

Sarcopenia, muscle wasting disorders and significant muscle weight loss may occur in the absence of cachexia, decreased appetite or body weight loss. In certain embodiments, therefore, one or more of the anti-GDF antibodies of the invention (for example, antibody 01G06, 03G05, 04F08, 06C11, 08G01, 14F11, or 17B11) can be used to treat a subject suffering from, or who has been diagnosed with, sarcopenia, a muscle wasting disorder and/or significant muscle weight loss, whether or not the subject has, or has been diagnosed with, cachexia or decreased appetite. Such a method comprises administering a therapeutically effective amount of one or more antibodies of the invention to the subject in need thereof.

The Fc-rhGDF15 fusion proteins disclosed herein can be used to treat obesity. In some embodiments, the hFc-rhGDF15 fusion proteins disclosed herein are used to inhibit weight gain or to reduce body weight by at least 5%, 10%, 15%, 20%, 25%, 30%, 35%, 40%, 45% or 50%. Use of an hFc-hGDF15 fusion protein to treat obesity in a mammal comprises administering to the mammal a therapeutically effective amount of the fusion protein.

As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of an active component (e.g., an antibody or a fusion protein) is in the range of 0.1 mg/kg to 100 mg/kg, e.g., 1 mg/kg to 100 mg/kg, e.g., 1 mg/kg to 10 mg/kg, e.g., 2.0 mg/kg to 10 mg/kg. The amount administered will depend on variables such as the type and extent of disease or indication to be treated, the overall health of the patient, the in vivo potency of the antibody or fusion protein, the pharmaceutical formulation, the serum half-life of the antibody or fusion protein, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody or fusion protein, and the disease being treated. Exemplary dosing frequencies are once per day, once per week and once every two weeks. In some embodiments, dosing is once every two weeks. A preferred route of administration is parenteral, e.g., intravenous infusion. Formulation of monoclonal antibody-based drugs and fusion protein-based drugs are within ordinary skill in the art. In some embodiments, the antibody or fusion protein is lyophilized, and then reconstituted in buffered saline, at the time of administration. The effective amount of a second active agent, for example, an anti-cancer agent or the other agents discussed below, will also follow the principles discussed hereinabove and will be chosen so as to elicit the required therapeutic benefit in the patient.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies or fusion proteins, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfate; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

In addition to the GDF15 (i.e., MIC-1/PLAB/PDF/NAG-1) pathway, other cytokines implicated in cachexia include Activin A and IL-6. Increased activin levels have been associated with cancer-associated cachexia and gonadal tumors. See, e.g., Marino et al. (2013) CYTOKINE & GROWTH FACTOR REV. 24:477-484. Activin A is a member of the TGF-beta family, and is a ligand of the activin type 2 receptor, ActRIIB. See, e.g., Zhou et al. (2010) CELL 142:531-543. Circulating levels of IL-6 have been shown to correlate with weight loss in cancer patients, as well as with reduced survival. See, e.g., Fearon et al. (2012) CELL METABOLISM 16:153-166.

Accordingly, in certain embodiments of the present invention, one or more inhibitors of Activin-A or the Activin-A receptor, ActRIIB, IL-6 or the IL-6 receptor (IL-6R), may be administered in combination with (for example, administered at the same time as, administered before, or administered after) an antibody of the present invention that inhibits GDF-15 activity. Exemplary inhibitors of Activin A or ActRIIB, include, for example, an anti-Activin-A antibody or an antigen binding fragment thereof, an anti-ActRIIB antibody or an antigen binding fragment thereof, a small molecule inhibitor of Activin-A, a small molecule inhibitor of ActRIIB, and a 'decoy' receptor of ActRIIB, such as a soluble ActRIIB receptor and a fusion of the soluble ActRIIB receptor with an Fc molecule (ActRIIB-Fc). See, for example, Zhou et al. (2010), supra. Suitable inhibitors of IL-6 or IL-6R, include an anti-IL-6 antibody or an antigen binding fragment thereof, an anti-IL-6R antibody or an antigen binding fragment thereof, a small molecule inhibitor of IL-6, a small molecule inhibitor of IL-6R, and a 'decoy' receptor of IL-6R, such as a soluble IL-6 receptor and a fusion of the soluble IL-6 receptor with an Fc molecule (IL6R-Fc). See, e.g., Enomoto et al. (2004) BIOCHEM. AND BIOPHYS. RES. COMM. 323:1096-1102; Argiles et al. (2011) EUR. J. PHARMACOL. 668:S81-S86; Tuca et al. (2013) ONCOLOGY/HEMATOLOGY 88:625-636. Suitable inhibitors of IL-6 or IL-6R may include, for example, Tocilizumab (Actemra®, Hoffmann-LaRoche), a humanized anti-IL-6R monoclonal antibody approved for treatment of rheumatoid arthritis, and Sarilumab/REGN88 (Regeneron), a humanized anti-IL6R antibody in clinical development for treatment of rheumatoid arthritis; and Selumetinib/AZD6244 (AstraZeneca), an allosteric inhibitor of MEK, which has been shown to inhibit IL-6 production. Prado et al. (2012) BRITISH J. CANCER 106:1583-1586.

TNFα and IL-1 are cytokines known to be involved in mediation of the proinflammatory response, which are also implicated in muscle depletion, anorexia and cachexia. Increased circulating levels of TNFα appear to inhibit myogenesis. TNFα, also known as "cachectin," stimulates interleukin-1 secretion and is implicated in the induction of cachexia. IL-1 is a potent trigger of the acute-phase inflammatory response, and it has been shown that infusion of IL-1 can lead to marked weight loss and appetite loss. IL-1 has been shown to contribute to the initiation of cancer cachexia in mice bearing a murine colon-26 adenocarcinoma (Strassmann et al. (1993) J. IMMUNOL. 150:2341). See also, Mathys and Billiau (1997) NUTRITION 13:763-770; Fong et al. (1989) AM. J. PHYSIOL—REGULATORY, INTEGRATIVE AND COMPARATIVE PHYSIOL, 256:R659-R665. Thus, TNFα inhibitors and IL-1 inhibitors that are used in the treatment of rheumatoid arthritis may also be useful in the treatment of cachexia.

Accordingly, in certain embodiments of the present invention, one or more inhibitors of TNFα or IL-1 may be administered in combination with (for example, administered at the same time as, administered before, or administered after) an antibody of the present invention that inhibits GDF-15 activity. Suitable inhibitors of TNFα or IL-1 include an anti-TNFα antibody or an antigen binding fragment thereof, an anti-IL-1 antibody or an antigen binding fragment thereof, a small molecule inhibitor of TNFα or IL-1, and a 'decoy' receptor of TNFα or IL-1, such as a soluble TNFα or IL-1 receptor and a fusion of the soluble form of TNFα or IL-1 with an Fc molecule. Suitable inhibitors of TNFα include for example, etanercept (Enbrel®, Pfizer/Amgen), infliximab (Remicade®, Janssen Biotech), adalimumab (Humira®, Abbvie), golimumab (Simponi®, Johnson and Johnson/Merck), and certolizumab pegol (Cimzia®, UCB). Suitable IL-1 inhibitors include, for example, Xilonix® antibody that targets IL-1α (XBiotech), anikinra (Kinaret®, Amgen), canakinumab (Ilaris®, Novartis), and rilonacept (Arcalyst®, Regeneron). In certain embodiments, the TNFα inhibitor or IL-1 inhibitor, which is typically administered systemically for the treatment of rheumatoid arthritis may be administered locally and directly to the tumor site.

Myostatin, also known as GDF-8, is a member of the TGF-β family of peptides that is a negative regulator of muscle mass, as shown by increased muscle mass in myostatin deficient mammals. Myostatin is a ligand of the activin type 2 receptor, ActRIIB. Accordingly, in certain embodiments of the present invention, one or more inhibitors of myostatin or its receptor may be administered in combination with (for example, administered at the same time as, administered before, or administered after) an antibody of the invention that inhibits GDF-15 activity. Suitable inhibitors of myostatin or ActRIIB, include an anti-myostatin antibody or an antigen binding fragment thereof, an anti-ActRIIB antibody or an antigen binding fragment thereof, a small molecule inhibitor of myostatin, a small molecule inhibitor of ActRIIB, and a 'decoy' receptor of GDF-8, such as a soluble ActRIIB and a fusion of the soluble form of ActRIIB with an Fc molecule. See, e.g., Lokireddy et al. (2012) BIOCHEM. J. 446 (1):23-26. Myostatin inhibitors that may be suitable for the present invention include REGN1033 (Regeneron); see Bauerlein et al. (2013) J. CACHEXIA SARCOPENIA MUSCLE: Abstracts of the $7^{th}$ Cachexia Conference, Kobe/Osaka, Japan, Dec. 9-11, 2013, Abstract 4-06; LY2495655 (Lilly), a humanized anti-myostatin antibody in clinical development by Eli Lilly; see also "A PHASE 2 STUDY OF LY2495655 IN PARTICIPANTS WITH PANCREATIC CANCER," available on the world wide web at clinicaltrials.gov/ct2/NCT01505530; NML identifier: NCT01505530; ACE-031 (Acceleron Pharma); and stamulumab (Pfizer).

Agents such as Ghrelin or ghrelin mimetics, or other growth hormone secretagogues (GHS) which are able to activate the GHS receptor (GHS-R1a), also known as the ghrelin receptor, may be useful for increasing food intake and body weight in humans. See Guillory et al. (2013) in VITAMINS AND HORMONES vol. 92, chap. 3; and Steinman and DeBoer (2013) VITAMINS AND HORMONES vol. 92, chap. 8. Suitable ghrelin mimetics include anamorelin (Helsinn, Lugano, CH); See Temel et al. (2013) J. CACHEXIA SARCOPENIA MUSCLE: Abstracts of the $7^{th}$ Cachexia Conference, Kobe/Osaka, Japan, Dec. 9-11, 2013, Abstract 5-01. Other suitable GHS molecules can be identified, for example, using the growth hormone secretagogue receptor Ghrelin competition assay described in PCT Publication Nos. WO2011/117254 and WO2012/113103.

Agonists of the androgen receptor, including small molecules and other selective androgen receptor modulators (SARMs) may be useful in treating cachexia and/or sarcopenia. See, e.g., Mohler et al. (2009) J. MED. CHEM. 52:3597-3617; Nagata et al. (2011) BIOORGANIC AND MED. CHEM. LETTERS 21:1744-1747; and Chen et al. (2005) MOL. INTERV. 5:173-188. Ideally, SARMs should act as full agonists, like testosterone, in anabolic target tissues, such as muscle and bone, but should demonstrate only partial or pure androgen receptor antagonistic activities on prostate tissue. See, e.g., Bovee et al. (2010) J. STEROID BIOCHEM. & MOL. BIOL. 118:85-92. Suitable SARMs can be identified, for example, by use of the methods and assays described in Zhang et al. (2006) BIOORG. MED. CHEM. LETT. 16:5763-5766; and Zhang et al. (2007) BIOORG. MED. CHEM. LETT. 17:439-443. Suitable SARMs include, for example, GTx-024 (enobosarm, Ostarine®, GTx, Inc.), a SARM in phase II clinical development by GTx, Inc. See also, Dalton et al. (2011) J. CACHEXIA SARCOPENIA MUSCLE 2:153-161. Other suitable SARMs include 2-(2,2,2)-trifluoroethyl-benzimidazoles (Ng et al. (2007) BIOORG. MED. CHEM. LETT. 17:1784-1787) and JNJ-26146900 (Allan et al. (2007) J. STEROID BIOCHEM. & MOL. BIOL. 103:76-83).

β-adrenergic receptor blockers, or beta-blockers, have been studied for their effect on body weight in cachexic subjects, and have been associated with partial reversal of cachexia in patients with congestive heart failure. See, e.g., Hryniewicz et al. (2003) J. CARDIAC FAILURE 9:464-468. Beta-blocker MT-102 (PsiOxus Therapeutics, Ltd.) has been evaluated in a phase 2 clinical trial for subjects with cancer cachexia. See Coats et al. (2011) J. CACHEXIA SARCOPENIA MUSCLE 2:201-207.

Melanocortin receptor-knockout mice with a genetic defect in melanocortin signaling exhibit a phenotype opposite that of cachexia: increased appetite, increased lean body mass, and decreased metabolism. Thus, melanocortin antagonism has emerged as a potential treatment for cachexia associated with chronic disease (DeBoer and Marks (2006) TRENDS IN ENDOCRINOLOGY AND METABOLISM 17:199-204). Accordingly, in certain embodiments of the present invention, one or more inhibitors of a melanocortin peptide or a melanocortin receptor may be administered in combination (for example, administered at the same time as, administered before, or administered after) with an antibody of the invention that inhibits GDF-15 activity. Suitable inhibitors of melanocortins or melanocortin receptors include an anti-melanocortin peptide antibody or an antigen binding fragment thereof, an anti-melanocortin receptor antibody or an antigen binding fragment thereof, a small molecule inhibitor of a melanocortin peptide, a small molecule inhibitor of a melanocortin receptor, and a 'decoy' receptor of a melanocortin receptor, such as soluble melanocortin receptor and a fusion of a soluble melanocortin receptor with an Fc molecule. Suitable melacortin receptor inhibitors include, for example, the melanocortin receptor antagonist agouri-related peptide (AgRP(83-132)), which has been demonstrated to prevent cachexia-related symptoms in a mouse model of cancer-related cachexia (Joppa et al. (2007) PEPTIDES 28:636-642).

Anti-cancer agents, especially those that can cause cachexia and elevate GDF-15 levels, such as cisplatin, may be used in methods of the present invention in combination with (for example, administered at the same time as, administered before, or administered after) an anti-GDF-15 antibody of the invention. Many cancer patients are weakened by harsh courses of radio- and/or chemotherapy, which can limit the ability of the patient to tolerate such therapies, and hence restrict the dosage regimen. Certain cancer agents themselves, such as fluorouracil, Adriamycin, methotrexate and cisplatin, may contribute to cachexia, for example by inducing severe gastrointestinal complications. See, e.g., Inui (2002) CANCER J. FOR CLINICIANS 52:72-91. By the methods of the present invention, in which an anti-cancer agent is administered in combination with an anti-GDF-15 antibody of the invention, it is possible to decrease the incidence and/or severity of cachexia, and ultimately increase the maximum tolerated dose of such an anti-cancer agent. Accordingly, efficacy of treatment with anti-cancer agents that may cause cachexia can be improved by reducing the incidence of cachexia as a dose-limiting adverse effect, and by allowing administration of higher doses of a given anti-cancer agent.

Thus, the present invention includes pharmaceutical compositions comprising an anti-GDF-15 antibody of the present invention in combination with an agent selected from the group consisting of: an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, a melanocortin receptor inhibitor, and an anti-cancer agent. The present invention also includes methods of treating, preventing or minimizing cachexia and/or sarcopenia in a mammal comprising administering to a mammal in need thereof a pharmaceutical composition or compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1α agonist, a SARM, a TNFα inhibitor, an IL-1α inhibitor, a myostatin inhibitor, a beta-blocker, a melanocortin peptide inhibitor, or a melanocortin receptor inhibitor.

In another embodiment, the invention comprises a method of inhibiting loss of muscle mass associated with an underlying disease comprising administering to a mammal in need thereof a pharmaceutical composition or compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1α agonist, a SARM, a TNFα inhibitor, an IL-1α inhibitor, a myostatin inhibitor, a beta-blocker, a melanocortin peptide inhibitor, or a melanocortin receptor inhibitor to prevent or reduce loss of muscle mass. The underlying disease may be selected from the group consisting of cancer, chronic heart failure, chronic kidney disease, COPD, AIDS, multiple sclerosis, rheumatoid arthritis, sepsis, and tuberculosis. Additionally, in certain embodiments, the loss of muscle mass is accompanied by a loss of fat mass.

In yet further embodiments, the present invention comprises a method of inhibiting or reducing involuntary weight loss in a mammal comprising administering to a mammal in need thereof a pharmaceutical composition or pharmaceutical compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1α agonist, a SARM, a TNFα inhibitor, a IL-1α inhibitor, a myostatin inhibitor, a beta-blocker, a melanocortin peptide inhibitor, or a melanocortin receptor inhibitor.

Certain anti-cancer agents, such as cisplatin, have one or more undesirable adverse effects that involve causing or increasing one or more syndromes such as cachexia, sarcopenia, muscle wasting, bone wasting or involuntary body weight loss. Accordingly, in certain embodiments, the present invention comprises a method of treating cancer, while preventing, minimizing or reducing the occurrence, frequency or severity of cachexia, sarcopenia, or muscle wasting, bone wasting or involuntary loss of body weight in a mammal, comprising administering to a mammal in need thereof a pharmaceutical composition comprising an effective amount of an anti-GDF-15 antibody of the present invention in combination with one or more anti-cancer agents. In particular embodiments, the invention comprises a method of treating cancer, while preventing, minimizing or reducing the occurrence, frequency or severity of cachexia, sarcopenia or muscle wasting, bone wasting or involuntary loss of body weight in a mammal, comprising administering to a mammal in need thereof a pharmaceutical composition comprising an effective amount of an anti-GDF-15 antibody of the invention in combination with one or more anti-cancer agents known to cause or increase the occurrence, frequency or severity of cachexia, sarcopenia, or muscle wasting, bone wasting or involuntary loss of body weight in a mammal.

EXAMPLES

The following Examples are merely illustrative and are not intended to limit the scope or content of the invention in any way.

Example 1

Human GDF15 Serum Levels in Mouse Xenograft Tumor Models

Figure 2:
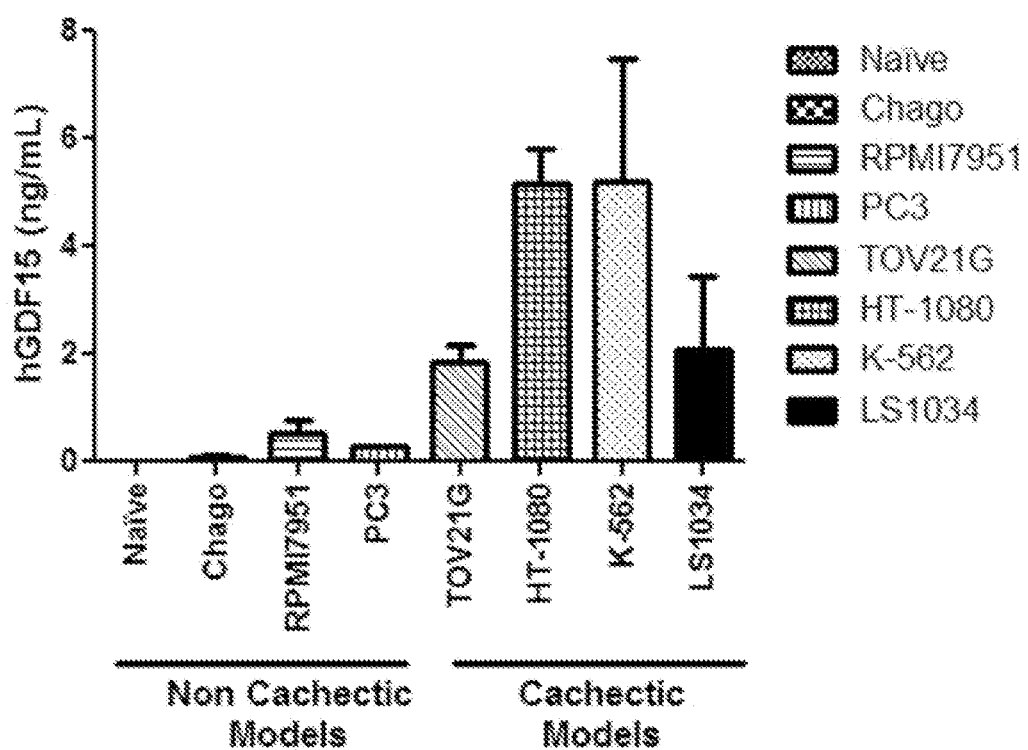
FIG. 2 is a graph representing results from an experiment to measure hGDF15 serum levels in naïve mice or mice bearing human xenograft tumors (Chago, RPMI7951, PC3, TOV21G, HT-1080, K-562, LS1034), as determined by ELISA.

In this example, the amount of hGDF15 in the serum of mice bearing various xenograft tumors was measured. Serum was collected from three mice for each of the following tumor xenograft models: Chago, RPMI7951, PC3, TOV21G, HT-1080, K-562, and LS1034. Serum was also collected from three naïve mice as a control. Human GDF15 serum levels were determined by ELISA (R&D Systems, Cat. No. DY957E). Mice bearing human xenograft tumors that induce cachexia had serum levels of hGDF15 above 2 ng/mL, while mice bearing human xenograft tumors that do not induce cachexia had serum levels of hGDF15 below 1 ng/mL (FIG. 2). Naïve mice had no detectable hGDF15 (control). These results indicate that a serum level of approximately 2 ng/mL GDF15 is a threshold for inducing cachexia in this mouse model. Similar levels of hGDF15 were also observed in plasma when determined by ELISA.

Example 2

Non-Tumor Bearing Mouse Model of Cachexia

Figure 3:
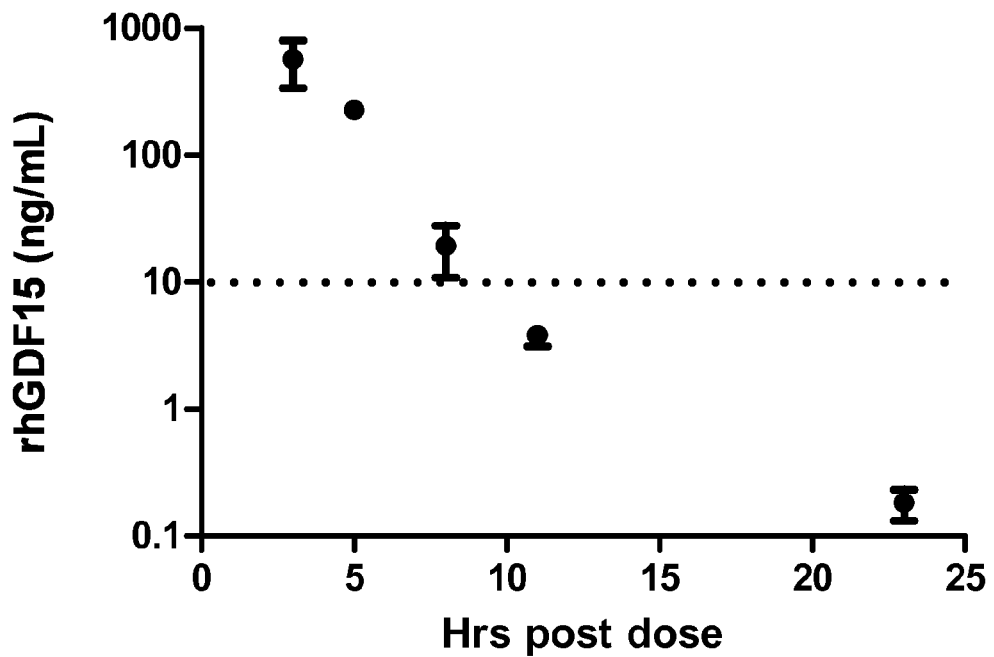
FIG. 3 is a plot representing results from an experiment to determine the plasma pharmacokinetics (PK) of cleaved rhGDF15 administered by subcutaneous injection (1 µg/g) in naïve ICR-SCID mice, as determined by ELISA.
Figure 4:
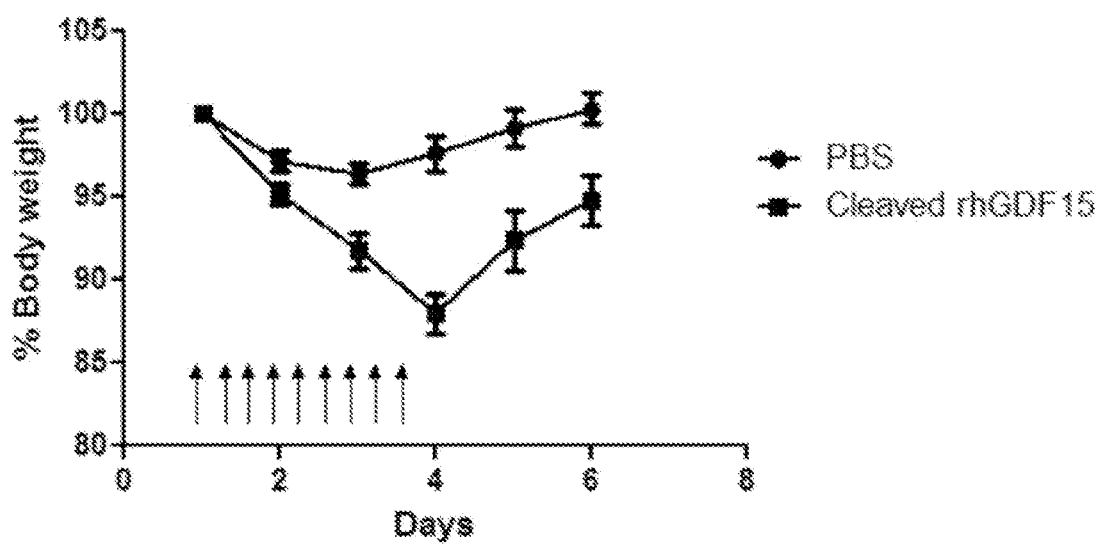
FIG. 4 is a graph summarizing results from an experiment to measure cachectic activity of cleaved rhGDF15 protein (■) and negative control (PBS (●)) to induce body weight loss in immune-incompetent mice, ICR-SCID. Arrows indicate subcutaneous doses of 1 µg/g of rhGDF15.

An existing non-tumor bearing mouse model of cachexia is based on the injection of mature rhGDF15 into a mouse (Johnen et al. (1997) NAT. MED. 13:1333-1340). Mature rhGDF15 corresponds to amino acids 197 to 308 of hGDF15 protein. Mature rhGDF15 can be produced in the yeast *Pichia pastoris* as described in Fairlie et al. (2000) GENE 254:67-76). Cleaved-rhGDF15 corresponds to amino acids 197 to 308 of hGDF15 protein released from an Fc-rhGDF15 fusion protein. In FIGS. 3-4 described below, cleaved-rhGDF15 was produced by enzymatic digestion of mFc-rhGDF15 fusion protein with Factor Xa, and subsequent purification, prior to injection in mice.

To investigate the half-life of cleaved-rhGDF15, plasma was collected from a group of three mice after single dose of cleaved-rhGDF15 (1 µg/g) at different time points (2, 5, 8, 11, and 23 hours). Human GDF15 plasma levels were determined by ELISA (R&D Systems, Cat. No. DY957E). As shown in FIG. 3, cleaved-rhGDF15 was rapidly cleared from the plasma following injection. Eleven hours post-injection, the amount of cleaved-rhGDF15 in the plasma was below 10 ng/mL, and, within 23-hours, cleaved-rhGDF15 was almost completely cleared from the plasma.

The rapid clearance of cleaved-rhGDF15 in non-tumor bearing mice was further investigated. Eight-week old female ICR-SCID mice were randomized into two groups of ten mice each. Mice were dosed subcutaneously into the flank every eight hours for three days (a total of nine doses) with one of the following treatments: PBS (control) or cleaved-rhGDF15 at 1 µg/g. Body weight was measured daily. Statistical analyses were performed using a two-way ANOVA.

As shown in FIG. 4, cleaved-rhGDF15 induced body weight loss. After nine doses over a three day period, percent body weight dropped to 88% at day 4 ($p<0.001$), but approximately 24 hours after the last dose the mice began to gain weight. On day 6, the last day of the experiment, percent body weight increased to 94.8 percent ($p<0.001$). These results indicate that weight loss induced by cleaved-rhGDF15 is not sustained over long periods of time. The activity observed with cleaved-rhGDF15 described herein was similar to that observed with mature rhGDF15 in the existing mouse model (Johnen et al., supra).

The existing non-tumor bearing mouse model for cachexia relies on the injection of large amounts of mature rhGDF15 delivered in multiple doses per day to induce muscle loss and body weight loss (Johnen et al., supra). It appears that if mature rhGDF15 or cleaved-rhGDF15 is used, the mice do not sustain muscle weight loss or body weight loss for long periods of time without continuous dosing. This limits the usefulness of such models. Moreover, repeated dosing requires frequent handling of these mice which introduces stress that can compromise the reliability of body weight loss measurements. For example, as shown in FIG. 4, mice treated with multiple doses of PBS demonstrated a body weight drop due to the stress of repeated dosing and handling.

Example 3

GDF15 Fusion Proteins

In view of the large amounts of mature rhGDF15 (or cleaved-rhGDF15) and the labor intensity required to induce non-tumor bearing cachexia mouse models (as well as the resulting limitations of these models), we investigated alternate forms of rhGDF15 to induce a cachetic phenotype in mice. This Example describes the construction and production of two fusion proteins consisting of GDF15 and an immunoglobulin Fc fragment, designated mFc-rhGDF15 (mouse IgG1 Fc fused to the amino terminus of mature human GDF15) and rFc-rmGDF15 (rabbit IgG1 Fc fused to the amino terminus of mature mouse GDF15). The GDF15 fusion proteins were designed using methods known in the art. The mFc-rhGDF15 DNA sequences were constructed from fragments using overlap extension PCR to include (in the following order): 5' HindIII restriction site, Kozak consensus sequence, amino terminal signal sequence, mouse IgG1 Fc, Factor Xa cleavage site, a polypeptide linker (GGGGS) (SEQ ID NO: 139), mature hGDF15, stop codon, and a 3' EcoRI restriction site. The rFc-rmGDF15 amino acid sequences were converted to codon-optimized DNA sequences and synthesized to include (in the following order): 5' HindIII restriction site, Kozak consensus sequence, amino terminal signal sequence, rabbit IgG1 Fc, a polypeptide linker (GGGG) (SEQ ID NO: 265), mature mouse GDF15, stop codon, and a 3' EcoRI restriction site.

The GDF15 fusion proteins were subcloned into the mammalian expression vector pEE14.4 (Lonza, Basel, Switzerland) via HindIII and EcoRI sites using In-Fusion™ PCR cloning (Clontech, Mountain View, Calif.). GDF15 fusion proteins were stably expressed in CHOK1SV cells using the GS System™ (Lonza Biologics) in order to produce large quantities of purified protein. Each expression vector was linearized and transfected into CHOK1SV cells. Stable clones were selected in the presence of methionine sulfoximine. Secreted proteins produced by CHOK1SV stably transfected cell lines were purified by Protein A and size exclusion chromatography.

The nucleic acid sequence and the encoded protein sequence defining the mouse IgG1 Fc-mature human GDF15 fusion protein (mFc-rhGDF15) are shown below. mFc-rhGDF15 contains mouse IgG1 Fc from amino acids 1-222, Factor Xa cleavage site from amino acids 223-228, an artificial linker sequence from amino acids 229-233, and mature hGDF15 from amino acids 234-345.

Nucleic Acid Sequence Encoding the Mouse IgG1 Fc—Mature Human GDF15 Fusion Protein (mFc-rhGDF15) (SEQ ID NO:219)

```
  1  gggtgtaaac cctgcatctg cacggtgccg gaggtgtcct
     ccgtctttat cttccctccc 61  aaacccaagg atgtgctgac aatcactttg actccaaaag
     tcacatgcgt agtcgtggac 121  atctcgaaag acgacccgga agtgcagttc tcgtggtttg
     ttgatgatgt agaagtgcat
```

```
 181 accgctcaaa cccagccgag ggaagaacag tttaacagca
     cgtttaggag tgtgtcggaa 241 ctgcccatta tgcaccagga ttggcttaat gggaaggagt
     tcaaatgtcg cgtgaatagt 301 gcggcgttcc cagcccctat tgaaaagact atttccaaaa
     cgaagggtcg gcccaaagct 361 ccccaagtat acacaatccc tccgccgaaa gaacaaatgg
     caaaagacaa agtgagtttg 421 acgtgcatga tcacggactt ttttcccggag gatatcaccg
     tcgaatggca atggaatggg 481 caacctgccg aaaactacaa gaatacacaa cccattatgg
     ataccgatgg atcgtatttc 541 gtctactcaa agttgaacgt acagaagtca aattgggagg
     cagggaatac gttcacttgc 601 agtgttttgc acgaaggcct ccataaccac catacggaaa
     agtcactgtc gcactccccg 661 ggaaaaatcg agggcagaat ggatggtgga ggagggtcgg
     cgcgcaacgg ggaccactgt 721 ccgctcgggc ccgggcgttg ctgccgtctg cacacggtcc
     gcgcgtcgct ggaagacctg 781 ggctgggccg attgggtgct gtcgccacgg gaggtgcaag
     tgaccatgtg catcggcgcg 841 tgcccgagcc agttccgggc ggcaaacatg cacgcgcaga
     tcaagacgag cctgcaccgc 901 ctgaagcccg acacggtgcc agcgccctgc tgcgtgcccg
     ccagctacaa tcccatggtg 961 ctcattcaaa agaccgacac cggggtgtcg ctccagacct
     atgatgactt gttagccaaa 1021 gactgccact gcata
```

Protein Sequence Defining the Mouse IgG1 Fc—Mature Human GDF15 Fusion Protein (mFc-rhGDF15) (SEQ ID NO:220)

```
  1 gckpcictvp evssvfifpp kpkdvltitl tpkvtcvvvd
    iskddpevqf swfvddvevh 61 taqtqpreeq fnstfrsvse lpimhqdwln gkefkcrvns
    aafpapiekt isktkgrpka 121 pqvytipppk eqmakdkvsl tcmitdffpe ditvewqwng
    qpaenykntq pimdtdgsyf 181 vysklnvqks nweagntftc svlheglhnh htekslshsp
    gkiegrmdgg ggsarngdhc 241 plgpgrccrl htvrasledl gwadwvlspr evqvtmciga
    cpsqfraanm haqiktslhr 301 lkpdtvpapc cvpasynpmv liqktdtgvs lqtyddllak
    dchci
```

The nucleic acid sequence and the encoded protein sequence defining the rabbit IgG1 Fc-mature mouse GDF15 fusion protein (rFc-rmGDF15) are shown below. rFc-rmGDF15 contains rabbit IgG1 Fc from amino acids 1-223, an artificial linker sequence from amino acids 224-227, and mature mouse GDF15 from amino acids 228-342.

Nucleic Acid Sequence Encoding the Rabbit IgG1 Fc—Mature Mouse GDF15 Fusion Protein (rFc-rmGDF15) (SEQ ID NO:221)

```
  1 tcgaaaccca cttgccctcc tccggagctg ttgggcggac
    cctccgtgtt tatctttccc 61 ccgaagccga aagataccct tatgatctca cggacgccgg
    aggtcacttg cgtagtagtg 121 gatgtgtcgg aggatgaccc cgaagtccag ttcacctggt
    atatcaataa cgagcaagtg 181 aggacagcga ggcccccact tagggagcag cagttcaact
    ccacaattcg ggtcgtcagc 241 actttgccca tcgctcatga ggactggctc cgcggaaaag
    agttcaagtg taaggtgcat 301 aacaaggcat tgccagcgcc tattgaaaag acaatctcga
    aggcgcgagg gcagccgctc 361 gagcccaaag tgtatacgat gggaccccg agggaagaat
    tgtcgtcgcg ctcagtaagc 421 cttacgtgca tgattaacgg tttctaccct agcgacatca
    gcgtagagtg ggaaaagaat 481 ggaaaggcgg aggataacta caagacgact cccgcggtgc
    tggattcgga tgggtcgtac 541 tttctgtata gcaaattgtc agtcccgacc tcagaatggc
    agaggggtga cgtgttcacg 601 tgctccgtga tgcacgaagc acttcacaat cactacaccc
    agaaaatcaat ctcgcggtcc 661 ccaggcaaag gtggaggagg gtcggctcac gcccaccctc
    gcgattcgtg tccgctgggg 721 cctggtagat gctgtcatct cgagacagtc caggccacgc
    tggaggacct cggggtggtca 781 gactgggtcc tgtccccacg acaactgcag ctttcgatgt
    gcgtgggga atgtccgcac 841 ttgtacagat cggcgaatac ccacgctcag attaaggcac
    gactccatgg tttgcagcca 901 gataaagtcc ccgcaccttg ctgtgtcccc agctcatata
    ctcctgtcgt actcatgcat 961 cggacagaca gcggcgtgtc gcttcaaacg tatgacgacc
    tcgtagcgag aggatgtcat 1021 tgcgcc
```

Protein Sequence Defining the Rabbit IgG1 Fc—Mature Mouse GDF15 Fusion Protein (rFc-rmGDF15) (SEQ ID NO:222)

```
  1 skptcpppel lggpsvfifp pkpkdtlmis rtpevtcvvv
    dvseddpevq ftwyinneqv 61 rtarpplreq qfnstirvvs tlpiahedwl rgkefkckvh
    nkalpapiek tiskargqpl 121 epkvytmgpp reelssrsvs ltcmingfyp sdisvewekn
    gkaednyktt pavldsdgsy 181 flysklsvpt sewqrgdvft csvmhealhn hytqksisrs
    pgkggggsah ahprdscplg 241 pgrcchletv qatledlgws dwvlsprqlq lsmcvgecph
    lyrsanthaq ikarlhglqp 301 dkvpapccvp ssytpvvlmh rtdsgvslqt yddlvargch
    ca
```

The following sequences represent exemplary protein sequences for human IgG1 Fc-mature human GDF15 fusion proteins (hFc-rhGDF15). hFc-rhGDF15 Xa consists of human IgG1 Fc from amino acids 1-227, Factor Xa cleavage site from amino acids 228-233, an artificial linker sequence from amino acids 234-238, and mature hGDF15 from amino acids 239-350. hFc-rhGDF15 consists of human IgG1 Fc from amino acids 1-227, an artificial linker sequence from amino acids 228-232, and mature hGDF15 from amino acids 233-344.

Protein Sequence Defining the Human IgG1 Fc—Mature Human GDF15 Fusion Protein with Xa Cleavage Site (hFc-hGDF15 Xa) (SEQ ID NO:223)

```
  1 dkthtcppcp apellggpsv flfppkpkdt lmisrtpevt
    cvvvdvshed pevkfnwyvd 61 gvevhnaktk preeqynsty rvvsvltvlh qdwlngkeyk
    ckvsnkalpa piektiskak 121 gqprepqvyt lppsreemtk nqvsltclvk gfypsdiave
    wesngqpenn ykttppvlds 181 dgsfflyskl tvdksrwqqg nvfscsvmhe alhnhytqks
    lslspgkieg rmdggggsar 241 ngdhcplgpg rccrlhtvra sledlgwadw vlsprevqvt
    mcigacpsqf raanmhaqik 301 tslhrlkpdt vpapccvpas ynpmvliqkt dtgvslqtyd
    dllakdchci
```

Protein Sequence Defining the Human IgG1 Fc—Mature Human GDF15 Fusion Protein with (hFc-hGDF15) (SEQ ID NO:224)

```
  1 dkthtcppcp apellggpsv flfppkpkdt lmisrtpevt
    cvvvdvshed pevkfnwyvd 61 gvevhnaktk preeqynsty rvvsvltvlh qdwlngkeyk
    ckvsnkalpa piektiskak 121 gqprepqvyt lppsreemtk nqvsltclvk gfypsdiave
    wesngqpenn ykttppvlds 181 dgsfflyskl tvdksrwqqg nvfscsvmhe alhnhytqks
    lslspgkggg gsarngdhcp 241 lgpgrccrlh tvrasledlg wadwvlspre vqvtmcigac
    psqfraanmh aqiktslhrl 301 kpdtvpapcc vpasynpmvl iqktdtgvsl qtyddllakd
    chci
```

Example 4

Fc-rhGDF15 Induced Cachexia Model

This Example describes the generation of an Fc-GDF15-induced cachexia model in mice Immune-competent (Balb/C) and immune-incompetent (CB17-Scid) mice were randomized into three groups of ten mice each. Each group received one of the following treatments: PBS (control), mFc-rhGDF15 (as described in Example 3), or rFc-rmGDF15 (as described in Example 3) at 1 µg/g. Eight-week old female mice were dosed subcutaneously into the flank for three days (Balb/C) or once (CB17-Scid). Body weight was measured daily.

Figure 5A:
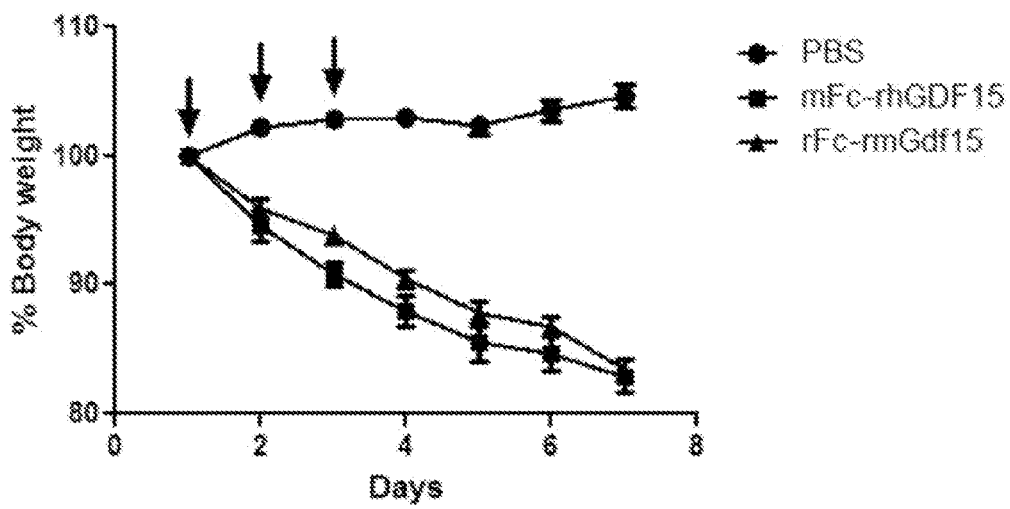
FIGS. 5A and 5B are graphs summarizing results from an experiment to measure cachectic activity of mFc-rhGDF15 (a mouse Fc fused to the amino terminus of a mature recombinant human GDF15; ■), rFc-rmGDF15 (a rabbit Fc fused to the amino terminus of a mature recombinant mouse GDF15; ▲), and negative control (PBS; ●) to induce body weight loss in immune-competent Balb/C mice (FIG. 5A) and immune-incompetent CB17-SCID mice (FIG. 5B). Arrows indicate subcutaneous doses of 1 µg/g of recombinant protein.
Figure 5B:
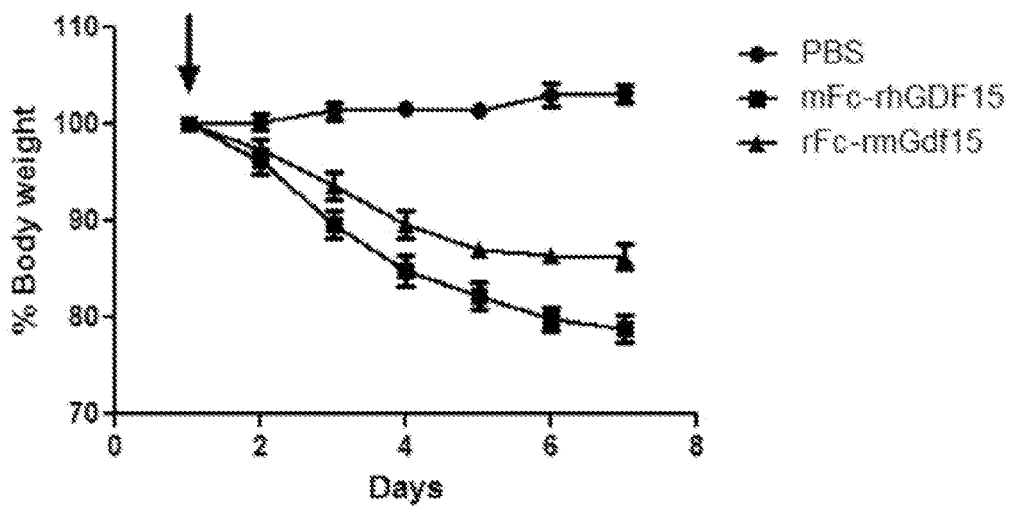

As shown in FIG. 5A and FIG. 5B, administration of mFc-rhGDF15 or rFc-rmGDF15 induced body weight loss in immune-competent mice (FIG. 5A) and immune-incompetent mice (FIG. 5B). These results indicate that a steady-state level of active rhGDF15 was achieved, because regardless of dose (one vs. three doses), both mFc-rhGDF15 and rFc-rmGDF15 induced sustained weight loss over the measured time course (7 days).

The fusion proteins, mFc-rhGDF15 and rFc-rmGDF15, were further tested in additional immune-competent (C57BL6, Swiss Webster) and immune-incompetent (ICR-SCID) mouse strains. In each tested mouse strain, the administration of mFc-rhGDF15 or rFc-rmGDF15 induced cachexia, as measured by body weight loss. Similar results were obtained regardless of whether mFc-rhGDF15 was dosed subcutaneously or intraperitoneally.

It was also investigated whether mFc-rhGDF15 induced weight loss regardless of the age of the mice treated with fusion protein. Swiss Webster (immune-competent) female mice of different ages (7, 13 and 25 weeks old) were divided into two groups of ten and treated with three doses per day of mFc-rhGDF15 or PBS (0.8 µg/g, 7 week old mice; 0.6 µg/g, 13 week old mice; or 0.4 µg/g, 25 week old mice). mFc-rhGDF15-induced weight loss was observed in all three mice age populations. In each age population, the mice lost approximately 10% of their body weight following treatment with mFc-rhGDF15 measured at ten days post treatment.

In another experiment, mFc-rhGDF15 induction of cachexia was investigated by measuring the loss of body weight, the loss of muscle mass, the loss of fat mass, and the expression levels of two molecular markers indicative of muscle degradation (i.e., mMuRF1 and mAtrogin). MuRF1 and Atrogin are E3-ubiquitin ligases that are upregulated in multiple models of muscle atrophy and cachexia (Glass, D. (2010) CURR. OPIN. CLIN. NUTR. MET. CARE 13:225-229).

Eight-week old female ICR-SCID mice were randomly divided into ten groups of ten mice each. Five groups (ten mice each) were dosed subcutaneously in the flank with PBS (control) and five groups (ten mice each) were dosed subcutaneously in the flank with mFc-rhGDF15 at 1.6 µg/g on day one. Body weight was measured daily for up to 17 days. One control group and one treatment group were sacrificed at different time points (0, 1, 3, 7 and 16 days post dose). Gonadal fat and gastrocnemius muscles were removed surgically from each group of mice at the indicated sacrifice time, and weighed. Tissues were snap frozen in liquid nitrogen, and RNA was isolated from the gastrocnemius muscle samples. Levels of mMuRF1 and mAtrogin mRNA were measured by qRT-PCR in samples corresponding to groups collected after 1, 7, and 16 days post dose. Statistical analyses were performed using a two-way ANOVA.

Figure 6A:
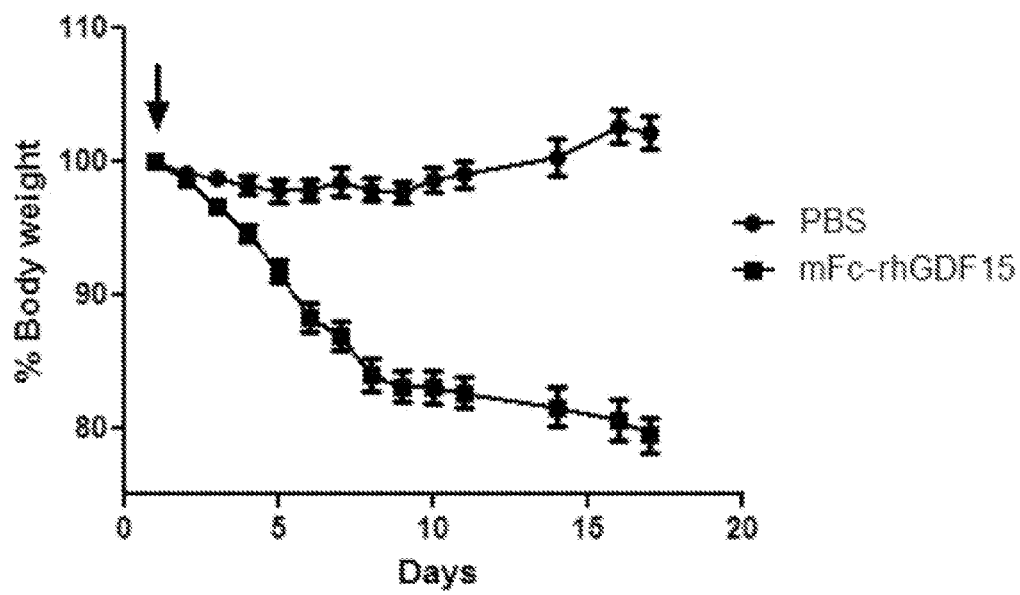
FIGS. 6A-6E are graphs summarizing results from an experiment to demonstrate cachectic activity of mFc-rhGDF15 (■) and negative control (PBS; ●) to induce body weight loss in immune-incompetent ICR-SCID mice (FIG. 6A; arrows indicate subcutaneous doses of 1 µg/g of mFc-rhGDF15); to induce loss of adipose tissue or gonadal fat mass (FIG. 6B); to induce loss of muscle mass of gastrocnemius muscle (FIG. 6C; Gastroc Mass); and to increase mRNA expression of muscle degradation molecular markers (mMuRF1 (FIG. 6D) and mAtrogin (FIG. 6E)).
Figure 6B:
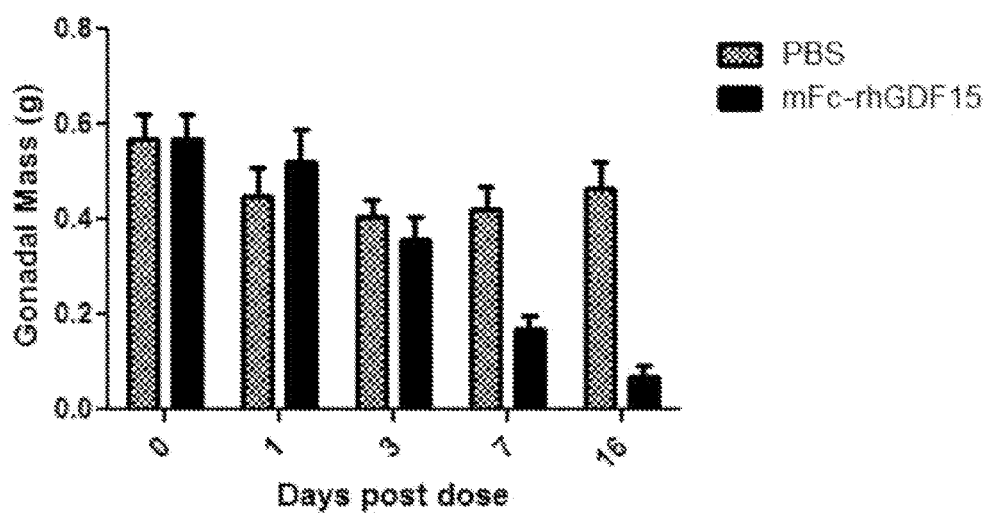
Figure 6C:
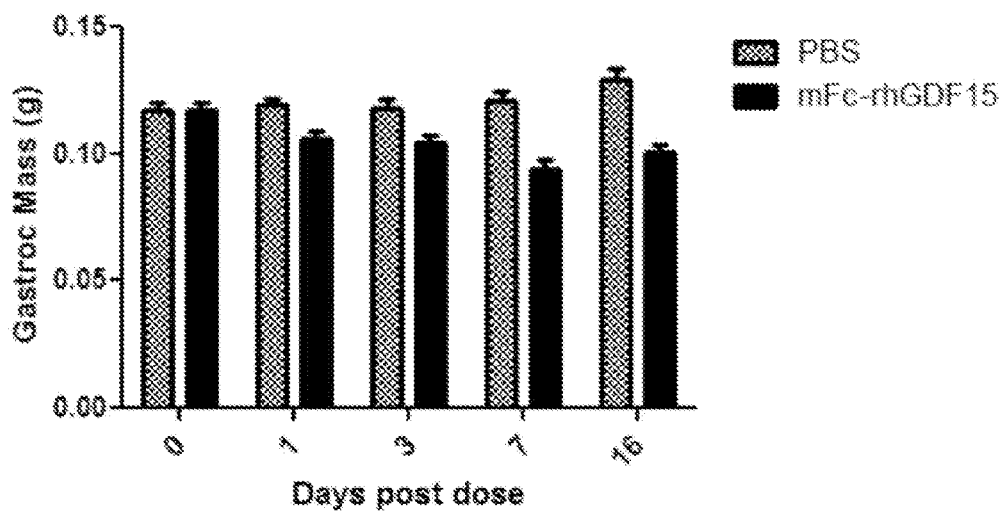
Figure 6D:
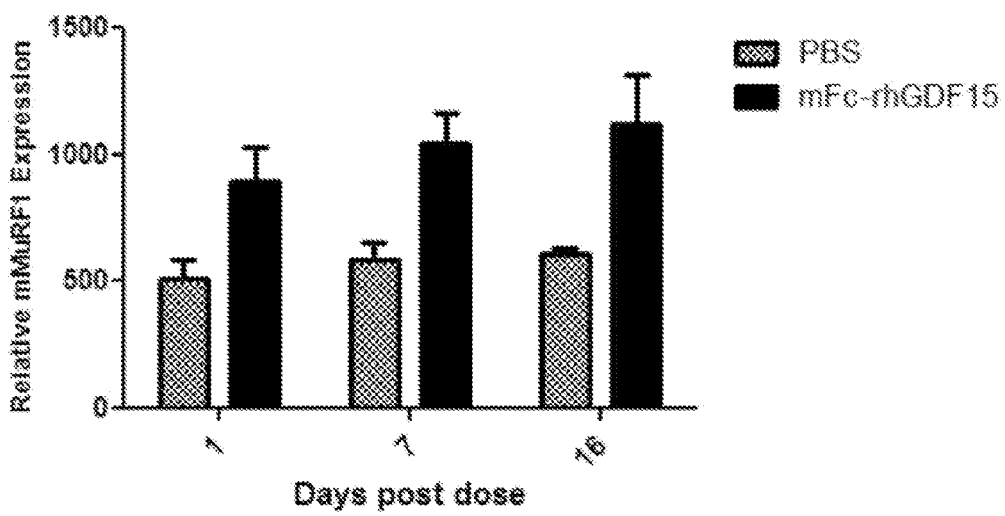
Figure 6E:
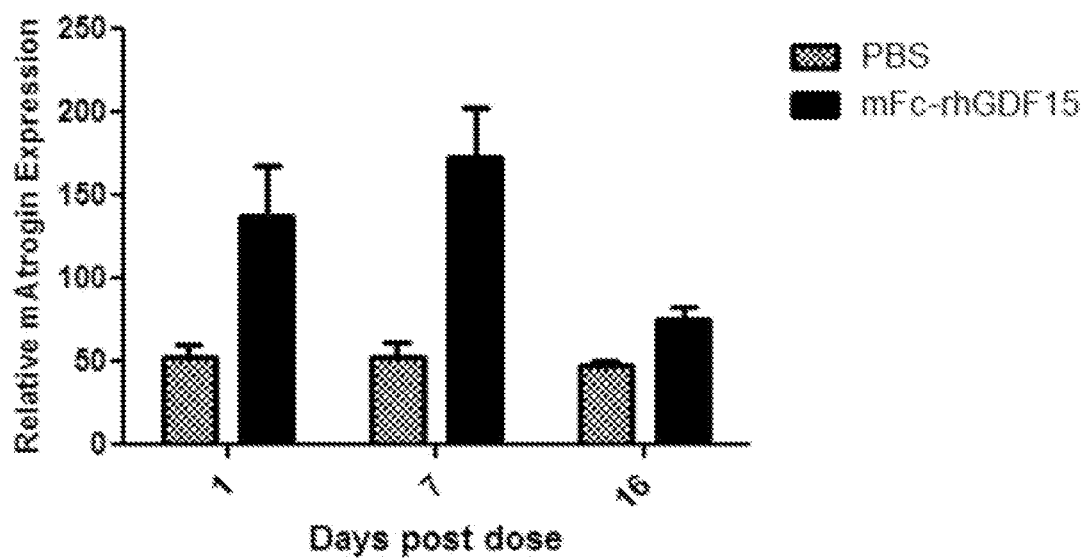

As shown in FIG. 6A, mFc-rhGDF15 induced body weight loss in ICR-SCID mice. Percent body weight was 79.4 percent when measured after 16 days following one dose of mFc-rhGDF15 ($p<0.001$). mFc-rhGDF15 also induced loss of fat (adipose tissue), as observed by the loss of gonadal fat (FIG. 6B; $p<0.01$ at day 7 and $p<0.001$ at day 16) and loss of muscle, as observed by the loss of gastrocnemius muscle (FIG. 6C; $p<0.05$ at days 1 and 3, and $p<0.0001$ at days 7 and 16). Administration of mFc-rhGDF15 also elevated gene expression of two enzymes associated with muscle degradation and cachexia, mMuRF1 (FIG. 6D; 6<0.001 at days 1, 7, and 16) and mAtrogin (FIG. 6E; $p<0.001$ at days 1 and 7, and $p<0.01$ at day 16).

These results indicated that mFc-rhGDF15 induces cachexia in mice.

Example 5 mFc-rhGDF15 Induces Cachexia with a Longer GDF15 Half-Life in Serum

Figure 7:
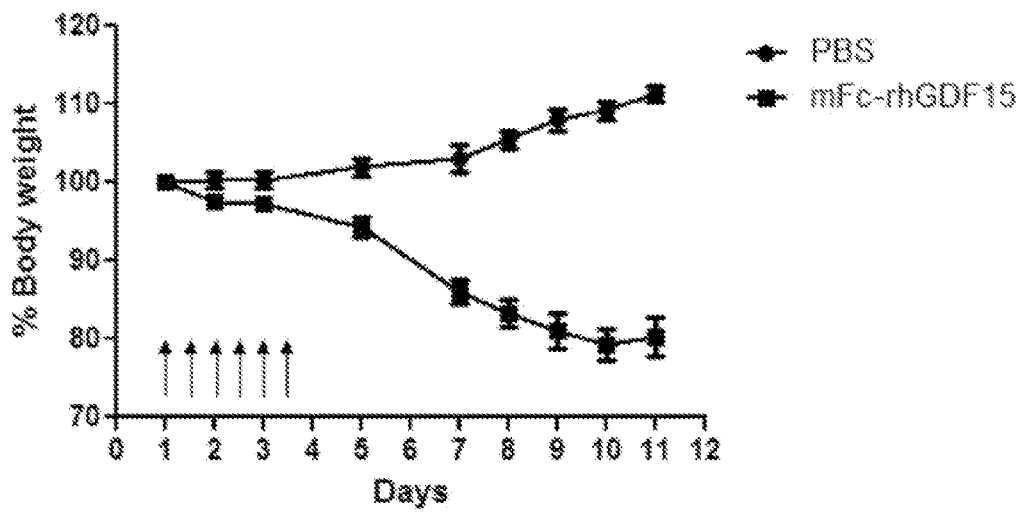
FIG. 7 is a graph summarizing results from an experiment to measure cachectic activity of mFc-rhGDF15 (■) and negative control (PBS; ●) to induce body weight loss in immune-incompetent Balb/C nude mice. Arrows indicate subcutaneous doses of 1.33 µg/g of mFc-rhGDF15.

In this Example, the serum hGDF15 levels were measured following administration of mFc-rhGDF15, to determine the half-life of rhGDF15 in this model. Eight-week old female Balb/C nude mice were randomly divided into two groups of twelve mice each. Mice were dosed subcutaneously in the flank every twelve hours for three days (a total of six doses) with one of the following treatments: PBS (control) or mFc-rhGDF15 at 1.33 µg/g. Body weight was measured daily. As shown in FIG. 7, mFc-rhGDF15 induced sustained body weight loss for at least one week after the final injection.

In this experiment, hGDF15 serum levels were measured 0.2, 5, and 8 days after the last dose of mFc-rhGDF15. Mice were sacrificed at the indicated time, and sera were collected. Human GDF15 serum levels were determined by ELISA (R&D Systems, Cat. No. DY957E). Table 1 provides the serum levels (µg/mL) for each mouse in the study.

TABLE 1

| Days post last dose | Mouse # | Treatment Agent | µg/g | Serum GDF15 (µg/mL); ELISA |
|---|---|---|---|---|
| 0.2 | 1 | mFc-rhGDF15 | 1.33 | 10.02 |
| 0.2 | 2 | mFc-rhGDF15 | 1.33 | 9.54 |
| 0.2 | 3 | mFc-rhGDF15 | 1.33 | 9.36 |
| 5 | 4 | mFc-rhGDF15 | 1.33 | 8.24 |
| 5 | 5 | mFc-rhGDF15 | 1.33 | 8.01 |
| 5 | 6 | mFc-rhGDF15 | 1.33 | 6.59 |
| 8 | 7 | mFc-rhGDF15 | 1.33 | 5.60 |
| 8 | 8 | mFc-rhGDF15 | 1.33 | 5.52 |
| 8 | 9 | mFc-rhGDF15 | 1.33 | 5.57 |

The results in Table 1 reveal that strong, sustained levels of hGDF15 are present in the serum at least eight days after the last dose of mFc-rhGDF15.

Figure 8:
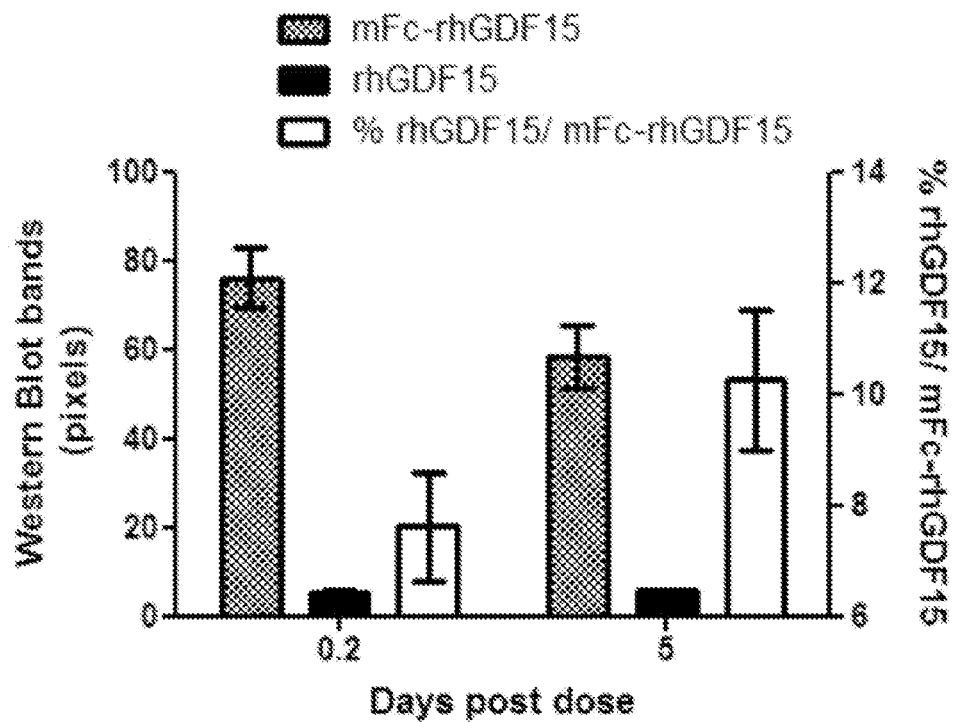
FIG. 8 is a graph summarizing results from an experiment to measure serum levels of mFc-rhGDF15 in mice dosed with the recombinant protein. The presence of mFc-rhGDF15 was determined by Western Blot. Two positive bands corresponding to mFc-rhGDF15 and rhGDF15 (according to the appropriate molecular size) were quantified by Licor. The percentage of released-rhGDF15 versus mFc-rhGDF15 was calculated.

Serum samples from day 0.2 and day 5 after the last dose were also analyzed by Western blot (reducing gel; blot with an antibody against hGDF15 (R&D Systems, Cat. No AF957)) and quantified by Licor to determine the stability of mFc-rhGDF15 in the serum. Unexpectedly, two bands were observed. The upper band was approximately 40 kDa, and appeared to be mFc-rhGDF15. The lower band was approximately 15 kDa, and appeared to be cleaved mature rhGDF15. This indicated that mature rhGDF15 was released from mFc-rhGDF15 in the serum. Quantification of the two bands showed that about 90% of the rhGDF15 present in the serum was in the form of mFc-rhGDF15, with about 10% of the total rhGDF15 in the serum being present as the cleaved mature form (FIG. 8). Quantification showed a slight decrease in mFc-rhGDF15 in the serum samples collected five days after the last dose, but, surprisingly, a constant level of mature rhGDF15 remained in the serum. The ratio of mature rhGDF15 to mFc-rhGDF15 slightly increased over time, as a result of a decrease in mFc-rhGDF15 in the serum. Similar results were observed when rFc-rmGDF15 was injected into mice.

The results presented in FIGS. 7-8 and Table 1 were unexpected. The expectation was that very little, if any, mature rhGDF15 would be cleaved (released) from the mFc-rhGDF15 by day 0.2, and that any cleaved rhGDF15 would be rapidly cleared from the serum, as had been previously observed. For example, in FIG. 4, a series of nine doses at 1 µg/g per dose (for a total of 9 µg/g) of cleaved-rhGDF15 was required to induce significant body weight loss in mice. These mice gained weight, almost immediately when dosing stopped. In contrast, a single dose of mFc-rhGDF15 at 0.1 µg/g was sufficient to induce significant body weight loss for at least eight days (FIG. 9A; ten ICR-SCID mice dosed intraperitoneally with 0.1 µg/g on day 1). The data in Table 1 revealed that rhGDF15 serum levels were stable for at least eight days, when rhGDF15 was administered as an mFc-rhGDF15 fusion protein.

Figure 9A:
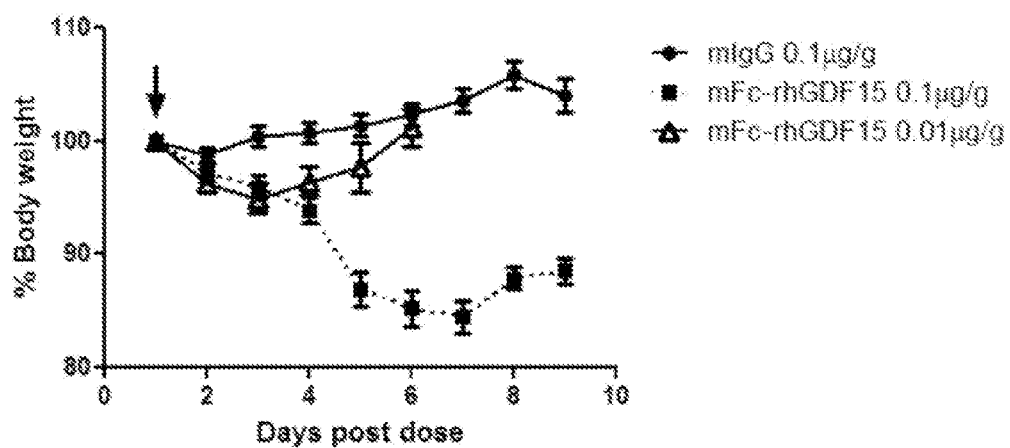
FIG. 9A is a graph summarizing results from an experiment to measure cachectic activity of mFc-rhGDF15 (0.1 µg/g (■), 0.01 µg/g (▲)) and negative control (mIgG 0.1 µg/g (●)) to induce body weight loss in immune-incompetent ICR-SCID mice. Arrows indicate the intraperitoneal dose of the recombinant protein.

To determine the source of activity resulting in sustained body weight loss, we investigated whether the observed rhGDF15 activity was attributable to the mFc-rhGDF15 fusion protein, the released mature rhGDF15 form, or both. As shown in FIG. 9A, a low dose of mFc-rhGDF15 (0.1 µg/g) resulted in body weight loss continuing for at least eight days. A lower dose of mFc-rhGDF15 (0.01 µg/g) also induced body weight loss, but the effect was not sustained for longer than 3 days post dose.

Figure 9B:
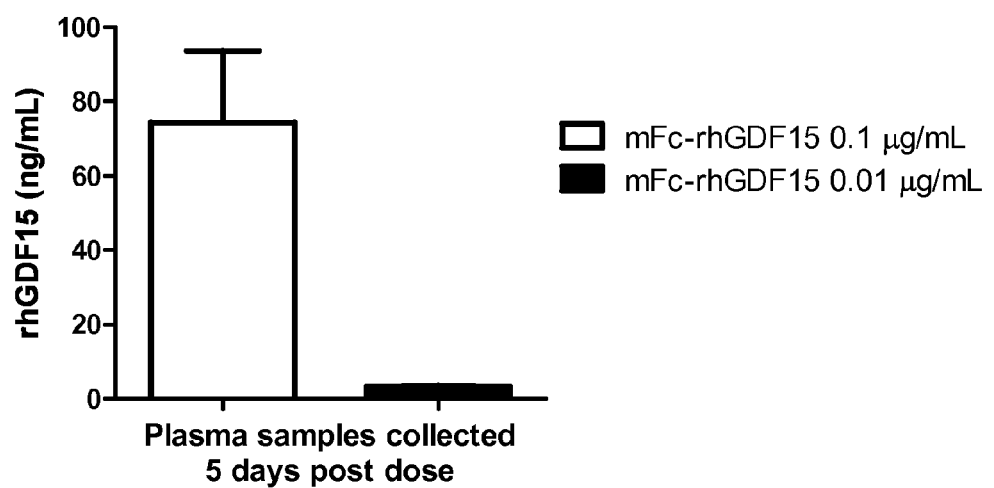
FIG. 9B is a graph representing the total level of rhGDF15 in the plasma of mice dosed with mFc-rhGDF15 (0.1 µg/g (□), 0.01 µg/g (■)) five days post dose, as determined by ELISA.

In this experiment, plasma was collected from three mice each dosed with 0.1 µg/g or 0.01 µg/g at 5 days post dose. Total rhGDF15 was measured by ELISA as described above. Total rhGDF15 plasma levels in the mice dosed with 0.1 µg/g were above 70 ng/mL, consistent with the observation that these mice had significant weight loss (FIG. 9B). Total rhGDF15 plasma levels in mice dosed with 0.01 µg/g were approximately 3.3 ng/mL, but it was observed that these mice were gaining weight (FIG. 9A and FIG. 9B). As described in FIG. 2, the threshold for hGDF15 to induce cachexia in tumor bearing mice is approximately 2 ng/mL. Thus, if both forms of rhGDF15 were active (i.e., mFc-rhGDF15 and released mature rhGDF15), then these mice should be losing weight, not gaining weight (i.e., 3.3 ng/mL total rhGDF15 is above the threshold of approximately 2 ng/mL hGDF15).

To determine which form was the active form (i.e., either mFc-rhGDF15 or released mature rhGDF15), we considered the data from FIG. 8 which showed that approximately 90% of the total rhGDF15 in serum was in the mFc-rhGDF15 form, and the remaining 10% was the released mature form. Based on this extrapolation, approximately 3.0 ng/mL of rhGDF15 in the plasma was in the mFc-rhGDF15 form (i.e., 90% of 3.3 ng/mL). Once again, if mFc-rhGDF15 were active, these mice would be losing weight, not gaining weight because 3.3 ng/mL mFc-rhGDF15 is above the threshold of approximately 2 ng/mL hGDF15. The mice dosed with 0.1 µg/g mFc-rhGDF15 served as an internal control, because these mice had sustained body weight loss indicating that at least one of the two forms must be active. A calculation of 10% of 70 ng/mL total rhGDF15 in these mice is 7 ng/mL released mature rhGDF15. This amount is consistent with inducing the observed body weight loss and the threshold observed in FIG. 2. Thus, the data indicate that the mFc-rhGDF15 is not an active form of the protein, and only the mature rhGDF15 is active. These results were unexpected, because: (a) there was no reason to predict that the Fc fusion protein (mFc-rhGDF15) would be inactive; and (b) there was no reason to predict that the Fc fusion protein would release mature rhGDF15 at the observed rate.

These results indicate that mFc-rhGDF15 sustains a cachetic phenotype by slowly releasing mature rhGDF15 into the serum. These results further indicate that a steady state level of mature rhGDF15 in the plasma or serum can be achieved in a non-tumor bearing mouse by administering mFc-rhGDF15 to the mouse. Therefore, administration of mFc-rhGDF15 to non-tumor bearing mice is particularly useful as a mouse model of cachexia with a robust and sustained loss of muscle mass, loss of fat mass, and body weight loss (see FIGS. 6A-C).

Example 6

Anti-GDF15 Antibodies

This Example describes the production of anti-GDF15 monoclonal antibodies. Immunizations, fusions, and primary screens were conducted using conventional methods following the Repetitive Immunization Multiple Sites (RIMMS) protocol. Five AJ mice and five Balb/c mice were immunized with 6×His (SEQ ID NO: 266) tagged recombinant human GDF15 (His-rhGDF15) (R&D Systems, Inc., Minneapolis, Minn.). Two Balb/c mice with sera displaying the highest anti-GDF15 activity by Enzyme Linked Immunosorbent Assay (ELISA) were chosen for subsequent fusion. Spleens and lymph nodes from the appropriate mice were harvested. B-cells were harvested and fused with a myeloma line. Fusion products were serially diluted onto forty 96-well plates to near clonality. Two AJ mice with sera displaying the highest anti-GDF15 activity by ELISA were chosen for subsequent fusion. Spleens and lymph nodes from the appropriate mice were harvested. B-cells were harvested and fused with a myeloma line. Fusion products were serially diluted onto forty 96-well plates to near clonality.

Approximately 3,840 supernatants from the cell fusions were screened by ELISA for binding to rhGDF15. A total of 172 supernatants containing antibodies against GDF15 were further characterized in vitro. A panel of hybridomas was selected, subcloned and expanded. Antibodies were expressed and subsequently purified by affinity chromatography on Protein G resin, under standard conditions.

Example 7

Antibody Sequence Analysis

The light chain isotype and heavy chain isotype of each monoclonal antibody in Example 6 was determined using the IsoStrip™ Mouse Monoclonal Antibody Isotyping Kit according the kit vendor's instructions (Roche Applied Science, Indianapolis, Ind.). All antibodies were found to be kappa light chain, and IgG1 or IgG2b heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNeasy® Miniprep kit according to the kit vendor's instructions (Qiagen, Valencia, Calif.). Full-length first strand cDNA containing 5' ends was generated using the SMARTer™ RACE cDNA Amplification Kit (Clontech, Mountain View, Calif.) according to the kit vendor's instructions for 5' RACE.

The variable regions of the light (kappa) and heavy (IgG1 or IgG2b) chains were amplified by PCR using KOD Hot Start Polymerase (EMD Chemicals, Gibbstown, N.J.) according to the kit vendor's instructions. For amplification of 5' cDNA ends in conjunction with the SMARTer™ RACE cDNA Amplification Kit, the Universal Primer Mix A primer (Clontech), a mix of: 5' CTAATACGACTCACTATAGGGCAAG-CAGTGGTATCAACGCAGAGT 3' (SEQ ID NO:233) and 5' CTAATAC-GACTCACTATAGGGC 3' (SEQ ID NO:225), was used as a 5' primer. Heavy chain variable regions were amplified using the above 5' primers and a 3' IgG1 constant region specific primer, 5' TATGCAAGGCTTACAACCACA 3' (SEQ ID NO:226), or a 3' IgG2b constant region specific primer, 5' AGGACAGGGGTTGATTGTTGA 3' (SEQ ID NO:227). Kappa chain variable regions were first amplified with the above 5' primers and a 3' kappa constant region specific primer, 5' CTCATTCCTGTTGAAGCTCTTGACAAT 3' (SEQ ID NO:228). The light chains were subjected to a second, nested, round of PCR using the Nested Universal Primer A (Clontech) 5' primer, 5' AAGCAGTGGTATCAACGCAGAGT 3' (SEQ ID NO:229) and a nested 3' kappa constant region specific primer, 5' CGACTGAGGCACCTCCAGATGTT 3' (SEQ ID NO:230). Individual PCR products were either purified using the Qiaquick® PCR Purification kit or isolated by agarose gel electrophoresis and purified using the Qiaquick® Gel Purification kit according to the kit vendor's instructions (Qiagen). The PCR products were subsequently cloned into the pCR®4Blunt plasmid using the Zero Blunt® TOPO® PCR Cloning according to the kit vendor's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO:231) and M13 Reverse primers (5' CAGGAAACAGC-TATGACC 3') (SEQ ID NO:232) by Beckman Genomics (Danvers, Mass.), using standard dideoxy DNA sequencing methods to identify the sequence of the variable region sequences. The sequences were analyzed using Vector NTI software (Invitrogen) and the IMGT/V-Quest web server (imgt-.cines.fr) to identify and confirm variable region sequences.

The nucleic acid sequences encoding and the protein sequences defining variable regions of the murine monoclonal antibodies are shown below (amino terminal signal peptide sequences are not shown). CDR sequences (Kabat definition) are indicated by bold font and underlining in the amino acid sequences.

Nucleic Acid Sequence Encoding the Heavy Chain Variable Region of the 01G06 Antibody (SEQ ID NO:39)

```
  1 gaggtcctgc tgcaacagtc tggacctgag ctggtgaagc
    ctggggcttc agtgaagata 61 ccctgcaagg cttctggata cacattcact gactacaaca
    tggactgggt gaagcagagc 121 catggaaaga gccttgagtg gattggacaa attaatccta
    acaatggtgg tatttctttc 181 aaccagaagt tcaagggcaa ggccacattg actgtagaca
    agtcctccaa tacagccttc 241 atggaggtcc gcagcctgac atctgaggac actgcagtct
    attactgtgc aagagaggca 301 attactacgg taggcgctat ggactactgg ggtcaaggaa
    cctcagtcac cgtctcctca
```

Protein Sequence Defining the Heavy Chain Variable Region of the 01G06 Antibody (SEQ ID NO:40)

```
  1 evllqqsgpe lvkpgasvki pckasgytft dynmdwvkqs
    hgkslewigq inpnnggiff 61 nqkfkgkatl tvdkssntaf mevrsltsed tavyycarea
    ittvgamdyw gqgtsvtvss
```

Nucleic Acid Sequence Encoding the Kappa Chain Variable Region of the 01G06 Antibody (SEQ ID NO:75)

```
  1 gacatccaga tgactcagtc tccagcctcc ctatctgcat
    ctgtgggaga aactgtcacc 61 atcacatgtc gaacaagtga gaatcttcac aattatttag
    catggtatca gcagaaacag 121 ggaaaatctc ctcagctcct ggtctatgat gcaaaaacct
    tagcagatgg tgtgccatca 181 aggttcagtg gcagtggatc aggaacacaa tattctctca
    agatcaacag cctgcagcct 241 gaagattttg ggagttatta ctgtcaacat ttttggagta
    gtccttacac gttcggaggg 301 gggaccaagc tggaaataaa a
```

Protein Sequence Defining the Kappa Chain Variable Region of the 01G06 Antibody (SEQ ID NO:76)

```
  1 diqmtqspas lsasvgetvt itcrtsenlh nylawyqqkq
    gkspqllvyd aktladgvps 61 rfsgsgsgtq yslkinslqp edfgsyycqh fwsspytfgg
    gtkleik
```

Nucleic Acid Sequence Encoding the Heavy Chain Variable Region of the 03G05 Antibody (SEQ ID NO:41)

```
  1 caggtccaac tgcagcagcc tggggctgaa ctggtgaagc
    ctggggcttc agtgaagctg 61 tcctgcaagg cttctggcta caccttcacc agctactgga
    ttcactgggt gaaccagagg 121 cctggacaag gccttgagtg gattggagac attaatccta
    gcaacggccg tagtaagtat 181 aatgagaagt tcaagaacaa ggccacaatg actgcagaca
    aatcctccaa cacagcctac 241 atgcaactca gcagcctgac atctgaggac tctgcggtct
    attactgtgc aagagaggtt 301 ctggatggtg ctatggacta ctggggtcaa ggaacctcag
    tcaccgtctc ctca
```

Protein Sequence Defining the Heavy Chain Variable Region of the 03G05 Antibody (SEQ ID NO:42)

```
  1 qvqlqqpgae lvkpgasvkl sckasgytft sywihwvnqr
    pgqglewigd inpsngrsky 61 nekfknkatm tadkssntay mqlssltsed savyycarev
    ldgamdywgq gtsvtvss
```

Nucleic Acid Sequence Encoding the Kappa Chain Variable Region of the 03G05 Antibody (SEQ ID NO:77)

```
  1 gacattgtgt tgacccaatc tccagcttct ttggctgtgt
    ctctagggca gagggccacc 61 atctcctgca gagccagcga aagtgttgat aattatggca
    ttagttttat gaactggttc 121 caacagaaac caggacagcc acccaaactc ctcatctatg
    ctgcatccaa ccaaggctcc 181 ggggtccctg ccaggtttag tggcagtggg tctgggacag
    acttcagcct caacatccat 241 cctatggagg aggatgatac tgcaatgtat ttctgtcagc
    aaagtaagga ggttccgtgg 301 acgttcggtg gaggctccaa gctggaaatc aaa
```

Protein Sequence Defining the Kappa Chain Variable Region of the 03G05 Antibody (SEQ ID NO:78)

```
  1 divltqspas lavslgqrat iscrasesvd nygisfmnwf
    qqkpgqppkl liyaasnqgs 61 gvparfsgsg sgtdfslnih pmeeddtamy
    fcqqskevpw tfgggsklei k
```

Nucleic Acid Sequence Encoding the Heavy Chain Variable Region of the 04F08 Antibody (SEQ ID NO:43)

```
  1 caggttactc tgaaagagtc tggccctggg atattgcagc
    cctcccagac cctcagtctg 61 acttgttctt tctctgggtt ttcactgagc acttatggta
    tgggtgtgac ctggattcgt 121 cagccttcag gaaagggtct ggagtggctg gcacacattt
    actgggatga tgacaagcgc 181 tataacccat ccctgaagag ccggctcaca atctccaagg
    atacctccaa caaccaggta 241 ttcctcaaga tcaccagtgt ggacactgca gatactgcca
    catactactg tgctcaaacg 301 gggtatagta acttgtttgc ttactgggc caagggactc
    tggtcactgt ctctgca
```

Protein Sequence Defining the Heavy Chain Variable Region of the 04F08 Antibody (SEQ ID NO:44)

```
  1 qvtlkesgpg ilqpsqtlsl tcsfsgfsls tygmgvtwir
    qpsgkglewl ahiywdddkr 61 ynpslksrlt iskdtsnnqv flkitsvdta dtatyycaqt
    gysnlfaywg qgtlvtvsa
```

Nucleic Acid Sequence Encoding the Kappa Chain Variable Region of the 04F08 Antibody (SEQ ID NO:79)

```
  1 gacattgtga tgacccagtc tcaaaaattc atgtccacat
    cagtaggaga cagggtcagc 61 gtcacctgca aggccagtca gaatgtgggt actaatgtag
    cctggtatca acagaaatta 121 ggacaatctc ctaaaacact gatttactcg gcatcctacc
    ggtacagtgg agtccctgat 181 cgcttcacag gcagtggatc tgggacagat ttcactctca
    ccatcagcaa tgtgcagtct 241 gaagacttgg cagagtattt ctgtcagcaa tataacagct
    atccgtacac gttcggaggg 301 gggaccaagc tggaaataaa a
```

Protein Sequence Defining the Kappa Chain Variable Region of the 04F08 Antibody (SEQ ID NO:80)

```
  1 divmtqsqkf mstsvgdrvs vtckasqnvg tnvawyqqkl
    gqspktliys asyrysgvpd 61 rftgsgsgtd ftltisnvqs edlaeyfcqq ynsypytfgg
    gtkleik
```

Nucleic Acid Sequence Encoding the Heavy Chain Variable Region of the 06C11 Antibody (SEQ ID NO:45)

```
  1 caggttactc tgaaagagtc tggccctggg atattgcagc
    cctcccagac cctcagtctg 61 acttgttctt tctctgggtt ttcactgaac acttatggta
    tgggtgtgag ctggattcgt 121 cagccttcag gaaagggtct ggagtggctg gcacacattt
    actgggatga tgacaagcgc 181 tataacccat ccctgaagag ccggctcaca atctccaagg
    atgcctccaa caacgggtc 241 ttcctcaaga tcaccagtgt ggacactgca gatactgcca
    catactactg tgctcaaaga
```

-continued

```
301 ggttatgatg attactgggg ttactggggc caagggactc
    tggtcactat ctctgca
```

Protein Sequence Defining the Heavy Chain Variable Region of the 06C11 Antibody (SEQ ID NO:46)

```
  1 qvtlkesgpg ilqpsqtlsl tcsfsgfsln tygmgvswir
    qpsgkglewl ahiywdddkr
 61 ynpslksrlt iskdasnnrv flkitsvdta dtatyycaqr
    gyddywgywg qgtlvtisa
```

Nucleic Acid Sequence Encoding the Kappa Chain Variable Region of the 06C11 Antibody (SEQ ID NO:81)

```
  1 gacattgtga tgacccagtc tcaaaaattc atgtccacat
    cagtaggaga cagggtcagc
 61 gtcacctgca aggccagtca gaatgtgggt actaatgtag
    cctggtttca acagaaacca
121 ggtcaatctc ctaaagcact gatttactcg gcatcttacc
    ggtacagtgg agtccctgat
181 cgcttcacag gcagtggatc tgggacagat ttcattctca
    ccatcagcaa tgtgcagtct
241 gaagacctgg cagagtattt ctgtcagcaa tataacaact
    atcctctcac gttcggtgct
301 gggaccaagc tggagctgaa a
```

Protein Sequence Defining the Kappa Chain Variable Region of the 06C11 Antibody (SEQ ID NO:82)

```
  1 divmtqsqkf mstsvgdrvs vtckasqnvg tnvawfqqkp
    gqspkaliys asyrysgvpd
 61 rftgsgsgtd filtisnvqs edlaeyfcqq ynnypltfga
    gtklelk
```

Nucleic Acid Sequence Encoding the Heavy Chain Variable Region of the 08G01 Antibody (SEQ ID NO:47)

```
  1 gaggtcctgc tgcaacagtc tggacctgag gtggtgaagc
    ctggggcttc agtgaagata
 61 ccctgcaagg cttctggata cacattcact gactacaaca
    tggactgggt gaagcagagc
121 catggaaaga gccttgagtg gattggagag attaatccta
    acaatggtgg tactttctac
181 aaccagaagt tcaagggcaa ggccacattg actgtagaca
    agtcctccag cacagcctac
241 atggagctcc gcagcctgac atctgaggac actgcagtct
    attactgtgc aagagaggca
301 attactacgg taggcgctat ggactactgg ggtcaaggaa
    cctcagtcac cgtctcctca
```

Protein Sequence Defining the Heavy Chain Variable Region of the 08G01 Antibody (SEQ ID NO:48)

```
  1 evllqqsgpe vvkpgasvki pckasgytft dynmdwvkqs
    hgkslewige inpnnggtfy
 61 nqkfkgkatl tvdkssstay melrsltsed tavyycarea
    ittvgamdyw gqgtsvtvss
```

Nucleic Acid Sequence Encoding the Kappa Chain Variable Region of the 08G01 Antibody (SEQ ID NO:83)

```
  1 gacatccaga tgactcagtc tccagcctcc ctatctgcat
    ctgtgggaga aactgtcacc
 61 atcacatgtc gagcaagtgg gaatattcac aattatttag
    catggtatca gcagaaacag
121 ggaaaatctc ctcagctcct ggtctataat gcaaaaacct
    tagcagatgg tgtgccatca
181 aggttcagtg gcagtggatc aggaacacaa tattctctca
    agatcaacag cctgcagcct
241 gaagattttg ggagttatta ctgtcaacat ttttggagtt
    ctccttacac gttcggaggg
301 gggaccaagc tggaaataaa a
```

Protein Sequence Defining the Kappa Chain Variable Region of the 08G01 Antibody (SEQ ID NO:84)

```
  1 diqmtqspas lsasvgetvt itcrasgnih nylawyqqkq
    gkspqllvyn aktladgvps
 61 rfsgsgsgtq yslkinslqp edfgsyycqh fwsspytfgg
    gtkleik
```

Nucleic Acid Sequence Encoding the Heavy Chain Variable Region of the 14F11 Antibody (SEQ ID NO:49)

```
  1 caggttactc tgaaagagtc tggccctgga atattgcagc
    cctcccagac cctcagtctg
 61 acttgttctt tctctgggtt ttcactgagc acttatggta
    tgggtgtagg ctggattcgt
121 cagccttcag gaaagggtct agagtggctg gcagacattt
    ggtgggatga cgataagtac
181 tataacccat ccctgaagag ccggctcaca atctccaagg
    atacctccag caatgaggta
241 ttcctcaaga tcgccattgt ggacactgca gatactgcca
    cttactactg tgctcgaaga
301 ggtcactact ctgctatgga ctactggggt caaggaacct
    cagtcaccgt ctcctca
```

Protein Sequence Defining the Heavy Chain Variable Region of the 14F11 Antibody (SEQ ID NO:50)

```
  1 qvtlkesgpg ilqpsqtlsl tcsfsgfsls tygmgvgwir
    qpsgkglewl adiwwdddky
 61 ynpslksrlt iskdtssnev flkiaivdta dtatyycarr
    ghysamdywg qgtsvtvss
```

Nucleic Acid Sequence Encoding the Kappa Chain Variable Region of the 14F11 Antibody (SEQ ID NO:85)

```
  1 gacattgtaa tgacccagtc tcaaaaattc atgtccacat
    cagtaggaga cagggtcagc
 61 gtcacctgca aggccagtca gaatgtgggt actaatgtag
    cctggtatca acagaaacca
121 gggcaatctc ctaaagcact gatttactcg ccatcctacc
    ggtacagtgg agtccctgat
181 cgcttcacag gcagtggatc tgggacagat ttcactctca
    ccatcagcaa tgtgcagtct
241 gaagacttgg cagaatattt ctgtcagcaa tataacagct
    atcctcacac gttcggaggg
301 gggaccaagc tggaaatgaa a
```

Protein Sequence Defining the Kappa Chain Variable Region of the 14F11 Antibody (SEQ ID NO:86)

```
  1 divmtqsqkf mstsvgdrvs vtckasqnvg tnvawyqqkp
    gqspkaliys psyrysgvpd 61 rftgsgsgtd ftltisnvqs edlaeyfcqq ynsyphtfgg
    gtklemk
```

Nucleic Acid Sequence Encoding the Heavy Chain Variable Region of the 17B11
Antibody (SEQ ID NO:51)

```
  1 caggttactc tgaaagagtc tggccctggg atattgcagc
    cctcccagac cctcagtctg 61 acttgttctt tctctgggtt ttcactgagc acttctggta
    tgggtgtgag ttggattcgt 121 cagccttcag gaaagggtct ggagtggctg gcacacaatg
    actgggatga tgacaagcgc 181 tataagtcat ccctgaagag ccggctcaca atatccaagg
    atacctccag aaaccaggta 241 ttcctcaaga tcaccagtgt ggacactgca gatactgcca
    catactactg tgctcgaaga 301 gttggggat tagagggcta ttttgattac tggggccaag
    gcaccactct cacagtctcc 361 tca
```

Protein Sequence Defining the Heavy Chain Variable Region of the 17B11
Antibody (SEQ ID NO:52)

```
  1 qvtlkesgpg ilqpsqtlsl tcsfsgfsls tsgmgvswir
    qpsgkglewl ahndwdddkr 61 yksslksrlt iskdtsrnqv flkitsvdta dtatyycarr
    vgglegyfdy wgqgttltvs 121 s
```

Nucleic Acid Sequence Encoding the Kappa Chain Variable Region of the 17B11 Antibody (SEQ ID NO:87)

```
  1 gacattgtgc tgacacagtc tcctgcttcc ttagctgtat
    ctctggggca gagggccacc 61 atctcatgca gggccagcca aagtgtcagt acatctaggt
    ttagttatat gcactggttc 121 caacagaaac caggacaggc acccaaactc ctcatcaagt
    atgcatccaa cctagaatct 181 ggggtccctg ccaggttcag tggcagtggg tctgggacag
    acttcaccct caacatccat 241 cctgtggagg gggaggatac tgcaacatat tactgtcagc
    acagttggga gattccgtac 301 acgttcggag gggggaccaa gctggaaata aaa
```

Protein Sequence Defining the Kappa Chain Variable Region of the 17B11 Antibody (SEQ ID NO:88)

```
  1 divltqspas lavslgqrat iscrasqsvs tsrfsymhwf
    qqkpgqapkl likyasnles 61 gvparfsgsg sgtdftlnih pvegedtaty ycqhsweipy
    tfgggtklei k
```

The amino acid sequences defining the immunoglobulin heavy chain variable regions for the antibodies produced in Example 6 are aligned in FIG. 10. Amino terminal signal peptide sequences (for expression/secretion) are not shown. $CDR_1$, $CDR_2$, and $CDR_3$ (Kabat definition) are identified by boxes. FIG. 11 shows an alignment of the separate $CDR_1$, $CDR_2$, and $CDR_3$ sequences for each antibody.

The amino acid sequences defining the immunoglobulin light chain variable regions of the antibodies in Example 6 are aligned in FIG. 12. Amino terminal signal peptide sequences (for expression/secretion) are not shown. $CDR_1$, $CDR_2$ and $CDR_3$ are identified by boxes. FIG. 13 shows an alignment of the separate $CDR_1$, $CDR_2$, and $CDR_3$ sequences for each antibody.

Table 2 shows the SEQ ID NO. of each sequence discussed in this Example.

TABLE 2

| SEQ. ID NO. | Nucleic Acid or Protein |
|---|---|
| 39 | 01G06 Heavy Chain Variable Region-nucleic acid |
| 40 | 01G06 Heavy Chain Variable Region-protein |
| 75 | 01G06 Light (kappa) Chain Variable Region-nucleic acid |
| 76 | 01G06 Light (kappa) Chain Variable Region-protein |
| 1 | 01G06 Heavy Chain $CDR_1$ |
| 7 | 01G06 Heavy Chain $CDR_2$ |
| 15 | 01G06 Heavy Chain $CDR_3$ |
| 21 | 01G06 Light (kappa) Chain $CDR_1$ |
| 26 | 01G06 Light (kappa) Chain $CDR_2$ |
| 32 | 01G06 Light (kappa) Chain $CDR_3$ |
| 41 | 03G05 Heavy Chain Variable Region-nucleic acid |
| 42 | 03G05 Heavy Chain Variable Region-protein |
| 77 | 03G05 Light (kappa) Chain Variable Region-nucleic acid |
| 78 | 03G05 Light (kappa) Chain Variable Region-protein |
| 2 | 03G05 Heavy Chain $CDR_1$ |
| 8 | 03G05 Heavy Chain $CDR_2$ |
| 16 | 03G05 Heavy Chain $CDR_3$ |
| 22 | 03G05 Light (kappa) Chain $CDR_1$ |
| 27 | 03G05 Light (kappa) Chain $CDR_2$ |
| 33 | 03G05 Light (kappa) Chain $CDR_3$ |
| 43 | 04F08 Heavy Chain Variable Region-nucleic acid |
| 44 | 04F08 Heavy Chain Variable Region-protein |
| 79 | 04F08 Light (kappa) Chain Variable Region-nucleic acid |
| 80 | 04F08 Light (kappa) Chain Variable Region-protein |
| 3 | 04F08 Heavy Chain $CDR_1$ |
| 9 | 04F08 Heavy Chain $CDR_2$ |
| 17 | 04F08 Heavy Chain $CDR_3$ |
| 23 | 04F08 Light (kappa) Chain $CDR_1$ |
| 28 | 04F08 Light (kappa) Chain $CDR_2$ |
| 34 | 04F08 Light (kappa) Chain $CDR_3$ |
| 45 | 06C11 Heavy Chain Variable Region-nucleic acid |
| 46 | 06C11 Heavy Chain Variable Region-protein |
| 81 | 06C11 Light (kappa) Chain Variable Region-nucleic acid |
| 82 | 06C11 Light (kappa) Chain Variable Region-protein |
| 4 | 06C11 Heavy Chain $CDR_1$ |
| 9 | 06C11 Heavy Chain $CDR_2$ |
| 18 | 06C11 Heavy Chain $CDR_3$ |
| 23 | 06C11 Light (kappa) Chain $CDR_1$ |
| 28 | 06C11 Light (kappa) Chain $CDR_2$ |
| 35 | 06C11 Light (kappa) Chain $CDR_3$ |
| 47 | 08G01 Heavy Chain Variable Region-nucleic acid |
| 48 | 08G01 Heavy Chain Variable Region-protein |
| 83 | 08G01 Light (kappa) Chain Variable Region-nucleic acid |
| 84 | 08G01 Light (kappa) Chain Variable Region-protein |
| 1 | 08G01 Heavy Chain $CDR_1$ |
| 10 | 08G01 Heavy Chain $CDR_2$ |
| 15 | 08G01 Heavy Chain $CDR_3$ |
| 24 | 08G01 Light (kappa) Chain $CDR_1$ |
| 29 | 08G01 Light (kappa) Chain $CDR_2$ |
| 32 | 08G01 Light (kappa) Chain $CDR_3$ |
| 49 | 14F11 Heavy Chain Variable Region-nucleic acid |
| 50 | 14F11 Heavy Chain Variable Region-protein |
| 85 | 14F11 Light (kappa) Chain Variable Region-nucleic acid |
| 86 | 14F11 Light (kappa) Chain Variable Region-protein |
| 5 | 14F11 Heavy Chain $CDR_1$ |
| 11 | 14F11 Heavy Chain $CDR_2$ |
| 19 | 14F11 Heavy Chain $CDR_3$ |

TABLE 2-continued

| SEQ. ID NO. | Nucleic Acid or Protein |
|---|---|
| 23 | 14F11 Light (kappa) Chain CDR$_1$ |
| 30 | 14F11 Light (kappa) Chain CDR$_2$ |
| 36 | 14F11 Light (kappa) Chain CDR$_3$ |
| 51 | 17B11 Heavy Chain Variable Region-nucleic acid |
| 52 | 17B11 Heavy Chain Variable Region-protein |
| 87 | 17B11 Light (kappa) Chain Variable Region-nucleic acid |
| 88 | 17B11 Light (kappa) Chain Variable Region-protein |
| 6 | 17B11 Heavy Chain CDR$_1$ |
| 12 | 17B11 Heavy Chain CDR$_2$ |
| 20 | 17B11 Heavy Chain CDR$_3$ |
| 25 | 17B11 Light (kappa) Chain CDR$_1$ |
| 31 | 17B11 Light (kappa) Chain CDR$_2$ |
| 37 | 17B11 Light (kappa) Chain CDR$_3$ |

Mouse monoclonal antibody heavy chain CDR sequences (Kabat, Chothia, and IMGT definitions) are shown in Table 3.

TABLE 3

| | CDR1 | CDR2 | CDR3 | Variable Region SEQ ID NO |
|---|---|---|---|---|
| | | Kabat | | |
| 01G06 | DYNMD (SEQ ID NO: 1) | QINPNNGGIFFNQKFKG (SEQ ID NO: 7) | EAITTVGAMDY (SEQ ID NO: 15) | 40 |
| 03G05 | SYWIH (SEQ ID NO: 2) | DINPSNGRSKYNEKFKN (SEQ ID NO: 8) | EVLDGAMDY (SEQ ID NO: 16) | 42 |
| 04F08 | TYGMGVT (SEQ ID NO: 3) | HIYWDDDKRYNPSLKS (SEQ ID NO: 9) | TGYSNLFAY (SEQ ID NO: 17) | 44 |
| 06C11 | TYGMGVS (SEQ ID NO: 4) | HIYWDDDKRYNPSLKS (SEQ ID NO: 9) | RGYDDYWGY (SEQ ID NO: 18) | 46 |
| 08G01 | DYNMD (SEQ ID NO: 1) | EINPNNGGTFYNQKFKG (SEQ ID NO: 10) | EAITTVGAMDY (SEQ ID NO: 15) | 48 |
| 14F11 | TYGMGVG (SEQ ID NO: 5) | DIWWDDDKYYNPSLKS (SEQ ID NO: 11) | RGHYSAMDY (SEQ ID NO: 19) | 50 |
| 17B11 | TSGMGVS (SEQ ID NO: 6) | HNDWDDDKRYKSSLKS (SEQ ID NO: 12) | RVGGLEGYFDY (SEQ ID NO: 20) | 52 |
| | | Chothia | | |
| 01G06 | GYTFTDY (SEQ ID NO: 38) | NPNNGG (SEQ ID NO: 143) | EAITTVGAMDY (SEQ ID NO: 15) | 40 |
| 03G05 | GYTFTSY (SEQ ID NO: 128) | NPSNGR (SEQ ID NO: 144) | EVLDGAMDY (SEQ ID NO: 16) | 42 |
| 04F08 | GFSLSTYGM (SEQ ID NO: 130) | YWDDD (SEQ ID NO: 145) | TGYSNLFAY (SEQ ID NO: 17) | 44 |
| 06C11 | GFSLNTYGM (SEQ ID NO: 132) | YWDDD (SEQ ID NO: 145) | RGYDDYWGY (SEQ ID NO: 18) | 46 |
| 08G01 | GYTFTDY (SEQ ID NO: 38) | NPNNGG (SEQ ID NO: 143) | EAITTVGAMDY (SEQ ID NO: 15) | 48 |
| 14F11 | GFSLSTYGM (SEQ ID NO: 130) | WWDDD (SEQ ID NO: 146) | RGHYSAMDY (SEQ ID NO: 19) | 50 |
| 17B11 | GFSLSTSGM (SEQ ID NO: 134) | DWDDD (SEQ ID NO: 147) | RVGGLEGYFDY (SEQ ID NO: 20) | 52 |
| | | IMGT | | |
| 01G06 | GYTFTDYN (SEQ ID NO: 136) | INPNNGGI (SEQ ID NO: 148) | AREAITTVGAMDY (SEQ ID NO: 154) | 40 |
| 03G05 | GYTFTSYW (SEQ ID NO: 138) | INPSNGRS (SEQ ID NO: 149) | AREVLDGAMDY (SEQ ID NO: 155) | 42 |
| 04F08 | GFSLSTYGMG (SEQ ID NO: 140) | IYWDDDK (SEQ ID NO: 150) | AQTGYSNLFAY (SEQ ID NO: 156) | 44 |

TABLE 3-continued

| | CDR1 | CDR2 | CDR3 | Variable Region SEQ ID NO |
|---|---|---|---|---|
| 06C11 | GFSLNTYGMG (SEQ ID NO: 141) | IYWDDDK (SEQ ID NO: 150) | AQRGYDDYWGY (SEQ ID NO: 157) | 46 |
| 08G01 | GYTFTDYN (SEQ ID NO: 136) | INPNNGGT (SEQ ID NO: 151) | AREAITTVGAMDY (SEQ ID NO: 154) | 48 |
| 14F11 | GFSLSTYGMG (SEQ ID NO: 140) | IWWDDDK (SEQ ID NO: 152) | ARRGHYSAMDY (SEQ ID NO: 158) | 50 |
| 17B11 | GFSLSTSGMG (SEQ ID NO: 142) | NDWDDDK (SEQ ID NO: 153) | ARRVGGLEGYFDY (SEQ ID NO: 159) | 52 |

Mouse monoclonal antibody Kappa light chain CDR sequences (Kabat, Chothia, and IMGT definitions) are shown in Table 4.

TABLE 4

| | CDR1 | CDR2 | CDR3 | Variable Region SEQ ID NO |
|---|---|---|---|---|
| | | Kabat/Chothia | | |
| 01G06 | RTSENLHNYLA (SEQ ID NO: 21) | DAKTLAD (SEQ ID NO: 26) | QHFWSSPYT (SEQ ID NO: 32) | 76 |
| 03G05 | RASESVDNYGISFMN (SEQ ID NO: 22) | AASNQGS (SEQ ID NO: 27) | QQSKEVPWT (SEQ ID NO: 33) | 78 |
| 04F08 | KASQNVGTNVA (SEQ ID NO: 23) | SASYRYS (SEQ ID NO: 28) | QQYNSYPYT (SEQ ID NO: 34) | 80 |
| 06C11 | KASQNVGTNVA (SEQ ID NO: 23) | SASYRYS (SEQ ID NO: 28) | QQYNNYPLT (SEQ ID NO: 35) | 82 |
| 08G01 | RASGNIHNYLA (SEQ ID NO: 24) | NAKTLAD (SEQ ID NO: 29) | QHFWSSPYT (SEQ ID NO: 32) | 84 |
| 14F11 | KASQNVGTNVA (SEQ ID NO: 23) | SPSYRYS (SEQ ID NO: 30) | QQYNSYPHT (SEQ ID NO: 36) | 86 |
| 17B11 | RASQSVSTSRFSYMH (SEQ ID NO: 25) | YASNLES (SEQ ID NO: 31) | QHSWEIPYT (SEQ ID NO: 37) | 88 |
| | | IMGT | | |
| 01G06 | ENLHNY (SEQ ID NO: 160) | DAK | QHFWSSPYT (SEQ ID NO: 32) | 76 |
| 03G05 | ESVDNYGISF (SEQ ID NO: 161) | AAS | QQSKEVPWT (SEQ ID NO: 33) | 78 |
| 04F08 | QNVGTN (SEQ ID NO: 162) | SAS | QQYNSYPYT (SEQ ID NO: 34) | 80 |
| 06C11 | QNVGTN (SEQ ID NO: 162) | SAS | QQYNNYPLT (SEQ ID NO: 35) | 82 |
| 08G01 | GNIHNY (SEQ ID NO: 163) | NAK | QHFWSSPYT (SEQ ID NO: 32) | 84 |
| 14F11 | QNVGTN (SEQ ID NO: 162) | SPS | QQYNSYPHT (SEQ ID NO: 36) | 86 |
| 17B11 | QSVSTSRFSY (SEQ ID NO: 164) | YAS | QHSWEIPYT (SEQ ID NO: 37) | 88 |

To create the complete heavy or kappa chain antibody sequences, each variable sequence above is combined with its respective constant region. For example, a complete heavy chain comprises a heavy variable sequence followed by the murine IgG1 or IgG2b heavy chain constant sequence, and a complete kappa chain comprises a kappa variable sequence followed by the murine kappa light chain constant sequence.

Nucleic Acid Sequence Encoding the Murine IgG1 Heavy Chain Constant Region (SEQ ID NO:165)

```
  1 gccaaaacga caccccatc tgtctatcca ctggcccctg
    gatctgctgc ccaaactaac
 61 tccatggtga ccctgggatg cctggtcaag ggctatttcc
    ctgagccagt gacagtgacc
121 tggaactctg gatccctgtc cagcggtgtg cacaccttcc
    cagctgtcct gcagtctgac
181 ctctacactc tgagcagctc agtgactgtc ccctccagca
    cctggcccag cgagaccgtc
241 acctgcaacg ttgcccaccc ggccagcagc accaaggtgg
    acaagaaaat tgtgcccagg
301 gattgtggtt gtaagccttg catatgtaca gtcccagaag
    tatcatctgt cttcatcttc
361 cccccaaagc ccaaggatgt gctcaccatt actctgactc
    ctaaggtcac gtgtgttgtg
421 gtagacatca gcaaggatga tcccgaggtc cagttcagct
    ggtttgtaga tgatgtggag
481 gtgcacacag ctcagacgca accccgggag gagcagttca
    acagcacttt ccgctcagtc
541 agtgaacttc ccatcatgca ccaggactgg ctcaatggca
    aggagttcaa atgcagggtc
601 aacagtgcag ctttccctgc ccccatcgag aaaaccatct
    ccaaaaccaa aggcagaccg
661 aaggctccac aggtgtacac cattccacct cccaaggagc
    agatggccaa ggataaagtc
721 agtctgacct gcatgataac agacttcttc cctgaagaca
    ttactgtgga gtggcagtgg
781 aatgggcagc cagcggagaa ctacaagaac actcagccca
    tcatggacac agatggctct
841 tacttcgtct acagcaagct caatgtgcag aagagcaact
    gggaggcagg aaatactttc
901 acctgctctg tgttacatga gggcctgcac aaccaccata
    ctgagaagag cctctcccac
961 tctcctggta aa
```

Protein Sequence Defining the Murine IgG1 Heavy Chain Constant Region (SEQ ID NO:166)

```
  1 akttppsvyp lapgsaaqtn smvtlgclvk gyfpepvtvt
    wnsgslssgv htfpavlqsd
 61 lytlsssvtv psstwpsetv tcnvahpass tkvdkkivpr
    dcgckpcict vpevssvfif
121 ppkpkdvlti tltpkvtcvv vdiskddpev qfswfvddve
    vhtaqtqpre eqfnstfrsv
181 selpimhqdw lngkefkcru nsaafpapie ktisktkgrp
    kapqvytipp pkeqmakdkv
241 sltcmitdff peditvewqw ngqpaenykn tqpimdtdgs
    yfvysklnvq ksnweagntf
301 tcsvlheglh nhhtekslsh spgk
```

Nucleic Acid Sequence Encoding the Murine IgG2b Heavy Chain Constant Region (SEQ ID NO:167)

```
  1 gccaaaacaa caccccatc agtctatcca ctggcccctg
    ggtgtggaga tacaactggt
 61 tcctccgtga ctctgggatg cctggtcaag ggctacttcc
    ctgagtcagt gactgtgact
121 tggaactctg gatccctgtc cagcagtgtg cacaccttcc
    cagctctcct gcagtctgga
181 ctctacacta tgagcagctc agtgactgtc ccctccagca
    cctggccaag tcagaccgtc
241 acctgcagcg ttgctcaccc agccagcagc accacggtgg
    acaaaaaact tgagcccagc
301 gggcccattt caacaatcaa cccctgtcct ccatgcaagg
    agtgtcacaa atgcccagct
361 cctaacctcg agggtggacc atccgtcttc atcttcctc
    caaatatcaa ggatgtactc
421 atgatctccc tgacacccaa ggtcacgtgt gtggtggtgg
    atgtgagcga ggatgaccca
481 gacgtccaga tcagctggtt tgtgaacaac gtggaagtac
    acacagctca gacacaaacc
541 catagagagg attacaacag tactatccgg gtggtcagca
    ccctcsccat ccagcaccag
601 gactggatga gtggcaagga gttcaaatgc aaggtcaaca
    acaaagacct cccatcaccc
661 atcgagagaa ccatctcaaa aattaaaggg ctagtcagag
    ctccacaagt atacatcttg
721 ccgccaccag cagagcagtt gtccaggaaa gatgtcagtc
    tcacttgcct ggtcgtgggc
781 ttcaaccctg gagacatcag tgtggagtgg accagcaatg
    ggcatacaga ggagaactac
841 aaggacaccg caccagtcct agactctgac ggttcttact
    tcatatatag caagctcaat
901 atgaaaacaa gcaagtggga gaaaacagat tccttctcat
    gcaacgtgag acacgagggt
961 ctgaaaaatt actacctgaa gaagaccatc tcccggtctc
    cgggtaaa
```

Protein Sequence Defining the Murine IgG2b Heavy Chain Constant Region (SEQ ID NO:168)

```
  1 akttppsvyp lapgcgdttg ssvtlgclvk gyfpesvtvt
    wnsgslsssv htfpallqsg
 61 lytmsssvtv psstwpsqtv tcsvahpass ttvdkkleps
    gpistinpcp pckechkcpa
121 pnleggpsvf ifppnikdvl misltpkvtc vvvdvseddp
    dvqiswfvnn vevhtaqtqt
181 hredynstir vvstlpiqhq dwmsgkefkc kvnnkdlpsp
    iertiskikg lvrapqvyil
241 pppaeqlsrk dvsltclvvg fnpgdisvew tsnghteeny
    kdtapvldsd gsyfiyskln
301 mktskwektd sfscnvrheg lknyylkkti srspgk
```

Nucleic Acid Sequence Encoding the Murine Kappa Light Chain Constant Region (SEQ ID NO:169)

```
  1 cgggctgatg ctgcaccaac tgtatccatc ttcccaccat
    ccagtgagca gttaacatct
 61 ggaggtgcct cagtcgtgtg cttcttgaac aacttctacc
    ccaaagacat caatgtcaag
```

```
121 tggaagattg atggcagtga acgacaaaat ggcgtcctga
    acagttggac tgatcaggac 181 agcaaagaca gcacctacag catgagcagc accctcacgt
    tgaccaagga cgagtatgaa 241 cgacataaca gctatacctg tgaggccact cacaagacat
    caacttcacc cattgtcaag 301 agcttcaaca ggaatgagtg t
```

Protein Sequence Defining the Murine Kappa Light Chain Constant Region (SEQ ID NO:170)

```
  1 radaaptvsi fppsseqlts ggasvvcfln nfypkdinvk
    wkidgserqn gvlnswtdqd 61 skdstysmss tltltkdeye rhnsytceat hktstspivk
    sfnrnec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Heavy Chain Sequence (Heavy Chain Variable Region and IgG1 Constant Region) of 01G06 (SEQ ID NO:99)

```
  1 gaggtcctgc tgcaacagtc tggacctgag ctggtgaagc
    ctggggcttc agtgaagata 61 ccctgcaagg cttctggata cacattcact gactacaaca
    tggactgggt gaagcagagc 121 catggaaaga gccttgagtg gattggacaa attaatccta
    acaatggtgg tatttttctc 181 aaccagaagt tcaagggcaa ggccacattg actgtagaca
    agtcctccaa tacagccttc 241 atggaggtcc gcagcctgac atctgaggac actgcagtct
    attactgtgc aagagaggca 301 attactacgg taggcgctat ggactactgg ggtcaaggaa
    cctcagtcac cgtctcctca 361 gccaaaacga cacccccatc tgtctatcca ctggcccctg
    gatctgctgc ccaaactaac 421 tccatggtga ccctgggatg cctggtcaag ggctatttcc
    ctgagccagt gacagtgacc 481 tggaactctg gatccctgtc cagcggtgtg cacaccttcc
    cagctgtcct gcagtctgac 541 ctctacactc tgagcagctc agtgactgtc ccctccagca
    cctggcccag cgagaccgtc 601 acctgcaacg ttgcccaccc ggccagcagc accaaggtgg
    acaagaaaat tgtgcccagg 661 gattgtggtt gtaagccttg catatgtaca gtcccagaag
    tatcatctgt cttcatcttc 721 cccccaaagc ccaaggatgt gctcaccatt actctgactc
    ctaaggtcac gtgtgttgtg 781 gtagacatca gcaaggatga tcccgaggtc cagttcagct
    ggtttgtaga tgatgtggag 841 gtgcacacag ctcagacgca accccgggag gagcagttca
    acagcacttt ccgctcagtc 901 agtgaacttc ccatcatgca ccaggactgg ctcaatggca
    aggagttcaa atgcagggtc 961 aacagtgcag ctttccctgc ccccatcgag aaaaccatct
    ccaaaaccaa aggcagaccg 1021 aaggctccac aggtgtacac cattccacct cccaaggagc
     agatggccaa ggataaagtc 1081 agtctgacct gcatgataac agacttcttc cctgaagaca
     ttactgtgga gtggcagtgg 1141 aatgggcagc cagcggagaa ctacaagaac actcagccca
     tcatggacac agatggctct 1201 tacttcgtct acagcaagct caatgtgcag aagagcaact
     gggaggcagg aaatactttc 1261 acctgctctg tgttacatga gggcctgcac aaccaccata
     ctgagaagag cctctcccac 1321 tctcctggta aa
```

Protein Sequence Defining the Full Length Heavy Chain Sequence (Heavy Chain Variable Region and IgG1 Constant Region) of 01G06 (SEQ ID NO:100)

```
  1 evllqqsgpe lvkpgasvki pckasgytft dynmdwvkqs
    hgkslewigq inpnnggiff 61 nqkfkgkatl tvdkssntaf mevrsltsed tavyycarea
    ittvgamdyw gqgtsvtvss 121 akttppsvyp lapgsaaqtn smvtlgclvk gyfpepvtvt
    wnsgslssgv htfpavlqsd 181 lytlsssvtv psstwpsetv tcnvahpass tkvdkkivpr
    dcgckpcict vpevssvfif 241 ppkpkdvlti tltpkvtcvv vdiskddpev qfswfvddve
    vhtaqtqpre eqfnstfrsv 301 selpimhqdw lngkefkcrv nsaafpapie ktisktkgrp
    kapqvytipp pkeqmakdkv 361 sltcmitdff peditvewqw ngqpaenykn tqpimdtdgs
    yfvysklnvq ksnweagntf 421 tcsvlheglh nhhtekslsh spgk
```

Nucleic Acid Sequence Encoding the Full Length Light Chain Sequence (Kappa Chain Variable Region and Constant Region) of 01G06 (SEQ ID NO:101)

```
  1 gacatccaga tgactcagtc tccagcctcc ctatctgcat
    ctgtgggaga aactgtcacc 61 atcacatgtc gaacaagtga gaatcttcac aattatttag
    catggtatca gcagaaacag 121 ggaaaatctc ctcagctcct ggtctatgat gcaaaaacct
    tagcagatgg tgtgccatca
```

```
181 aggttcagtg gcagtggatc aggaacacaa tattctctca
    agatcaacag cctgcagcct 241 gaagattttg ggagttatta ctgtcaacat ttttggagta
    gtccttacac gttcggaggg 301 gggaccaagc tggaaataaa acgggctgat gctgcaccaa
    ctgtatccat cttcccacca 361 tccagtgagc agttaacatc tggaggtgcc tcagtcgtgt
    gcttcttgaa caacttctac 421 cccaaagaca tcaatgtcaa gtggaagatt gatggcagtg
    aacgacaaaa tggcgtcctg 481 aacagttgga ctgatcagga cagcaaagac agcacctaca
    gcatgagcag cacccctcacg 541 ttgaccaagg acgagtatga acgacataac agctatacct
    gtgaggccac tcacaagaca 601 tcaacttcac ccattgtcaa gagcttcaac aggaatgagt gt
```

Protein Sequence Defining the Full Length Light Chain Sequence (Kappa Chain Variable Region and Constant Region) of 01G06 (SEQ ID NO:102)

```
  1 diqmtqspas lsasvgetvt itcrtsenlh nylawyqqkq
    gkspqllvyd aktladgvps 61 rfsgsgsgtq yslkinslqp edfgsyycqh fwsspytfgg
    gtkleikrad aaptvsifpp 121 sseqltsgga svvcflnnfy pkdinvkwki dgserqngvl
    nswtdqdskd stysmsstlt 181 ltkdeyerhn sytceathkt stspivksfn rnec
```

Nucleic Acid Sequence Encoding the Full Length Heavy Chain Sequence (Heavy Chain Variable Region and IgG1 Constant Region) of 03G05 (SEQ ID NO:103)

```
  1 caggtccaac tgcagcagcc tggggctgaa ctggtgaagc
    ctggggcttc agtgaagctg 61 tcctgcaagg cttctggcta caccttcacc agctactgga
    ttcactgggt gaaccagagg 121 cctggacaag gccttgagtg gattggagac attaatccta
    gcaacggccg tagtaagtat 181 aatgagaagt tcaagaacaa ggccacaatg actgcagaca
    aatcctccaa cacagcctac 241 atgcaactca gcagcctgac atctgaggac tctgcggtct
    attactgtgc aagagaggtt 301 ctggatggtg ctatggacta ctggggtcaa ggaacctcag
    tcaccgtctc ctcagccaaa 361 acgacacccc catctgtcta tccactggcc cctggatctg
    ctgcccaaac taactccatg 421 gtgaccctgg gatgcctggt caagggctat tccctgagc
    cagtgacagt gacctggaac 481 tctggatccc tgtccagcgg tgtgcacacc ttcccagctg
    tcctgcagtc tgacctctac 541 actctgagca gctcagtgac tgtcccctcc agcacctggc
    ccagcgagac cgtcacctgc 601 aacgttgccc acccggccag cagcaccaag gtggacaaga
    aaattgtgcc cagggattgt 661 ggttgtaagc cttgcatatg tacagtccca gaagtatcat
    ctgtcttcat cttccccca
```

```
721 aagcccaagg atgtgctcac cattactctg actcctaagg
    tcacgtgtgt tgtggtagac 781 atcagcaagg atgatcccga ggtccagttc agctggtttg
    tagatgatgt ggaggtgcac 841 acagctcaga cgcaacccg ggaggagcag ttcaacagca
    ctttccgctc agtcagtgaa 901 cttcccatca tgcaccagga ctggctcaat ggcaaggagt
    tcaaatgcag ggtcaacagt 961 gcagctttcc ctgcccccat cgagaaaacc atctccaaaa
    ccaaaggcag accgaaggct 1021 ccacaggtgt acaccattcc acctcccaag gagcagatgg
     ccaaggataa agtcagtctg 1081 acctgcatga taacagactt cttccctgaa gacattactg
     tggagtggca gtggaatggg 1141 cagccagcgg agaactacaa gaacactcag cccatcatgg
     acacagatgg ctcttacttc 1201 gtctacagca agctcaatgt gcagaagagc aactgggagg
     caggaaatac tttcacctgc 1261 tctgtgttac atgagggcct gcacaaccac atactgaga
     agagcctctc ccactctcct 1321 ggtaaa
```

Protein Sequence Defining the Full Length Heavy Chain Sequence (Heavy Chain Variable Region and IgG1 Constant Region) of 03G05 (SEQ ID NO:104)

```
  1 qvqlqqpgae lvkpgasvkl sckasgytft sywihwvnqr
    pgqglewigd inpsngrsky 61 nekfknkatm tadkssntay mqlssltsed savyycarev
    ldgamdywgq gtsvtvssak 121 ttppsvypla pgsaaqtnsm vtlgclvkgy fpepvtvtwn
    sgslssgvht fpavlqsdly 181 tlsssvtvps stwpsetvtc nvahpasstk vdkkivprdc
    gckpcictvp evssvfifpp 241 kpkdvltitl tpkvtcvvvd iskddpevqf swfvddvevh
    taqtqpreeq fnstfrsvse 301 lpimhqdwln gkefkcrvns aafpapiekt isktkgrpka
    pqvytipppk eqmakdkvsl 361 tcmitdffpe ditvewqwng qpaenykntq pimdtdgsyf
    vysklnvqks nweagntftc 421 svlheglhnh htekslshsp gk
```

Nucleic Acid Sequence Encoding the Full Length Light Chain Sequence (Kappa Chain Variable Region and Constant Region) of 03G05 (SEQ ID NO:105)

```
  1 gacattgtgt tgacccaatc tccagcttct ttggctgtgt
    ctctagggca gagggccacc 61 atctcctgca gagccagcga aagtgttgat aattatggca
    ttagttttat gaactggttc 121 caacagaaac caggacagcc acccaaactc ctcatctatg
    ctgcatccaa ccaaggctcc 181 ggggtccctg ccaggtttag tggcagtggg tctgggacag
    acttcagcct caacatccat 241 cctatggagg aggatgatac tgcaatgtat ttctgtcagc
    aaagtaagga ggttccgtgg
```

```
301 acgttcggtg gaggctccaa gctggaaatc aaacgggctg
    atgctgcacc aactgtatcc 361 atcttccac catccagtga gcagttaaca tctggaggtg
    cctcagtcgt gtgcttcttg 421 aacaacttct accccaaaga catcaatgtc aagtggaaga
    ttgatggcag tgaacgacaa 481 aatgcgtcc tgaacagttg gactgatcag acagcaaag
    acagcaccta cagcatgagc 541 agcaccctca cgttgaccaa ggacgagtat gaacgacata
    acagctatac ctgtgaggcc 601 actcacaaga catcaacttc acccattgtc aagagcttca
    acaggaatga gtgt
```

Protein Sequence Defining the Full Length Light Chain Sequence (Kappa Chain Variable Region and Constant Region) of 03G05 (SEQ ID NO:106)

```
  1 divltqspas lavslgqrat iscrasesvd nygisfmnwf
    qqkpgqppkl liyaasnqgs 61 gvparfsgsg sgtdfslnih pmeeddtamy fcqqskevpw
    tfgggsklei kradaaptvs 121 ifppsseqlt sggasvvcfl nnfypkdinv kwkidgserq
    ngvlnswtdq dskdstysms 181 stltltkdey erhnsytcea thktstspiv ksfnrnec
```

Nucleic Acid Sequence Encoding the Full Length Heavy Chain Sequence (Heavy Chain Variable Region and IgG1 Constant Region) of 04F08 (SEQ ID NO:107)

```
  1 caggttactc tgaaagagtc tggccctggg atattgcagc
    cctcccagac cctcagtctg 61 acttgttctt tctctgggtt ttcactgagc acttatggta
    tgggtgtgac ctggattcgt 121 cagccttcag gaaagggtct ggagtggctg gcacacattt
    actgggatga tgacaagcgc 181 tataacccat ccctgaagag ccggctcaca atctccaagg
    atacctccaa caaccaggta 241 ttcctcaaga tcaccagtgt ggacactgca gatactgcca
    catactactg tgctcaaacg 301 gggtatagta acttgttttgc ttactgggc caagggactc
    tggtcactgt ctctgcagcc 361 aaaacgacac cccatctgt ctatccactg gcccctggat
    ctgctgccca aactaactcc 421 atggtgaccc tgggatgcct ggtcaagggc tatttccctg
    agccagtgac agtgacctgg 481 aactctggat ccctgtccag cggtgtgcac accttcccag
    ctgtcctgca gtctgacctc 541 tacactctga gcagctcagt gactgtcccc tccagcacct
    ggcccagcga gaccgtcacc 601 tgcaacgttg cccacccggc cagcagcacc aaggtggaca
    agaaaattgt gcccaggga 661 tgtggttgta agccttgcat atgtacagtc ccagaagtat
    catctgtctt catcttcccc 721 ccaaagccca aggatgtgct caccattact ctgactccta
    aggtcacgtg tgttgtggta
```

```
781 gacatcagca aggatgatcc cgaggtccag ttcagctggt
    ttgtagatga tgtggaggtg 841 cacacagctc agacgcaacc ccgggaggag cagttcaaca
    gcactttccg ctcagtcagt 901 gaacttccca tcatgcacca ggactggctc aatggcaagg
    agttcaaatg cagggtcaac 961 agtgcagctt tccctgcccc catcgagaaa accatctcca
    aaaccaaagg cagaccgaag 1021 gctccacagg tgtacaccat tccacctccc aaggagcaga
     tggccaagga taaagtcagt 1081 ctgacctgca tgataacaga cttcttccct gaagacatta
     ctgtggagtg cagtggaat 1141 gggcagccca cggagaacta caagaacact cagcccatca
     tggacacaga tggctcttac 1201 ttcgtctaca gcaagctcaa tgtgcagaag agcaactggg
     aggcaggaaa tacttcacc 1261 tgctctgtgt tacatgaggg cctgcacaac caccatactg
     agaagagcct ctcccactct 1321 cctggtaaa
```

Protein Sequence Defining the Full Length Heavy Chain Sequence (Heavy Chain Variable Region and IgG1 Constant Region) of 04F08 (SEQ ID NO:108)

```
  1 qvtlkesgpg ilqpsqtlsl tcsfsgfsls tygmgvtwir
    qpsgkglewl ahiywdddkr 61 ynpslksrlt iskdtsnnqv flkitsvdta dtatyycaqt
    gysnlfaywg qgtlvtvsaa 121 kttppsvypl apgsaaqtns mvtlgclvkg yfpepvtvtw
    nsgslssgvh tfpavlqsdl 181 ytlsssvtvp sstwpsetvt cnvahpasst kvdkkivprd
    cgckpcictv pevssvfifp 241 pkpkdvltit ltpkvtcvvv diskddpevq fswfvddvev
    htaqtqpree qfnstfrsvs 301 elpimhqdwl ngkefkcrvn saafpapiek tisktkgrpk
    apqvytippp keqmakdkvs 361 ltcmitdffp editvewqwn gqpaenyknt qpimdtdgsy
    fvysklnvqk snweagntft 421 csvlheglhn hhtekslshs pgk
```

Nucleic Acid Sequence Encoding the Full Length Light Chain Sequence (Kappa Chain Variable Region and Constant Region) of 04F08 (SEQ ID NO:109)

```
  1 gacattgtga tgacccagtc tcaaaaattc atgtccacat
    cagtaggaga cagggtcagc 61 gtcacctgca aggccagtca gaatgtgggt actaatgtag
    cctggtatca acagaaatta 121 ggacaatctc ctaaaacact gatttactcg gcatcctacc
    ggtacagtgg agtccctgat 181 cgcttcacag gcagtggatc tgggacagat ttcactctca
    ccatcagcaa tgtgcagtct 241 gaagacttgg cagagtattt ctgtcagcaa tataacagct
    atccgtacac gttcggaggg 301 gggaccaagc tggaaataaa acgggctgat gctgcaccaa
    ctgtatccat cttcccacca
```

```
361 tccagtgagc agttaacatc tggaggtgcc tcagtcgtgt
    gcttcttgaa caacttctac 421 cccaaagaca tcaatgtcaa gtggaagatt gatggcagtg
    aacgacaaaa tggcgtcctg 481 aacagttgga ctgatcagga cagcaaagac agcacctaca
    gcatgagcag caccctcacg 541 ttgaccaagg acgagtatga acgacataac agctatacct
    gtgaggccac tcacaagaca 601 tcaacttcac ccattgtcaa gagcttcaac aggaatgagt gt
```

Protein Sequence Defining the Full Length Light Chain Sequence (Kappa Chain Variable Region and Constant Region) of 04F08 (SEQ ID NO:110)

```
  1 divmtqsqkf mstsvgdrvs vtckasqnvg tnvawyqqkl
    gqspktliys asyrysgvpd 61 rftgsgsgtd ftltisnvqs edlaeyfcqq ynsypytfgg
    gtkleikrad aaptvsifpp 121 sseqltsgga svvcflnnfy pkdinvkwki dgserqngvl
    nswtdqdskd stysmsstlt 181 ltkdeyerhn sytceathkt stspivksfn rnec
```

Nucleic Acid Sequence Encoding the Full Length Heavy Chain Sequence (Heavy Chain Variable Region and IgG1 Constant Region) of 06C11 (SEQ ID NO:111)

```
  1 caggttactc tgaaagagtc tggccctggg atattgcagc
    cctcccagac cctcagtctg 61 acttgttctt tctctgggtt ttcactgaac acttatggta
    tgggtgtgag ctggattcgt 121 cagccttcag gaaagggtct ggagtggctg gcacacattt
    actgggatga tgacaagcgc 181 tataacccat ccctgaagag ccggctcaca atctccaagg
    atgcctccaa caaccgggtc 241 ttcctcaaga tcaccagtgt ggacactgca gatactgcca
    catactactg tgctcaaaga 301 ggttatgatg attactgggg ttactggggc caagggactc
    tggtcactat ctctgcagcc 361 aaaacgacac cccatctgt ctatccactg gcccctggat
    ctgctgccca aactaactcc 421 atggtgaccc tgggatgcct ggtcaagggc tatttccctg
    agccagtgac agtgacctgg 481 aactctggat ccctgtccag cggtgtgcac accttcccag
    ctgtcctgca gtctgacctc 541 tacactctga gcagctcagt gactgtcccc tccagcacct
    ggcccagcga gaccgtcacc 601 tgcaacgttg cccacccggc cagcagcacc aaggtggaca
    gaaaattgt gcccagggat 661 tgtggttgta agccttgcat atgtacagtc ccagaagtat
    catctgtctt catcttcccc 721 ccaaagccca aggatgtgct caccattact ctgactccta
    aggtcacgtg tgttgtggta 781 gacatcagca aggatgatcc cgaggtccag ttcagctggt
    ttgtagatga tgtggaggtg
```

```
841 cacacagctc agacgcaacc ccgggaggag cagttcaaca
    gcactttccg ctcagtcagt 901 gaacttccca tcatgcacca ggactggctc aatggcaagg
    agttcaaatg cagggtcaac 961 agtgcagctt tccctgcccc catcgagaaa accatctcca
    aaaccaaagg cagaccgaag 1021 gctccacagg tgtacaccat tccacctccc aaggagcaga
    tggccaagga taaagtcagt 1081 ctgacctgca tgataacaga cttcttccct gaagacatta
    ctgtggagtg gcagtggaat 1141 gggcagccag cggagaacta caagaacact cagcccatca
    tggacacaga tggctcttac 1201 ttcgtctaca gcaagctcaa tgtgcagaag agcaactggg
    aggcaggaaa tactttcacc 1261 tgctctgtgt tacatgaggg cctgcacaac caccatactg
    agaagagcct ctcccactct 1321 cctggtaaa
```

Protein Sequence Defining the Full Length Heavy Chain Sequence (Heavy Chain Variable Region and IgG1 Constant Region) of 06C11 (SEQ ID NO:112)

```
  1 qvtlkesgpg ilqpsqtlsl tcsfsgfsln tygmgvswir
    qpsgkglewl ahiywdddkr 61 ynpslksrlt iskdasnnrv flkitsvdta dtatyycaqr
    gyddywgywg qgtlvtisaa 121 kttppsvypl apgsaaqtns mvtlgclvkg yfpepvtvtw
    nsgslssgvh tfpavlqsdl 181 ytlsssvtvp sstwpsetvt cnvahpasst kvdkkivprd
    cgckpcictv pevssvfifp 241 pkpkdvltit ltpkvtcvvv diskddpevq fswfvddvev
    htaqtqpree qfnstfrsvs 301 elpimhqdwl ngkefkcrvn saafpapiek tisktkgrpk
    apqvytippp keqmakdkvs 361 ltcmitdffp editvewqwn gqpaenyknt qpimdtdgsy
    fvysklnvqk snweagntft 421 csvlheglhn hhtekslshs pgk
```

Nucleic Acid Sequence Encoding the Full Length Light Chain Sequence (Kappa Chain Variable Region and Constant Region) of 06C11 (SEQ ID NO:113)

```
  1 gacattgtga tgacccagtc tcaaaaattc atgtccacat
    cagtaggaga cagggtcagc 61 gtcacctgca aggccagtca gaatgtgggt actaatgtag
    cctggtttca acagaaacca 121 ggtcaatctc ctaaagcact gatttactcg gcatcttacc
    ggtacagtgg agtccctgat 181 cgcttcacag gcagtggatc tgggacagat ttcattctca
    ccatcagcaa tgtgcagtct 241 gaagacctgg cagagtattt ctgtcagcaa tataacaact
    atcctctcac gttcggtgct 301 gggaccaagc tggagctgaa acgggctgat gctgcaccaa
    ctgtatccat cttcccacca 361 tccagtgagc agttaacatc tggaggtgcc tcagtcgtgt
    gcttcttgaa caacttctac
```

```
421 cccaaagaca tcaatgtcaa gtggaagatt gatggcagtg
    aacgacaaaa tggcgtcctg 481 aacagttgga ctgatcagga cagcaaagac agcacctaca
    gcatgagcag caccctcacg 541 ttgaccaagg acgagtatga acgacataac agctatacct
    gtgaggccac tcacaagaca 601 tcaacttcac ccattgtcaa gagcttcaac aggaatgagt gt
```

Protein Sequence Defining the Full Length Light Chain Sequence (Kappa Chain Variable Region and Constant Region) of 06C11 (SEQ ID NO:114)

```
  1 divmtqsqkf mstsvgdrvs vtckasqnvg tnvawfqqkp
    gqspkaliys asyrysgvpd 61 rftgsgsgtd filtisnvqs edlaeyfcqq ynnypltfga
    gtklelkrad aaptvsifpp 121 sseqltsgga svvcflnnfy pkdinvkwki dgserqngvl
    nswtdqdskd stysmsstlt 181 ltkdeyerhn sytceathkt stspivksfn rnec
```

Nucleic Acid Sequence Encoding the Full Length Heavy Chain Sequence (Heavy Chain Variable Region and IgG2b Constant Region) of 08G01 (SEQ ID NO:115)

```
  1 gaggtcctgc tgcaacagtc tggacctgag gtggtgaagc
    ctggggcttc agtgaagata 61 ccctgcaagg cttctggata cacattcact gactacaaca
    tggactgggt gaagcagagc 121 catggaaaga gccttgagtg gattggagag attaatccta
    acaatggtgg tactttctac 181 aaccagaagt tcaagggcaa ggccacattg actgtagaca
    agtcctccag cacagcctac 241 atggagctcc gcagcctgac atctgaggac actgcagtct
    attactgtgc aagagaggca 301 attactacgg taggcgctat ggactactgg ggtcaaggaa
    cctcagtcac cgtctcctca 361 gccaaaacaa cccccccatc agtctatcca ctggcccctg
    ggtgtggaga tacaactggt 421 tcctccgtga ctctgggatg cctggtcaag ggctacttcc
    ctgagtcagt gactgtgact 481 tggaactctg gatccctgtc cagcagtgtg cacaccttcc
    cagctctcct gcagtctgga 541 ctctacacta tgagcagctc agtgactgtc ccctccagca
    cctggccaag tcagaccgtc 601 acctgcagcg ttgctcaccc agccagcagc accacggtgg
    acaaaaaact tgagcccagc 661 gggcccattt caacaatcaa cccctgtcct ccatgcaagg
    agtgtcacaa atgcccagct 721 cctaacctcg agggtgacc atccgtcttc atcttccctc
    caaatatcaa ggatgtactc 781 atgatctccc tgacacccaa ggtcacgtgt gtggtggtgg
    atgtgagcga ggatgaccca 841 gacgtccaga tcagctggtt tgtgaacaac gtggaagtac
    acacagctca gacacaaacc 901 catagagagg attacaacag tactatccgg gtggtcagca
    ccctcccat ccagcaccag
```

```
961 gactggatga gtggcaagga gttcaaatgc aaggtcaaca
    acaaagacct cccatcaccc 1021 atcgagagaa ccatctcaaa aattaaaggg ctagtcagag
     ctccacaagt atacatcttg 1081 ccgccaccag cagagcagtt gtccaggaaa gatgtcagtc
     tcacttgcct ggtcgtgggc 1141 ttcaaccctg gagacatcag tgtggagtgg accagcaatg
     ggcatacaga ggagaactac 1201 aaggacaccg caccagtcct agactctgac ggttcttact
     tcatatatag caagctcaat 1261 atgaaaacaa gcaagtggga gaaaacagat tccttctcat
     gcaacgtgag acacgagggt 1321 ctgaaaaatt actacctgaa gaagaccatc tcccggtctc
     cgggtaaa
```

Protein Sequence Defining the Full Length Heavy Chain Sequence (Heavy Chain Variable Region and IgG2b Constant Region) of 08G01 (SEQ ID NO:116)

```
  1 evllqqsgpe vvkpgasvki pckasgytft dynmdwvkqs
    hgkslewige inpnnggtfy 61 nqkfkgkatl tvdkssstay melrsltsed tavyycarea
    ittvgamdyw gqgtsvtvss 121 akttppsvyp lapgcgdttg ssvtlgclvk gyfpesvtvt
    wnsgslsssv htfpallqsg 181 lytmsssvtv psstwpsqtv tcsvahpass ttvdkkleps
    gpistinpcp pckechkcpa 241 pnleggpsvf ifppnikdvl misltpkvtc vvvdvseddp
    dvqiswfvnn vevhtaqtqt 301 hredynstir vvstlpiqhq dwmsgkefkc kvnnkdlpsp
    iertiskikg lvrapqvyil 361 pppaeqlsrk dvsltclvvg fnpgdisvew tsnghteeny
    kdtapvldsd gsyfiyskln 421 mktskwektd sfscnvrheg lknyylkkti srspgk
```

Nucleic Acid Sequence Encoding the Full Length Light Chain Sequence (Kappa Chain Variable Region and Constant Region) of 08G01 (SEQ ID NO:117)

```
  1 gacatccaga tgactcagtc tccagcctcc ctatctgcat
    ctgtgggaga aactgtcacc 61 atcacatgtc gagcaagtgg gaatattcac aattatttag
    catggtatca gcagaaacag 121 ggaaaatctc ctcagctcct ggtctataat gcaaaaacct
    tagcagatgg tgtgccatca 181 aggttcagtg gcagtggatc aggaacacaa tattctctca
    agatcaacag cctgcagcct 241 gaagattttg ggagttatta ctgtcaacat ttttggagtt
    ctccttacac gttcggaggg 301 gggaccaagc tggaaataaa acgggctgat gctgcaccaa
    ctgtatccat cttcccacca 361 tccagtgagc agttaacatc tggaggtgcc tcagtcgtgt
    gcttcttgaa caacttctac 421 cccaaagaca tcaatgtcaa gtggaagatt gatggcagtg
    aacgacaaaa tggcgtcctg
```

```
481 aacagttgga ctgatcagga cagcaaagac agcacctaca
    gcatgagcag caccctcacg 541 ttgaccaagg acgagtatga acgacataac agctatacct
    gtgaggccac tcacaagaca 601 tcaacttcac ccattgtcaa gagcttcaac aggaatgagt gt
```

Protein Sequence Defining the Full Length Light Chain Sequence (Kappa Chain Variable Region and Constant Region) of 08G01 (SEQ ID NO:118)

```
  1 diqmtqspas lsasvgetvt itcrasgnih nylawyqqkq
    gkspqllvyn aktladgvps 61 rfsgsgsgtq yslkinslqp edfgsyycqh fwsspytfgg
    gtkleikrad aaptvsifpp 121 sseqltsgga svvcflnnfy pkdinvkwki dgserqngvl
    nswtdqdskd stysmsstlt 181 ltkdeyerhn sytceathkt stspivksfn rnec
```

Nucleic Acid Sequence Encoding the Full Length Heavy Chain Sequence (Heavy Chain Variable Region and IgG1 Constant Region) of 14F11 (SEQ ID NO:119)

```
  1 caggttactc tgaaagagtc tggccctgga atattgcagc
    cctcccagac cctcagtctg 61 acttgttctt tctctgggtt ttcactgagc acttatggta
    tgggtgtagg ctggattcgt 121 cagccttcag gaaagggtct agagtggctg gcagacattt
    ggtgggatga cgataagtac 181 tataacccat ccctgaagag ccggctcaca atctccaagg
    atacctccag caatgaggta 241 ttcctcaaga tcgccattgt ggacactgca gatactgcca
    cttactactg tgctcgaaga 301 ggtcactact ctgctatgga ctactggggt caaggaacct
    cagtcaccgt ctcctcagcc 361 aaaacgacac ccccatctgt ctatccactg gcccctggat
    ctgctgccca aactaactcc 421 atggtgaccc tgggatgcct ggtcaagggc tatttccctg
    agccagtgac agtgacctgg 481 aactctggat ccctgtccag cggtgtgcac accttcccag
    ctgtcctgca gtctgacctc 541 tacactctga gcagctcagt gactgtcccc tccagcacct
    ggcccagcga gaccgtcacc 601 tgcaacgttg cccacccggc cagcagcacc aaggtggaca
    agaaaattgt gcccaggga t 661 tgtggttgta agccttgcat atgtacagtc ccagaagtat
    catctgtctt catcttcccc 721 ccaaagccca aggatgtgct caccattact ctgactccta
    aggtcacgtg tgttgtggta 781 gacatcagca aggatgatcc cgaggtccag ttcagctggt
    ttgtagatga tgtggaggtg 841 cacacagctc agacgcaacc ccgggaggag cagttcaaca
    gcactttccg ctcagtcagt 901 gaacttccca tcatgcacca ggactggctc aatggcaagg
    agttcaaatg cagggtcaac 961 agtgcagctt tccctgcccc catcgagaaa accatctcca
    aaaccaaagg cagaccgaag
```

```
1021 gctccacagg tgtacaccat tccacctccc aaggagcaga
     tggccaagga taaagtcagt 1081 ctgacctgca tgataacaga cttcttccct gaagacatta
     ctgtggagtg gcagtggaat 1141 gggcagccag cggagaacta caagaacact cagcccatca
     tggacacaga tggctcttac 1201 ttcgtctaca gcaagctcaa tgtgcagaag agcaactggg
     aggcaggaaa tactttcacc 1261 tgctctgtgt tacatgaggg cctgcacaac caccatactg
     agaagagcct ctcccactct 1321 cctggtaaa
```

Protein Sequence Defining the Full Length Heavy Chain Sequence (Heavy Chain Variable Region and IgG1 Constant Region) of 14F11 (SEQ ID NO:120)

```
  1 qvtlkesgpg ilqpsqtlsl tcsfsgfsls tygmgvgwir
    qpsgkglewl adiwwdddky 61 ynpslksrlt iskdtssnev flkiaivdta dtatyycarr
    ghysamdywg qgtsvtvssa 121 kttppsvypl apgsaaqtns mvtlgclvkg yfpepvtvtw
    nsgslssgvh tfpavlqsdl 181 ytlsssvtvp sstwpsetvt cnvahpasst kvdkkivprd
    cgckpcictv pevssvfifp 241 pkpkdvltit ltpkvtcvvv diskddpevq fswfvddvev
    htaqtqpree qfnstfrsvs 301 elpimhqdwl ngkefkcrvn saafpapiek tisktkgrpk
    apqvytippp keqmakdkvs 361 ltcmitdffp editvewqwn gqpaenyknt qpimdtdgsy
    fvysklnvqk snweagntft 421 csvlheglhn hhtekslshs pgk
```

Nucleic Acid Sequence Encoding the Full Length Light Chain Sequence (Kappa Chain Variable Region and Constant Region) of 14F11 (SEQ ID NO:121)

```
  1 gacattgtaa tgacccagtc tcaaaaattc atgtccacat
    cagtaggaga cagggtcagc 61 gtcacctgca aggccagtca gaatgtgggt actaatgtag
    cctggtatca acagaaacca 121 gggcaatctc ctaaagcact gatttactcg ccatcctacc
    ggtacagtgg agtccctgat 181 cgcttcacag gcagtggatc tgggacagat ttcactctca
    ccatcagcaa tgtgcagtct 241 gaagacttgg cagaatattt ctgtcagcaa tataacagct
    atcctcacac gttcggaggg 301 gggaccaagc tggaaatgaa acgggctgat gctgcaccaa
    ctgtatccat cttcccacca 361 tccagtgagc agttaacatc tggaggtgcc tcagtcgtgt
    gcttcttgaa caacttctac 421 cccaaagaca tcaatgtcaa gtggaagatt gatggcagtg
    aacgacaaaa tggcgtcctg 481 aacagttgga ctgatcagga cagcaaagac agcacctaca
    gcatgagcag caccctcacg
```

-continued

```
541 ttgaccaagg acgagtatga acgacataac agctatacct
    gtgaggccac tcacaagaca 601 tcaacttcac ccattgtcaa gagcttcaac aggaatgagt gt
```

Protein Sequence Defining the Full Length Light Chain Sequence (Kappa Chain Variable Region and Constant Region) of 14F11 (SEQ ID NO:122)

```
  1 divmtqsqkf mststvgdrvs vtckasqnvg tnvawyqqkp
    gqspkaliys psyrysgvpd 61 rftgsgsgtd ftltisnvqs edlaeyfcqq ynsyphtfgg
    gtklemkrad aaptvsifpp 121 sseqltsgga svvcflnnfy pkdinvkwki dgserqngvl
    nswtdqdskd stysmsstlt 181 ltkdeyerhn sytceathkt stspivksfn rnec
```

Nucleic Acid Sequence Encoding the Full Length Heavy Chain Sequence (Heavy Chain Variable Region and IgG1 Constant Region) of 17B11 (SEQ ID NO:123)

```
  1 caggttactc tgaaagagtc tggccctggg atattgcagc
    cctcccagac cctcagtctg 61 acttgttctt tctctgggtt ttcactgagc acttctggta
    tgggtgtgag ttggattcgt 121 cagccttcag gaaagggtct ggagtggctg gcacacaatg
    actgggatga tgacaagcgc 181 tataagtcat ccctgaagag ccggctcaca atatccaagg
    atacctccag aaaccaggta 241 ttcctcaaga tcaccagtgt ggacactgca gatactgcca
    catactactg tgctcgaaga 301 gttggggat tagagggcta ttttgattac tggggccaag
    gcaccactct cacagtctcc 361 tcagccaaaa cgacaccccc atctgtctat ccactggccc
    ctggatctgc tgcccaaact 421 aactccatgt gaccctggg atgcctggtc aagggctatt
    tccctgagcc agtgacagtg 481 acctggaact ctggatccct gtccagcggt gtgcacacct
    tcccagctgt cctgcagtct 541 gacctctaca ctctgagcag ctcagtgact gtcccctcca
    gcacctggcc cagcgagacc 601 gtcacctgca acgttgccca cccggccagc agcaccaagg
    tggacaagaa aattgtgccc 661 agggattgtg gttgtaagcc ttgcatatgt acagtcccag
    aagtatcatc tgtcttcatc 721 ttccccccaa agcccaagga tgtgctcacc attactctga
    ctcctaaggt cacgtgtgtt 781 gtggtagaca tcagcaagga tgatcccgag gtccagttca
    gctggtttgt agatgatgtg 841 gaggtgcaca cagctcagac gcaacccccgg gaggagcagt
    tcaacagcac tttccgctca 901 gtcagtgaac ttcccatcat gcaccaggac tggctcaatg
    gcaaggagtt caaatgcagg 961 gtcaacagtg cagctttccc tgcccccatc gagaaaacca
    tctccaaaac caaaggcaga
```

```
1021 ccgaaggctc cacaggtgta caccattcca cctcccaagg
     agcagatggc caaggataaa 1081 gtcagtctga cctgcatgat aacagacttc ttccctgaag
     acattactgt ggagtggcag 1141 tggaatgggc agccagcgga gaactacaag aacactcagc
     ccatcatgga cacagatggc 1201 tcttacttcg tctacagcaa gctcaatgtg cagaagagca
     actgggaggc aggaaatact 1261 ttcacctgct ctgtgttaca tgagggcctg cacaaccacc
     atactgagaa gagcctctcc 1321 cactctcctg gtaaa
```

Protein Sequence Defining the Full Length Heavy Chain Sequence (Heavy Chain Variable Region and IgG1 Constant Region) of 17B11 (SEQ ID NO:124)

```
  1 qvtlkesgpg ilqpsqtlsl tcsfsgfsls tsgmgvswir
    qpsgkglewl ahndwdddkr 61 yksslksrlt iskdtsrnqv flkitsvdta dtatyycarr
    vgglegyfdy wgqgttltvs 121 sakttppsvy plapgsaaqt nsmvtlgclv kgyfpepvtv
    twnsgslssg vhtfpavlqs 181 dlytlsssvt vpsstwpset vtcnvahpas stkvdkkivp
    rdcgckpcic tvpevssvfi 241 fppkpkdvlt itltpkvtcv vvdiskddpe vqfswfvddv
    evhtaqtqpr eeqfnstfrs 301 vselpimhqd wlngkefkcr vnsaafpapi ektisktkgr
    pkapqvytip ppkeqmakdk 361 vsltcmitdf fpeditvewq wngqpaenyk ntqpimdtdg
    syfvysklnv qksnweagnt 421 ftcsvlhegl hnhhteksls hspgk
```

Nucleic Acid Sequence Encoding the Full Length Light Chain Sequence (Kappa Chain Variable Region and Constant Region) of 17B11 (SEQ ID NO:125)

```
  1 gacattgtgc tgacacagtc tcctgcttcc ttagctgtat
    ctctggggca gagggccacc 61 atctcatgca gggccagcca aagtgtcagt acatctaggt
    tagttatat gcactggttc 121 caacagaaac caggacaggc acccaaactc ctcatcaagt
    atgcatccaa cctagaatct 181 ggggtccctg ccaggttcag tggcagtggg tctgggacag
    acttcaccct caacatccat 241 cctgtggagg gggaggatac tgcaacatat tactgtcagc
    acagttggga gattccgtac 301 acgttcggag gggggaccaa gctggaaata aaacgggctg
    atgctgcacc aactgtatcc 361 atcttcccac catccagtga gcagttaaca tctggaggtg
    cctcagtcgt gtgcttcttg 421 aacaacttct accccaaaga catcaatgtc aagtggaaga
    ttgatggcag tgaacgacaa 481 aatggcgtcc tgaacagttg gactgatcag gacagcaaag
    acagcaccta cagcatgagc 541 agcaccctca cgttgaccaa ggacgagtat gaacgacata
    acagctatac ctgtgaggcc
```

-continued
```
601 actcacaaga catcaacttc acccattgtc aagagcttca
    acaggaatga gtgt
```

Protein Sequence Defining the Full Length Light Chain Sequence (Kappa Chain Variable Region and Constant Region) of 17B11 (SEQ ID NO:126)

```
  1 divltqspas lavslgqrat iscrasqsvs tsrfsymhwf
    qqkpgqapkl likyasnles 61 gvparfsgsg sgtdftlnih pvegedtaty ycqhsweipy
    tfgggtklei kradaaptvs 121 ifppsseqlt sggasvvcfl nnfypkdinv kwkidgserq
    ngvlnswtdq dskdstysms 181 stltltkdey erhnsytcea thktstspiv ksfnrnec
```

Table 5 shows the correspondence between the full-length sequences of the antibodies discussed in this Example with those presented in the Sequence Listing.

TABLE 5

| SEQ ID NO. | Nucleic Acid or Protein |
|---|---|
| 99  | 01G06_Heavy Variable + IgG1 Constant-nucleic acid |
| 100 | 01G06_Heavy Variable + IgG1 Constant-protein |
| 101 | 01G06_Kappa Variable + Constant-nucleic acid |
| 102 | 01G06_Kappa Variable + Constant-protein |
| 103 | 03G05 Heavy Variable + IgG1 Constant-nucleic acid |
| 104 | 03G05 Heavy Variable + IgG1 Constant-protein |
| 105 | 03G05 Kappa Variable + Constant-nucleic acid |
| 106 | 03G05 Kappa Variable + Constant-protein |
| 107 | 04F08 Heavy Variable + IgG1 Constant-nucleic acid |
| 108 | 04F08 Heavy Variable + IgG1 Constant-protein |
| 109 | 04F08 Kappa Variable + Constant-nucleic acid |
| 110 | 04F08 Kappa Variable + Constant-protein |
| 111 | 06C11 Heavy Variable + IgG1 Constant-nucleic acid |
| 112 | 06C11 Heavy Variable + IgG1 Constant-protein |
| 113 | 06C11 Kappa Variable + Constant-nucleic acid |
| 114 | 06C11 Kappa Variable + Constant-protein |
| 115 | 08G01 Heavy Variable + IgG2b Constant-nucleic acid |
| 116 | 08G01 Heavy Variable + IgG2b Constant-protein |
| 117 | 08G01 Kappa Variable + Constant-nucleic acid |
| 118 | 08G01 Kappa Variable + Constant-protein |
| 119 | 14F11 Heavy Variable + IgG1 Constant-nucleic acid |
| 120 | 14F11 Heavy Variable + IgG1 Constant-protein |
| 121 | 14F11 Kappa Variable + Constant-nucleic acid |
| 122 | 14F11 Kappa Variable + Constant-protein |
| 123 | 17B11 Heavy Variable + IgG1 Constant-nucleic acid |
| 124 | 17B11 Heavy Variable + IgG1 Constant-protein |
| 125 | 17B11 Kappa Variable + Constant-nucleic acid |
| 126 | 17B11 Kappa Variable + Constant-protein |

Example 8

Binding Affinities

The binding affinities and kinetics of binding of antibodies to 6xHis tagged (SEQ ID NO: 266) recombinant human GDF15 (His-rhGDF15 (R&D Systems, Inc.)), untagged recombinant human GDF15 (rhGDF15 (Peprotech, Rocky Hill, N.J.), and recombinant human GDF15 produced as either mouse Fc fused to human GDF15 (mFc-rhGDF15) or a version in which the Fc was enzymatically removed (cleaved-rhGDF15) were measured by surface plasmon resonance, using a Biacore® T100 instrument (GE Healthcare, Piscataway, N.J.).

Rabbit anti-mouse IgGs (GE Healthcare) were immobilized on carboxymethylated dextran CM4 sensor chips (GE Healthcare) by amine coupling, according to a standard protocol. Analyses were performed at 37° C. using PBS containing 0.05% surfactant P20 as running buffer. The antibodies were captured in individual flow cells at a flow rate of 10 µL/minute. Injection time was varied for each antibody to yield an Rmax between 30 and 60 RU. 250 µg/mL mouse Fc (Jackson ImmunoResearch, West Grove, Pa.) was injected at 30 µL/minute for 120 seconds to block non-specific binding of capture antibodies to mouse Fc portion of the recombinant GDF15 protein when needed. Buffer, mFc-rhGDF15, cleaved-rhGDF15, His-rhGDF15, or rhGDF15 diluted in running buffer was injected sequentially over a reference surface (no antibody captured) and the active surface (antibody to be tested) for 240 seconds at 60 µL/minute. The dissociation phase was monitored for up to 1500 seconds. The surface was then regenerated with two 60-second injections of 10 mM Glycine-HCl, pH 1.7, at a flow rate of 30 µL/minute. The GDF15 concentration range tested was 30 nM to 0.625 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined Kinetic values of the monoclonal antibodies on mFc-rhGDF15, cleaved rhGDF15, His-rhGDF15, or rhGDF15 are summarized in Tables 6, 7, 8, and 9, respectively.

TABLE 6

Antibody Binding to mFc-rhGDF15

| Antibody | $k_a$ (1/Ms) | $k_d$ (1/s) | $K_D$ (M) | n |
|---|---|---|---|---|
| 01G06 | 5.6E+06 | 7.0E−04 | 2.1E−10 | 7 |
| 03G05 | 1.0E+07 | 6.4E−04 | 6.9E−11 | 3 |
| 04F08 | 3.6E+06 | 6.4E−04 | 1.9E−10 | 3 |
| 06C11 | 4.5E+06 | 6.8E−04 | 1.7E−10 | 5 |
| 08G01 | 6.0E+06 | 1.1E−03 | 1.9E−10 | 4 |
| 14F11 | 1.7E+06 | 3.3E−04 | 2.2E−10 | 4 |
| 17B11 | 3.7E+06 | 5.1E−04 | 1.4E−10 | 3 |

The data in Table 6 demonstrate that antibodies bind mFc-rhGDF15 with a $K_D$ of about 250 pM or less, 200 pM or less, 150 pM or less, 100 pM or less, 75 pM or less, or 50 pM or less.

Kinetic values of the monoclonal antibodies on cleaved-rhGDF15 are summarized in Table 7.

TABLE 7

Antibody Binding to Cleaved-rhGDF15

| Antibody | $k_a$ (1/Ms) | $k_d$ (1/s) | $K_D$ (M) | n |
|---|---|---|---|---|
| 01G06 | 7.5E+06 | 8.6E−04 | 1.1E−10 | 1 |
| 06C11 | 1.2E+07 | 2.0E−03 | 1.7E−10 | 2 |
| 14F11 | 5.7E+06 | 6.0E−04 | 1.1E−10 | 1 |

The data in Table 7 demonstrate that antibodies 01G06, 06C11 and 14F11 bind cleaved-rhGDF15 with a $K_D$ of about 200 pM or less, 150 pM or less, or 100 pM or less.

Kinetic values of the monoclonal antibodies on His-rhGDF15 are summarized in Table 8.

TABLE 8

Antibody Binding to His-rhGDF15

| Antibody | $k_a$ (1/Ms) | $k_d$ (1/s) | $K_D$ (M) | n |
|---|---|---|---|---|
| 01G06 | 1.4E+07 | 1.1E−03 | 8.1E−11 | 2 |
| 06C11 | 2.9E+07 | 1.5E−03 | 5.1E−11 | 2 |
| 14F11 | 4.4E+06 | 4.2E−04 | 9.6E−11 | 1 |

The data in Table 8 demonstrate that antibodies 01G06, 06C11 and 14F11 bind His-rhGDF15 with a $K_D$ of about 150 pM or less, 100 pM or less, 75 pM or less, or 50 pM or less.

Kinetic values of the monoclonal antibodies on rhGDF15 are summarized in Table 9.

TABLE 9

Antibody Binding to rhGDF15

| Antibody | $k_a$ (1/Ms) | $k_d$ (1/s) | $K_D$ (M) | n |
|---|---|---|---|---|
| 01G06 | 2.1E+07 | 1.9E−03 | 9.3E−11 | 1 |
| 06C11 | 2.2E+07 | 4.6E−03 | 2.1E−10 | 1 |
| 14F11 | 3.1E+07 | 2.2E−03 | 7.1E−11 | 1 |

The data in Table 9 demonstrate that antibodies 01G06, 06C11 and 14F11 bind rhGDF15 with a $K_D$ of about 250 pM or less, 200 pM or less, 150 pM or less, 100 pM or less, 75 pM or less, or 50 pM or less.

Example 9

Reversal of Cachexia in an mFc-rhGDF15-Induced Model

This Example demonstrates the reversal of cachexia (as indicated by body weight loss) by antibody 01G06, 03G05, 04F08, 06C11, 14F11, or 17B11 in an mFc-rhGDF15-induced cachexia model. mFc-rhGDF15 (2 µg/g) was administered subcutaneously into the flank of 8-week old female ICR-SCID mice. Body weight was measured daily. When body weight reached 93%, the mice were randomized into seven groups of ten mice each. Each group received one of the following treatments: murine IgG control, 01G06, 03G05, 04F08, 06C11, 14F11, or 17B11 at 10 mg/kg. Treatment was administered once by intra-peritoneal injection. Treatment with antibody 01G06, 03G05, 04F08, 06C11, 14F11, or 17B11 resulted in body weight increase relative to initial weight or about 100% (p<0.001) (FIG. 14 and Table 10).

TABLE 10

| | Treatment | | % Body | ANOVA Analysis |
|---|---|---|---|---|
| Gr. | Agent | mg/kg | weight | (compared to mIgG) |
| 1 | mIgG | 10 | 77.1 | NA |
| 2 | 01G06 | 10 | 94.1 | p < 0.001 |
| 3 | 03G05 | 10 | 95.1 | p < 0.001 |
| 4 | 04F08 | 10 | 95.8 | p < 0.001 |
| 5 | 06C11 | 10 | 93.8 | p < 0.001 |
| 7 | 14F11 | 10 | 95.4 | p < 0.001 |
| 8 | 17B11 | 10 | 92.8 | p < 0.001 |

Figure 14:
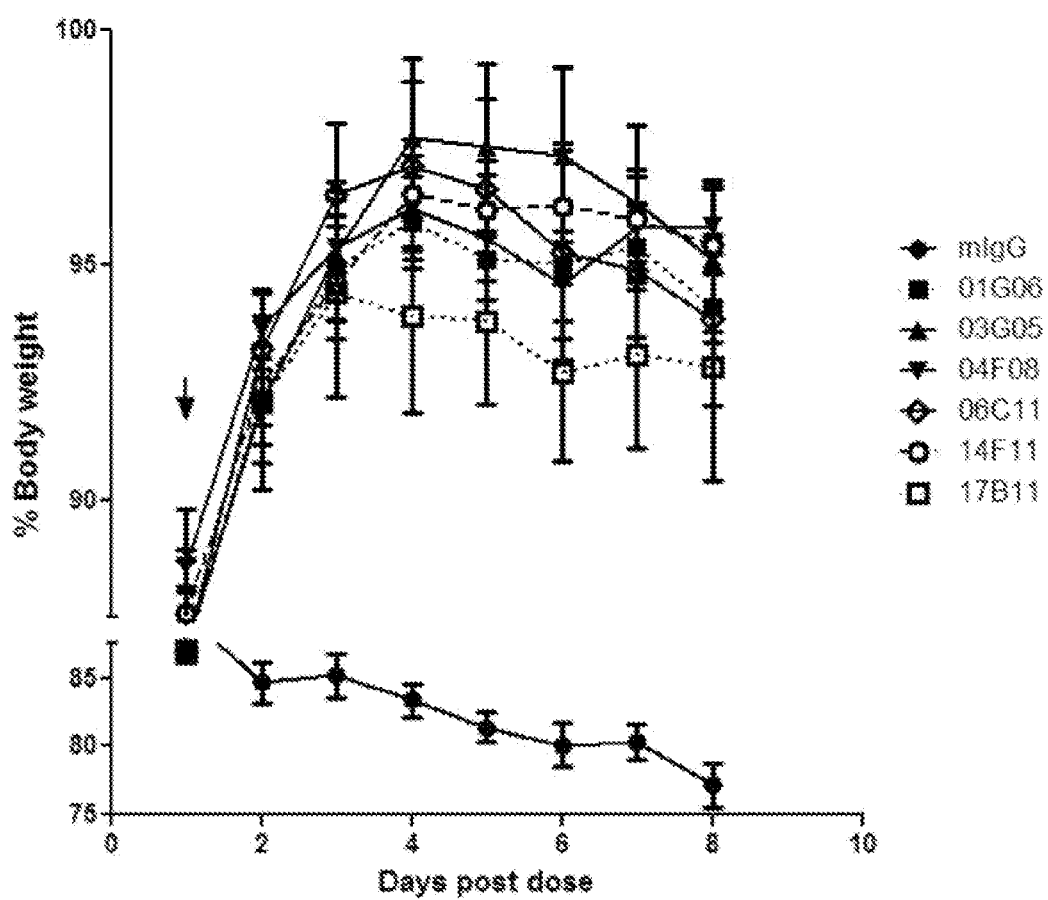
FIG. 14 is a graph summarizing results from an experiment to measure cachectic inhibitory activity of anti-GDF15 antibodies 01G06 (■), 03G05 (▲), 04F08 (▼), 06C11 (◇), 14F11 (⌑), and 17B11 (□), and a murine IgG control (■; mIgG) dosed at 10 mg/kg in an mFc-rhGDF15 cachectic model in ICR-SCID mice. The arrow indicates intra-peritoneal injection of antibody.

The data in FIG. 14 and Table 10 indicate that the disclosed anti-GDF15 antibodies can reverse cachexia in an mFc-rhGDF15-induced mouse model (i.e., a non-tumor bearing mouse model).

Example 10

Reversal of Cachexia in an HT-1080 Xenograft Tumor Model

This Example demonstrates the reversal of cachexia (as indicated by body weight loss) by antibody 01G06, 03G05, 04F08, 06C11, 08G01, 14F11 or 17B11 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. Body weight was measured daily. When body weight reached 93%, the mice were randomized into eight groups of ten mice each. Each group received one of the following treatments: murine IgG control, 01G06, 03G05, 04F08, 06C11, 08G01, 14F11 or 17B11 at 10 mg/kg. Treatment was administered every three days by intra-peritoneal injection. Treatment with antibody 01G06, 03G05, 04F08, 06C11, 08G01, 14F11 or 17B11 resulted in body weight increase relative to initial weight or about 100% (p<0.001) (FIG. 15 and Table 11).

TABLE 11

| | Treatment | | % Body | ANOVA Analysis |
|---|---|---|---|---|
| Gr. | Agent | mg/kg | weight | (compared to mIgG) |
| 1 | mIgG | 10 | 81.4 | NA |
| 2 | 01G06 | 10 | 103.3 | p < 0.001 |
| 3 | 03G05 | 10 | 106.1 | p < 0.001 |
| 4 | 04F08 | 10 | 104.3 | p < 0.001 |
| 5 | 06C11 | 10 | 106.6 | p < 0.001 |
| 6 | 08G01 | 10 | 105.3 | p < 0.001 |
| 7 | 14F11 | 10 | 99.6 | p < 0.001 |
| 8 | 17B11 | 10 | 103.7 | p < 0.001 |

Figure 15:
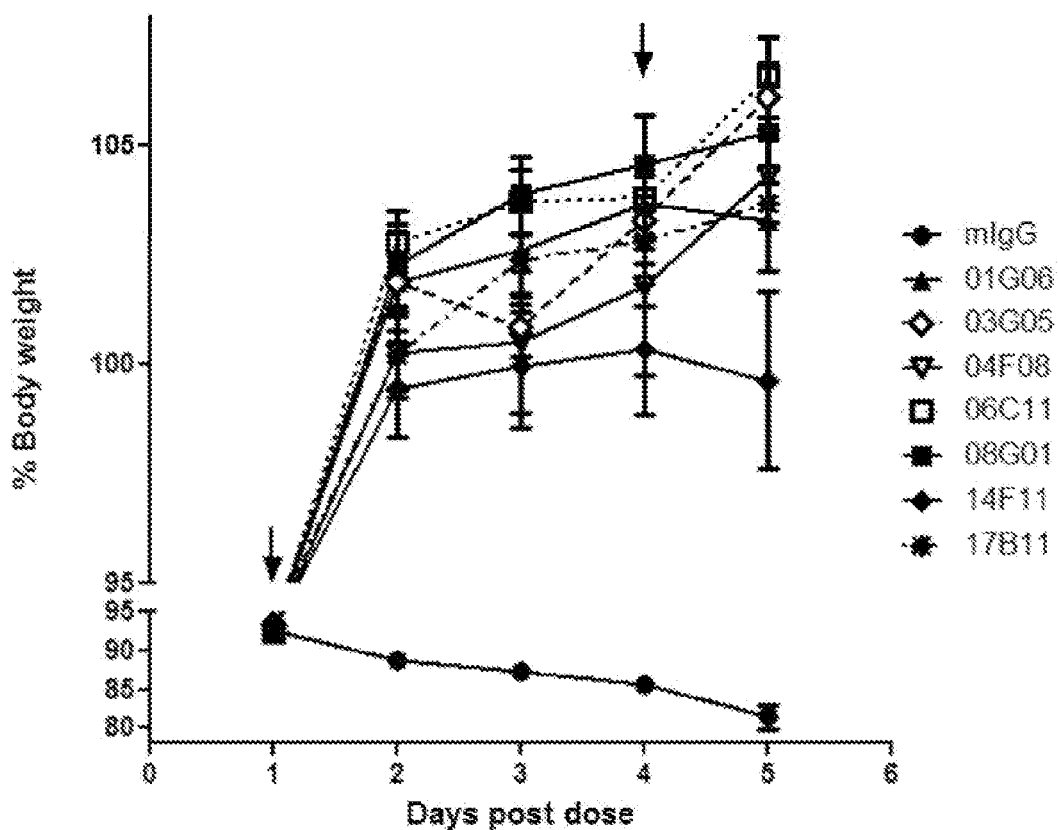
FIG. 15 is a graph summarizing results from an experiment to measure cachectic inhibitory activity of anti-GDF15 antibodies 01G06 (▲), 03G05 (◇), 04F08 (∇), 06C11 (□), 08G01 (■), 14F11 (♦), and 17B11 (*), and a murine IgG control (■; mIgG), dosed at 10 mg/kg in an HT-1080 fibrosarcoma tumor xenograft model in ICR-SCID mice. The arrows indicate intra-peritoneal injection of antibody every three days.

The data in FIG. 15 and Table 11 indicate that the disclosed anti-GDF15 antibodies can reverse cachexia in an HT-1080 fibrosarcoma xenograft model.

Figure 16A:
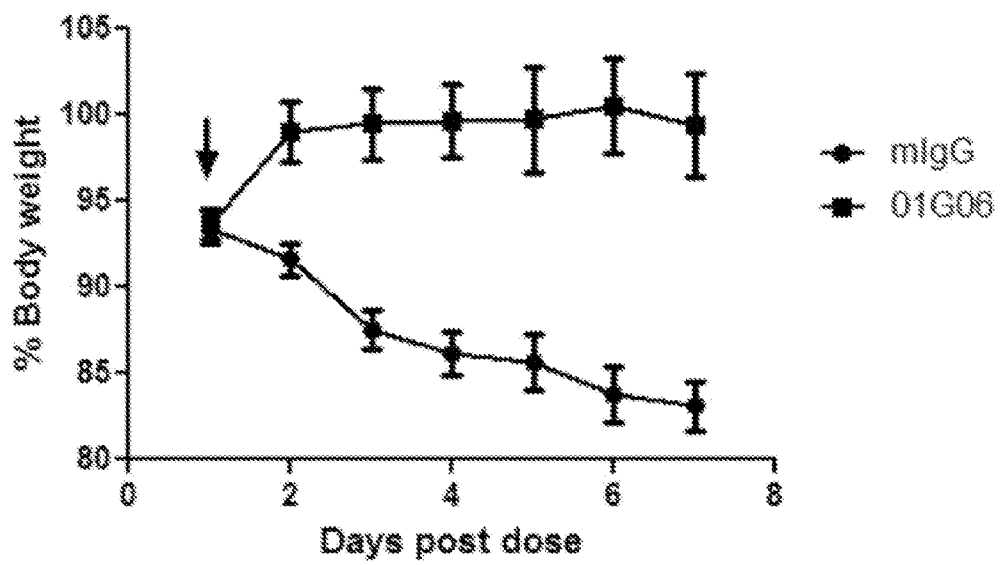
FIGS. 16A-16E are graphs summarizing results from an experiment to demonstrate anti-cachectic activity of anti-GDF15 antibody 01G06 (■), dosed at 10 mg/kg, in immune-incompetent mice (ICR-SCID) bearing an HT-1080 fibrosarcoma tumor xenograft model. Treatment with antibody 01G06 reversed body weight loss (FIG. 16A); induced a significant increase in food consumption for up to three days post dose (FIG. 16B); induced a gain of gonadal fat mass (FIG. 16C); induced a gain of muscle mass of gastrocnemius muscle (FIG. 16D); and decreased mRNA expression of muscle degradation molecular markers (mMuRF1 and mAtrogin (FIG. 16E)) compared to negative control (murine IgG (●)).

Additional studies were conducted with antibody 01G06 to demonstrate the reversal of cachexia in this mouse model. HT-1080 cells were grown and inoculated subcutaneously into the flank of 8-week old female ICR SCID mice as described above. When body weight reached 93%, the mice were randomized into two groups of ten mice each. Each group received one of the following treatments: murine IgG control or 01G06 at 10 mg/kg. Treatment was administered once by intra-peritoneal injection. As shown in FIG. 16A, treatment with antibody 01G06 resulted in body weight increase to initial weight or 100% (p<0.001) (FIG. 16A).

Figure 16B:
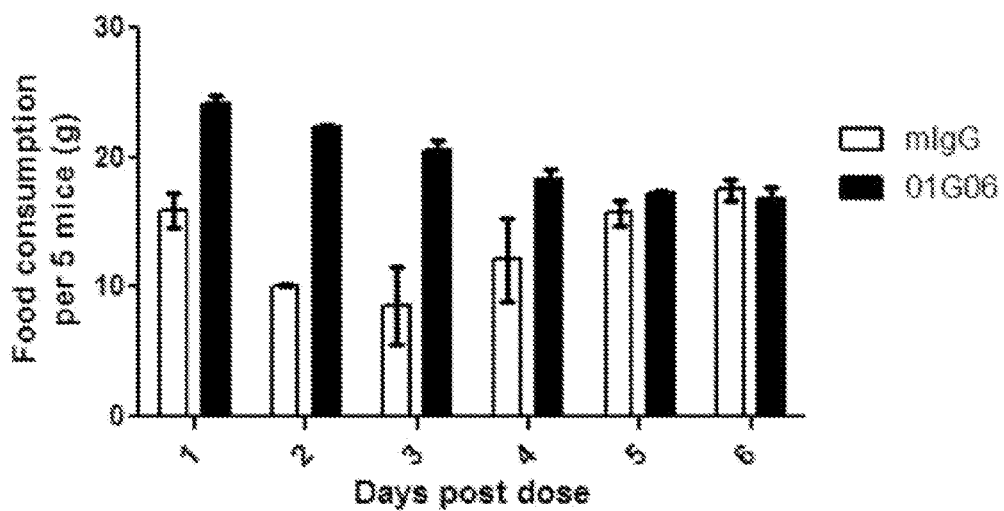

Food consumption was determined by weighing the food supply given to the mice daily (FIG. 16B). A significant increase in food consumption was observed in the 01G06 treated group for the first three days post treatment. After that time, no significant change was observed compared to the control group (mIgG).

Water consumption was determined by weighing the water supply given to the mice daily. No significant change in water consumption was observed between groups.

In this experiment, a group of ten mice were sacrificed at the time of the dose (baseline or 93% body weight, without treatment) and at the end of study (seven days post dose, either mIgG or 01G06). Gonadal fat and the gastrocnemius muscles were removed surgically and weighed as described above in Example 4 and tissues were snap frozen in liquid nitrogen. RNA was isolated from the gastrocnemius muscle samples to determine the levels of mMuRF1 and mAtrogin mRNA by RT-PCR, as described in Example 4.

Figure 16C:
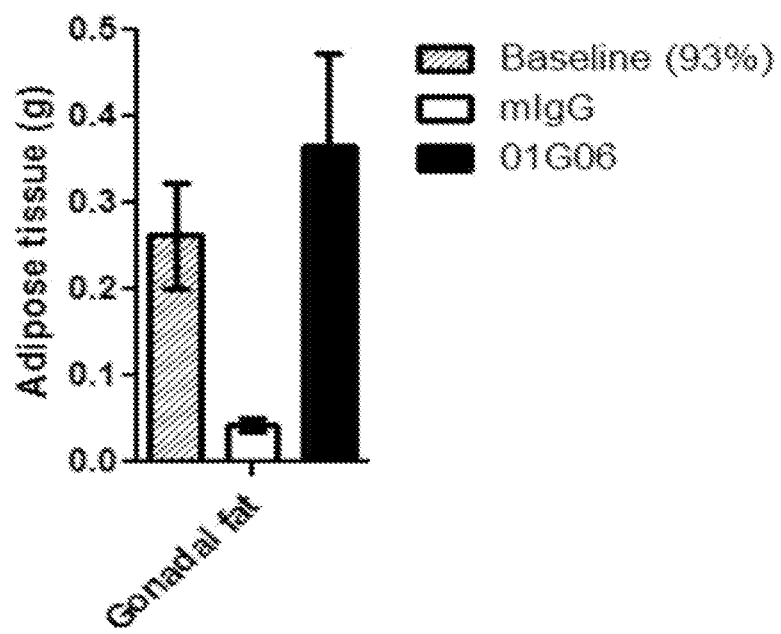
Figure 16D:
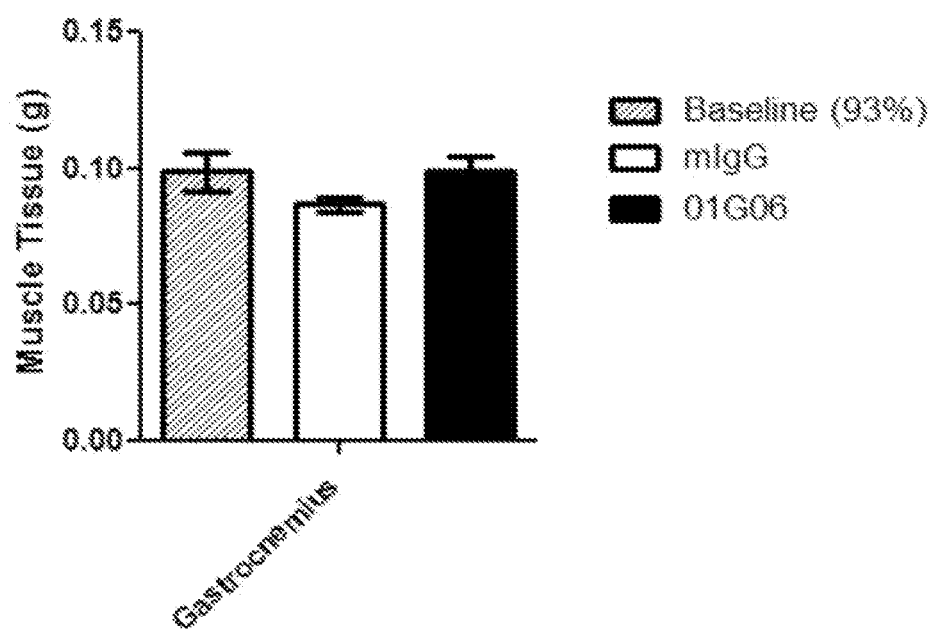
Figure 16E:
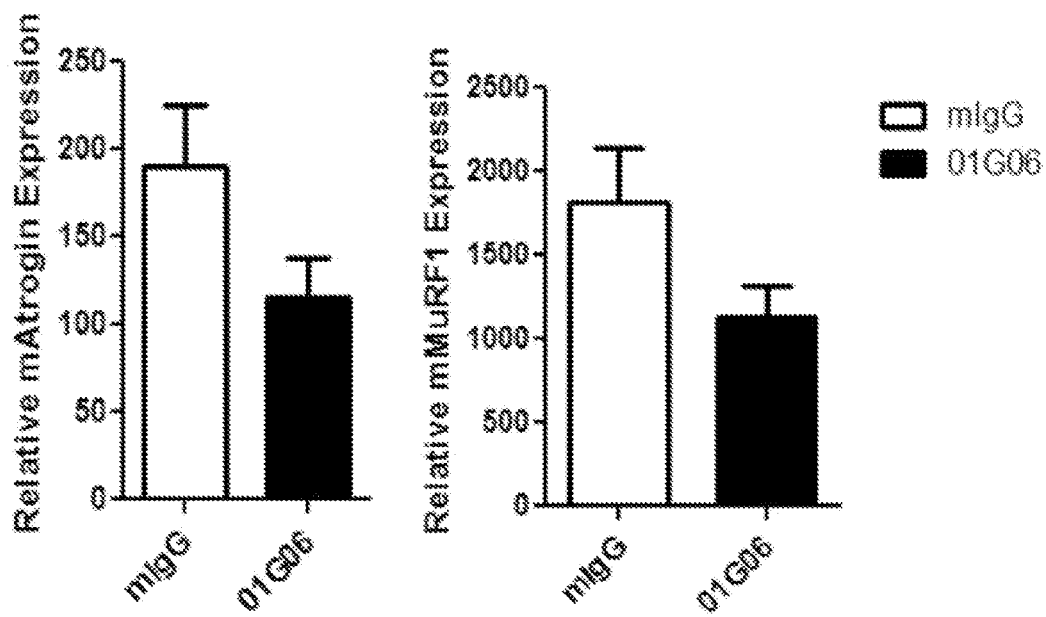

As shown in FIG. 16C, a significant reduction in gonadal fat mass was observed seven days post dose with mIgG, but not in the group treated with antibody 01G06. In addition, mice treated with mIgG displayed significant gastrocnemius muscle loss compared to the baseline group, while the group of mice treated with antibody 01G06 did not (FIG. 16D). Further, the levels of muscular degradation markers, mMuRF1 and mAtrogin, were significantly higher in the mIgG group compared to the 01G06 group (FIG. 16E).

These results indicate that the disclosed anti-GDF15 antibodies can reverse cachexia measured by the loss of muscle mass, the loss of fat and involuntary weight loss in an HT-1080 xenograft tumor model.

Example 11

Reversal of Cachexia in an HT-1080 Xenograft Tumor Model

This Example demonstrates the reversal of cachexia (as indicated by body weight loss) by antibody 01G06 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. Body weight was measured daily. When body weight reached 80%, the mice were randomized into two groups of five mice each. Each group received one of the following treatments: murine IgG control, 01G06 dosed at 2 mg/kg on day 1 and day 7. Treatment was administered by intra-peritoneal injection. Treatment with antibody 01G06 resulted in body weight increase relative to initial weight or about 100% (p<0.001) (FIG. 17A and Table 12).

TABLE 12

| | Treatment | | % Body | ANOVA Analysis |
|---|---|---|---|---|
| Gr. | Agent | mg/kg | weight | (compared to mIgG) |
| 1 | mIgG | 2 | 66.4 | NA |
| 2 | 01G06 | 2 | 97.16 | p < 0.001 |

Figure 17A:
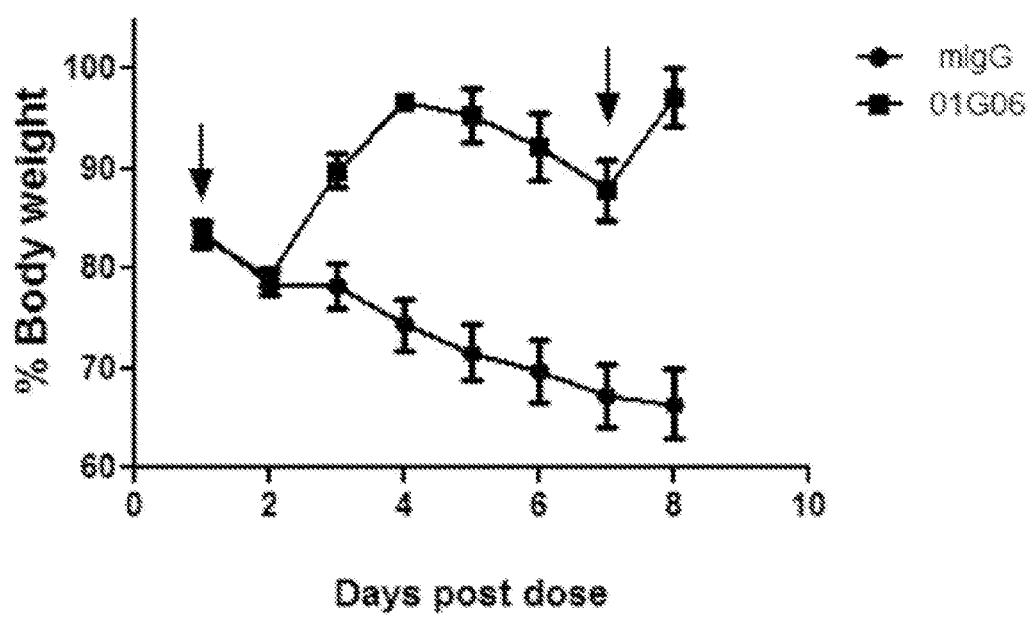
FIGS. 17A-17B are graphs summarizing results from an experiment to demonstrate anti-cachectic activity of anti-GDF15 antibody 01G06 (■), dosed at 2 mg/kg, in immune-incompetent mice (ICR-SCID) bearing an HT-1080 fibrosarcoma tumor xenograft model. Treatment with antibody 01G06 reversed body weight loss compared to murine IgG (●) (FIG. 17A); and induced a gain of organ mass (liver, heart, spleen, kidney) and induced a gain of tissue mass (gonadal and gastrocnemius) (FIG. 17B) compared to negative control (murine IgG) and baseline (day 1). The arrows in FIG. 17A indicate intra-peritoneal injection of antibody.
Figure 17B:
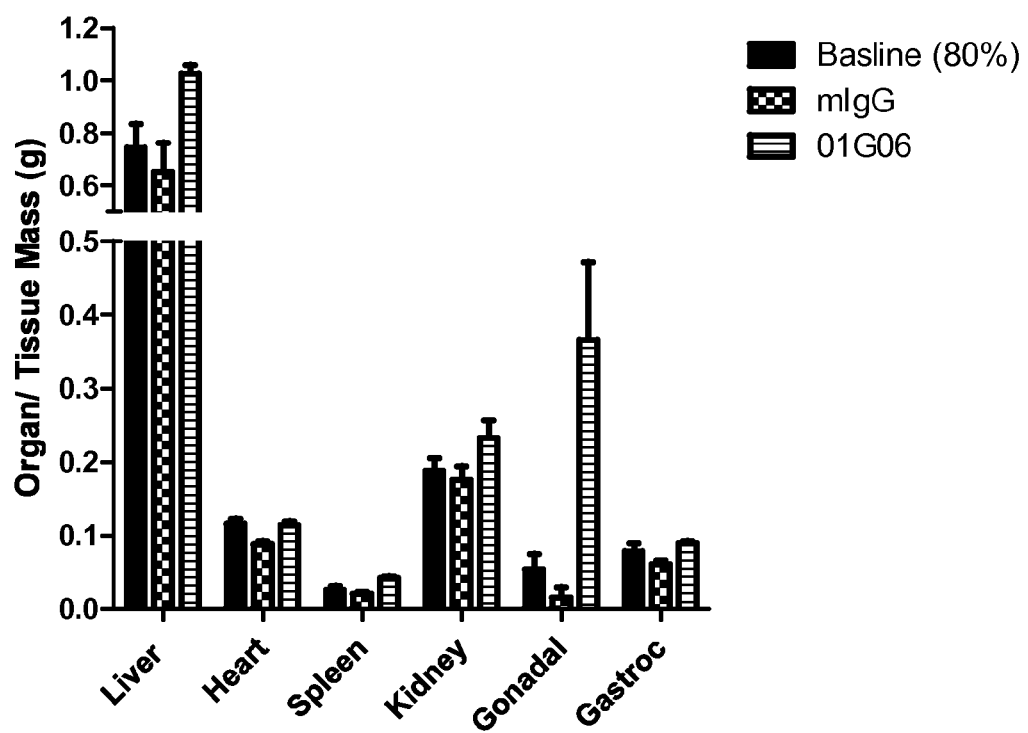

The data in FIGS. 17A-B and Table 12 indicate that the disclosed anti-GDF15 antibodies can reverse cachexia in an HT-1080 fibrosarcoma xenograft model.

In this experiment, a group of five mice were sacrificed at the time of dosing (baseline or 80% body weight loss, without treatment) and at the end of study (seven days post dose, either mIgG or 01G06). Liver, heart, spleen, kidney, gonadal fat and the gastrocnemius muscles were removed surgically and weighed. As shown in FIG. 17B, a significant loss in liver, heart, spleen, kidney, gonadal fat and gastrocnemius muscle mass was observed seven days post dose with mIgG, but not in the group treated with antibody 01G06. In addition, mice treated with antibody 01G06 displayed significant liver and gonadal muscle gain compared to the baseline group (FIG. 17B).

These results indicate that the disclosed anti-GDF15 antibodies can reverse cachexia measured by the loss of key organ mass, loss of muscle mass, loss of fat and involuntary weight loss in an HT-1080 xenograft tumor model.

Example 12

Reversal of Cachexia in a K-562 Xenograft Tumor Model

This Example demonstrates the reversal of cachexia (as indicated by body weight loss) by antibody 01G06, 03G05, 04F08, 06C11, 08G01, 14F11 or 17B11 in a K-562 leukemia xenograft model. K-562 cells were grown in culture at 37° C. in an atmosphere containing 5% $CO_2$, using Iscove's Modified Dulbecco's Medium (ATCC Catalog No. 30-2005) containing 10% FBS. Cells were inoculated subcutaneously into the flank of 8-week old female CB17SCRFMF mice with $2.5 \times 10^6$ cells per mouse in 50% matrigel. Body weight was measured daily. When body weight reached 93%, the mice were randomly distributed into eight groups of ten mice each. Each group received one of the following treatments: murine IgG control, 01G06, 03G05, 04F08, 06C11, 08G01, 14F11 or 17B11 at 10 mg/kg. Treatment was administered every three days by intra-peritoneal injection. Treatment with antibody 01G06, 03G05, 04F08, 06C11, 08G01, 14F11 or 17B11 resulted in body weight increase relative to initial weight or about 100% (p<0.001) (FIG. 18 and Table 13).

TABLE 13

| | Treatment | | % Body | ANOVA Analysis |
|---|---|---|---|---|
| Gr. | Agent | mg/kg | weight | (compared to mIgG) |
| 1 | mIgG | 10 | 90.4 | NA |
| 2 | 01G06 | 10 | 106.5 | p < 0.001 |
| 3 | 03G05 | 10 | 109.8 | p < 0.001 |
| 4 | 04F08 | 10 | 108.9 | p < 0.001 |
| 5 | 06C11 | 10 | 109.5 | p < 0.001 |
| 6 | 08G01 | 10 | 107.2 | p < 0.001 |
| 7 | 14F11 | 10 | 107.0 | p < 0.001 |
| 8 | 17B11 | 10 | 105.3 | p < 0.001 |

Figure 18:
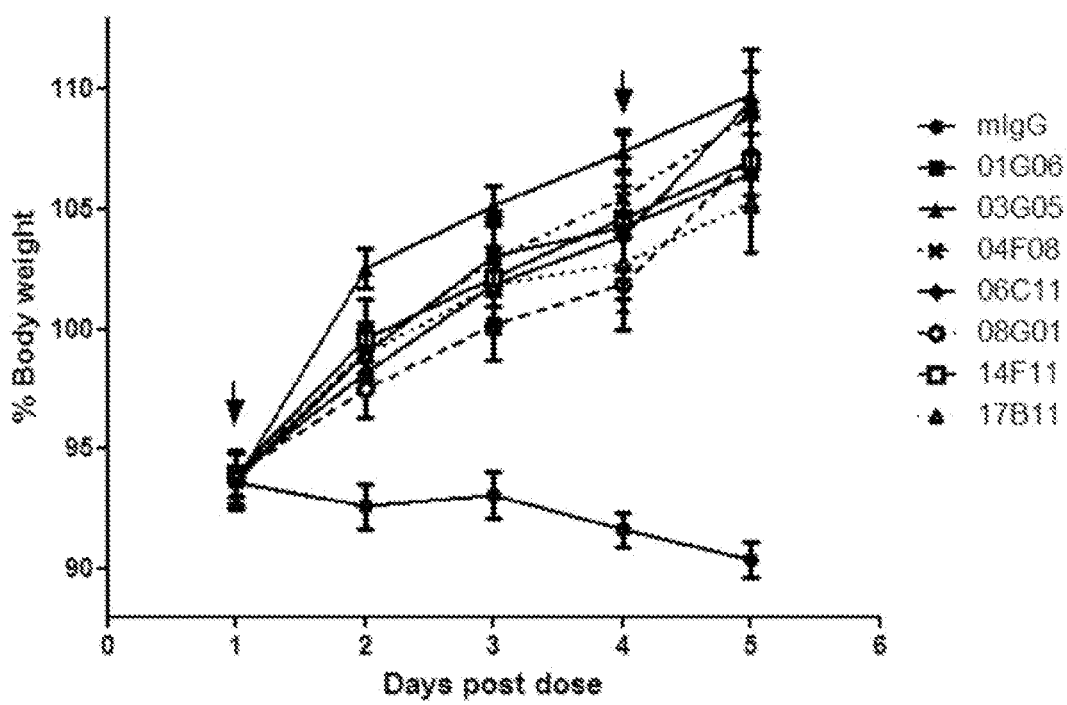
FIG. 18 is a graph summarizing results from an experiment to measure cachectic inhibitory activity of anti-GDF15 antibodies 01G06 (■), 03G05 (▲), 04F08 (X), 06C11 (◆), 08G01 (○), 14F11 (□), and 17B11 (Δ), and a murine IgG control (●) dosed at 10 mg/kg in a K-562 leukemia tumor xenograft model in immune-incompetent (CB17SCRFMF) mice. The arrows indicate intra-peritoneal injection of antibody.

The data in FIG. 18 and Table 13 indicate that the disclosed anti-GDF15 antibodies can reverse cachexia in a K-562 xenograft tumor model.

Example 13

Additional Xenograft Tumor Models

Antibody 01G06 was tested in additional tumor xenograft models including the TOV-21G ovarian xenograft model and the LS1034 colon xenograft model. In each model, antibody 01G06 reversed body weight loss compared to a PBS control (p<0.001 for the TOV-21G model and p<0.01 for the LS1034 model).

Example 14

Humanization of Anti-GDF15 Antibodies

This Example describes the humanization and chimerization of three murine antibodies, designated 01G06, 06C11, and 14F11, and the characterization of the resulting humanized antibodies. The humanized anti-GDF15 antibodies were designed, affinity matured by targeted CDR mutagenesis, and optimized using methods known in the art. The amino acid sequences were converted to codon-optimized DNA sequences and synthesized to include (in the following order): 5' HindIII restriction site, Kozak consensus sequence, amino terminal signal sequence, humanized variable region, human IgG1 or Kappa constant region, stop codon, and a 3' EcoRI restriction site.

Chimeric (murine variable region and human constant region) 01G06, 06C11, and 14F11 heavy (human IgG1) and light (human Kappa) chains were also constructed. To generate chimeric antibodies, the murine variable regions were fused to the human constant region, and codon-optimized DNA sequences were synthesized, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza, Basel, Switzerland) via HindIII and EcoRI sites using In-Fusion™ PCR cloning (Clontech, Mountain View, Calif.). The humanized and chimeric Kappa light chains were subcloned into pEE14.4 (Lonza) via HindIII and EcoRI sites using In-Fusion™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human GDF15 was measured as described below. The results are summarized in Tables 24-27.

Each of the possible combinations of the chimeric or humanized 01G06 immunoglobulin heavy chain and immunoglobulin light chain variable regions is set forth below in Table 14.

TABLE 14

| Antibody Name | Light Chain Variable Region | Heavy Chain Variable Region |
|---|---|---|
| Hu01G06-1 | Ch01G06 Chimeric Kappa (SEQ ID NO: 76) | Ch01G06 Chimeric Heavy (SEQ ID NO: 40) |
| Hu01G06-14 | Ch01G06 Chimeric Kappa (SEQ ID NO: 76) | Hu01G06 IGHV1-18 Heavy (SEQ ID NO: 54) |
| Hu01G06-15 | Ch01G06 Chimeric Kappa (SEQ ID NO: 76) | Hu01G06 IGHV1-69 Heavy (SEQ ID NO: 56) |
| Hu01G06-147 | Ch01G06 Chimeric Kappa (SEQ ID NO: 76) | Sh01G06 IGHV1-18 M69L Heavy (SEQ ID NO: 58) |
| Hu01G06-148 | Ch01G06 Chimeric Kappa (SEQ ID NO: 76) | Sh01G06 IGHV1-18 M69L K64Q G44S Heavy (SEQ ID NO: 60) |
| Hu01G06-149 | Ch01G06 Chimeric Kappa (SEQ ID NO: 76) | Sh01G06 IGHV1-18 M69L K64Q Heavy (SEQ ID NO: 62) |
| Hu01G06-150 | Ch01G06 Chimeric Kappa (SEQ ID NO: 76) | Sh01G06 IGHV1-69 T30S I69L Heavy (SEQ ID NO: 64) |
| Hu01G06-151 | Ch01G06 Chimeric Kappa (SEQ ID NO: 76) | Sh01G06 IGHV1-69 T30S K64Q I69L Heavy (SEQ ID NO: 66) |
| Hu01G06-4 | Hu01G06 IGKV1-39 Kappa (SEQ ID NO: 90) | Ch01G06 Chimeric Heavy (SEQ ID NO: 40) |
| Hu01G06-46 | Hu01G06 IGKV1-39 Kappa (SEQ ID NO: 90) | Hu01G06 IGHV1-18 Heavy (SEQ ID NO: 54) |
| Hu01G06-52 | Hu01G06 IGKV1-39 Kappa (SEQ ID NO: 90) | Hu01G06 IGHV1-69 Heavy (SEQ ID NO: 56) |
| Hu01G06-100 | Hu01G06 IGKV1-39 Kappa (SEQ ID NO: 90) | Sh01G06 IGHV1-18 M69L Heavy (SEQ ID NO: 58) |
| Hu01G06-102 | Hu01G06 IGKV1-39 Kappa (SEQ ID NO: 90) | Sh01G06 IGHV1-18 M69L K64Q G44S Heavy (SEQ ID NO: 60) |
| Hu01G06-101 | Hu01G06 IGKV1-39 Kappa (SEQ ID NO: 90) | Sh01G06 IGHV1-18 M69L K64Q Heavy (SEQ ID NO: 62) |
| Hu01G06-103 | Hu01G06 IGKV1-39 Kappa (SEQ ID NO: 90) | Sh01G06 IGHV1-69 T30S I69L Heavy (SEQ ID NO: 64) |
| Hu01G06-104 | Hu01G06 IGKV1-39 Kappa (SEQ ID NO: 90) | Sh01G06 IGHV1-69 T30S K64Q I69L Heavy (SEQ ID NO: 66) |
| Hu01G06-152 | Hu01G06 IGKV1-39 S43A V48I Kappa (SEQ ID NO: 92) | Ch01G06 Chimeric Heavy (SEQ ID NO: 40) |
| Hu01G06-71 | Hu01G06 IGKV1-39 S43A V48I Kappa (SEQ ID NO: 92) | Hu01G06 IGHV1-18 Heavy (SEQ ID NO: 54) |
| Hu01G06-77 | Hu01G06 IGKV1-39 S43A V48I Kappa (SEQ ID NO: 92) | Hu01G06 IGHV1-69 Heavy (SEQ ID NO: 56) |
| Hu01G06-110 | Hu01G06 IGKV1-39 S43A V48I Kappa (SEQ ID NO: 92) | Sh01G06 IGHV1-18 M69L Heavy (SEQ ID NO: 58) |
| Hu01G06-112 | Hu01G06 IGKV1-39 S43A V48I Kappa (SEQ ID NO: 92) | Sh01G06 IGHV1-18 M69L K64Q G44S Heavy (SEQ ID NO: 60) |
| Hu01G06-111 | Hu01G06 IGKV1-39 S43A V48I Kappa (SEQ ID NO: 92) | Sh01G06 IGHV1-18 M69L K64Q Heavy (SEQ ID NO: 62) |
| Hu01G06-113 | Hu01G06 IGKV1-39 S43A V48I Kappa(SEQ ID NO: 92) | Sh01G06 IGHV1-69 T30S I69L Heavy (SEQ ID NO: 64) |
| Hu01G06-114 | Hu01G06 IGKV1-39 S43A V48I Kappa (SEQ ID NO: 92) | Sh01G06 IGHV1-69 T30S K64Q I69L Heavy (SEQ ID NO: 66) |
| Hu01G06-122 | Hu01G06 IGKV1-39 S43A V48I Kappa(SEQ ID NO: 92) | Hu01G06 IGHV1-18 F1 Heavy (SEQ ID NO: 246) |
| Hu01G06-119 | Hu01G06 IGKV1-39 S43A V48I Kappa(SEQ ID NO: 92) | Hu01G06 IGHV1-18 F2 Heavy (SEQ ID NO: 248) |
| Hu01G06-135 | Hu01G06 IGKV1-39 S43A V48I Kappa(SEQ ID NO: 92) | Hu01G06 IGHV1-69 F1 Heavy (SEQ ID NO: 250) |
| Hu01G06-138 | Hu01G06 IGKV1-39 S43A V48I Kappa(SEQ ID NO: 92) | Hu01G06 IGHV1-69 F2 Heavy (SEQ ID NO: 252) |
| Hu01G06-153 | Hu01G06 IGKV1-39 V48I Kappa (SEQ ID NO: 94) | Ch01G06 Chimeric Heavy (SEQ ID NO: 40) |

TABLE 14-continued

| Antibody Name | Light Chain Variable Region | Heavy Chain Variable Region |
| --- | --- | --- |
| Hu01G06-69 | Hu01G06 IGKV1-39 V48I Kappa (SEQ ID NO: 94) | Hu01G06 IGHV1-18 Heavy (SEQ ID NO: 54) |
| Hu01G06-75 | Hu01G06 IGKV1-39 V48I Kappa (SEQ ID NO: 94) | Hu01G06 IGHV1-69 Heavy (SEQ ID NO: 56) |
| Hu01G06-105 | Hu01G06 IGKV1-39 V48I Kappa (SEQ ID NO: 94) | Sh01G06 IGHV1-18 M69L Heavy (SEQ ID NO: 58) |
| Hu01G06-107 | Hu01G06 IGKV1-39 V48I Kappa (SEQ ID NO: 94) | Sh01G06 IGHV1-18 M69L K64Q G44S Heavy (SEQ ID NO: 60) |
| Hu01G06-106 | Hu01G06 IGKV1-39 V48I Kappa (SEQ ID NO: 94) | Sh01G06 IGHV1-18 M69L K64Q Heavy (SEQ ID NO: 62) |
| Hu01G06-108 | Hu01G06 IGKV1-39 V48I Kappa (SEQ ID NO: 94) | Sh01G06 IGHV1-69 T30S I69L Heavy (SEQ ID NO: 64) |
| Hu01G06-109 | Hu01G06 IGKV1-39 V48I Kappa (SEQ ID NO: 94) | Sh01G06 IGHV1-69 T30S K64Q I69L Heavy (SEQ ID NO: 66) |
| Hu01G06-154 | Hu01G06 IGKV1-39 F2 Kappa (SEQ ID NO: 254) | Ch01G06 Chimeric Heavy (SEQ ID NO: 40) |
| Hu01G06-155 | Hu01G06 IGKV1-39 F2 Kappa (SEQ ID NO: 254) | Hu01G06 IGHV1-18 Heavy (SEQ ID NO: 54) |
| Hu01G06-156 | Hu01G06 IGKV1-39 F2 Kappa (SEQ ID NO: 254) | Hu01G06 IGHV1-69 Heavy (SEQ ID NO: 56) |
| Hu01G06-157 | Hu01G06 IGKV1-39 F2 Kappa (SEQ ID NO: 254) | Sh01G06 IGHV1-18 M69L Heavy (SEQ ID NO: 58) |
| Hu01G06-158 | Hu01G06 IGKV1-39 F2 Kappa (SEQ ID NO: 254) | Sh01G06 IGHV1-18 M69L K64Q G44S Heavy (SEQ ID NO: 60) |
| Hu01G06-159 | Hu01G06 IGKV1-39 F2 Kappa (SEQ ID NO: 254) | Sh01G06 IGHV1-18 M69L K64Q Heavy (SEQ ID NO: 62) |
| Hu01G06-160 | Hu01G06 IGKV1-39 F2 Kappa (SEQ ID NO: 254) | Sh01G06 IGHV1-69 T30S I69L Heavy (SEQ ID NO: 64) |
| Hu01G06-161 | Hu01G06 IGKV1-39 F2 Kappa (SEQ ID NO: 254) | Sh01G06 IGHV1-69 T30S K64Q I69L Heavy (SEQ ID NO: 66) |
| Hu01G06-130 | Hu01G06 IGKV1-39 F2 Kappa (SEQ ID NO: 254) | Hu01G06 IGHV1-18 F1 Heavy (SEQ ID NO: 246) |
| Hu01G06-127 | Hu01G06 IGKV1-39 F2 Kappa (SEQ ID NO: 254) | Hu01G06 IGHV1-18 F2 Heavy (SEQ ID NO: 248) |
| Hu01G06-143 | Hu01G06 IGKV1-39 F2 Kappa (SEQ ID NO: 254) | Hu01G06 IGHV1-69 F1 Heavy (SEQ ID NO: 250) |
| Hu01G06-146 | Hu01G06 IGKV1-39 F2 Kappa (SEQ ID NO: 254) | Hu01G06 IGHV1-69 F2 Heavy (SEQ ID NO: 252) |

Each of the possible combinations of the chimeric or humanized 06C11 immunoglobulin heavy chain and immunoglobulin light chain variable regions is set forth below in Table 15.

TABLE 15

| Antibody Name | Light Chain Variable Region | Heavy Chain Variable Region |
| --- | --- | --- |
| Hu06C11-1 | Ch06C11 Chimeric Kappa (SEQ ID NO: 82) | Ch06C11 Chimeric Heavy (SEQ ID NO: 46) |
| Hu06C11-7 | Ch06C11 Chimeric Kappa (SEQ ID NO: 82) | HE LM 06C11 IGHV2-70 Heavy (SEQ ID NO: 68) |
| Hu06C11-10 | Ch06C11 Chimeric Kappa (SEQ ID NO: 82) | Hu06C11 IGHV2-5 Heavy (SEQ ID NO: 70) |
| Hu06C11-12 | Sh06C11 IGKV1-16 Kappa (SEQ ID NO: 96) | Ch06C11 Chimeric Heavy (SEQ ID NO: 46) |
| Hu06C11-27 | Sh06C11 IGKV1-16 Kappa (SEQ ID NO: 96) | HE LM 06C11 IGHV2-70 Heavy (SEQ ID NO: 68) |
| Hu06C11-30 | Sh06C11 IGKV1-16 Kappa (SEQ ID NO: 96) | Hu06C11 IGHV2-5 Heavy (SEQ ID NO: 70) |

Each of the possible combinations of the chimeric or humanized 14F11 immunoglobulin heavy chain and immunoglobulin light chain variable regions is set forth below in Table 16.

TABLE 16

| Antibody Name | Light Chain Variable Region | Heavy Chain Variable Region |
| --- | --- | --- |
| Hu14F11-1 | Ch14F11 Chimeric Kappa (SEQ ID NO: 86) | Ch14F11 Chimeric Heavy (SEQ ID NO: 50) |
| Hu14F11-14 | Ch14F11 Chimeric Kappa (SEQ ID NO: 86) | Sh14F11 IGHV2-5 Heavy (SEQ ID NO: 72) |
| Hu14F11-15 | Ch14F11 Chimeric Kappa (SEQ ID NO: 86) | Sh14F11 IGHV2-70 Heavy (SEQ ID NO: 74) |
| Hu14F11-11 | Hu14F11 IGKV1-16 Kappa (SEQ ID NO: 98) | Ch14F11 Chimeric Heavy (SEQ ID NO: 50) |
| Hu14F11-39 | Hu14F11 IGKV1-16 Kappa (SEQ ID NO: 98) | Sh14F11 IGHV2-5 Heavy (SEQ ID NO: 72) |
| Hu14F11-47 | Hu14F11 IGKV1-16 Kappa (SEQ ID NO: 98) | Sh14F11 IGHV2-70 Heavy (SEQ ID NO: 74) |

Each of the possible combinations of the chimeric 04F08, 06C11, and 14F11 immunoglobulin heavy chain and immunoglobulin light chain variable regions is set forth below in Table 17.

TABLE 17

| Light Chain Variable Region | Heavy Chain Variable Region |
| --- | --- |
| 04F08 Chimeric Kappa (SEQ ID NO: 80) | Ch06C11 Chimeric Heavy (SEQ ID NO: 46) |
| 04F08 Chimeric Kappa (SEQ ID NO: 80) | Ch14F11 Chimeric Heavy (SEQ ID NO: 50) |
| Ch06C11 Chimeric Kappa (SEQ ID NO: 82) | 04F08 Chimeric Heavy (SEQ ID NO: 44) |

TABLE 17-continued

| Light Chain Variable Region | Heavy Chain Variable Region |
|---|---|
| Ch06C11 Chimeric Kappa (SEQ ID NO: 82) | Ch14F11 Chimeric Heavy (SEQ ID NO: 50) |
| Ch14F11 Chimeric Kappa (SEQ ID NO: 86) | 04F08 Chimeric Heavy (SEQ ID NO: 44) |
| Ch14F11 Chimeric Kappa (SEQ ID NO: 86) | Ch06C11 Chimeric Heavy (SEQ ID NO: 46) |

Each of the possible combinations of the chimeric 01G06 and chimeric 08G01 immunoglobulin heavy chain and immunoglobulin light chain variable regions is set forth below in Table 18.

TABLE 18

| Light Chain Variable Region | Heavy Chain Variable Region |
|---|---|
| Ch01G06 Chimeric Kappa (SEQ ID NO: 76) | 08G01 Chimeric Heavy (SEQ ID NO: 48) |
| 08G01 Chimeric Kappa (SEQ ID NO: 84) | Ch01G06 Chimeric Heavy (SEQ ID NO: 40) |

The nucleic acid sequences and the encoded protein sequences defining variable regions of the chimeric and humanized 01G06, 06C11, and 14F11 antibodies are summarized below (amino terminal signal peptide sequences are not shown). CDR sequences (Kabat definition) are shown in bold and are underlined in the amino acid sequences.

Nucleic Acid Sequence Encoding the Ch01G06 Chimeric Heavy Chain Variable Region (SEQ ID NO:127)

```
  1 gaagtgttgt tgcagcagtc agggccggag ttggtaaaac
    cgggagcgtc ggtgaaaatc 61 ccgtgcaaag cgtcggggta tacgtttacg gactataaca
    tggattgggt gaaacagtcg 121 catgggaaat cgcttgaatg gattggtcag atcaatccga
    ataatggagg aatcttcttt 181 aatcagaagt ttaaaggaaa agcgacgctt acagtcgata
    agtcgtcgaa cacggcgttc 241 atggaagtac ggtcgcttac gtcggaagat acggcggtct
    attactgtgc gagggaggcg 301 attacgacgg tgggagcgat ggactattgg ggacaaggga
    cgtcggtcac ggtatcgtcg
```

Protein Sequence Defining the Ch01G06 Chimeric Heavy Chain Variable Region (SEQ ID NO:40)

```
  1 evllqqsgpe lvkpgasvki pckasgytft dynmdwvkqs
    hgkslewigg inpnnggiff 61 nqkfkgkatl tvdkssntaf mevrsltsed tavyycarea
    ittvgamdyw gqgtsvtvss
```

Nucleic Acid Sequence Encoding the Hu01G06 IGHV1-18 Heavy Chain Variable Region (SEQ ID NO:53)

```
  1 caagtgcaac ttgtgcagtc gggtgcggaa gtcaaaaagc
    cgggagcgtc ggtgaaagta 61 tcgtgtaaag cgtcggggta tacgtttacg gactataaca
    tggactgggt acgacaggca 121 ccggggaaat cgttggaatg gatcggacag attaatccga
    acaatggggg aattttcttt 181 aatcagaaat tcaaaggacg ggcgacgttg acggtcgata
    catcgacgaa tacggcgtat 241 atggaattga ggtcgcttcg ctcggacgat acggcggtct
    attactgcgc cagggaggcg 301 atcacgacgg tagggcgat ggattattgg ggacagggga
    cgcttgtgac ggtatcgtcg
```

Protein Sequence Defining the Hu01G06 IGHV1-18 Heavy Chain Variable Region (SEQ ID NO:54)

```
  1 qvqlvqsgae vkkpgasvkv sckasgytft dynmdwvrqa
    pgkslewigg inpnnggiff 61 nqkfkgratl tvdtstntay melrslrsdd tavyycarea
    ittvgamdyw gqgtlvtvss
```

Nucleic Acid Sequence Encoding the Hu01G06 IGHV1-69 Heavy Chain Variable Region (SEQ ID NO:55)

```
  1 caagtccagc ttgtccagtc gggagcggaa gtgaagaaac
    cggggtcgtc ggtcaaagta 61 tcgtgtaaag cgtcgggata tacgtttacg gactataaca
    tggattgggt acgacaggct 121 ccgggaaaat cattggaatg gattggacag attaatccga
    ataatggggg tatcttcttt 181 aatcaaaagt ttaaaggag ggcgacgttg acggtggaca
    aatcgacaaa tacggcgtat 241 atggaattgt cgtcgcttcg gtcggaggac acggcggtgt
    attactgcgc gagggaggcg 301 atcacgacgg tcgggcgat ggattattgg ggacagggaa
    cgcttgtgac ggtatcgtcg
```

Protein Sequence Defining the Hu01G06 IGHV1-69 Heavy Chain Variable Region (SEQ ID NO:56)

```
  1 qvqlvqsgae vkkpgssvkv sckasgytft dynmdwvrqa
    pgkslewigg inpnnggiff 61 nqkfkgratl tvdkstntay melsslrsed tavyycarea
    ittvgamdyw gqgtlvtvss
```

Nucleic Acid Sequence Encoding the Sh01G06 IGHV1-18 M69L Heavy Chain Variable Region (SEQ ID NO:57)

```
  1 caggtccagc ttgtgcaatc gggagcggaa gtgaagaaac
    cgggagcgtc ggtaaaagtc 61 tcgtgcaaag cgtcggggta tacgtttacg gactataaca
    tggactgggt gcgccaagcg 121 cctggacagg gtcttgaatg gatgggcag attaatccga
    ataatggagg gatcttcttt 181 aatcagaaat tcaaaggaag ggtaacgctg acgacagaca
    cgtcaacatc gacggcctat 241 atggaattgc ggtcgttgcg atcagatgat acggcggtct
    actattgtgc gagggaggcg 301 attacgacgg tgggagcgat ggattattgg ggacagggga
    cgttggtaac ggtatcgtcg
```

Protein Sequence Defining the Sh01G06 IGHV1-18 M69L Heavy Chain Variable Region (SEQ ID NO:58)

```
  1 qvqlvqsgae vkkpgasvkv sckasgytft dynmdwvrqa
    pgqglewmgg inpnnggiff 61 nqkfkgrvtl ttdtststay melrslrsdd tavyycarea
    ittvgamdyw gqgtlvtvss
```

Nucleic Acid Sequence Encoding the Sh01G06 IGHV1-18 M69L K64Q G44S Heavy Chain Variable Region (SEQ ID NO:59)

```
  1 caggtccagc ttgtgcaatc gggagcggaa gtgaagaaac
    cgggagcgtc ggtaaaagtc 61 tcgtgcaaag cgtcgggta tacgtttacg gactataaca
    tggactgggt gcgccaagcg 121 cctggacaga gccttgaatg gatggggcag attaatccga
    ataatggagg gatcttcttt 181 aatcagaaat tccagggaag ggtaacgctg acgacagaca
    cgtcaacatc gacggcctat 241 atggaattgc ggtcgttgcg atcagatgat acggcggtct
    actattgtgc gagggaggcg 301 attacgacgg tgggagcgat ggattattgg gacagggga
    cgttggtaac ggtatcgtcg
```

Protein Sequence Defining the Sh01G06 IGHV1-18 M69L K64Q G44S Heavy Chain Variable Region (SEQ ID NO:60)

```
  1 qvqlvqsgae vkkpgasvkv sckasgytft dynmdwvrqa
    pgqslewmgg inpnnggiff 61 nqkfqgrvtl ttdtststay melrslrsdd tavyycarea
    ittvgamdyw gqgtlvtvss
```

Nucleic Acid Sequence Encoding the Sh01G06 IGHV1-18 M69L K64Q Heavy Chain Variable Region (SEQ ID NO:61)

```
  1 caggtccagc ttgtgcaatc gggagcggaa gtgaagaaac
    cgggagcgtc ggtaaaagtc 61 tcgtgcaaag cgtcgggta tacgtttacg gactataaca
    tggactgggt gcgccaagcg 121 cctggacagg tcttgaatg gatggggcag attaatccga
    ataatggagg gatcttcttt 181 aatcagaaat tccagggaag ggtaacgctg acgacagaca
    cgtcaacatc gacggcctat 241 atggaattgc ggtcgttgcg atcagatgat acggcggtct
    actattgtgc gagggaggcg 301 attacgacgg tgggagcgat ggattattgg gacagggga
    cgttggtaac ggtatcgtcg
```

Protein Sequence Defining the Sh01G06 IGHV1-18 M69L K64Q Heavy Chain Variable Region (SEQ ID NO:62)

```
  1 qvqlvqsgae vkkpgasvkv sckasgytft dynmdwvrqa
    pgqglewmgg inpnnggiff 61 nqkfqgrvtl ttdtststay melrslrsdd tavyycarea
    ittvgamdyw gqgtlvtvss
```

Nucleic Acid Sequence Encoding the Sh01G06 IGHV1-69 T30S I69L Heavy Chain Variable Region (SEQ ID NO:63)

```
  1 caagtacagc ttgtacagtc gggagcggaa gtcaagaaac
    cgggatcgtc ggtcaaagtg 61 tcgtgtaaag cgtcgggata tacgtttagc gactataaca
    tggattgggt gcgacaagcg 121 cctgggcagg gacttgaatg gatgggtcag atcaatccga
    ataatggggg aatctttttc 181 aatcagaagt ttaaagggag ggtaacgctg acggcggata
    aaagcacgtc aacggcgtat 241 atggagttgt cgtcgttgcg gtcggaggac acggcggtct
    attactgcgc gagggaagcg 301 attacgacgg tgggagcgat ggattattgg gggcagggaa
    cgcttgtaac ggtgtcatcg
```

Protein Sequence Defining the Sh01G06 IGHV1-69 T30S I69L Heavy Chain Variable Region (SEQ ID NO:64)

```
  1 qvqlvqsgae vkkpgssvkv sckasgytfs dynmdwvrqa
    pgqglewmgq inpnnggiff 61 nqkfkgrvtl tadkststay melsslrsed tavyycarea
    ittvgamdyw gqgtlvtvss
```

Nucleic Acid Sequence Encoding the Sh01G06 IGHV1-69 T30S K64Q I69L Heavy Chain Variable Region (SEQ ID NO:65)

```
  1 caagtacagc ttgtacagtc gggagcggaa gtcaagaaac
    cgggatcgtc ggtcaaagtg 61 tcgtgtaaag cgtcgggata tacgtttagc gactataaca
    tggattgggt gcgacaagcg 121 cctgggcagg gacttgaatg gatgggtcag atcaatccga
    ataatggggg aatctttttc 181 aatcagaagt tcaggggag ggtaacgctg acggcggata
    aaagcacgtc aacggcgtat 241 atggagttgt cgtcgttgcg gtcggaggac acggcggtct
    attactgcgc gagggaagcg 301 attacgacgg tgggagcgat ggattattgg gggcagggaa
    cgcttgtaac ggtgtcatcg
```

Protein Sequence Defining the Sh01G06 IGHV1-69 T30S K64Q I69L Heavy Chain Variable Region (SEQ ID NO:66)

```
  1 qvqlvqsgae vkkpgssvkv sckasgytfs dynmdwvrqa
    pgqglewmgq inpnnggiff 61 nqkfqgrvtl tadkststay melsslrsed tavyycarea
    ittvgamdyw gqgtlvtvss
```

Nucleic Acid Sequence Encoding the Hu01G06 IGHV1-18 F1 Heavy Chain Variable Region (SEQ ID NO:245)

```
  1 caggtccagc ttgtgcaatc gggagcggaa gtgaagaaac
    cgggagcgtc ggtaaaagtc 61 tcgtgcaaag cgtcgggta tacgtttacg gactataaca
    tggactgggt gcgccaagcg 121 cctggacaga gccttgaatg gatggggcag attaatccgt
    acaatcacct gatcttcttt 181 aatcagaaat tccagggaag ggtaacgctg acgacagaca
    cgtcaacatc gacggcctat 241 atggaattgc ggtcgttgcg atcagatgat acggcggtct
    actattgtgc gagggaggcg
```

```
301 attacgacgg tgggagcgat ggattattgg ggacagggga
    cgttggtaac ggtatcgtcg
```

Protein Sequence Defining the Hu01G06 IGHV1-18 F1 Heavy Chain Variable Region (SEQ ID NO:246)

```
  1 qvqlvqsgae vkkpgasvkv sckasgytft dynmdwvrqa
    pgqslewmgq inpynhliff
 61 nqkfqgrvtl ttdtststay melrslrsdd tavyycarea
    ittvgamdyw gqgtlvtvss
```

Nucleic Acid Sequence Encoding the Hu01G06 IGHV1-18 F2 Heavy Chain Variable Region (SEQ ID NO:247)

```
  1 caggtccagc ttgtgcaatc gggagcggaa gtgaagaaac
    cgggagcgtc ggtaaaagtc
 61 tcgtgcaaag cgtcggggta tacgtttacg gactataaca
    tggactgggt gcgccaagcg
121 cctggacaga gccttgaatg gatggggcag attaatccga
    ataatggact gatcttcttt
181 aatcagaaat tccagggaag ggtaacgctg acgacagaca
    cgtcaacatc gacggcctat
241 atggaattgc ggtcgttgcg atcagatgat acggcggtct
    actattgtgc gagggaggcg
301 attacgacgg tgggagcgat ggattattgg ggacagggga
    cgttggtaac ggtatcgtcg
```

Protein Sequence Defining the Hu01G06 IGHV1-18 F2 Heavy Chain Variable Region (SEQ ID NO:248)

```
  1 qvglvqsgae vkkpgasvkv sckasgytft dynmdwvrqa
    pgqslewmgq inpnngliff
 61 nqkfqgrvtl ttdtststay melrslrsdd tavyycarea
    ittvgamdyw gqgtlvtvss
```

Nucleic Acid Sequence Encoding the Hu01G06 IGHV1-69 F1 Heavy Chain Variable Region (SEQ ID NO:249)

```
  1 caagtacagc ttgtacagtc gggagcggaa gtcaagaaac
    cgggatcgtc ggtcaaagtg
 61 tcgtgtaaag cgtcgggata tacgtttagc gactataaca
    tggattgggt gcgacaagcg
121 cctgggcagg gacttgaatg gatgggtcag atcaatccga
    ataatgggct gatcttttc
181 aatcagaagt ttaaagggag ggtaacgctg acggcggata
    aaagcacgtc aacggcgtat
241 atggagttgt cgtcgttgcg gtcggaggac acggcggtct
    attactgcgc gagggaagcg
301 attacgacgg tgggagcgat ggattattgg gggcagggaa
    cgcttgtaac ggtgtcatcg
```

Protein Sequence Defining the Hu01G06 IGHV1-69 F1 Heavy Chain Variable Region (SEQ ID NO:250)

```
  1 qvqlvqsgae vkkpgssvkv sckasgytfs dynmdwvrqa
    pgqglewmgq inpnngliff
 61 nqkfkgrvtl tadkststay melsslrsed tavyycarea
    ittvgamdyw gqgtlvtvss
```

Nucleic Acid Sequence Encoding the Hu01G06 IGHV1-69 F2 Heavy Chain Variable Region (SEQ ID NO:251)

```
  1 caagtacagc ttgtacagtc gggagcggaa gtcaagaaac
    cgggatcgtc ggtcaaagtg
 61 tcgtgtaaag cgtcgggata tacgtttagc gactataaca
    tggattgggt gcgacaagcg
121 cctgggcagg gacttgaatg gatgggtcag atcaatccgt
    acaatcacct gatcttttc
181 aatcagaagt ttaaagggag ggtaacgctg acggcggata
    aaagcacgtc aacggcgtat
241 atggagttgt cgtcgttgcg gtcggaggac acggcggtct
    attactgcgc gagggaagcg
301 attacgacgg tgggagcgat ggattattgg gggcagggaa
    cgcttgtaac ggtgtcatcg
```

Protein Sequence Defining the Hu01G06 IGHV1-69 F2 Heavy Chain Variable Region (SEQ ID NO:252)

```
  1 qvqlvqsgae vkkpgssvkv sckasgytfs dynmdwvrqa
    pgqglewmgq inpynhliff
 61 nqkfkgrvtl tadkststay melsslrsed tavyycarea
    ittvgamdyw gqgtlvtvss
```

Nucleic Acid Sequence Encoding the Ch06C11 Chimeric Heavy Chain Variable Region (SEQ ID NO:129)

```
  1 caggtgacac tcaaagaatc aggacccgga atccttcagc
    ccagccagac cttgtcgctg
 61 acttgttcgt tctccggttt cagcctgaat acttatggga
    tgggtgtgtc atggatcagg
121 caaccgtccg ggaaaggatt ggagtggctc gcgcacatct
    actgggacga tgacaaacgc
181 tacaatcctt cgctgaagag ccgattgacg atttccaagg
    atgcctcgaa caaccgggta
241 tttcttaaga tcacgtcggt cgatacggca gacacggcga
    cctattactg cgcccaaaga
301 gggtacgatg actattgggg atattggggc caggggacac
    tcgtcacaat ttcagct
```

Protein Sequence Defining the Ch06C11 Chimeric Heavy Chain Variable Region (SEQ ID NO:46)

```
  1 qvtlkesgpg ilqpsqtlsl tcsfsgfsln tygmgvswir
    qpsgkglewl ahiywdddkr
 61 ynpslksrlt iskdasnnrv flkitsvdta dtatyycaqr
    gyddywgywg qgtlvtisa
```

Nucleic Acid Sequence Encoding the HE LM 06C11 IGHV2-70 Heavy Chain Variable Region (SEQ ID NO:67)

```
  1 caggtgactt tgaaagaatc cggtcccgca ttggtaaagc
    caacccagac acttacgctc
 61 acatgtacat tttccggatt cagcttgaac acttacggga
    tgggagtgtc gtggattcgg
121 caacctccgg ggaaggctct ggagtggctc gcgcacatct
    actgggatga tgacaaaagg
```

```
181 tataacccct cacttaaaac gagactgacg atctcgaagg
    acacaagcaa gaatcaggtc
241 gtcctcacga ttacgaatgt agacccggtg gatactgccg
    tctattactg cgcgcaacgc
301 gggtatgatg actactgggg atattggggt cagggcaccc
    tcgtgaccat ctcgtca
```

Protein Sequence Defining the HE LM 06C11 IGHV2-70 Heavy Chain Variable Region (SEQ ID NO:68)

```
  1 qvtlkesgpa lvkptqtltl tctfsgfsln tygmgvswir
    qppgkalewl ahiywdddkr
 61 ynpslktrlt iskdtsknqv vltitnvdpv dtavyycaqr
    gyddywgywg qgtivtiss
```

Nucleic Acid Sequence Encoding the Hu06C11 IGHV2-5 Heavy Chain Variable Region (SEQ ID NO:69)

```
  1 caagtaacgc tcaaggagtc cggacccacc ttggtgaagc
    cgacgcagac cttgactctt
 61 acgtgcactt tctcggggtt ttcactgaat acgtacggga
    tgggtgtctc atggatcagg
121 caacctccgg ggaaaggatt ggaatggctg gcgcacatct
    actgggatga cgataagaga
181 tataacccaa gcctcaagtc gcggctcacc attacaaaag
    atacatcgaa aaatcaggtc
241 gtacttacta tcacgaacat ggaccccgtg gacacagcaa
    catattactg tgcccagcgc
301 ggctatgacg attattgggg ttactgggga cagggaacac
    tggtcacggt gtccagc
```

Protein Sequence Defining the Hu06C11 IGHV2-5 Heavy Chain Variable Region (SEQ ID NO:70)

```
  1 qvtlkesgpt lvkptqtltl tctfsgfsln tygmgvswir
    qppgkglewl ahiywdddkr
 61 ynpslksrlt itkdtsknqv vltitnmdpv dtatyycaqr
    gyddywgywg qgtlvtvss
```

Nucleic Acid Sequence Encoding the Ch14F11 Chimeric Heavy Chain Variable Region (SEQ ID NO:131)

```
  1 caggtcacgc tgaaagagtc aggtcccgga atccttcaac
    cttcgcagac attgtcactc
 61 acatgttcct tctccgggtt ctcgctctcg acttatggca
    tgggtgtagg atggattcgg
121 cagcccagcg ggaaggggct tgagtggttg gcggatatct
    ggtgggacga cgacaaatac
181 tacaatccga gcctgaagtc ccgcctcacc atttcgaaag
    atacgtcatc aaacgaagtc
241 tttttgaaga tcgccatcgt ggacacggcg gatacagcga
    cgtattactg cgccagaagg
301 ggacactaca gcgcaatgga ttattgggga caggggaccc
    cggtgactgt gtcgtcc
```

Protein Sequence Defining the Ch14F11 Chimeric Heavy Chain Variable Region (SEQ ID NO:50)

```
  1 qvtlkesgpg ilqpsqtlsl tcsfsgfsls tygmgvgwir
    qpsgkglewl adiwwdddky
 61 ynpslksrlt iskdtssnev flkiaivdta dtatyycarr
    ghysamdywg qgtsvtvss
```

Nucleic Acid Sequence Encoding the Sh14F11 IGHV2-5 Heavy Chain Variable Region (SEQ ID NO:71)

```
  1 cagatcactt tgaaagaaag cggaccgacc ttggtcaagc
    ccacacaaac cctcacgctc
 61 acgtgtacat tttcggggtt ctcgctttca acttacggga
    tgggagtagg gtggattcgc
121 cagccgcctg gtaaagcgtt ggagtggctt gcagacatct
    ggtgggacga cgataagtac
181 tataatccct cgctcaagtc cagactgacc atcacgaaag
    atacgagcaa gaaccaggtc
241 gtgctgacaa tgactaacat ggacccagtg gatacggcta
    catattactg cgccaggcgg
301 ggtcactact cagcgatgga ttattggggc cagggaacac
    tggtaacggt gtcgtcc
```

Protein Sequence Defining the Sh14F11 IGHV2-5 Heavy Chain Variable Region (SEQ ID NO:72)

```
  1 qitlkesgpt lvkptqtltl tctfsgfsls tygmgvgwir
    qppgkalewl adiwwdddky
 61 ynpslksrlt itkdtsknqv vltmtnmdpv dtatyycarr
    ghysamdywg qgtlvtvss
```

Nucleic Acid Sequence Encoding the Sh14F11 IGHV2-70 Heavy Chain Variable Region (SEQ ID NO:73)

```
  1 caagtgactc tcaaggagtc cggacccgcc ctggtcaaac
    caacgcagac actgacgctc
 61 acatgcacct tcagcggatt ttcgttgtca acgtacggca
    tgggtgtggg gtggattcgc
121 cagcctccgg ggaaagccct tgaatggttg gcggacatct
    ggtgggatga tgacaagtac
181 tataatccct cacttaagtc acggttgacg atctcgaaag
    acaccagcaa gaaccaggta
241 gtgctgacaa tgactaacat ggacccggtc gatacagcgg
    tctactattg tgctagaagg
301 ggacactact ccgcaatgga ttattggggt caggggacgc
    tcgtaaccgt gtcgtcg
```

Protein Sequence Defining the Sh14F11 IGHV2-70 Heavy Chain Variable Region (SEQ ID NO:74)

```
  1 qvtlkesgpa lvkptqtltl tctfsgfsls tygmgvgwir
    qppgkalewl adiwwdddky
 61 ynpslksrlt iskdtsknqv vltmtnmdpv dtavyycarr
    ghysamdywg qgtlvtvss
```

Nucleic Acid Sequence Encoding the Ch01G06 Chimeric Kappa Chain Variable Region (SEQ ID NO:133)

```
  1 gacatccaaa tgacccagtc acccgcgagc ctttcggcgt
    cggtcggaga aacggtcacg
```

-continued

```
 61 atcacgtgcc ggacatcaga gaatctccat aactacctcg
    cgtggtatca acagaagcag 121 gggaagtcgc cccagttgct tgtatacgat gcgaaaacgt
    tggcggatgg ggtgccgtcc 181 agattctcgg gatcgggctc ggggacgcag tactcgctca
    agatcaattc gctgcagccg 241 gaggactttg gtcgtacta ttgtcagcat ttttggtcat
    caccgtatac atttggaggt 301 ggaacgaaac ttgagattaa g
```

Protein Sequence Defining the Ch01G06 Chimeric Kappa Chain Variable Region (SEQ ID NO:76)

```
  1 diqmtqspas lsasvgetvt itcrtsenlh nylawyqqkq
    gkspqllvyd aktladgvps 61 rfsgsgsgtq yslkinslqp edfgsyycqh fwsspytfgg
    gtkleik
```

Nucleic Acid Sequence Encoding the Hu01G06 IGKV1-39 Kappa Chain Variable Region (SEQ ID NO:89)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaagtcac cgaaactcct tgtctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgt
    cgccctacac atttgggcag 301 gggaccaagt tggaaatcaa g
```

Protein Sequence Defining the Hu01G06 IGKV1-39 Kappa Chain Variable Region (SEQ ID NO:90)

```
  1 diqmtqspss lsasvgdrvt itcrtsenlh nylawyqqkp
    gkspkllvyd aktladgvps 61 rfsgsgsgtd ytltisslqp edfatyycqh fwsspytfgq
    gtkleik
```

Nucleic Acid Sequence Encoding the Hu01G06 IGKV1-39 S43A V48I Kappa Chain Variable Region (also referred to herein as Hu01G06 IGKV1-39 F1 Kappa Chain Variable Region; SEQ ID NO:91)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaaggccc cgaaactcct tatctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgt
    cgccctacac atttgggcag 301 gggaccaagt tggaaatcaa g
```

Protein Sequence Defining the Hu01G06 IGKV1-39 S43A V48I Kappa Chain Variable Region (also referred to herein as Hu01G06 IGKV1-39 F1 Kappa Chain Variable Region; SEQ ID NO:92)

```
  1 diqmtqspss lsasvgdrvt itcrtsenlh nylawyqqkp
    gkapklliyd aktladgvps 61 rfsgsgsgtd ytltisslqp edfatyycqh fwsspytfgq
    gtkleik
```

Nucleic Acid Sequence Encoding the Hu01G06 IGKV1-39 V48I Kappa Chain Variable Region (SEQ ID NO:93)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaagtcac cgaaactcct tatctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgt
    cgccctacac atttgggcag 301 gggaccaagt tggaaatcaa g
```

Protein Sequence Defining the Hu01G06 IGKV1-39 V48I Kappa Chain Variable Region (SEQ ID NO:94)

```
  1 diqmtqspss lsasvgdrvt itcrtsenlh nylawyqqkp
    gkspklliyd aktladgvps 61 rfsgsgsgtd ytltisslqp edfatyycqh fwsspytfgq
    gtkleik
```

Nucleic Acid Sequence Encoding the Hu01G06 IGKV1-39 F1 Kappa Chain Variable Region (also referred to herein as Hu01G06 IGKV1-39 S43A V48I Kappa Chain Variable Region; SEQ ID NO:91)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaaggccc cgaaactcct tatctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgt
    cgccctacac atttgggcag 301 gggaccaagt tggaaatcaa g
```

Protein Sequence Defining the Hu01G06 IGKV1-39 F1 Kappa Chain Variable Region (also referred to herein as Hu01G06 IGKV1-39 S43A V48I Kappa Chain Variable Region; SEQ ID NO:92)

```
  1 diqmtqspss lsasvgdrvt itcrtsenlh nylawyqqkp
    gkapklliyd aktladgvps 61 rfsgsgsgtd ytltisslqp edfatyycqh fwsspytfgq
    gtkleik
```

Nucleic Acid Sequence Encoding the Hu01G06 IGKV1-39 F2 Kappa Chain Variable Region (SEQ ID NO:253)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaagtcac cgaaactcct tatctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgg
    accccctacac atttgggcag 301 gggaccaagt tggaaatcaa g
```

Protein Sequence Defining the Hu01G06 IGKV1-39 F2 Kappa Chain Variable Region (SEQ ID NO:254)

```
  1 diqmtqspss lsasvgdrvt itcrtsenlh nylawyqqkp
    gkspklliyd aktladgvps 61 rfsgsgsgtd ytltisslqp edfatyycqh fwsdpytfgq
    gtkleik
```

Nucleic Acid Sequence Encoding the Ch06C11 Chimeric Kappa Chain Variable Region (SEQ ID NO:135)

```
  1 gatatcgtca tgacccagtc ccagaagttc atgtcaactt
    cagtgggaga cagagtgtcc 61 gtcacatgta aagcctcgca aaatgtggga accaacgtag
    cgtggttcca gcagaaacct 121 ggccaatcac cgaaggcact gatctactcg gccagctata
    ggtactcggg agtaccagat 181 cggtttacgg ggtcggggag cgggacggac tttatcctca
    ctatttccaa tgtccagtcg 241 gaggaccttg cggaatactt ctgccagcag tataacaact
    atccctcac gtttggtgct 301 ggtacaaaat tggagttgaa g
```

Protein Sequence Defining the Ch06C11 Chimeric Kappa Chain Variable Region (SEQ ID NO:82)

```
  1 divmtqsqkf mstsvgdrvs vtckasqnvg tnvawfqqkp
    gqspkaliys asyrysgvpd 61 rftgsgsgtd filtisnvqs edlaeyfcqq ynnvpltfga
    gtklelk
```

Nucleic Acid Sequence Encoding the Sh06C11 IGKV1-16 Kappa Chain Variable Region (SEQ ID NO:95)

```
  1 gacatccaaa tgacccaatc gccctcctcc ctctccgcat
    cagtagggga ccgcgtcaca 61 attacttgca aagcctcgca gaacgtcgga acgaatgtgg
    cgtggtttca gcagaagccc 121 ggaaaagctc cgaagagctt gatctactcg gcctcatata
    ggtattcggg tgtgccgagc 181 cggtttagcg ggtcggggtc aggtactgat ttcacgctca
    caatttcatc gttgcagcca
```

241 gaagatttcg ccacatatta ctgtcagcag tacaacaatt
    acccctctgac gttcggccag 301 ggaaccaaac ttgagatcaa g Protein Sequence Defining the Sh06C11 IGKV1-16 Kappa Chain Variable Region (SEQ ID NO:96)

```
  1 diqmtqspss lsasvgdrvt itckasqnvg tnvawfqqkp
    gkapksliys asyrysgvps 61 rfsgsgsgtd ftltisslqp edfatyycqq ynnypltfgq
    gtkleik
```

Nucleic Acid Sequence Encoding the Ch14F11 Chimeric Kappa Chain Variable Region (SEQ ID NO:137)

```
  1 gacatcgtga tgacacagtc acagaaattc atgtccacat
    ccgtcggtga tagagtatcc 61 gtcacgtgta aggcctcgca aaacgtagga actaatgtgg
    cgtggtatca acagaagcca 121 ggacagtcac ccaaagcact catctacagc ccctcatatc
    ggtacagcgg ggtgccggac 181 aggttcacgg gatcggggag cgggaccgat tttacactga
    ccatttcgaa tgtccagtcg 241 gaggaccttg cggaatactt ctgccagcag tataactcgt
    acccctcacac gtttggaggt 301 ggcactaagt tggagatgaa a
```

Protein Sequence Defining the Ch14F11 Chimeric Kappa Chain Variable Region (SEQ ID NO:86)

```
  1 divmtqsqkf mstsvgdrvs vtckasqnvg tnvawyqqkp
    gqspkaliys psyrysgvpd 61 rftgsgsgtd ftltisnvqs edlaeyfcqq ynsvphtfgg
    gtklemk
```

Nucleic Acid Sequence Encoding the Hu14F11 IGKV1-16 Kappa Chain Variable Region (SEQ ID NO:97)

```
  1 gatatccaga tgacacagtc accctcgtcg ctctcagctt
    ccgtaggcga cagggtcact 61 attacgtgta aagcatcaca gaacgtcgga acgaatgtgg
    cgtggtttca gcagaagccc 121 gggaagagcc ccaaagcgct tatctactcc ccgtcgtatc
    ggtattccgg tgtgccaagc 181 agattttcgg ggtcaggttc gggaactgac tttaccctga
    ccatctcgtc cctccaaccg 241 gaagatttcg ccacgtactt ctgccagcag tataacagct
    atcctcacac attcggacaa 301 gggacaaagt tggagattaa a
```

Protein Sequence Defining the Hu14F11 IGKV1-16 Kappa Chain Variable Region (SEQ ID NO:98)

```
  1 diqmtqspss lsasvgdrvt itckasqnvg tnvawfqqkp
    gkspkaliys psyrysgvps 61 rfsgsgsgtd ftltisslqp edfatyfcqq ynsyphtfgq
    gtkleik
```

The amino acid sequences defining the immunoglobulin heavy chain variable regions for the antibodies produced in Example 13 are aligned in FIG. 19. Amino terminal signal peptide sequences (for proper expression/secretion) are not shown. CDR$_1$, CDR$_2$, and CDR$_3$ (Kabat definition) are identified by boxes. FIG. 20 show an alignment of the separate CDR$_1$, CDR$_2$, and CDR$_3$ sequences for each of the variable region sequences shown in FIG. 19.

The amino acid sequences defining the immunoglobulin light chain variable regions for the antibodies in Example 13 are aligned in FIG. 21. Amino terminal signal peptide sequences (for proper expression/secretion) are not shown. CDR$_1$, CDR$_2$ and CDR$_3$ are identified by boxes. FIG. 22 shows an alignment of the separate CDR$_1$, CDR$_2$, and CDR$_3$ sequences for each of the variable region sequences shown in FIG. 21.

Table 19 is a concordance chart showing the SEQ ID NO. of each sequence discussed in this Example.

TABLE 19

| SEQ. ID NO. | Nucleic Acid or Protein |
|---|---|
| 127 | Ch01G06 Chimeric Heavy Chain Variable Region-nucleic acid |
| 40 | Ch01G06 Chimeric Heavy Chain Variable Region-protein |
| 1 | Ch01G06 Chimeric Heavy Chain CDR$_1$ |
| 7 | Ch01G06 Chimeric Heavy Chain CDR$_2$ |
| 15 | Ch01G06 Chimeric Heavy Chain CDR$_3$ |
| 53 | Hu01G06 IGHV1-18 Heavy Chain Variable Region-nucleic acid |
| 54 | Hu01G06 IGHV1-18 Heavy Chain Variable Region-protein |
| 1 | Hu01G06 IGHV1-18 Heavy Chain CDR$_1$ |
| 7 | Hu01G06 IGHV1-18 Heavy Chain CDR$_2$ |
| 15 | Hu01G06 IGHV1-18 Heavy Chain CDR$_3$ |
| 55 | Hu01G06 IGHV1-69 Heavy Chain Variable Region-nucleic acid |
| 56 | Hu01G06 IGHV1-69 Heavy Chain Variable Region-protein |
| 1 | Hu01G06 IGHV1-69 Heavy Chain CDR$_1$ |
| 7 | Hu01G06 IGHV1-69 Heavy Chain CDR$_2$ |
| 15 | Hu01G06 IGHV1-69 Heavy Chain CDR$_3$ |
| 57 | Sh01G06 IGHV1-18 M69L Heavy Chain Variable Region-nucleic acid |
| 58 | Sh01G06 IGHV1-18 M69L Heavy Chain Variable Region-protein |
| 1 | Sh01G06 IGHV1-18 M69L Heavy Chain CDR$_1$ |
| 7 | Sh01G06 IGHV1-18 M69L Heavy Chain CDR$_2$ |
| 15 | Sh01G06 IGHV1-18 M69L Heavy Chain CDR$_3$ |
| 59 | Sh01G06 IGHV1-18 M69L K64Q G44S Heavy Chain Variable Region-nucleic acid |
| 60 | Sh01G06 IGHV1-18 M69L K64Q G44S Heavy Chain Variable Region-protein |
| 1 | Sh01G06 IGHV1-18 M69L K64Q G44S Heavy Chain CDR$_1$ |
| 13 | Sh01G06 IGHV1-18 M69L K64Q G44S Heavy Chain CDR$_2$ |
| 15 | Sh01G06 IGHV1-18 M69L K64Q G44S Heavy Chain CDR$_3$ |
| 61 | Sh01G06 IGHV1-18 M69L K64Q Heavy Chain Variable Region-nucleic acid |
| 62 | Sh01G06 IGHV1-18 M69L K64Q Heavy Chain Variable Region-protein |
| 1 | Sh01G06 IGHV1-18 M69L K64Q Heavy Chain CDR$_1$ |
| 13 | Sh01G06 IGHV1-18 M69L K64Q Heavy Chain CDR$_2$ |
| 15 | Sh01G06 IGHV1-18 M69L K64Q Heavy Chain CDR$_3$ |
| 63 | Sh01G06 IGHV1-69 T30S I69L Heavy Chain Variable Region-nucleic acid |
| 64 | Sh01G06 IGHV1-69 T30S I69L Heavy Chain Variable Region-protein |
| 1 | Sh01G06 IGHV1-69 T30S I69L Heavy Chain CDR$_1$ |
| 7 | Sh01G06 IGHV1-69 T30S I69L Heavy Chain CDR$_2$ |
| 15 | Sh01G06 IGHV1-69 T30S I69L Heavy Chain CDR$_3$ |
| 65 | Sh01G06 IGHV1-69 T30S K64Q I69L Heavy Chain Variable Region-nucleic acid |
| 66 | Sh01G06 IGHV1-69 T30S K64Q I69L Heavy Chain Variable Region-protein |
| 1 | Sh01G06 IGHV1-69 T30S K64Q I69L Heavy Chain CDR$_1$ |
| 13 | Sh01G06 IGHV1-69 T30S K64Q I69L Heavy Chain CDR$_2$ |
| 15 | Sh01G06 IGHV1-69 T30S K64Q I69L Heavy Chain CDR$_3$ |
| 245 | Hu01G06 IGHV1-18 F1 Heavy Chain Variable Region-nucleic acid |
| 246 | Hu01G06 IGHV1-18 F1 Heavy Chain Variable Region-protein |
| 1 | Hu01G06 IGHV1-18 F1 Heavy Chain CDR$_1$ |
| 236 | Hu01G06 IGHV1-18 F1 Heavy Chain CDR$_2$ |
| 15 | Hu01G06 IGHV1-18 F1 Heavy Chain CDR$_3$ |
| 247 | Hu01G06 IGHV1-18 F2 Heavy Chain Variable Region-nucleic acid |
| 248 | Hu01G06 IGHV1-18 F2 Heavy Chain Variable Region-protein |
| 1 | Hu01G06 IGHV1-18 F2 Heavy Chain CDR$_1$ |
| 237 | Hu01G06 IGHV1-18 F2 Heavy Chain CDR$_2$ |
| 15 | Hu01G06 IGHV1-18 F2 Heavy Chain CDR$_3$ |
| 259 | Hu01G06 IGHV1-69 F1 Heavy Chain Variable Region-nucleic acid |
| 250 | Hu01G06 IGHV1-69 F1 Heavy Chain Variable Region-protein |
| 1 | Hu01G06 IGHV1-69 F1 Heavy Chain CDR$_1$ |
| 238 | Hu01G06 IGHV1-69 F1 Heavy Chain CDR$_2$ |
| 15 | Hu01G06 IGHV1-69 F1 Heavy Chain CDR$_3$ |
| 251 | Hu01G06 IGHV1-69 F2 Heavy Chain Variable Region-nucleic acid |
| 252 | Hu01G06 IGHV1-69 F2 Heavy Chain Variable Region-protein |
| 1 | Hu01G06 IGHV1-69 F2 Heavy Chain CDR$_1$ |
| 239 | Hu01G06 IGHV1-69 F2 Heavy Chain CDR$_2$ |
| 15 | Hu01G06 IGHV1-69 F2 Heavy Chain CDR$_3$ |
| 129 | Ch06C11 Chimeric Heavy Chain Variable Region-nucleic acid |
| 46 | Ch06C11 Chimeric Heavy Chain Variable Region-protein |
| 4 | Ch06C11 Chimeric Heavy Chain CDR$_1$ |
| 9 | Ch06C11 Chimeric Heavy Chain CDR$_2$ |
| 18 | Ch06C11 Chimeric Heavy Chain CDR$_3$ |
| 67 | HE LM 06C11 IGHV2-70 Heavy Chain Variable Region-nucleic acid |
| 68 | HE LM 06C11 IGHV2-70 Heavy Chain Variable Region-protein |

TABLE 19-continued

| SEQ. ID NO. | Nucleic Acid or Protein |
|---|---|
| 4 | HE LM 06C11 IGHV2-70 Heavy Chain CDR$_1$ |
| 14 | HE LM 06C11 IGHV2-70 Heavy Chain CDR$_2$ |
| 18 | HE LM 06C11 IGHV2-70 Heavy Chain CDR$_3$ |
| 69 | Hu06C11 IGHV2-5 Heavy Chain Variable Region-nucleic acid |
| 70 | Hu06C11 IGHV2-5 Heavy Chain Variable Region-protein |
| 4 | Hu06C11 IGHV2-5 Heavy Chain CDR$_1$ |
| 9 | Hu06C11 IGHV2-5 Heavy Chain CDR$_2$ |
| 18 | Hu06C11 IGHV2-5 Heavy Chain CDR$_3$ |
| 131 | Ch14F11 Chimeric Heavy Chain Variable Region-nucleic acid |
| 50 | Ch14F11 Chimeric Heavy Chain Variable Region-protein |
| 5 | Ch14F11 Chimeric Heavy Chain CDR$_1$ |
| 11 | Ch14F11 Chimeric Heavy Chain CDR$_2$ |
| 19 | Ch14F11 Chimeric Heavy Chain CDR$_3$ |
| 71 | Sh14F11 IGHV2-5 Heavy Chain Variable Region-nucleic acid |
| 72 | Sh14F11 IGHV2-5 Heavy Chain Variable Region-protein |
| 5 | Sh14F11 IGHV2-5 Heavy Chain CDR$_1$ |
| 11 | Sh14F11 IGHV2-5 Heavy Chain CDR$_2$ |
| 19 | Sh14F11 IGHV2-5 Heavy Chain CDR$_3$ |
| 73 | Sh14F11 IGHV2-70 Heavy Chain Variable Region-nucleic acid |
| 74 | Sh14F11 IGHV2-70 Heavy Chain Variable Region-protein |
| 5 | Sh14F11 IGHV2-70 Heavy Chain CDR$_1$ |
| 11 | Sh14F11 IGHV2-70 Heavy Chain CDR$_2$ |
| 19 | Sh14F11 IGHV2-70 Heavy Chain CDR$_3$ |
| 133 | Ch01G06 Chimeric Light (kappa) Chain Variable Region-nucleic acid |
| 76 | Ch01G06 Chimeric Light (kappa) Chain Variable Region-protein |
| 21 | Ch01G06 Chimeric Light (kappa) Chain CDR$_1$ |
| 26 | Ch01G06 Chimeric Light (kappa) Chain CDR$_2$ |
| 32 | Ch01G06 Chimeric Light (kappa) Chain CDR$_3$ |
| 89 | Hu01G06 IGKV1-39 Light (kappa) Chain Variable Region-nucleic acid |
| 90 | Hu01G06 IGKV1-39 Light (kappa) Chain Variable Region-protein |
| 21 | Hu01G06 IGKV1-39 Light (kappa) Chain CDR$_1$ |
| 26 | Hu01G06 IGKV1-39 Light (kappa) Chain CDR$_2$ |
| 32 | Hu01G06 IGKV1-39 Light (kappa) Chain CDR$_3$ |
| 91 | Hu01G06 IGKV1-39 S43A V48I Light (kappa) Chain Variable Region-nucleic acid |
| 92 | Hu01G06 IGKV1-39 S43A V48I Light (kappa) Chain Variable Region-protein |
| 21 | Hu01G06 IGKV1-39 S43A V48I Light (kappa) Chain CDR$_1$ |
| 26 | Hu01G06 IGKV1-39 S43A V48I Light (kappa) Chain CDR$_2$ |
| 32 | Hu01G06 IGKV1-39 S43A V48I Light (kappa) Chain CDR$_3$ |
| 93 | Hu01G06 IGKV1-39 V48I Light (kappa) Chain Variable Region-nucleic acid |
| 94 | Hu01G06 IGKV1-39 V48I Light (kappa) Chain Variable Region-protein |
| 21 | Hu01G06 IGKV1-39 V48I Light (kappa) Chain CDR$_1$ |
| 26 | Hu01G06 IGKV1-39 V48I Light (kappa) Chain CDR$_2$ |
| 32 | Hu01G06 IGKV1-39 V48I Light (kappa) Chain CDR$_3$ |
| 91 | Hu01G06 IGKV1-39 F1 Light (kappa) Chain Variable Region-nucleic acid |
| 92 | Hu01G06 IGKV1-39 F1 Light (kappa) Chain Variable Region-protein |
| 21 | Hu01G06 IGKV1-39 F1 Light (kappa) Chain CDR$_1$ |
| 26 | Hu01G06 IGKV1-39 F1 Light (kappa) Chain CDR$_2$ |
| 32 | Hu01G06 IGKV1-39 F1 Light (kappa) Chain CDR$_3$ |
| 253 | Hu01G06 IGKV1-39 F2 Light (kappa) Chain Variable Region-nucleic acid |
| 254 | Hu01G06 IGKV1-39 F2 Light (kappa) Chain Variable Region-protein |
| 21 | Hu01G06 IGKV1-39 F2 Light (kappa) Chain CDR$_1$ |
| 26 | Hu01G06 IGKV1-39 F2 Light (kappa) Chain CDR$_2$ |
| 244 | Hu01G06 IGKV1-39 F2 Light (kappa) Chain CDR$_3$ |
| 135 | Ch06C11 Chimeric Light (kappa) Chain Variable Region-nucleic acid |
| 82 | Ch06C11 Chimeric Light (kappa) Chain Variable Region-protein |
| 23 | Ch06C11 Chimeric Light (kappa) Chain CDR$_1$ |
| 28 | Ch06C11 Chimeric Light (kappa) Chain CDR$_2$ |
| 35 | Ch06C11 Chimeric Light (kappa) Chain CDR$_3$ |
| 95 | Sh06C11 IGKV1-16 Light (kappa) Chain Variable Region-nucleic acid |
| 96 | Sh06C11 IGKV1-16 Light (kappa) Chain Variable Region-protein |
| 23 | Sh06C11 IGKV1-16 Light (kappa) Chain CDR$_1$ |
| 28 | Sh06C11 IGKV1-16 Light (kappa) Chain CDR$_2$ |
| 35 | Sh06C11 IGKV1-16 Light (kappa) Chain CDR$_3$ |
| 137 | Ch14F11 Chimeric Light (kappa) Chain Variable Region-nucleic acid |
| 86 | Ch14F11 Chimeric Light (kappa) Chain Variable Region-protein |
| 23 | Ch14F11 Chimeric Light (kappa) Chain CDR$_1$ |
| 30 | Ch14F11 Chimeric Light (kappa) Chain CDR$_2$ |
| 36 | Ch14F11 Chimeric Light (kappa) Chain CDR$_3$ |
| 97 | Hu14F11 IGKV1-16 Light (kappa) Chain Variable Region-nucleic acid |
| 98 | Hu14F11 IGKV1-16 Light (kappa) Chain Variable Region-protein |
| 23 | Hu14F11 IGKV1-16 Light (kappa) Chain CDR$_1$ |
| 30 | Hu14F11 IGKV1-16 Light (kappa) Chain CDR$_2$ |
| 36 | Hu14F11 IGKV1-16 Light (kappa) Chain CDR$_3$ |

Humanized monoclonal antibody heavy chain CDR sequences (Kabat, Chothia, and IMGT definitions) are shown in Table 20.

TABLE 20

| | CDR1 | CDR2 | CDR3 | Variable Region SEQ ID NO: |
|---|---|---|---|---|
| Kabat | | | | |
| Ch01G06 Chimeric | DYNMD (SEQ ID NO: 1) | QINPNNGGIFFNQKFKG (SEQ ID NO: 7) | EAITTVGAMDY (SEQ ID NO: 15) | 40 |
| Hu01G06 IGHV1-18 | DYNMD (SEQ ID NO: 1) | QINPNNGGIFFNQKFKG (SEQ ID NO: 7) | EAITTVGAMDY (SEQ ID NO: 15) | 54 |
| Hu01G06 IGHV1-69 | DYNMD (SEQ ID NO: 1) | QINPNNGGIFFNQKFKG (SEQ ID NO: 7) | EAITTVGAMDY (SEQ ID NO: 15) | 56 |
| Sh01G06 IGHV1-18 M69L | DYNMD (SEQ ID NO: 1) | QINPNNGGIFFNQKFKG (SEQ ID NO: 7) | EAITTVGAMDY (SEQ ID NO: 15) | 58 |
| Sh01G06 IGHV1-18 M69L K64Q G44S | DYNMD (SEQ ID NO: 1) | QINPNNGGIFFNQKFQG (SEQ ID NO: 13) | EAITTVGAMDY (SEQ ID NO: 15) | 60 |
| Sh01G06 IGHV1-18 M69L K64Q | DYNMD (SEQ ID NO: 1) | QINPNNGGIFFNQKFQG (SEQ ID NO: 13) | EAITTVGAMDY (SEQ ID NO: 15) | 62 |
| Sh01G06 IGHV1-69 T30S I69L | DYNMD (SEQ ID NO: 1) | QINPNNGGIFFNQKFKG (SEQ ID NO: 7) | EAITTVGAMDY (SEQ ID NO: 15) | 64 |
| Sh01G06 IGHV1-69 T30S K64Q I69L | DYNMD (SEQ ID NO: 1) | QINPNNGGIFFNQKFQG (SEQ ID NO: 13) | EAITTVGAMDY (SEQ ID NO: 15) | 66 |
| Hu01G06 IGHV1-18 F1 | DYNMD (SEQ ID NO: 1) | QINPYNHLIFFNQKFQG (SEQ ID NO: 236) | EAITTVGAMDY (SEQ ID NO: 15) | 246 |
| Hu01G06 IGHV1-18 F2 | DYNMD (SEQ ID NO: 1) | QINPNNGLIFFNQKFQG (SEQ ID NO: 237) | EAITTVGAMDY (SEQ ID NO: 15) | 248 |
| Hu01G06 IGHV1-69 F1 | DYNMD (SEQ ID NO: 1) | QINPNNGLIFFNQKFKG (SEQ ID NO: 238) | EAITTVGAMDY (SEQ ID NO: 15) | 250 |
| Hu01G06 IGHV1-69 F2 | DYNMD (SEQ ID NO: 1) | QINPYNHLIFFNQKFKG (SEQ ID NO: 239) | EAITTVGAMDY (SEQ ID NO: 15) | 252 |
| Ch06C11 Chimeric | TYGMGVS (SEQ ID NO: 4) | HIYWDDDKRYNPSLKS (SEQ ID NO: 9) | RGYDDYWGY (SEQ ID NO: 18) | 46 |
| HE LM 06C11 IGHV2-70 | TYGMGVS (SEQ ID NO: 4) | HIYWDDDKRYNPSLKT (SEQ ID NO: 14) | RGYDDYWGY (SEQ ID NO: 18) | 68 |
| Hu06C11 IGHV2-5 | TYGMGVS (SEQ ID NO: 4) | HIYWDDDKRYNPSLKS (SEQ ID NO: 9) | RGYDDYWGY (SEQ ID NO: 18) | 70 |
| Ch14F11 Chimeric | TYGMGVG (SEQ ID NO: 5) | DIWWDDDKYYNPSLKS (SEQ ID NO: 11) | RGHYSAMDY (SEQ ID NO: 19) | 50 |
| Sh14F11 IGHV2-5 | TYGMGVG (SEQ ID NO: 5) | DIWWDDDKYYNPSLKS (SEQ ID NO: 11) | RGHYSAMDY (SEQ ID NO: 19) | 72 |
| Sh14F11 IGHV2-70 | TYGMGVG (SEQ ID NO: 5) | DIWWDDDKYYNPSLKS (SEQ ID NO: 11) | RGHYSAMDY (SEQ ID NO: 19) | 74 |
| Chothia | | | | |
| Ch01G06 Chimeric | GYTFTDY (SEQ ID NO: 38) | NPNNGG (SEQ ID NO: 143) | EAITTVGAMDY (SEQ ID NO: 15) | 40 |
| Hu01G06 IGHV1-18 | GYTFTDY (SEQ ID NO: 38) | NPNNGG (SEQ ID NO: 143) | EAITTVGAMDY (SEQ ID NO: 15) | 54 |
| Hu01G06 IGHV1-69 | GYTFTDY (SEQ ID NO: 38) | NPNNGG (SEQ ID NO: 143) | EAITTVGAMDY (SEQ ID NO: 15) | 56 |
| Sh01G06 IGHV1-18 M69L | GYTFTDY (SEQ ID NO: 38) | NPNNGG (SEQ ID NO: 143) | EAITTVGAMDY (SEQ ID NO: 15) | 58 |

TABLE 20-continued

| | CDR1 | CDR2 | CDR3 | Variable Region SEQ ID NO: |
|---|---|---|---|---|
| Sh01G06 IGHV1-18 M69L K64Q G44S | GYTFTDY (SEQ ID NO: 38) | NPNNGG (SEQ ID NO: 143) | EAITTVGAMDY (SEQ ID NO: 15) | 60 |
| Sh01G06 IGHV1-18 M69L K64Q | GYTFTDY (SEQ ID NO: 38) | NPNNGG (SEQ ID NO: 143) | EAITTVGAMDY (SEQ ID NO: 15) | 62 |
| Sh01G06 IGHV1-69 T30S I69L | GYTFSDY (SEQ ID NO: 234) | NPNNGG (SEQ ID NO: 143) | EAITTVGAMDY (SEQ ID NO: 15) | 64 |
| Sh01G06 IGHV1-69 T30S K64Q I69L | GYTFSDY (SEQ ID NO: 234) | NPNNGG (SEQ ID NO: 143) | EAITTVGAMDY (SEQ ID NO: 15) | 66 |
| Hu01G06 IGHV1-18 F1 | GYTFTDY (SEQ ID NO: 38) | NPYNHL (SEQ ID NO: 240) | EAITTVGAMDY (SEQ ID NO: 15) | 246 |
| Hu01G06 IGHV1-18 F2 | GYTFTDY (SEQ ID NO: 38) | NPNNGL (SEQ ID NO: 241) | EAITTVGAMDY (SEQ ID NO: 15) | 248 |
| Hu01G06 IGHV1-69 F1 | GYTFSDY (SEQ ID NO: 234) | NPNNGL (SEQ ID NO: 241) | EAITTVGAMDY (SEQ ID NO: 15) | 250 |
| Hu01G06 IGHV1-69 F2 | GYTFSDY (SEQ ID NO: 234) | NPYNHL (SEQ ID NO: 240) | EAITTVGAMDY (SEQ ID NO: 15) | 252 |
| Ch06C11 Chimeric | GFSLNTYGM (SEQ ID NO: 132) | YWDDD (SEQ ID NO: 145) | RGYDDYWGY (SEQ ID NO: 18) | 46 |
| HE LM 06C11 IGHV2-70 | GFSLNTYGM (SEQ ID NO: 132) | YWDDD (SEQ ID NO: 145) | RGYDDYWGY (SEQ ID NO: 18) | 68 |
| Hu06C11 IGHV2-5 | GFSLNTYGM (SEQ ID NO: 132) | YWDDD (SEQ ID NO: 145) | RGYDDYWGY (SEQ ID NO: 18) | 70 |
| Ch14F11 Chimeric | GFSLSTYGM (SEQ ID NO: 130) | WWDDD (SEQ ID NO: 146) | RGHYSAMDY (SEQ ID NO: 19) | 50 |
| Sh14F11 IGHV2-5 | GFSLSTYGM (SEQ ID NO: 130) | WWDDD (SEQ ID NO: 146) | RGHYSAMDY (SEQ ID NO: 19) | 72 |
| Sh14F11 IGHV2-70 | GFSLSTYGM (SEQ ID NO: 130) | WWDDD (SEQ ID NO: 146) | RGHYSAMDY (SEQ ID NO: 19) | 74 |
| IMGT | | | | |
| Ch01G06 Chimeric | GYTFTDYN (SEQ ID NO: 136) | INPNNGGI (SEQ ID NO: 148) | AREAITTVGAMDY (SEQ ID NO: 154) | 40 |
| Hu01G06 IGHV1-18 | GYTFTDYN (SEQ ID NO: 136) | INPNNGGI (SEQ ID NO: 148) | AREAITTVGAMDY (SEQ ID NO: 154) | 54 |
| Hu01G06 IGHV1-69 | GYTFTDYN (SEQ ID NO: 136) | INPNNGGI (SEQ ID NO: 148) | AREAITTVGAMDY (SEQ ID NO: 154) | 56 |
| Sh01G06 IGHV1-18 M69L | GYTFTDYN (SEQ ID NO: 136) | INPNNGGI (SEQ ID NO: 148) | AREAITTVGAMDY (SEQ ID NO: 154) | 58 |
| Sh01G06 IGHV1-18 M69L K64Q G44S | GYTFTDYN (SEQ ID NO: 136) | INPNNGGI (SEQ ID NO: 148) | AREAITTVGAMDY (SEQ ID NO: 154) | 60 |
| Sh01G06 IGHV1-18 M69L K64Q | GYTFTDYN (SEQ ID NO: 136) | INPNNGGI (SEQ ID NO: 148) | AREAITTVGAMDY (SEQ ID NO: 154) | 62 |
| Sh01G06 IGHV1-69 T30S I69L | GYTFSDYN (SEQ ID NO: 235) | INPNNGGI (SEQ ID NO: 148) | AREAITTVGAMDY (SEQ ID NO: 154) | 64 |
| Sh01G06 IGHV1-69 T30S K64Q I69L | GYTFSDYN (SEQ ID NO: 235) | INPNNGGI (SEQ ID NO: 148) | AREAITTVGAMDY (SEQ ID NO: 154) | 66 |
| Hu01G06 IGHV1-18 F1 | GYTFTDYN (SEQ ID NO: 136) | INPYNHLI (SEQ ID NO: 242) | AREAITTVGAMDY (SEQ ID NO: 154) | 246 |

TABLE 20-continued

|  | CDR1 | CDR2 | CDR3 | Variable Region SEQ ID NO: |
|---|---|---|---|---|
| Hu01G06 IGHV1-18 F2 | GYTFTDYN (SEQ ID NO: 136) | INPNNGLI (SEQ ID NO: 243) | AREAITTVGAMDY (SEQ ID NO: 154) | 248 |
| Hu01G06 IGHV1-69 F1 | GYTFSDYN (SEQ ID NO: 235) | INPNNGLI (SEQ ID NO: 243) | AREAITTVGAMDY (SEQ ID NO: 154) | 250 |
| Hu01G06 IGHV1-69 F2 | GYTFSDYN (SEQ ID NO: 235) | INPYNHLI (SEQ ID NO: 242) | AREAITTVGAMDY (SEQ ID NO: 154) | 252 |
| Ch06C11 Chimeric | GFSLNTYGMG (SEQ ID NO: 141) | IYWDDDK (SEQ ID NO: 150) | AQRGYDDYWGY (SEQ ID NO: 157) | 46 |
| HE LM 06C11 IGHV2-70 | GFSLNTYGMG (SEQ ID NO: 141) | IYWDDDK (SEQ ID NO: 150) | AQRGYDDYWGY (SEQ ID NO: 157) | 68 |
| Hu06C11 IGHV2-5 | GFSLNTYGMG (SEQ ID NO: 141) | IYWDDDK (SEQ ID NO: 150) | AQRGYDDYWGY (SEQ ID NO: 157) | 70 |
| Ch14F11 Chimeric | GFSLSTYGMG (SEQ ID NO: 140) | IWWDDDK (SEQ ID NO: 152) | ARRGHYSAMDY (SEQ ID NO: 158) | 50 |
| Sh14F11 IGHV2-5 | GFSLSTYGMG (SEQ ID NO: 140) | IWWDDDK (SEQ ID NO: 152) | ARRGHYSAMDY (SEQ ID NO: 158) | 72 |
| Sh14F11 IGHV2-70 | GFSLSTYGMG (SEQ ID NO: 140) | IWWDDDK (SEQ ID NO: 152) | ARRGHYSAMDY (SEQ ID NO: 158) | 74 |

Humanized monoclonal antibody Kappa light chain CDR sequences (Kabat, Chothia, and IMGT definitions) are shown in Table 21.

TABLE 21

|  | CDR1 | CDR2 | CDR3 | Variable Region SEQ ID NO: |
|---|---|---|---|---|
| Kabat/Chothia | | | | |
| Ch01G06 Chimeric | RTSENLHNYLA (SEQ ID NO: 21) | DAKTLAD (SEQ ID NO: 26) | QHFWSSPYT (SEQ ID NO: 32) | 76 |
| Hu01G06 IGKV1-39 | RTSENLHNYLA (SEQ ID NO: 21) | DAKTLAD (SEQ ID NO: 26) | QHFWSSPYT (SEQ ID NO: 32) | 90 |
| Hu01G06 IGKV1-39 S43A V48I (also known as Hu01G06 IGKV1-39 F1) | RTSENLHNYLA (SEQ ID NO: 21) | DAKTLAD (SEQ ID NO: 26) | QHFWSSPYT (SEQ ID NO: 32) | 92 |
| Hu01G06 IGKV1-39 V48I | RTSENLHNYLA (SEQ ID NO: 21) | DAKTLAD (SEQ ID NO: 26) | QHFWSSPYT (SEQ ID NO: 32) | 94 |
| Hu01G06 IGKV1-39 F1 (also known as Hu01G06 IGKV1-39 S43A V48I) | RTSENLHNYLA (SEQ ID NO: 21) | DAKTLAD (SEQ ID NO: 26) | QHFWSSPYT (SEQ ID NO: 32) | 92 |
| Hu01G06 IGKV1-39 F2 | RTSENLHNYLA (SEQ ID NO: 21) | DAKTLAD (SEQ ID NO: 26) | QHFWSDPYT (SEQ ID NO: 244) | 254 |
| Ch06C11 Chimeric | KASQNVGTNVA (SEQ ID NO: 23) | SASYRYS (SEQ ID NO: 28) | QQYNNYPLT (SEQ ID NO: 35) | 82 |
| Sh06C11 IGKV1-16 | KASQNVGTNVA (SEQ ID NO: 23) | SASYRYS (SEQ ID NO: 28) | QQYNNYPLT (SEQ ID NO: 35) | 96 |
| Ch14F11 Chimeric | KASQNVGTNVA (SEQ ID NO: 23) | SPSYRYS (SEQ ID NO: 30) | QQYNSYPHT (SEQ ID NO: 36) | 86 |
| Hu14F11 IGKV1-16 | KASQNVGTNVA (SEQ ID NO: 23) | SPSYRYS (SEQ ID NO: 30) | QQYNSYPHT (SEQ ID NO: 36) | 98 |

TABLE 21-continued

| | CDR1 | CDR2 | CDR3 | Variable Region SEQ ID NO: |
|---|---|---|---|---|
| | | IMGT | | |
| Ch01G06 Chimeric | ENLHNY (SEQ ID NO: 160) | DAK | QHFWSSPYT (SEQ ID NO: 32) | 76 |
| Hu01G06 IGKV1-39 | ENLHNY (SEQ ID NO: 160) | DAK | QHFWSSPYT (SEQ ID NO: 32) | 90 |
| Hu01G06 IGKV1-39 S43A V48I (also known as Hu01G06 IGKV1-39 F1) | ENLHNY (SEQ ID NO: 160) | DAK | QHFWSSPYT (SEQ ID NO: 32) | 92 |
| Hu01G06 IGKV1-39 V48I | ENLHNY (SEQ ID NO: 160) | DAK | QHFWSSPYT (SEQ ID NO: 32) | 94 |
| Hu01G06 IGKV1-39 F1 (also known as Hu01G06 IGKV1-39 S43A V48I) | ENLHNY (SEQ ID NO: 160) | DAK | QHFWSSPYT (SEQ ID NO: 32) | 92 |
| Hu01G06 IGKV1-39 F2 | ENLHNY (SEQ ID NO: 160) | DAK | QHFWSDPYT (SEQ ID NO: 244) | 254 |
| Ch06C11 Chimeric | QNVGTN (SEQ ID NO: 162) | SAS | QQYNNYPLT (SEQ ID NO: 35) | 82 |
| Sh06C11 IGKV1-16 | QNVGTN (SEQ ID NO: 162) | SAS | QQYNNYPLT (SEQ ID NO: 35) | 96 |
| Ch14F11 Chimeric | QNVGTN (SEQ ID NO: 162) | SPS | QQYNSYPHT (SEQ ID NO: 36) | 86 |
| Hu14F11 IGKV1-16 | QNVGTN (SEQ ID NO: 162) | SPS | QQYNSYPHT (SEQ ID NO: 36) | 98 |

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

Nucleic Acid Sequence Encoding the Human IgG1 Heavy Chain Constant Region (SEQ ID NO:171)

```
  1 gcctcaacaa aaggaccaag tgtgttccca ctcgcccta
    gcagcaagag tacatccggg 61 ggcactgcag cactcggctg cctcgtcaag gattattttc
    cagagccagt aaccgtgagc 121 tggaacagtg gagcactcac ttctggtgtc catactttc
    ctgctgtcct gcaaagctct 181 ggcctgtact cactcagctc cgtcgtgacc gtgccatctt
    catctctggg cactcagacc 241 tacatctgta atgtaaacca caagcctagc aatactaagg
    tcgataagc ggtggaaccc 301 aagagctgcg acaagactca cacttgtccc ccatgccctg
    cccctgaact tctgggcggt 361 cccagcgtct ttttgttccc accaaagcct aaagatactc
    tgatgataag tagaacaccc 421 gaggtgacat gtgttgttgt agacgtttcc cacgaggacc
    cagaggttaa gttcaactgg 481 tacgttgatg gagtcgaagt acataatgct aagaccaagc
    ctagagagga gcagtataat 541 agtacatacc gtgtagtcag tgttctcaca gtgctgcacc
    aagactggct caacggcaaa 601 gaatacaat gcaaagtgtc caacaaagca ctcccagccc
    ctatcgagaa gactattagt 661 aaggcaaagg ggcagcctcg tgaaccacag gtgtacactc
    tgccacccag tagagaggaa 721 atgacaaaga accaagtctc attgacctgc ctggtgaaag
    gcttctaccc cagcgacatc 781 gccgttgagt gggagagtaa cggtcagcct gagaacaatt
    acaagacaac ccccccagtg 841 ctggatagtg acgggtcttt ctttctgtac agtaagctga
    ctgtggacaa gtcccgctgg 901 cagcagggta acgtcttcag ctgttccgtg atgcacgagg
    cattgcacaa ccactacacc 961 cagaagtcac tgagcctgag cccagggaag
```

Protein Sequence Defining the Human IgG1 Heavy Chain Constant Region (SEQ ID NO:172)

```
  1 astkgpsvfp lapsskstsg gtaalgclvk dyfpepvtvs
    wnsgaltsgv htfpavlqss 61 glyslssvvt vpssslgtqt yicnvnhkps ntkvdkrvep
    kscdkthtcp pcpapellgg
```

```
121 psvflfppkp kdtlmisrtp evtcvvvdvs hedpevkfnw
    yvdgvevhna ktkpreeqyn 181 styrvvsvlt vlhqdwlngk eykckvsnka lpapiektis
    kakgqprepq vytlppsree 241 mtknqvsltc lvkgfypsdi avewesngqp ennykttppv
    ldsdgsffly skltvdksrw 301 qqgnvfscsv mhealhnhyt qkslslspgk
```

Nucleic Acid Sequence Encoding the Human Kappa Light Chain Constant Region (SEQ ID NO:173)

```
  1 cgcacagttg ctgcccccag cgtgttcatt ttcccaccta
    gcgatgagca gctgaaaagc 61 ggtactgcct ctgtcgtatg cttgctcaac aactttacc
    cacgtgaggc taaggtgcag 121 tggaaagtgg ataatgcact tcaatctgga aacagtcaag
    agtccgtgac agaacaggac 181 agcaaagact caacttattc actctcttcc accctgactc
    tgtccaaggc agactatgaa 241 aaacacaagg tatacgcctg cgaggttaca caccagggtt
    tgtctagtcc tgtcaccaag 301 tccttcaata ggggcgaatg t
```

Protein Sequence Defining the Human Kappa Light Chain Constant Region (SEQ ID NO:174)

```
  1 rtvaapsvfi fppsdeqlks gtasvvclln nfypreakvq
    wkvdnalqsg nsqesvteqd 61 skdstyslss tltlskadye khkvyacevt hqglsspvtk
    sfnrgec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Ch01G06 Chimeric Heavy Chain (Mouse Heavy Chain Variable Region and Human IgG1 Constant Region) (SEQ ID NO:175)

```
  1 gaagtgttgt tgcagcagtc agggccggag ttggtaaaac
    cgggagcgtc ggtgaaaatc 61 ccgtgcaaag cgtcggggta tacgtttacg gactataaca
    tggattgggt gaaacagtcg 121 catgggaaat cgcttgaatg gattggtcag atcaatccga
    ataatggagg aatcttcttt
```

```
181 aatcagaagt ttaaaggaaa agcgacgctt acagtcgata
    agtcgtcgaa cacggcgttc 241 atggaagtac ggtcgcttac gtcggaagat acggcggtct
    attactgtgc gagggaggcg 301 attacgacgg tgggagcgat ggactattgg ggacaaggga
    cgtcggtcac ggtatcgtcg 361 gcctcaacaa aaggaccaag tgtgttccca ctcgcccta
    gcagcaagag tacatccggg 421 ggcactgcag cactcggctg cctcgtcaag gattattttc
    cagagccagt aaccgtgagc 481 tggaacagtg gagcactcac ttctggtgtc catactttc
    ctgctgtcct gcaaagctct 541 ggcctgtact cactcagctc cgtcgtgacc gtgccatctt
    catctctggg cactcagacc 601 tacatctgta atgtaaacca caagcctagc aatactaagg
    tcgataagcg ggtggaaccc 661 aagagctgcg acaagactca cacttgtccc ccatgccctg
    cccctgaact tctgggcggt 721 cccagcgtct ttttgttccc accaaagcct aaagatactc
    tgatgataag tagaacaccc 781 gaggtgacat gtgttgttgt agacgtttcc cacgaggacc
    cagaggttaa gttcaactgg 841 tacgttgatg gagtcgaagt acataatgct aagaccaagc
    ctagagagga gcagtataat 901 agtacatacc gtgtagtcag tgttctcaca gtgctgcacc
    aagactggct caacggcaaa 961 gaatacaaat gcaaagtgtc caacaaagca ctcccagccc
    ctatcgaaga gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acgggtcttt cttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Ch01G06 Chimeric Heavy Chain (Mouse Heavy Chain Variable Region and Human IgG1 Constant Region) (SEQ ID NO:176)

```
  1 evllqqsgpe lvkpgasvki pckasgytft dynmdwvkqs
    hgkslewigq inpnnggiff 61 nqkfkgkatl tvdkssntaf mevrsltsed tavyycarea
    ittvgamdyw gqgtsvtvss 121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn
```

-continued

```
301 styrvvsvlt vlhqdwlngk eykckvsnka lpapiektis
    kakgqprepq vytlppsree 361 mtknqvsltc lvkgfypsdi avewesngqp ennykttppv
    ldsdgsffly skltvdksrw 421 qqgnvfscsv mhealhnhyt qkslslspgk
```

Nucleic Acid Sequence Encoding the Full Length Hu01G06 IGHV1-18 Heavy Chain (Humanized Heavy Chain Variable Region and Human IgG1 Constant Region) (SEQ ID NO:177)

```
   1 caagtgcaac ttgtgcagtc gggtgcggaa gtcaaaagc
     cgggagcgtc ggtgaaagta 61 tcgtgtaaag cgtcgggata tacgtttacg gactataaca
     tggactgggt acgacaggca 121 ccggggaaat cgttggaatg gatcggacag attaatccga
     acaatggggg aatttcttt 181 aatcagaaat tcaaaggacg ggcgacgttg acggtcgata
     catcgacgaa tacggcgtat 241 atggaattga ggtcgcttcg ctcggacgat acggcggtct
     attactgcgc cagggaggcg 301 atcacgacgg taggggcgat ggattattgg ggacagggga
     cgcttgtgac ggtatcgtcg 361 gcctcaacaa aaggaccaag tgtgttccca ctcgcccta
     gcagcaagag tacatccggg 421 ggcactgcag cactcggctg cctcgtcaag gattattttc
     cagagccagt aaccgtgagc 481 tggaacagtg gagcactcac ttctggtgtc catactttc
     ctgctgtcct gcaaagctct 541 ggcctgtact cactcagctc cgtcgtgacc gtgccatctt
     catctctggg cactcagacc 601 tacatctgta atgtaaacca caagcctagc aatactaagg
     tcgataagcg ggtgaaccc 661 aagagctgcg acaagactca cacttgtccc ccatgccctg
     cccctgaact tctgggcggt 721 cccagcgtct ttttgttccc accaaagcct aaagatactc
     tgatgataag tagaacaccc 781 gaggtgacat gtgttgttgt agacgtttcc cacgaggacc
     cagaggttaa gttcaactgg 841 tacgttgatg gagtcgaagt acataatgct aagaccaagc
     ctagagagga gcagtataat 901 agtacatacc gtgtagtcag tgttctcaca gtgctgcacc
     aagactggct caacggcaaa 961 gaatacaaat gcaaagtgtc caacaaagca ctcccagccc
     ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac ccccccagtg 1201 ctggatagtg acgggtcttt ctttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Hu01G06 IGHV1-18 Heavy Chain (Humanized Heavy Chain Variable Region and Human IgG1 Constant Region) (SEQ ID NO:178)

```
   1 qvqlvqsgae vkkpgasvkv sckasgytft dynmdwvrqa
     pgkslewigq inpnnggiff 61 nqkfkgratl tvdtstntay melrslrsdd tavyycarea
     ittvgamdyw gqgtivtvss 121 astkgpsvfp lapsskstsg gtaalgclvk dyfpepvtvs
     wnsgaltsgv htfpavlqss 181 glyslssvvt vpssslgtqt yicnvnhkps ntkvdkrvep
     kscdkthtcp pcpapellgg 241 psvflfppkp kdtlmisrtp evtcvvvdvs hedpevkfnw
     yvdgvevhna ktkpreeqyn 301 styrvvsvlt vlhqdwlngk eykckvsnka lpapiektis
     kakgqprepq vytlppsree 361 mtknqvsltc lvkgfypsdi avewesngqp ennykttppv
     ldsdgsffly skltvdksrw 421 qqgnvfscsv mhealhnhyt qkslslspgk
```

Nucleic Acid Sequence Encoding the Full Length Hu01G06 IGHV1-69 Heavy Chain (Humanized Heavy Chain Variable Region and Human IgG1 Constant Region) (SEQ ID NO:179)

```
   1 caagtccagc ttgtccagtc gggagcggaa gtgaagaaac
     cggggtcgtc ggtcaaagta 61 tcgtgtaaag cgtcgggata tacgtttacg gactataaca
     tggattgggt acgacaggct 121 ccggaaaat cattggaatg gattggacag attaatccga
     ataatggggg tatcttcttt 181 aatcaaaagt ttaaagggag ggcgacgttg acggtggaca
     aatcgacaaa tacggcgtat 241 atggaattgc gtcgcttcg gtcggaggac acggcggtgt
     attactgcgc gagggaggcg 301 atcacgacgg tcggggcgat ggattattgg ggacagggaa
     cgcttgtgac ggtatcgtcg 361 gcctcaacaa aaggaccaag tgtgttccca ctcgcccta
     gcagcaagag tacatccggg 421 ggcactgcag cactcggctg cctcgtcaag gattattttc
     cagagccagt aaccgtgagc 481 tggaacagtg gagcactcac ttctggtgtc catactttc
     ctgctgtcct gcaaagctct 541 ggcctgtact cactcagctc cgtcgtgacc gtgccatctt
     catctctggg cactcagacc 601 tacatctgta atgtaaacca caagcctagc aatactaagg
     tcgataagcg ggtgaaccc 661 aagagctgcg acaagactca cacttgtccc ccatgccctg
     cccctgaact tctgggcggt 721 cccagcgtct ttttgttccc accaaagcct aaagatactc
     tgatgataag tagaacaccc 781 gaggtgacat gtgttgttgt agacgtttcc cacgaggacc
     cagaggttaa gttcaactgg 841 tacgttgatg gagtcgaagt acataatgct aagaccaagc
     ctagagagga gcagtataat
```

```
901  agtacatacc gtgtagtcag tgttctcaca gtgctgcacc
     aagactggct caacggcaaa 961  gaatacaaat gcaaagtgtc caacaaagca ctcccagccc
     ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acgggtcttt ctttctgtac agtaagctga
     ctgtggacaa gtcccgctgg 1261 cagcaggta  acgtcttcag ctgttccgtg atgcacgagg
     cattgcacaa ccactacacc 1321 cagaagtcac tgagcctgag cccagggaag
```

Protein Sequence Defining the Full Length Hu01G06 IGHV1-69 Heavy Chain (Humanized Heavy Chain Variable Region and Human IgG1 Constant Region) (SEQ ID NO:180)

```
  1 qvqlvqsgae vkkpgssvkv sckasgytft dynmdwvrqa
    pgkslewigq inpnnggiff 61 nqkfkgratl tvdkstntay melsslrsed tavyycarea
    ittvgamdyw gqgtivtvss 121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn 301 styrvvsvlt vlhqdwlngk eykckvsnka lpapiektis
    kakgqprepq vytlppsree 361 mtknqvsltc lvkgfypsdi avewesngqp ennyktttppv
    ldsdgsffly skltvdksrw 421 qqgnvfscsv mhealhnhyt qkslslspgk
```

Nucleic Acid Sequence Encoding the Full Length Sh01G06 IGHV1-18 M69L Heavy Chain (Humanized Heavy Chain Variable Region and Human IgG1 Constant Region) (SEQ ID NO:181)

```
  1 caggtccagc ttgtgcaatc gggagcggaa gtgaagaaac
    cgggagcgtc ggtaaaagtc 61 tcgtgcaaag cgtcggggta tacgtttacg gactataaca
    tggactgggt gcgccaagcg 121 cctggacagg gtcttgaatg gatggggcag attaatccga
    ataatggagg gatcttcttt 181 aatcagaaat tcaaaggaag ggtaacgctg acgacagaca
    cgtcaacatc gacggcctat 241 atgaattgc  ggtcgttgcg atcagatgat acggcggtct
    actattgtgc gagggaggcg 301 attacgacgg tgggagcgat ggattattgg ggacagggga
    cgttggtaac ggtatcgtcg 361 gcctcaacaa aaggaccaag tgtgttccca ctcgccccta
    gcagcaagag tacatccggg
```

```
421 ggcactgcag cactcggctg cctcgtcaag gattattttc
    cagagccagt aaccgtgagc 481 tggaacagtg gagcactcac ttctggtgtc catactttc
    ctgctgtcct gcaaagctct 541 ggcctgtact cactcagctc cgtcgtgacc gtgccatctt
    catctctggg cactcagacc 601 tacatctgta atgtaaacca caagcctagc aatactaagg
    tcgataagcg ggtggaaccc 661 aagagctgcg acaagactca cacttgtccc ccatgccctg
    cccctgaact tctgggcggt 721 cccagcgtct ttttgttccc accaaagcct aaagatactc
    tgatgataag tagaacaccc 781 gaggtgacat gtgttgttgt agacgtttcc cacgaggacc
    cagaggttaa gttcaactgg 841 tacgttgatg gagtcgaagt acataatgct aagaccaagc
    ctagagagga gcagtataat 901 agtacatacc gtgtagtcag tgttctcaca gtgctgcacc
    aagactggct caacggcaaa 961 gaatacaaat gcaaagtgtc caacaaagca ctcccagccc
    ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acgggtcttt ctttctgtac agtaagctga
     ctgtggacaa gtcccgctgg 1261 cagcaggta  acgtcttcag ctgttccgtg atgcacgagg
     cattgcacaa ccactacacc 1321 cagaagtcac tgagcctgag cccagggaag
```

Protein Sequence Defining the Full Length Sh01G06 IGHV1-18 M69L Heavy Chain (Humanized Heavy Chain Variable Region and Human IgG1 Constant Region) (SEQ ID NO:182)

```
  1 qvqlvqsgae vkkpgasvkv sckasgytft dynmdwvrqa
    pgqglewmgq inpnnggiff 61 nqkfkgrvtl ttdtststay melrslrsdd tavyycarea
    ittvgamdyw gqgtivtvss 121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn 301 styrvvsvlt vlhqdwlngk eykckvsnka lpapiektis
    kakgqprepq vytlppsree 361 mtknqvsltc lvkgfypsdi avewesngqp ennyktttppv
    ldsdgsffly skltvdksrw 421 qqgnvfscsv mhealhnhyt qkslslspgk
```

Nucleic Acid Sequence Encoding the Full Length Sh01G06 IGHV1-18 M69L K64Q G44S Heavy Chain (Humanized Heavy Chain Variable Region and Human IgG1 Constant Region) (SEQ ID NO:183)

```
   1 caggtccagc ttgtgcaatc gggagcggaa gtgaagaaac
     cgggagcgtc ggtaaaagtc 61 tcgtgcaaag cgtcggggta tacgtttacg gactataaca
     tggactgggt gcgccaagcg 121 cctggacaga gccttgaatg gatggggcag attaatccga
     ataatggagg gatcttcttt 181 aatcagaaat tccagggaag ggtaacgctg acgacagaca
     cgtcaacatc gacggcctat 241 atggaattgc ggtcgttgcg atcagatgat acggcggtct
     actattgtgc gagggaggcg 301 attacgacgg tgggagcgat ggattattgg ggacagggga
     cgttggtaac ggtatcgtcg 361 gcctcaacaa aaggaccaag tgtgttccca ctcgcccta
     gcagcaagag tacatccggg 421 ggcactgcag cactcggctg cctcgtcaag gattattttc
     cagagccagt aaccgtgagc 481 tggaacagtg gagcactcac ttctggtgtc catactttc
     ctgctgtcct gcaaagctct 541 ggcctgtact cactcagctc cgtcgtgacc gtgccatctt
     catctctggg cactcagacc 601 tacatctgta atgtaaacca caagcctagc aatactaagg
     tcgataagcg ggtggaaccc 661 aagagctgcg acaagactca cacttgtccc ccatgccctg
     cccctgaact tctgggcggt 721 cccagcgtct ttttgttccc accaaagcct aaagatactc
     tgatgataag tagaacaccc 781 gaggtgacat gtgttgttgt agacgtttcc cacgaggacc
     cagaggttaa gttcaactgg 841 tacgttgatg gagtcgaagt acataatgct aagaccaagc
     ctagagagga gcagtataat 901 agtacatacc gtgtagtcag tgttctcaca gtgctgcacc
     aagactggct caacggcaaa 961 gaatacaaat gcaaagtgtc caacaaagca ctcccagccc
     ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acggtctttt ctttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Sh01G06 IGHV1-18 M69L K64Q G44S Heavy Chain (Humanized Heavy Chain Variable Region and Human IgG1 Constant Region) (SEQ ID NO:184)

```
   1 qvqlvqsgae vkkpgasvkv sckasgytft dynmdwvrqa
     pgqslewmgq inpnnggiff
```

```
  61 nqkfqgrvtl ttdtststay melrslrsdd tavyycarea
     ittvgamdyw gqgtivtvss 121 astkgpsvfp lapsskstsg gtaalgclvk dyfpepvtvs
     wnsgaltsgv htfpavlqss 181 glyslssvvt vpssslgtqt yicnvnhkps ntkvdkrvep
     kscdkthtcp pcpapellgg 241 psvflfppkp kdtlmisrtp evtcvvvdvs hedpevkfnw
     yvdgvevhna ktkpreeqyn 301 styrvvsvlt vlhqdwlngk eykckvsnka lpapiektis
     kakgqprepq vytlppsree 361 mtknqvsltc lvkgfypsdi avewesngqp ennykttppv
     ldsdgsffly skltvdksrw 421 qqgnvfscsv mhealhnhyt qkslslspgk
```

Nucleic Acid Sequence Encoding the Full Length Sh01G06 IGHV1-18 M69L K64Q Heavy Chain (Humanized Heavy Chain Variable Region and Human IgG1 Constant Region) (SEQ ID NO:185)

```
   1 caggtccagc ttgtgcaatc gggagcggaa gtgaagaaac
     cgggagcgtc ggtaaaagtc 61 tcgtgcaaag cgtcggggta tacgtttacg gactataaca
     tggactgggt gcgccaagcg 121 cctggacagg gtcttgaatg gatggggcag attaatccga
     ataatggagg gatcttcttt 181 aatcagaaat tccagggaag ggtaacgctg acgacagaca
     cgtcaacatc gacggcctat 241 atggaattgc ggtcgttgcg atcagatgat acggcggtct
     actattgtgc gagggaggcg 301 attacgacgg tgggagcgat ggattattgg ggacagggga
     cgttggtaac ggtatcgtcg 361 gcctcaacaa aaggaccaag tgtgttccca ctcgcccta
     gcagcaagag tacatccggg 421 ggcactgcag cactcggctg cctcgtcaag gattattttc
     cagagccagt aaccgtgagc 481 tggaacagtg gagcactcac ttctggtgtc catactttc
     ctgctgtcct gcaaagctct 541 ggcctgtact cactcagctc cgtcgtgacc gtgccatctt
     catctctggg cactcagacc 601 tacatctgta atgtaaacca caagcctagc aatactaagg
     tcgataagcg ggtggaaccc 661 aagagctgcg acaagactca cacttgtccc ccatgccctg
     cccctgaact tctgggcggt 721 cccagcgtct ttttgttccc accaaagcct aaagatactc
     tgatgataag tagaacaccc 781 gaggtgacat gtgttgttgt agacgtttcc cacgaggacc
     cagaggttaa gttcaactgg 841 tacgttgatg gagtcgaagt acataatgct aagaccaagc
     ctagagagga gcagtataat 901 agtacatacc gtgtagtcag tgttctcaca gtgctgcacc
     aagactggct caacggcaaa 961 gaatacaaat gcaaagtgtc caacaaagca ctcccagccc
     ctatcgagaa gactattagt
```

```
1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acgggtcttt ctttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Sh01G06 IGHV1-18 M69L K64Q Heavy Chain (Humanized Heavy Chain Variable Region and Human IgG1 Constant Region) (SEQ ID NO:186)

```
  1 qvqlvqsgae vkkpgasvkv sckasgytft dynmdwvrqa
    pgqglewmgq inpnnggiff 61 nqkfqgrvtl ttdtststay melrslrsdd tavyycarea
    ittvgamdyw gqgtlvtvss 121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn 301 styrvvsvlt vlhqdwlngk eykckvsnka lpapiektis
    kakgqprepq vytlppsree 361 mtknqvsltc lvkgfypsdi avewesngqp ennykttppv
    ldsdgsffly skltvdksrw 421 qqgnvfscsv mhealhnhyt qkslslspgk
```

Nucleic Acid Sequence Encoding the Full Length Sh01G06 IGHV1-69 T30S I69L Heavy Chain (Humanized Heavy Chain Variable Region and Human IgG1 Constant Region) (SEQ ID NO:187)

```
  1 caagtacagc ttgtacagtc gggagcggaa gtcaagaaac
    cgggatcgtc ggtcaaagtg 61 tcgtgtaaag cgtcgggata tacgtttagc gactataaca
    tggattgggt gcgacaagcg 121 cctggcagg acttgaatg gatgggtcag atcaatccga
    ataatggggg aatctttttc 181 aatcagaagt ttaaagggag ggtaacgctg acggcggata
    aaagcacgtc aacggcgtat 241 atggagttgt cgtcgttgcg gtcggaggac acggcggtct
    attactgcgc gagggaagcg 301 attacgacgg tgggagcgat ggattattgg gggcagggaa
    cgcttgtaac ggtgtcatcg 361 gcctcaacaa aaggaccaag tgtgttccca ctcgcccta
    gcagcaagag tacatccggg 421 ggcactgcag cactcggctg cctcgtcaag gattattttc
    cagagccagt aaccgtgagc 481 tggaacagtg gagcactcac ttctggtgtc catacttttc
    ctgctgtcct gcaaagctct
```

```
541 ggcctgtact cactcagctc cgtcgtgacc gtgccatctt
    catctctggg cactcagacc 601 tacatctgta atgtaaacca caagcctagc aatactaagg
    tcgataagcg ggtggaaccc 661 aagagctgcg acaagactca cacttgtccc ccatgccctg
    cccctgaact tctgggcggt 721 cccagcgtct ttttgttccc accaaagcct aaagatactc
    tgatgataag tagaacaccc 781 gaggtgacat gtgttgttgt agacgtttcc cacgaggacc
    cagaggttaa gttcaactgg 841 tacgttgatg gagtcgaagt acataatgct aagaccaagc
    ctagagagga gcagtataat 901 agtacatacc gtgtagtcag tgttctcaca gtgctgcacc
    aagactggct caacggcaaa 961 gaatacaaat gcaaagtgtc caacaaagca ctcccagccc
    ctatcgaaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acgggtcttt ctttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Sh01G06 IGHV1-69 T30S I69L Heavy Chain (Humanized Heavy Chain Variable Region and Human IgG1 Constant Region) (SEQ ID NO:188)

```
  1 qvqlvqsgae vkkpgssvkv sckasgytfs dynmdwvrqa
    pgqglewmgq inpnnggiff 61 nqkfkgrvtl tadkststay melsslrsed tavyycarea
    ittvgamdyw gqgtlvtvss 121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn 301 styrvvsvlt vlhqdwlngk eykckvsnka lpapiektis
    kakgqprepq vytlppsree 361 mtknqvsltc lvkgfypsdi avewesngqp ennykttppv
    ldsdgsffly skltvdksrw 421 qqgnvfscsv mhealhnhyt qkslslspgk
```

Nucleic Acid Sequence Encoding the Full Length Sh01G06 IGHV1-69 T30S K64Q I69L Heavy Chain (Humanized Heavy Chain Variable Region and Human IgG1 Constant Region) (SEQ ID NO:189)

```
  1 caagtacagc ttgtacagtc gggagcggaa gtcaagaaac
    cgggatcgtc ggtcaaagtg 61 tcgtgtaaag cgtcgggata tacgtttagc gactataaca
    tggattgggt gcgacaagcg 121 cctgggcagg acttgaatg gatgggtcag atcaatccga
    ataatggggg aatcttttc 181 aatcagaagt tcaggggag ggtaacgctg acggcggata
    aaagcacgtc aacggcgtat 241 atggagttgt cgtcgttgcg gtcggaggac acggcggtct
    attactgcgc gagggaagcg 301 attacgacgg tgggagcgat ggattattgg gggcagggaa
    cgcttgtaac ggtgtcatcg 361 gcctcaacaa aggaccaag tgtgttccca ctcgcccta
    gcagcaagag tacatccggg 421 ggcactgcag cactcggctg cctcgtcaag gattattttc
    cagagccagt aaccgtgagc 481 tggaacagtg gagcactcac ttctggtgtc catactttc
    ctgctgtcct gcaaagctct 541 ggcctgtact cactcagctc cgtcgtgacc gtgccatctt
    catctctggg cactcagacc 601 tacatctgta atgtaaacca caagcctagc aatactaagg
    tcgataagcg ggtggaaccc 661 aagagctgcg acaagactca cacttgtccc ccatgccctg
    cccctgaact tctgggcggt 721 cccagcgtct ttttgttccc accaaagcct aaagatactc
    tgatgataag tagaacaccc 781 gaggtgacat gtgttgttgt agacgtttcc cacgaggacc
    cagaggttaa gttcaactgg 841 tacgttgatg gagtcgaagt acataatgct aagaccaagc
    ctagagagga gcagtataat 901 agtacatacc gtgtagtcag tgttctcaca gtgctgcacc
    aagactggct caacggcaaa 961 gaatacaaat gcaaagtgtc caacaaagca ctcccagccc
    ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac cccccagtg 1201 ctggatagtg acgggtcttt ctttctgtac agtaagctga
     ctgtggacaa gtcccgctgg 1261 cagcaggta acgtcttcag ctgttccgtg atgcacgagg
     cattgcacaa ccactacacc 1321 cagaagtcac tgagcctgag cccagggaag
```

Protein Sequence Defining the Full Length Sh01G06 IGHV1-69 T30S K64Q I69L Heavy Chain (Humanized Heavy Chain Variable Region and Human IgG1 Constant Region) (SEQ ID NO:190)

```
  1 qvqlvqsgae vkkpgssvkv sckasgytfs dynmdwvrqa
    pgqglewmgq inpnnggiff 61 nqkfqgrvtl tadkststay melsslrsed tavyycarea
    ittvgamdyw gqgtlvtvss
```

```
121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn 301 styrvvsvlt vlhqdwlngk eykckvsnka lpapiektis
    kakgqprepq vytlppsree 361 mtknqvsltc lvkgfypsdi avewesngqp ennykttppv
    ldsdgsffly skltvdksrw 421 qqgnvfscsv mhealhnhyt qkslslspgk
```

Nucleic Acid Sequence Encoding the Full Length Hu01G06 IGHV1-18 F1 Heavy Chain (Humanized Heavy Chain Variable Region and Human IgG1 Constant Region) (SEQ ID NO:255)

```
  1 caggtccagc ttgtgcaatc gggagcggaa gtgaagaaac
    cgggagcgtc ggtaaaagtc 61 tcgtgcaaag cgtcgggta tacgtttacg gactataaca
    tggactgggt gcgccaagcg 121 cctggacaga gccttgaatg gatggggcag attaatccgt
    acaatcacct gatcttcttt 181 aatcagaaat tccagggaag ggtaacgctg acgacagaca
    cgtcaacatc gacggcctat 241 atggaattgc ggtcgttgcg atcagatgat acggcggtct
    actattgtgc gagggaggcg 301 attacgacgg tgggagcgat ggattattgg ggacagggga
    cgttggtaac ggtatcgtcg 361 gcctcaacaa aggaccaag tgtgttccca ctcgcccta
    gcagcaagag tacatccggg 421 ggcactgcag cactcggctg cctcgtcaag gattattttc
    cagagccagt aaccgtgagc 481 tggaacagtg gagcactcac ttctggtgtc catactttc
    ctgctgtcct gcaaagctct 541 ggcctgtact cactcagctc cgtcgtgacc gtgccatctt
    catctctggg cactcagacc 601 tacatctgta atgtaaacca caagcctagc aatactaagg
    tcgataagcg ggtggaaccc 661 aagagctgcg acaagactca cacttgtccc ccatgccctg
    cccctgaact tctgggcggt 721 cccagcgtct ttttgttccc accaaagcct aaagatactc
    tgatgataag tagaacaccc 781 gaggtgacat gtgttgttgt agacgtttcc cacgaggacc
    cagaggttaa gttcaactgg 841 tacgttgatg gagtcgaagt acataatgct aagaccaagc
    ctagagagga gcagtataat 901 agtacatacc gtgtagtcag tgttctcaca gtgctgcacc
    aagactggct caacggcaaa 961 gaatacaaat gcaaagtgtc caacaaagca ctcccagccc
    ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc
```

```
1141  gccgttgagt gggagagtaa cggtcagcct gagaacaatt
      acaagacaac ccccccagtg 1201  ctggatagtg acgggtcttt ctttctgtac agtaagctga
      ctgtggacaa gtcccgctgg 1261  cagcagggta acgtcttcag ctgttccgtg atgcacgagg
      cattgcacaa ccactacacc 1321  cagaagtcac tgagcctgag cccagggaag
```

Protein Sequence Defining the Full Length Hu01G06 IGHV1-18 F1 Heavy Chain (Humanized Heavy Chain Variable Region and Human IgG1 Constant Region) (SEQ ID NO:256)

```
  1  qvqlvqsgae vkkpgasvkv sckasgytft dynmdwvrqa
     pgqslewmgq inpynhliff 61  nqkfqgrvtl ttdtststay melrslrsdd tavyycarea
     ittvgamdyw gqgtlvtvss 121  astkgpsvfp lapsskstsg gtaalgclvk dyfpepvtvs
     wnsgaltsgv htfpavlqss 181  glyslssvvt vpssslgtqt yicnvnhkps ntkvdkrvep
     kscdkthtcp pcpapellgg 241  psvflfppkp kdtlmisrtp evtcvvvdvs hedpevkfnw
     yvdgvevhna ktkpreeqyn 301  styrvvsvlt vlhqdwlngk eykckvsnka lpapiektis
     kakgqprepq vytlppsree 361  mtknqvsltc lvkgfypsdi avewesngqp ennykttppv
     ldsdgsffly skltvdksrw 421  qqgnvfscsv mhealhnhyt qkslslspgk
```

Nucleic Acid Sequence Encoding the Full Length Hu01G06 IGHV1-18 F2 Heavy Chain (Humanized Heavy Chain Variable Region and Human IgG1 Constant Region) (SEQ ID NO:257)

```
  1  caggtccagc ttgtgcaatc gggagcggaa gtgaagaaac
     cgggagcgtc ggtaaaagtc 61  tcgtgcaaag cgtcggggta tacgtttacg gactataaca
     tggactgggt gcgccaagcg 121  cctggacaga gccttgaatg gatggggcag attaatccga
     ataatggact gatcttcttt 181  aatcagaaat tccaggggaag ggtaacgctg acgacagaca
     cgtcaacatc gacggcctat 241  atggaattgc ggtcgttgcg atcagatgat acggcggtct
     actattgcg gagggaggcg 301  attacgacgg tgggagcgat ggattattgg gacagggga
     cgttggtaac ggtatcgtcg 361  gcctcaacaa aaggaccaag tgtgttccca ctcgcccta
     gcagcaagag tacatccggg 421  ggcactgcag cactcggctg cctcgtcaag gattattttc
     cagagccagt aaccgtgagc 481  tggaacagtg gagcactcac ttctggtgtc catactttc
     ctgctgtcct gcaaagctct 541  ggcctgtact cactcagctc cgtcgtgacc gtgccatctt
     catctctggg cactcagacc 601  tacatctgta atgtaaacca caagcctagc aatactaagg
     tcgataagcg ggtggaaccc 661  aagagctgcg acaagactca cacttgtccc ccatgccctg
     ccctgaact tctgggcggt 721  cccagcgtct ttttgttccc accaaagcct aaagatactc
     tgatgataag tagaacaccc 781  gaggtgacat gtgttgttgt agacgtttcc cacgaggacc
     cagaggttaa gttcaactgg 841  tacgttgatg gagtcgaagt acataatgct aagaccaagc
     ctagagagga gcagtataat 901  agtacatacc gtgtagtcag tgttctcaca gtgctgcacc
     aagactggct caacggcaaa 961  gaatacaaat gcaaagtgtc caacaaagca ctcccagccc
     ctatcgaaga gactattagt 1021 aaggcaaagg ggcagcctcg tgaaccacag gtgtacactc
     tgccacccag tagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac ccccccagtg 1201 ctggatagtg acgggtcttt ctttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Hu01G06 IGHV1-18 F2 Heavy Chain (Humanized Heavy Chain Variable Region and Human IgG1 Constant Region) (SEQ ID NO:258)

```
  1  qvqlvqsgae vkkpgasvkv sckasgytft dynmdwvrqa
     pgqslewmgq inpnngliff 61  nqkfqgrvtl ttdtststay melrslrsdd tavyycarea
     ittvgamdyw gqgtlvtvss 121  astkgpsvfp lapsskstsg gtaalgclvk dyfpepvtvs
     wnsgaltsgv htfpavlqss 181  glyslssvvt vpssslgtqt yicnvnhkps ntkvdkrvep
     kscdkthtcp pcpapellgg 241  psvflfppkp kdtlmisrtp evtcvvvdvs hedpevkfnw
     yvdgvevhna ktkpreeqyn 301  styrvvsvlt vlhqdwlngk eykckvsnka lpapiektis
     kakgqprepq vytlppsree 361  mtknqvsltc lvkgfypsdi avewesngqp ennykttppv
     ldsdgsffly skltvdksrw 421  qqgnvfscsv mhealhnhyt qkslslspgk
```

Nucleic Acid Sequence Encoding the Full Length Hu01G06 IGHV1-69 F1 Heavy Chain (Humanized Heavy Chain Variable Region and Human IgG1 Constant Region) (SEQ ID NO:259)

```
  1  caagtacagc ttgtacagtc gggagcggaa gtcaagaaac
     cgggatcgtc ggtcaaagtg 61  tcgtgtaaag cgtcgggata tacgtttagc gactataaca
     tggattgggt gcgacaagcg
```

-continued

```
121  cctgggcagg gacttgaatg gatgggtcag atcaatccga
     ataatgggct gatctttttc 181  aatcagaagt ttaaagggag ggtaacgctg acggcggata
     aaagcacgtc aacggcgtat 241  atggagttgt cgtcgttgcg gtcggaggac acggcggtct
     attactgcgc gagggaagcg 301  attacgacgg tgggagcgat ggattattgg gggcagggaa
     cgcttgtaac ggtgtcatcg 361  gcctcaacaa aaggaccaag tgtgttccca ctcgcccta
     gcagcaagag tacatccggg 421  ggcactgcag cactcggctg cctcgtcaag gattattttc
     cagagccagt aaccgtgagc 481  tggaacagtg gagcactcac ttctggtgtc catactttc
     ctgctgtcct gcaaagctct 541  ggcctgtact cactcagctc cgtcgtgacc gtgccatctt
     catctctggg cactcagacc 601  tacatctgta atgtaaacca caagcctagc aatactaagg
     tcgataagcg ggtggaaccc 661  aagagctgcg acaagactca cacttgtccc ccatgccctg
     cccctgaact tctgggcggt 721  cccagcgtct ttttgttccc accaaagcct aaagatactc
     tgatgataag tagaacaccc 781  gaggtgacat gtgttgttgt agacgtttcc cacgaggacc
     cagaggttaa gttcaactgg 841  tacgttgatg gagtcgaagt acataatgct aagaccaagc
     ctagagagga gcagtataat 901  agtacatacc gtgtagtcag tgttctcaca gtgctgcacc
     aagactggct caacggcaaa 961  gaatacaaat gcaaagtgtc caacaaagca ctcccagccc
     ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac ccccccagtg 1201 ctggatagtg acgggtcttt ctttctgtac agtaagctga
     ctgtggacaa gtcccgctgg 1261 cagcagggta acgtcttcag ctgttccgtg atgcacgagg
     cattgcacaa ccactacacc 1321 cagaagtcac tgagcctgag cccagggaag
```

Protein Sequence Defining the Full Length Hu01G06 IGHV1-69 F1 Heavy Chain (Humanized Heavy Chain Variable Region and Human IgG1 Constant Region) (SEQ ID NO:260)

```
  1  qvqlvqsgae vkkpgssvkv sckasgytfs dynmdwvrqa
     pgqglewmgq inpnngliff 61  nqkfkgrvtl tadkststay melsslrsed tavyycarea
     ittvgamdyw gqgtivtvss 121  astkgpsvfp lapssktstsg gtaalgclvk dyfpepvtvs
     wnsgaltsgv htfpavlqss 181  glyslssvvt vpssslgtqt yicnvnhkps ntkvdkrvep
     kscdkthtcp pcpapellgg
```

-continued
```
241  psvflfppkp kdtlmisrtp evtcvvvdvs hedpevkfnw
     yvdgvevhna ktkpreeqyn 301  styrvvsvlt vlhqdwlngk eykckvsnka lpapiektis
     kakgqprepq vytlppsree 361  mtknqvsltc lvkgfypsdi avewesngqp ennykttppv
     ldsdgsffly skltvdksrw 421  qqgnvfscsv mhealhnhyt qkslslspgk
```

Nucleic Acid Sequence Encoding the Full Length Hu01G06 IGHV1-69 F2 Heavy Chain (Humanized Heavy Chain Variable Region and Human IgG1 Constant Region) (SEQ ID NO:261)

```
  1  caagtacagc ttgtacagtc gggagcggaa gtcaagaaac
     cgggatcgtc ggtcaaagtg 61  tcgtgtaaag cgtcgggata tacgtttagc gactataaca
     tggattgggg gcgacaagcg 121  cctgggcagg gacttgaatg gatgggtcag atcaatccgt
     acaatcacct gatctttttc 181  aatcagaagt ttaaagggag ggtaacgctg acggcggata
     aaagcacgtc aacggcgtat 241  atggagttgt cgtcgttgcg gtcggaggac acggcggtct
     attactgcgc gagggaagcg 301  attacgacgg tgggagcgat ggattattgg gggcagggaa
     cgcttgtaac ggtgtcatcg 361  gcctcaacaa aaggaccaag tgtgttccca ctcgcccta
     gcagcaagag tacatccggg 421  ggcactgcag cactcggctg cctcgtcaag gattattttc
     cagagccagt aaccgtgagc 481  tggaacagtg gagcactcac ttctggtgtc catactttc
     ctgctgtcct gcaaagctct 541  ggcctgtact cactcagctc cgtcgtgacc gtgccatctt
     catctctggg cactcagacc 601  tacatctgta atgtaaacca caagcctagc aatactaagg
     tcgataagcg ggtggaaccc 661  aagagctgcg acaagactca cacttgtccc ccatgccctg
     cccctgaact tctgggcggt 721  cccagcgtct ttttgttccc accaaagcct aaagatactc
     tgatgataag tagaacaccc 781  gaggtgacat gtgttgttgt agacgtttcc cacgaggacc
     cagaggttaa gttcaactgg 841  tacgttgatg gagtcgaagt acataatgct aagaccaagc
     ctagagagga gcagtataat 901  agtacatacc gtgtagtcag tgttctcaca gtgctgcacc
     aagactggct caacggcaaa 961  gaatacaaat gcaaagtgtc caacaaagca ctcccagccc
     ctatcgagaa gactattagt 1021 aaggcaaagg ggcagcctcg tgaaccacag gtgtacactc
     tgccacccag tagagaggaa 1081 atgacaaaga accaagtctc attgacctgc ctggtgaaag
     gcttctaccc cagcgacatc 1141 gccgttgagt gggagagtaa cggtcagcct gagaacaatt
     acaagacaac ccccccagtg
```

```
     -continued
1201 ctggatagtg acgggtcttt ctttctgtac agtaagctga
     ctgtggacaa gtcccgctgg 1261 cagcagggta acgtcttcag ctgttccgtg atgcacgagg
     cattgcacaa ccactcacc 1321 cagaagtcac tgagcctgag cccagggaag
```

Protein Sequence Defining the Full Length Hu01G06 IGHV1-69 F2 Heavy Chain (Humanized Heavy Chain Variable Region and Human IgG1 Constant Region) (SEQ ID NO:262)

```
  1 qvqlvqsgae vkkpgssvkv sckasgytfs dynmdwvrqa
    pgqglewmgq inpynhliff 61 nqkfkgrvtl tadkststay melsslrsed tavyycarea
    ittvgamdyw gqgtivtvss 121 astkgpsvfp lapsskstsg gtaalgclvk dyfpepvtvs
    wnsgaltsgv htfpavlqss 181 glyslssvvt vpssslgtqt yicnvnhkps ntkvdkrvep
    kscdkthtcp pcpapellgg 241 psvflfppkp kdtlmisrtp evtcvvvdvs hedpevkfnw
    yvdgvevhna ktkpreeqyn 301 styrvvsvlt vlhqdwlngk eykckvsnka lpapiektis
    kakgqprepq vytlppsree 361 mtknqvsltc lvkgfypsdi avewesngqp ennyktttppv
    ldsdgsffly skltvdksrw 421 qqgnvfscsv mhealhnhyt qkslslspgk
```

Nucleic Acid Sequence Encoding the Full Length Ch06C11 Chimeric Heavy Chain (Mouse Heavy Chain Variable Region and Human IgG1 Constant Region) (SEQ ID NO:191)

```
  1 caggtgacac tcaaagaatc aggacccgga atccttcagc
    ccagccagac cttgtcgctg 61 acttgttcgt tctccggttt cagcctgaat acttatggga
    tgggtgtgtc atggatcagg 121 caaccgtccg ggaaaggatt ggagtggctc gcgcacatct
    actgggacga tgacaaacgc 181 tacaatcctc cgctgaagag ccgattgacg atttccaagg
    atgcctcgaa caaccgggta 241 tttcttaaga tcacgtcggt cgatacggca gacacggcga
    cctattactg cgcccaaaga 301 gggtacgatg actattgggg atattgggc caggggacac
    tcgtcacaat ttcagctgcc 361 tcaacaaaag gaccaagtgt gttcccactc gcccctagca
    gcaagagtac atccggggc 421 actgcagcac tcggctgcct cgtcaaggat tattttccag
    agccagtaac cgtgagctgg 481 aacagtggag cactcacttc tggtgtccat acttttcctg
    ctgtcctgca aagctctggc 541 ctgtactcac tcagctccgt cgtgaccgtg ccatcttcat
    ctctgggcac tcagacctac 601 atctgtaatg taaaccacaa gcctagcaat actaaggtcg
    ataagcgggt ggaacccaag 661 agctgcgaca agactcacac ttgtccccca tgccctgccc
    ctgaacttct gggcggtccc
```

```
     -continued
 721 agcgtcttt tgttcccacc aaagcctaaa gatactctga
     tgataagtag aacacccgag 781 gtgacatgtg ttgttgtaga cgtttccac gaggacccag
     aggttaagtt caactggtac 841 gttgatggag tcgaagtaca taatgctaag accaagccta
     gagaggagca gtataatagt 901 acataccgtg tagtcagtgt tctcacagtg ctgcaccaag
     actggctcaa cggcaaagaa 961 tacaaatgca aagtgtccaa caaagcactc ccagcccta
     tcgagaagac tattagtaag 1021 gcaaggggc agcctcgtga accacaggtg tacactctgc
     cacccagtag agaggaaatg 1081 acaaagaacc aagtctcatt gacctgcctg gtgaaaggct
     tctaccccga cgacatcgcc 1141 gttgagtggg agagtaacgg tcagcctgag aacaattaca
     agacaacccc cccagtgctg 1201 gatagtgacg ggtctttctt tctgtacagt aagctgactg
     tggacaagtc ccgctggcag 1261 cagggtaacg tcttcagctg ttccgtgatg cacgaggcat
     tgcacaacca ctacacccag 1321 aagtcactga gcctgagccc agggaag
```

Protein Sequence Defining the Full Length Ch06C11 Chimeric Heavy Chain (Mouse Heavy Chain Variable Region and Human IgG1 Constant Region) (SEQ ID NO:192)

```
  1 qvtlkesgpg ilqpsqtlsl tcsfsgfsln tygmgvswir
    qpsgkglewl ahiywdddkr 61 ynpslksrlt iskdasnnrv flkitsvdta dtatyycaqr
    gyddywgywg qgtlvtisaa 121 stkgpsvfpl apsskstsgg taalgclvkd yfpepvtvsw
    nsgaltsgvh tfpavlqssg 181 lyslssvvtv pssslgtqty icnvnhkpsn tkvdkrvepk
    scdkthtcpp cpapellggp 241 svflfppkpk dtlmisrtpe vtcvvvdvsh edpevkfnwy
    vdgvevhnak tkpreeqyns 301 tyrvvsvltv lhqdwlngke ykckvsnkal papiektisk
    akgqprepqv ytlppsreem 361 tknqvsltcl vkgfypsdia vewesngqpe nnyktttppvl
    dsdgsfflys kltvdksrwq 421 qgnvfscsvm healhnhytq kslslspgk
```

Nucleic Acid Sequence Encoding the Full Length HE LM 06C11 IGHV2-70 Heavy Chain (Humanized Heavy Chain Variable Region and Human IgG1 Constant Region) (SEQ ID NO:193)

```
  1 caggtgactt tgaaagaatc cggtcccgca ttggtaaagc
    caacccagac acttacgctc 61 acatgtacat tttccggatt cagcttgaac acttacggga
    tgggagtgtc gtggattcgg 121 caacctccgg ggaaggctct ggagtggctg gcgcacatct
    actgggatga tgacaaaagg 181 tataacccct cacttaaaac gagactgacg atctcgaagg
    acacaagcaa gaatcaggtc
```

```
241 gtcctcacga ttacgaatgt agacccggtg gatactgccg
    tctattactg cgcgcaacgc 301 gggtatgatg actactgggg atattggggt cagggcaccc
    tcgtgaccat ctcgtcagcc 361 tcaacaaaag gaccaagtgt gttcccactc gcccctagca
    gcaagagtac atccgggggc 421 actgcagcac tcggctgcct cgtcaaggat tattttccag
    agccagtaac cgtgagctgg 481 aacagtggag cactcacttc tggtgtccat acttttcctg
    ctgtcctgca aagctctggc 541 ctgtactcac tcagctccgt cgtgaccgtg ccatcttcat
    ctctgggcac tcagacctac 601 atctgtaatg taaaccacaa gcctagcaat actaaggtcg
    ataagcgggt ggaacccaag 661 agctgcgaca agactcacac ttgtccccca tgccctgccc
    ctgaacttct gggcggtccc 721 agcgtctttt tgttcccacc aaagcctaaa gatactctga
    tgataagtag aacacccgag 781 gtgacatgtg ttgttgtaga cgtttcccac gaggacccag
    aggttaagtt caactggtac 841 gttgatggag tcgaagtaca taatgctaag accaagccta
    gagaggagca gtataatagt 901 acataccgtg tagtcagtgt tctcacagtg ctgcaccaag
    actggctcaa cggcaaagaa 961 tacaaatgca aagtgtccaa caaagcactc ccagcccta
    tcgagaagac tattagtaag 1021 gcaaaggggc agcctcgtga accacaggtg tacactctgc
     cacccagtag agaggaaatg 1081 acaaagaacc aagtctcatt gacctgcctg gtgaaaggct
     tctacccag cgacatcgcc 1141 gttgagtggg agagtaacgg tcagcctgag aacaattaca
     agacaacccc cccagtgctg 1201 gatagtgacg ggtctttctt tctgtacagt aagctgactg
     tggacaagtc ccgctggcag 1261 cagggtaacg tcttcagctg ttccgtgatg cacgaggcat
     tgcacaacca ctacacccag 1321 aagtcactga gcctgagccc agggaag
```

Protein Sequence Defining the Full Length HE LM 06C11 IGHV2-70 Heavy Chain (Humanized Heavy Chain Variable Region and Human IgG1 Constant Region) (SEQ ID NO:194)

```
  1 qvtlkesgpa lvkptqtltl tctfsgfsln tygmgvswir
    qppgkalewl ahiywdddkr 61 ynpslktrlt iskdtsknqv vltitnvdpv dtavyycaqr
    gyddywgywg qgtlvtissa 121 stkgpsvfpl apssкstsgg taalgclvkd yfpepvtvsw
    nsgaltsgvh tfpavlqssg 181 lyslssvvtv pssslgtqty icnvnhkpsn tkvdkrvepk
    scdkthtcpp cpapellggp 241 svflfppkpk dtlmisrtpe vtcvvvdvsh edpevkfnwy
    vdgvevhnak tkpreeqyns 301 tyrvvsvltv lhqdwlngke ykckvsnkal papiektisk
    akgqprepqv ytlppsreem 361 tknqvsltcl vkgfypsdia vewesngqpe nnykttppvl
    dsdgsfflys kltvdksrwq 421 qgnvfscsvm healhnhytq kslslspgk
```

Nucleic Acid Sequence Encoding the Full Length Hu06C11 IGHV2-5 Heavy Chain (Humanized Heavy Chain Variable Region and Human IgG1 Constant Region) (SEQ ID NO:195)

```
  1 caagtaacgc tcaaggagtc cggacccacc ttggtgaagc
    cgacgcagac cttgactctt 61 acgtgcactt tctcgggggtt ttcactgaat acgtacggga
    tgggtgtctc atggatcagg 121 caacctccgg ggaaaggatt ggaatggctg gcgcacatct
    actgggatga cgataagaga 181 tataacccaa gcctcaagtc gcggctcacc attacaaaag
    atacatcgaa aaatcaggtc 241 gtacttacta tcacgaacat ggaccccgtg gacacagcaa
    catattactg tgcccagcgc 301 ggctatgacg attattgggg ttactgggga cagggaacac
    tggtcacggt gtccagcgcc 361 tcaacaaaag gaccaagtgt gttcccactc gcccctagca
    gcaagagtac atccgggggc 421 actgcagcac tcggctgcct cgtcaaggat tattttccag
    agccagtaac cgtgagctgg 481 aacagtggag cactcacttc tggtgtccat acttttcctg
    ctgtcctgca aagctctggc 541 ctgtactcac tcagctccgt cgtgaccgtg ccatcttcat
    ctctgggcac tcagacctac 601 atctgtaatg taaaccacaa gcctagcaat actaaggtcg
    ataagcgggt ggaacccaag 661 agctgcgaca agactcacac ttgtccccca tgccctgccc
    ctgaacttct gggcggtccc 721 agcgtctttt tgttcccacc aaagcctaaa gatactctga
    tgataagtag aacacccgag 781 gtgacatgtg ttgttgtaga cgtttcccac gaggacccag
    aggttaagtt caactggtac 841 gttgatggag tcgaagtaca taatgctaag accaagccta
    gagaggagca gtataatagt 901 acataccgtg tagtcagtgt tctcacagtg ctgcaccaag
    actggctcaa cggcaaagaa 961 tacaaatgca aagtgtccaa caaagcactc ccagcccta
    tcgagaagac tattagtaag 1021 gcaaaggggc agcctcgtga accacaggtg tacactctgc
     cacccagtag agaggaaatg 1081 acaaagaacc aagtctcatt gacctgcctg gtgaaaggct
     tctacccag cgacatcgcc 1141 gttgagtggg agagtaacgg tcagcctgag aacaattaca
     agacaacccc cccagtgctg 1201 gatagtgacg ggtctttctt tctgtacagt aagctgactg
     tggacaagtc ccgctggcag 1261 cagggtaacg tcttcagctg ttccgtgatg cacgaggcat
     tgcacaacca ctacacccag 1321 aagtcactga gcctgagccc agggaag
```

Protein Sequence Defining the Full Length Hu06C11 IGHV2-5 Heavy Chain (Humanized Heavy Chain Variable Region and Human IgG1 Constant Region) (SEQ ID NO:196)

```
  1 qvtlkesgpt lvkptqtltl tctfsgfsln tygmgvswir
    qppgkglewl ahiywdddkr 61 ynpslksrlt itkdtsknqv vltitnmdpv dtatyycaqr
    gyddywgywg qgtlvtvssa 121 stkgpsvfpl apsskstsgg taalgclvkd yfpepvtvsw
    nsgaltsgvh tfpavlqssg 181 lyslssvvtv pssslgtqty icnvnhkpsn tkvdkrvepk
    scdkthtcpp cpapellggp 241 svflfppkpk dtlmisrtpe vtcvvvdvsh edpevkfnwy
    vdgvevhnak tkpreeqyns 301 tyrvvsvltv lhqdwlngke ykckvsnkal papiektisk
    akgqprepqv ytlppsreem 361 tknqvsltcl vkgfypsdia vewesngqpe nnyktttppvl
    dsdgsfflys kltvdksrwq 421 qgnvfscsvm healhnhytq kslslspgk
```

Nucleic Acid Sequence Encoding the Full Length Ch14F11 Chimeric Heavy Chain (Mouse Heavy Chain Variable Region and Human IgG1 Constant Region) (SEQ ID NO:197)

```
  1 caggtcacgc tgaaagagtc aggtcccgga atccttcaac
    cttcgcagac attgtcactc 61 acatgttcct tctccgggtt ctcgctctcg acttatggca
    tgggtgtagg atggattcgg 121 cagcccagcg ggaaggggct tgagtggttg gcggatatct
    ggtgggacga cgacaaatac 181 tacaatccga gcctgaagtc ccgcctcacc atttcgaaag
    atacgtcatc aaacgaagtc 241 tttttgaaga tcgccatcgt ggacacggcg gatacagcga
    cgtattactg cgccagaagg 301 ggacactaca gcgcaatgga ttattgggga caggggacct
    cggtgactgt gtcgtccgcc 361 tcaacaaaag gaccaagtgt gttcccactc gcccctagca
    gcaagagtac atccggggc 421 actgcagcac tcggctgcct cgtcaaggat tattttccag
    agccagtaac cgtgagctgg 481 aacagtggag cactcacttc tggtgtccat acttttcctg
    ctgtcctgca aagctctggc 541 ctgtactcac tcagctccgt cgtgaccgtg ccatcttcat
    ctctgggcac tcagacctac 601 atctgtaatg taaaccacaa gcctagcaat actaaggtcg
    ataagcgggt ggaacccaag 661 agctgcgaca agactcacac ttgtcccca tgccctgccc
    ctgaacttct gggcggtccc 721 agcgtctttt tgttcccacc aaagcctaaa gatactctga
    tgataagtag aacacccgag 781 gtgacatgtg ttgttgtaga cgtttcccac gaggaccag
    aggttaagtt caactggtac 841 gttgatggag tcgaagtaca taatgctaag accaagccta
    gagaggagca gtataatagt
```

```
 901 acataccgtg tagtcagtgt tctcacagtg ctgcaccaag
     actggctcaa cggcaaagaa 961 tacaaatgca aagtgtccaa caaagcactc ccagcccta
     tcgagaagac tattagtaag 1021 gcaaaggggc agcctcgtga accacaggtg tacactctgc
     cacccagtag agaggaaatg 1081 acaaagaacc aagtctcatt gacctgcctg gtgaaaggct
     tctaccccag cgacatcgcc 1141 gttgagtggg agagtaacgg tcagcctgag aacaattaca
     agacaaccc cccagtgctg 1201 gatagtgacg ggtctttctt tctgtacagt aagctgactg
     tggacaagtc ccgctggcag 1261 cagggtaacg tcttcagctg ttccgtgatg cacgaggcat
     tgcacaacca ctacacccag 1321 aagtcactga gcctgagccc agggaag
```

Protein Sequence Defining the Full Length Ch14F11 Chimeric Heavy Chain (Mouse Heavy Chain Variable Region and Human IgG1 Constant Region) (SEQ ID NO:198)

```
  1 qvtlkesgpg ilqpsqtlsl tcsfsgfsls tygmgvgwir
    qpsgkglewl adiwwdddky 61 ynpslksrlt iskdtssnev flkiaivdta dtatyycarr
    ghysamdywg qgtsvtvssa 121 stkgpsvfpl apsskstsgg taalgclvkd yfpepvtvsw
    nsgaltsgvh tfpavlqssg 181 lyslssvvtv pssslgtqty icnvnhkpsn tkvdkrvepk
    scdkthtcpp cpapellggp 241 svflfppkpk dtlmisrtpe vtcvvvdvsh edpevkfnwy
    vdgvevhnak tkpreeqyns 301 tyrvvsvltv lhqdwlngke ykckvsnkal papiektisk
    akgqprepqv ytlppsreem 361 tknqvsltcl vkgfypsdia vewesngqpe nnykttppvl
    dsdgsfflys kltvdksrwq 421 qgnvfscsvm healhnhytq kslslspgk
```

Nucleic Acid Sequence Encoding the Full Length Sh14F11 IGHV2-5 Heavy Chain (Humanized Heavy Chain Variable Region and Human IgG1 Constant Region) (SEQ ID NO:199)

```
  1 cagatcactt tgaaagaaag cggaccgacc ttggtcaagc
    ccacacaaac cctcacgctc 61 acgtgtacat tttcggggtt ctcgctttca acttacggga
    tgggagtagg gtggattcgc 121 cagccgcctg gtaaagcgtt ggagtggctt gcagacatct
    ggtgggacga cgataagtac 181 tataatccct cgctcaagtc cagactgacc atcacgaaag
    atacgagcaa gaaccaggtc 241 gtgctgacaa tgactaacat ggacccagtg gatacggcta
    catattactg cgccaggcgg 301 ggtcactact cagcgatgga ttattgggc caggggaacac
    tggtaacggt gtcgtccgcc 361 tcaacaaaag gaccaagtgt gttcccactc gcccctagca
    gcaagagtac atccggggc
```

-continued

```
 421 actgcagcac tcggctgcct cgtcaaggat tattttccag
     agccagtaac cgtgagctgg 481 aacagtggag cactcacttc tggtgtccat acttttcctg
     ctgtcctgca aagctctggc 541 ctgtactcac tcagctccgt cgtgaccgtg ccatcttcat
     ctctgggcac tcagacctac 601 atctgtaatg taaaccacaa gcctagcaat actaaggtcg
     ataagcgggt ggaacccaag 661 agctgcgaca agactcacac ttgtccccca tgccctgccc
     ctgaacttct gggcggtccc 721 agcgtctttt tgttcccacc aaagcctaaa gatactctga
     tgataagtag aacacccgag 781 gtgacatgtg ttgttgtaga cgtttcccac gaggacccag
     aggttaagtt caactggtac 841 gttgatggag tcgaagtaca taatgctaag accaagccta
     gagaggagca gtataatagt 901 acataccgtg tagtcagtgt tctcacagtg ctgcaccaag
     actggctcaa cggcaaagaa 961 tacaaatgca aagtgtccaa caaagcactc ccagccccta
     tcgagaagac tattagtaag 1021 gcaaaggggc agcctcgtga accacaggtg tacactctgc
     cacccagtag agaggaaatg 1081 acaaagaacc aagtctcatt gacctgcctg gtgaaaggct
     tctacccag cgacatcgcc 1141 gttgagtggg agagtaacgg tcagcctgag aacaattaca
     agacaacccc cccagtgctg 1201 gatagtgacg ggtctttctt tctgtacagt aagctgactg
     tggacaagtc ccgctggcag 1261 cagggtaacg tcttcagctg ttccgtgatg cacgaggcat
     tgcacaacca ctacacccag 1321 aagtcactga gcctgagccc agggaag
```

Protein Sequence Defining the Full Length Sh14F11 IGHV2-5 Heavy Chain (Humanized Heavy Chain Variable Region and Human IgG1 Constant Region) (SEQ ID NO:200)

```
  1 qitlkesgpt lvkptqtltl tctfsgfsls tygmgvgwir
    qppgkalewl adiwwdddky 61 ynpslksrlt itkdtsknqv vltmtnmdpv dtatyycarr
    ghysamdywg qgtlvtvssa 121 stkgpsvfpl apsskstsgg taalgclvkd yfpepvtvsw
    nsgaltsgvh tfpavlqssg 181 lyslssvvtv pssslgtqty icnvnhkpsn tkvdkrvepk
    scdkthtcpp cpapellggp 241 svflfppkpk dtlmisrtpe vtcvvvdvsh edpevkfnwy
    vdgvevhnak tkpreeqyns 301 tyrvvsvltv lhqdwlngke ykckvsnkal papiektisk
    akgqprepqv ytlppsreem 361 tknqvsltcl vkgfypsdia vewesngqpe nnykttppvl
    dsdgsfflys kltvdksrwq 421 qgnvfscsvm healhnhytq kslslspgk
```

Nucleic Acid Sequence Encoding the Full Length Sh14F11 IGHV2-70 Heavy Chain (Humanized Heavy Chain Variable Region and Human IgG1 Constant Region) (SEQ ID NO:201)

```
   1 caagtgactc tcaaggagtc cggacccgcc ctggtcaaac
     caacgcagac actgacgctc 61 acatgcacct tcagcggatt ttcgttgtca acgtacggca
     tgggtgtggg gtggattcgc 121 cagcctccgg ggaaagccct tgaatggttg gcggacatct
     ggtgggatga tgacaagtac 181 tataatccct cacttaagtc acggttgacg atctcgaaag
     acaccagcaa gaaccaggta 241 gtgctgacaa tgactaacat ggacccggtc gatacagcgg
     tctactattg tgctagaagg 301 ggacactact ccgcaatgga ttattgggt caggggacgc
     tcgtaaccgt gtcgtcggcc 361 tcaacaaaag gaccaagtgt gttcccactc gcccctagca
     gcaagagtac atccggggc 421 actgcagcac tcggctgcct cgtcaaggat tattttccag
     agccagtaac cgtgagctgg 481 aacagtggag cactcacttc tggtgtccat acttttcctg
     ctgtcctgca aagctctggc 541 ctgtactcac tcagctccgt cgtgaccgtg ccatcttcat
     ctctgggcac tcagacctac 601 atctgtaatg taaaccacaa gcctagcaat actaaggtcg
     ataagcgggt ggaacccaag 661 agctgcgaca agactcacac ttgtccccca tgccctgccc
     ctgaacttct gggcggtccc 721 agcgtctttt tgttcccacc aaagcctaaa gatactctga
     tgataagtag aacacccgag 781 gtgacatgtg ttgttgtaga cgtttcccac gaggacccag
     aggttaagtt caactggtac 841 gttgatggag tcgaagtaca taatgctaag accaagccta
     gagaggagca gtataatagt 901 acataccgtg tagtcagtgt tctcacagtg ctgcaccaag
     actggctcaa cggcaaagaa 961 tacaaatgca aagtgtccaa caaagcactc ccagccccta
     tcgagaagac tattagtaag 1021 gcaaaggggc agcctcgtga accacaggtg tacactctgc
     cacccagtag agaggaaatg 1081 acaaagaacc aagtctcatt gacctgcctg gtgaaaggct
     tctacccag cgacatcgcc 1141 gttgagtggg agagtaacgg tcagcctgag aacaattaca
     agacaacccc cccagtgctg 1201 gatagtgacg ggtctttctt tctgtacagt aagctgactg
     tggacaagtc ccgctggcag 1261 cagggtaacg tcttcagctg ttccgtgatg cacgaggcat
     tgcacaacca ctacacccag 1321 aagtcactga gcctgagccc agggaag
```

Protein Sequence Defining the Full Length Sh14F11 IGHV2-70 Heavy Chain (Humanized Heavy Chain Variable Region and Human IgG1 Constant Region) (SEQ ID NO:202)

```
  1 qvtlkesgpa lvkptqtltl tctfsgfsls tygmgvgwir
    qppgkalewl adiwwdddky 61 ynpslksrlt iskdtsknqv vltmtnmdpv dtavyycarr
    ghysamdywg qgtlvtvssa 121 stkgpsvfpl apsskstsgg taalgclvkd yfpepvtvsw
    nsgaltsgvh tfpavlqssg 181 lyslssvvtv pssslgtqty icnvnhkpsn tkvdkrvepk
    scdkthtcpp cpapellggp 241 svflfppkpk dtlmisrtpe vtcvvvdvsh edpevkfnwy
    vdgvevhnak tkpreeqyns 301 tyrvvsvltv lhqdwlngke ykckvsnkal papiektisk
    akgqprepqv ytlppsreem 361 tknqvsltcl vkgfypsdia vewesngqpe nnykttppvl
    dsdgsfflys kltvdksrwq 421 qgnvfscsvm healhnhytq kslslspgk
```

Nucleic Acid Sequence Encoding the Full Length Ch01G06 Chimeric Light Chain (Mouse Kappa Chain Variable Region and Human Kappa Constant Region) (SEQ ID NO:203)

```
  1gacatccaaa tgacccagtc acccgcgagc ctttcggcgt
   cggtcggaga aacggtcacg

61atcacgtgcc ggacatcaga gaatctccat aactacctcg
   cgtggtatca acagaagcag

121gggaagtcgc cccagttgct tgtatacgat gcgaaaacgt
   tggcggatgg ggtgccgtcc

181agattctcgg gatcgggctc ggggacgcag tactcgctca
   agatcaattc gctgcagccg

241gaggactttg ggtcgtacta ttgtcagcat ttttggtcat
   caccgtatac atttggaggt

301ggaacgaaac ttgagattaa gcgcacagtt gctgccccca
   gcgtgttcat ttcccacct

361agcgatgagc agctgaaaag cggtactgcc tctgtcgtat
   gcttgctcaa caacttttac

421ccacgtgagg ctaaggtgca gtggaaagtg gataatgcac
   ttcaatctgg aaacagtcaa

481gagtccgtga cagaacagga cagcaaagac tcaacttatt
   cactctcttc caccctgact

541ctgtccaagg cagactatga aaaacacaag gtatacgcct
   gcgaggttac acaccagggt

601ttgtctagtc ctgtcaccaa gtccttcaat aggggcgaat gt
```

Protein Sequence Defining the Full Length Ch01G06 Chimeric Light Chain (Mouse Kappa Chain Variable Region and Human Kappa Constant Region) (SEQ ID NO:204)

```
  1 diqmtqspas lsasvgetvt itcrtsenlh nylawyqqkq
    gkspqllvyd aktladgvps 61 rfsgsgsgtq yslkinslqp edfgsyycqh fwsspytfgg
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Hu01G06 IGKV1-39 Light Chain (Humanized Kappa Chain Variable Region and Human Kappa Constant Region) (SEQ ID NO:205)

```
  1gacatccaaa tgacccagtc gccgtcgtcg ctttcagcgt
   cggtagggga tcgggtcaca

61attacgtgcc gaacgtcaga gaatttgcat aactacctcg
   cgtggtatca gcagaagccc

121gggaagtcac cgaaactcct tgtctacgat gcgaaaacgc
   tggcggatgg agtgccgtcg

181agattctcgg gaagcggatc cggtacggac tatacgctta
   cgatctcatc gctccagccc

241gaggactttg cgacgtacta ttgtcagcat ttttggtcgt
   cgccctacac atttgggcag

301gggaccaagt tggaaatcaa gcgcacagtt gctgccccca
   gcgtgttcat ttcccacct

361agcgatgagc agctgaaaag cggtactgcc tctgtcgtat
   gcttgctcaa caacttttac

421ccacgtgagg ctaaggtgca gtggaaagtg gataatgcac
   ttcaatctgg aaacagtcaa

481gagtccgtga cagaacagga cagcaaagac tcaacttatt
   cactctcttc caccctgact

541ctgtccaagg cagactatga aaaacacaag gtatacgcct
   gcgaggttac acaccagggt

601ttgtctagtc ctgtcaccaa gtccttcaat aggggcgaat gt
```

Protein Sequence Defining the Full Length Hu01G06 IGKV1-39 Light Chain (Humanized Kappa Chain Variable Region and Human Kappa Constant Region) (SEQ ID NO:206)

```
  1 diqmtqspss lsasvgdrvt itcrtsenlh nylawyqqkp
    gkspkllvyd aktladgvps 61 rfsgsgsgtd ytltisslqp edfatyycqh fwsspytfgq
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Hu01G06 IGKV1-39 S43A V48I Light Chain (Humanized Kappa Chain Variable Region and Human Kappa Constant Region) (also referred to herein as the full length Hu01G06 IGFV1-39 F1 Light Chain; SEQ ID NO:207)

```
  1gacatccaaa tgacccagtc gccgtcgtcg ctttcagcgt
   cggtagggga tcgggtcaca

61attacgtgcc gaacgtcaga gaatttgcat aactacctcg
   cgtggtatca gcagaagccc

121gggaaggccc cgaaactcct tatctacgat gcgaaaacgc
   tggcggatgg agtgccgtcg

181agattctcgg gaagcggatc cggtacggac tatacgctta
   cgatctcatc gctccagccc

241gaggactttg cgacgtacta ttgtcagcat ttttggtcgt
   cgccctacac atttgggcag

301gggaccaagt tggaaatcaa gcgcacagtt gctgccccca
   gcgtgttcat ttcccacct

361agcgatgagc agctgaaaag cggtactgcc tctgtcgtat
   gcttgctcaa caacttttac
```

```
421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Hu01G06 IGKV1-39 S43A V48I Light Chain (Humanized Kappa Chain Variable Region and Human Kappa Constant Region) (also referred to herein as the full length Hu01G06 IGFV1-39 F1 Light Chain; SEQ ID NO:208)

```
  1 diqmtqspss lsasvgdrvt itcrtsenlh nylawyqqkp
    gkapklliyd aktladgvps 61 rfsgsgsgtd ytltisslqp edfatyycqh fwsspytfgq
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Hu01G06 IGKV1-39 V48I Light Chain (Humanized Kappa Chain Variable Region and Human Kappa Constant Region) (SEQ ID NO:209)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaagtcac cgaaactcct tatctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgt
    cgccctacac atttgggcag 301 gggaccaagt tggaaatcaa gcgcacagtt gctgccccca
    gcgtgttcat tttcccacct 361 agcgatgagc agctgaaaag cggtactgcc tctgtcgtat
    gcttgctcaa caacttttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Hu01G06 IGKV1-39 V48I Light Chain (Humanized Kappa Chain Variable Region and Human Kappa Constant Region) (SEQ ID NO:210)

```
  1 diqmtqspss lsasvgdrvt itcrtsenlh nylawyqqkp
    gkspklliyd aktladgvps 61 rfsgsgsgtd ytltisslqp edfatyycqh fwsspytfgq
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Hu01G06 IGKV1-39 F1 Light Chain (Humanized Kappa Chain Variable Region and Human Kappa Constant Region) (also referred to herein as the Full Length Hu01G06 IGKV1-39 S43A V48I Light Chain; SEQ ID NO:207)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaaggccc cgaaactcct tatctacgat gcgaaaacgc
    tggcggatgg agtgccgtcg 181 agattctcgg gaagcggatc cggtacggac tatacgctta
    cgatctcatc gctccagccc 241 gaggactttg cgacgtacta ttgtcagcat ttttggtcgt
    cgccctacac atttgggcag 301 gggaccaagt tggaaatcaa gcgcacagtt gctgccccca
    gcgtgttcat tttcccacct 361 agcgatgagc agctgaaaag cggtactgcc tctgtcgtat
    gcttgctcaa caacttttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Hu01G06 IGKV1-39 F1 Light Chain (Humanized Kappa Chain Variable Region and Human Kappa Constant Region) (also referred to herein as the Full Length Hu01G06 IGKV1-39 S43A V48I Light Chain; SEQ ID NO:208)

```
  1 diqmtqspss lsasvgdrvt itcrtsenlh nylawyqqkp
    gkapklliyd aktladgvps 61 rfsgsgsgtd ytltisslqpedfatyycqh
    fwsspytfgqgtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Hu01G06 IGKV1-39 F2 Light Chain (Humanized Kappa Chain Variable Region and Human Kappa Constant Region) (SEQ ID NO:263)

```
  1 gacatccaaa tgacccagtc gccgtcgtcg ctttcagcgt
    cggtagggga tcgggtcaca 61 attacgtgcc gaacgtcaga gaatttgcat aactacctcg
    cgtggtatca gcagaagccc 121 gggaagtcac cgaaactcct tatctacgat gcgaaaacgc
    tggcggatgg agtgccgtcg
```

```
181 agattctcgg gaagcggatc cggtacggac tatacgctta
    cgatctcatc gctccagccc 241 gaggactttg cgacgtacta ttgtcagcat ttttggtcgg
    accoctacac atttgggcag 301 gggaccaagt tggaaatcaa gcgcacagtt gctgccccca
    gcgtgttcat tttcccacct 361 agcgatgagc agctgaaaag cggtactgcc tctgtcgtat
    gcttgctcaa caacttttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Hu01G06 IGKV1-39 F2 Light Chain (Humanized Kappa Chain Variable Region and Human Kappa Constant Region) (SEQ ID NO:264)

```
  1 diqmtqspss lsasvgdrvt itcrtsenlh nylawyqqkp
    gkspklliyd aktladgvps 61 rfsgsgsgtd ytltisslqp edfatyycqh fwsdpytfgq
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Ch06C11 Chimeric Light Chain (Mouse Kappa Chain Variable Region and Human Kappa Constant Region) (SEQ ID NO:211)

```
  1 gatatcgtca tgacccagtc ccagaagttc atgtcaactt
    cagtgggaga cagagtgtcc 61 gtcacatgta aagcctcgca aaatgtggga accaacgtag
    cgtggttcca gcagaaacct 121 ggccaatcac cgaaggcact gatctactcg gccagctata
    ggtactcggg agtaccagat 181 cggtttacgg ggtcggggag cgggacggac tttatcctca
    ctatttccaa tgtccagtcg 241 gaggaccttg cggaatactt ctgccagcag tataacaact
    atcccctcac gtttggtgct 301 ggtacaaaat tggagttgaa gcgcacagtt gctgccccca
    gcgtgttcat tttcccacct 361 agcgatgagc agctgaaaag cggtactgcc tctgtcgtat
    gcttgctcaa caacttttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Ch06C11 Chimeric Light Chain (Mouse Kappa Chain Variable Region and Human Kappa Constant Region) (SEQ ID NO:212)

```
  1 divmtqsqkf mstsvgdrvs vtckasqnvg tnvawfqqkp
    gqspkaliys asyrysgvpd 61 rftgsgsgtd filtisnvqs edlaeyfcqq ynnypltfga
    gtklelkrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Sh06C11 IGKV1-16 Light Chain (Humanized Kappa Chain Variable Region and Human Kappa Constant Region) (SEQ ID NO:213)

```
  1 gacatccaaa tgacccaatc gccctcctcc ctctccgcat
    cagtagggga ccgcgtcaca 61 attacttgca aagcgtcgca gaacgtcgga acgaatgtgg
    cgtggtttca gcagaagccc 121 ggaaaagctc cgaagagctt gatctactcg gcctcatata
    ggtattcggg tgtgccgagc 181 cggtttagcg ggtcggggtc aggtactgat ttcacgctca
    caatttcatc gttgcagcca 241 gaagatttcg ccacatatta ctgtcagcag tacaacaatt
    accctctgac gttcggccag 301 ggaaccaaac ttgagatcaa gcgcacagtt gctgccccca
    gcgtgttcat tttcccacct 361 agcgatgagc agctgaaaag cggtactgcc tctgtcgtat
    gcttgctcaa caacttttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Sh06C11 IGKV1-16 Light Chain (Humanized Kappa Chain Variable Region and Human Kappa Constant Region) (SEQ ID NO:214)

```
  1 diqmtqspss lsasvgdrvt itckasqnvg tnvawfqqkp
    gkapksliys asyrysgvps 61 rfsgsgsgtd ftltisslqp edfatyycqq ynnypltfgq
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Ch14F11 Chimeric Light Chain (Mouse Kappa Chain Variable Region and Human Kappa Constant Region) (SEQ ID NO:215)

```
  1 gacatcgtga tgacacagtc acagaaattc atgtccacat
    ccgtcggtga tagagtatcc 61 gtcacgtgta aggcctcgca aaacgtagga actaatgtgg
    cgtggtatca acagaagcca 121 ggacagtcac ccaaagcact catctacagc ccctcatatc
    ggtacagcgg ggtgccggac 181 aggttcacgg gatcggggag cgggaccgat tttacactga
    ccatttcgaa tgtccagtcg 241 gaggaccttg cggaatactt ctgccagcag tataactcgt
    accctcacac gtttggaggt 301 ggcactaagt tggagatgaa acgcacagtt gctgccccca
    gcgtgttcat tttcccacct 361 agcgatgagc agctgaaaag cggtactgcc tctgtcgtat
    gcttgctcaa caactttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Ch14F11 Chimeric Light Chain (Mouse Kappa Chain Variable Region and Human Kappa Constant Region) (SEQ ID NO:216)

```
  1 divmtqsqkf mstsvgdrvs vtckasqnvg tnvawyqqkp
    gqspkaliys psyrysgvpd 61 rftgsgsgtd ftltisnvqs edlaeyfcqq ynsyphtfgg
    gtklemkrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Nucleic Acid Sequence Encoding the Full Length Hu14F11 IGKV1-16 Light Chain (Humanized Kappa Chain Variable Region and Human Kappa Constant Region) (SEQ ID NO:217)

```
  1 gatatccaga tgcacacagtc accctcgtcg ctctcagctt
    ccgtaggcga cagggtcact 61 attacgtgta aagcatcaca gaacgtcgga acgaatgtgg
    cgtggtttca gcagaagccc 121 gggaagagcc ccaaagcgct tatctactcc ccgtcgtatc
    ggtattccgg tgtgccaagc 181 agattttcgg ggtcaggttc gggaactgac tttaccctga
    ccatctcgtc cctccaaccg 241 gaagatttcg ccacgtactt ctgccagcag tacaacagct
    atcctcacac attcggacaa 301 gggacaaagt tggagattaa acgcacagtt gctgccccca
    gcgtgttcat tttcccacct 361 agcgatgagc agctgaaaag cggtactgcc tctgtcgtat
    gcttgctcaa caactttac 421 ccacgtgagg ctaaggtgca gtggaaagtg gataatgcac
    ttcaatctgg aaacagtcaa 481 gagtccgtga cagaacagga cagcaaagac tcaacttatt
    cactctcttc caccctgact 541 ctgtccaagg cagactatga aaaacacaag gtatacgcct
    gcgaggttac acaccagggt 601 ttgtctagtc ctgtcaccaa gtccttcaat aggggcgaat gt
```

Protein Sequence Defining the Full Length Hu14F11 IGKV1-16 Light Chain (Humanized Kappa Chain Variable Region and Human Kappa Constant Region) (SEQ ID NO:218)

```
  1 diqmtqspss lsasvgdrvt itckasqnvg tnvawfqqkp
    gkspkaliys psyrysgvps 61 rfsgsgsgtd ftltisslqp edfatyfcqq ynsyphtfgq
    gtkleikrtv aapsvfifpp 121 sdeqlksgta svvcllnnfy preakvqwkv dnalqsgnsq
    esvteqdskd styslsstlt 181 lskadyekhk vyacevthqg lsspvtksfn rgec
```

Table 22 is a concordance chart showing the SEQ ID NO. of each sequence discussed in this Example.

TABLE 22

| SEQ ID NO. | Nucleic Acid or Protein |
|---|---|
| 171 | Human IgG1 constant-nucleic acid |
| 172 | Human IgG1 constant-protein |
| 173 | Human Kappa constant-nucleic acid |
| 174 | Human Kappa constant-protein |
| 175 | Humanized Ch01G06 Chimeric Heavy Human Variable + Human IgG1 constant-nucleic acid |
| 176 | Humanized Ch01G06 Chimeric Heavy Human Variable + Human IgG1 constant-protein |
| 177 | Humanized Hu01G06 IGHV1-18 Heavy Human Variable + Human IgG1 constant-nucleic acid |
| 178 | Humanized Hu01G06 IGHV1-18 Heavy Human Variable + Human IgG1 constant-protein |
| 179 | Humanized Hu01G06 IGHV1-69 Heavy Human Variable + Human IgG1 constant-nucleic acid |
| 180 | Humanized Hu01G06 IGHV1-69 Heavy Human Variable + Human IgG1 constant-protein |
| 181 | Humanized Sh01G06 IGHV1-18 M69L Heavy Human Variable + Human IgG1 constant-nucleic acid |
| 182 | Humanized Sh01G06 IGHV1-18 M69L Heavy Human Variable + Human IgG1 constant-protein |
| 183 | Humanized Sh01G06 IGHV1-18 M69L K64Q G44S Heavy Human Variable + Human IgG1 constant-nucleic acid |
| 184 | Humanized Sh01G06 IGHV1-18 M69L K64Q G44S Heavy Human Variable + Human IgG1 constant-protein |
| 185 | Humanized Sh01G06 IGHV1-18 M69L K64Q Heavy Human Variable + Human IgG1 constant-nucleic acid |
| 186 | Humanized Sh01G06 IGHV1-18 M69L K64Q Heavy Human Variable + Human IgG1 constant-protein |
| 187 | Humanized Sh01G06 IGHV1-69 T30S I69L Heavy Human Variable + Human IgG1 constant-nucleic acid |
| 188 | Humanized Sh01G06 IGHV1-69 T30S I69L Heavy Human Variable + Human IgG1 constant-protein |
| 189 | Humanized Sh01G06 IGHV1-69 T30S K64Q I69L Heavy Human Variable + Human IgG1 constant-nucleic acid |
| 190 | Humanized Sh01G06 IGHV1-69 T30S K64Q I69L Heavy Human Variable + Human IgG1 constant-protein |
| 255 | Humanized Hu01G06 IGHV1-18 F1 Heavy Human Variable + Human IgG1 constant-nucleic acid |
| 256 | Humanized Hu01G06 IGHV1-18 F1 Heavy Human Variable + Human IgG1 constant-protein |

TABLE 22-continued

| SEQ ID NO. | Nucleic Acid or Protein |
|---|---|
| 257 | Humanized Hu01G06 IGHV1-18 F2 Heavy Human Variable + Human IgG1 constant-nucleic acid |
| 258 | Humanized Hu01G06 IGHV1-18 F2 Heavy Human Variable + Human IgG1 constant-protein |
| 259 | Humanized Hu01G06 IGHV1-69 F1 Heavy Human Variable + Human IgG1 constant-nucleic acid |
| 260 | Humanized Hu01G06 IGHV1-69 F1 Heavy Human Variable + Human IgG1 constant-protein |
| 261 | Humanized Hu01G06 IGHV1-69 F2 Heavy Human Variable + Human IgG1 constant-nucleic acid |
| 262 | Humanized Hu01G06 IGHV1-69 F2 Heavy Human Variable + Human IgG1 constant-protein |
| 191 | Humanized Ch06C11 Chimeric Heavy Human Variable + Human IgG1 constant-nucleic acid |
| 192 | Humanized Ch06C11 Chimeric Heavy Human Variable + Human IgG1 constant-protein |
| 193 | Humanized HE LM 06C11 IGHV2-70 Heavy Human Variable + Human IgG1 constant-nucleic acid |
| 194 | Humanized HE LM 06C11 IGHV2-70 Heavy Human Variable + Human IgG1 constant-protein |
| 195 | Humanized Hu06C11 IGHV2-5 Heavy Human Variable + Human IgG1 constant-nucleic acid |
| 196 | Humanized Hu06C11 IGHV2-5 Heavy Human Variable + Human IgG1 constant-protein |
| 197 | Humanized Ch14F11 Chimeric Heavy Human Variable + Human IgG1 constant-nucleic acid |
| 198 | Humanized Ch14F11 Chimeric Heavy Human Variable + Human IgG1 constant-protein |
| 199 | Humanized Sh14F11 IGHV2-5 Heavy Human Variable + Human IgG1 constant-nucleic acid |
| 200 | Humanized Sh14F11 IGHV2-5 Heavy Human Variable + Human IgG1 constant-protein |
| 201 | Humanized Sh14F11-IGHV2-70 Heavy Human Variable + Human IgG1 constant-nucleic acid |
| 202 | Humanized Sh14F11-IGHV2-70 Heavy Human Variable + Human IgG1 constant-protein |
| 203 | Humanized Ch01G06 Chimeric Human Variable + Human Kappa constant-nucleic acid |
| 204 | Humanized Ch01G06 Chimeric Human Variable + Human Kappa constant-protein |
| 205 | Humanized Hu01G06 IGKV1-39 Human Variable + Human Kappa constant-nucleic acid |
| 206 | Humanized Hu01G06 IGKV1-39 Human Variable + Human Kappa constant-protein |
| 207 | Humanized Hu01G06 IGKV1-39 S43A V48I Human Variable + Human Kappa constant-nucleic acid |
| 208 | Humanized Hu01G06 IGKV1-39 S43A V48I Human Variable + Human Kappa constant-protein |
| 209 | Humanized Hu01G06 IGKV1-39 V48I Human Variable + Human Kappa constant-nucleic acid |
| 210 | Humanized Hu01G06 IGKV1-39 V48I Human Variable + Human Kappa constant-protein |
| 207 | Humanized Hu01G06 IGKV1-39 F1 Human Variable + Human Kappa constant-nucleic acid |
| 208 | Humanized Hu01G06 IGKV1-39 F1 Human Variable + Human Kappa constant-protein |
| 263 | Humanized Hu01G06 IGKV1-39 F2 Human Variable + Human Kappa constant-nucleic acid |
| 264 | Humanized Hu01G06 IGKV1-39 F2 Human Variable + Human Kappa constant-protein |
| 211 | Humanized Ch06C11 Chimeric Human Variable + Human Kappa constant-nucleic acid |
| 212 | Humanized Ch06C11 Chimeric Human Variable + Human Kappa constant-protein |
| 213 | Humanized Sh06C11 IGKV1-16 Human Variable + Human Kappa constant-nucleic acid |
| 214 | Humanized Sh06C11 IGKV1-16 Human Variable + Human Kappa constant-protein |
| 215 | Humanized Ch14F11 Chimeric Human Variable + Human Kappa constant-nucleic acid |
| 216 | Humanized Ch14F11 Chimeric Human Variable + Human Kappa constant-protein |
| 217 | Humanized Hu14F11 IGKV1-16 Human Variable + Human Kappa constant-nucleic acid |
| 218 | Humanized Hu14F11 IGKV1-16 Human Variable + Human Kappa constant-protein |

Table 23 below shows antibodies containing chimeric immunoglobulin heavy and light chains and exemplary combinations of the full-length chimeric or humanized immunoglobulin heavy and light chains.

TABLE 23

| Antibody Name | Light Chain | Heavy Chain |
|---|---|---|
| Hu01G06-1 | Humanized Ch01G06 Chimeric Human Variable + Human Kappa constant (SEQ ID NO: 204) | Humanized Ch01G06 Chimeric Heavy Human Variable + Human IgG1 constant (SEQ ID NO: 176) |
| Hu01G06-46 | Humanized Hu01G06 IGKV1-39 Human Variable + Human Kappa constant (SEQ ID NO: 206) | Humanized Hu01G06 IGHV1-18 Heavy Human Variable + Human IgG1 constant (SEQ ID NO: 178) |
| Hu01G06-52 | Humanized Hu01G06 IGKV1-39 Human Variable + Human Kappa constant (SEQ ID NO: 206) | Humanized Hu01G06 IGHV1-69 Heavy Human Variable + Human IgG1 constant (SEQ ID NO: 180) |
| Hu01G06-100 | Humanized Hu01G06 IGKV1-39 Human Variable + Human Kappa constant (SEQ ID NO: 206) | Humanized Sh01G06 IGHV1-18 M69L Heavy Human Variable + Human IgG1 constant (SEQ ID NO: 182) |
| Hu01G06-101 | Humanized Hu01G06 IGKV1-39 Human Variable + Human Kappa constant (SEQ ID NO: 206) | Humanized Sh01G06 IGHV1-18 M69L K64Q Heavy Human Variable + Human IgG1 constant (SEQ ID NO: 186) |
| Hu01G06-102 | Humanized Hu01G06 IGKV1-39 Human Variable + Human Kappa constant (SEQ ID NO: 206) | Humanized Sh01G06 IGHV1-18 M69L K64Q G44S Heavy Human Variable + Human IgG1 constant (SEQ ID NO: 184) |
| Hu01G06-103 | Humanized Hu01G06 IGKV1-39 Human Variable + Human Kappa constant (SEQ ID NO: 206) | Humanized Sh01G06 IGHV1-69 T30S I69L Heavy Human Variable + Human IgG1 constant (SEQ ID NO: 188) |
| Hu01G06-104 | Humanized Hu01G06 IGKV1-39 Human Variable + Human Kappa constant (SEQ ID NO: 206) | Humanized Sh01G06 IGHV1-69 T30S K64Q I69L Heavy Human Variable + Human IgG1 constant (SEQ ID NO: 190) |
| Hu01G06-105 | Humanized Hu01G06 IGKV1-39 V48I Human Variable + Human Kappa constant (SEQ ID NO: 210) | Humanized Sh01G06 IGHV1-18 M69L Heavy Human Variable + Human IgG1 constant (SEQ ID NO: 182) |

TABLE 23-continued

| Antibody Name | Light Chain | Heavy Chain |
| --- | --- | --- |
| Hu01G06-106 | Humanized Hu01G06 IGKV1-39 V48I Human Variable + Human Kappa constant (SEQ ID NO: 210) | Humanized Sh01G06 IGHV1-18 M69L K64Q Heavy Human Variable + Human IgG1 constant (SEQ ID NO: 186) |
| Hu01G06-107 | Humanized Hu01G06 IGKV1-39 V48I Human Variable + Human Kappa constant (SEQ ID NO: 210) | Humanized Sh01G06 IGHV1-18 M69L K64Q G44S Heavy Human Variable + Human IgG1 constant (SEQ ID NO: 184) |
| Hu01G06-108 | Humanized Hu01G06 IGKV1-39 V48I Human Variable + Human Kappa constant (SEQ ID NO: 210) | Humanized Sh01G06 IGHV1-69 T30S I69L Heavy Human Variable + Human IgG1 constant (SEQ ID NO: 188) |
| Hu01G06-109 | Humanized Hu01G06 IGKV1-39 V48I Human Variable + Human Kappa constant (SEQ ID NO: 210) | Humanized Sh01G06 IGHV1-69 T30S K64Q I69L Heavy Human Variable + Human IgG1 constant (SEQ ID NO: 190) |
| Hu01G06-110 | Humanized Hu01G06 IGKV1-39 S43A V48I Human Variable + Human Kappa constant (SEQ ID NO: 208) | Humanized Sh01G06 IGHV1-18 M69L Heavy Human Variable + Human IgG1 constant (SEQ ID NO: 182) |
| Hu01G06-111 | Humanized Hu01G06 IGKV1-39 S43A V48I Human Variable + Human Kappa constant (SEQ ID NO: 208) | Humanized Sh01G06 IGHV1-18 M69L K64Q Heavy Human Variable + Human IgG1 constant (SEQ ID NO: 186) |
| Hu01G06-112 | Humanized Hu01G06 IGKV1-39 S43A V48I Human Variable + Human Kappa constant (SEQ ID NO: 208) | Humanized Sh01G06 IGHV1-18 M69L K64Q G44S Heavy Human Variable + Human IgG1 constant (SEQ ID NO: 184) |
| Hu01G06-113 | Humanized Hu01G06 IGKV1-39 S43A V48I Human Variable + Human Kappa constant (SEQ ID NO: 208) | Humanized Sh01G06 IGHV1-69 T30S I69L Heavy Human Variable + Human IgG1 constant (SEQ ID NO: 188) |
| Hu01G06-114 | Humanized Hu01G06 IGKV1-39 S43A V48I Human Variable + Human Kappa constant (SEQ ID NO: 208) | Humanized Sh01G06 IGHV1-69 T30S K64Q I69L Heavy Human Variable + Human IgG1 constant (SEQ ID NO: 190) |
| Hu01G06-122 | Humanized Hu01G06 IGKV1-39 F1 Human Variable + Human Kappa constant (SEQ ID NO: 208) | Humanized Hu01G06 IGHV1-18 F1 Heavy Human Variable + Human IgG1 constant (SEQ ID NO: 256) |
| Hu01G06-127 | Humanized Hu01G06 IGKV1-39 F2 Human Variable + Human Kappa constant (SEQ ID NO: 264) | Humanized Hu01G06 IGHV1-18 F2 Heavy Human Variable + Human IgG1 constant (SEQ ID NO: 258) |
| Hu01G06-135 | Humanized Hu01G06 IGKV1-39 F1 Human Variable + Human Kappa constant (SEQ ID NO: 208) | Humanized Hu01G06 IGHV1-69 F1 Heavy Human Variable + Human IgG1 constant (SEQ ID NO: 260) |
| Hu01G06-138 | Humanized Hu01G06 IGKV1-39 F1 Human Variable + Human Kappa constant (SEQ ID NO: 208) | Humanized Hu01G06 IGHV1-69 F2 Heavy Human Variable + Human IgG1 constant (SEQ ID NO: 262) |
| Hu01G06-146 | Humanized Hu01G06 IGKV1-39 F2 Human Variable + Human Kappa constant (SEQ ID NO: 264) | Humanized Hu01G06 IGHV1-69 F2 Heavy Human Variable + Human IgG1 constant (SEQ ID NO: 262) |
| Hu06C11-1 | Humanized Ch06C11 Chimeric Human Variable + Human Kappa constant (SEQ ID NO: 212) | Humanized Ch06C11 Chimeric Heavy Human Variable + Human IgG1 constant (SEQ ID NO:176) |
| Hu06C11-27 | Humanized Sh06C11 IGKV1-16 Human Variable + Human Kappa constant (SEQ ID NO: 214) | Humanized HE LM 06C11 IGHV2-70 Heavy Human Variable + Human IgG1 constant (SEQ ID NO: 194) |
| Hu06C11-30 | Humanized Sh06C11 IGKV1-16 Human Variable + Human Kappa constant (SEQ ID NO: 214) | Humanized Hu06C11 IGHV2-5 Heavy Human Variable + Human IgG1 constant (SEQ ID NO: 196) |
| Hu14F11-1 | Humanized Ch14F11 Chimeric Human Variable + Human Kappa constant (SEQ ID NO: 216) | Humanized Ch14F11 Chimeric Heavy Human Variable + Human IgG1 constant (SEQ ID NO: 198) |
| Hu14F11-23 | Humanized Ch14F11 Chimeric Human Variable + Human Kappa constant (SEQ ID NO: 216) | Humanized Ch06C11 Chimeric Heavy Human Variable + Human IgG1 constant (SEQ ID NO: 192) |
| Hu14F11-24 | Humanized Ch06C11 Chimeric Human Variable + Human Kappa constant (SEQ ID NO: 212) | Humanized Ch14F11 Chimeric Heavy Human Variable + Human IgG1 constant (SEQ ID NO: 198) |
| Hu14F11-39 | Humanized Hu14F11 IGKV1-16 Human Variable + Human Kappa constant (SEQ ID NO: 218) | Humanized Sh14F11 IGHV2-5 Heavy Human Variable + Human IgG1 constant (SEQ ID NO: 200) |
| Hu14F11-47 | Humanized Hu14F11 IGKV1-16 Human Variable + Human Kappa constant (SEQ ID NO: 218) | Humanized Sh14F11-IGHV2-70 Heavy Human Variable + Human IgG1 constant (SEQ ID NO: 202) |

The antibody constructs containing the full length chimeric heavy and light chains are designated below:

Chimeric 01G06 (Hu01G06-1)=Full Length Ch01G06 Chimeric Heavy Chain (Mouse Heavy Chain Variable Region and Human IgG1 Constant Region) (SEQ ID NO:176) plus Full Length Ch01G06 Chimeric Light Chain (Mouse Kappa Chain Variable Region and Human Kappa Constant Region) (SEQ ID NO:204)

Chimeric 06C11 (Hu06C11-1)=Full Length Ch06C11 Chimeric Heavy Chain (Mouse Heavy Chain Variable Region and Human IgG1 Constant Region) (SEQ ID NO:192) plus Full Length Ch06C11 Chimeric Light Chain (Mouse Kappa Chain Variable Region and Human Kappa Constant Region) (SEQ ID NO:212)

Chimeric 14F11 (Hu14F11-1)=Full Length Ch14F11 Chimeric Heavy Chain (Mouse Heavy Chain Variable Region and Human IgG1 Constant Region) (SEQ ID NO:198) plus Full Length Ch14F11 Chimeric Light Chain (Mouse Kappa Chain Variable Region and Human Kappa Constant Region) (SEQ ID NO:216)

Fifteen of the possible antibody constructs containing the full length immunoglobulin heavy and light chains containing humanized variable regions are designated below:

Hu01G06-46=Full Length Hu01G06 IGHV1-18 Heavy Chain (Humanized Heavy Chain Variable Region and Human IgG1 Constant Region) (SEQ ID NO:178) plus Full Length Hu01G06 IGKV1-39 Light Chain (Humanized Kappa Chain Variable Region and Human Kappa Constant Region) (SEQ ID NO:206)

Hu01G06-52=Full Length Hu01G06 IGHV1-69 Heavy Chain (Humanized Heavy Chain Variable Region and Human IgG1 Constant Region) (SEQ ID NO:180) plus Full Length Hu01G06 IGKV1-39 Light Chain (Humanized Kappa Chain Variable Region and Human Kappa Constant Region) (SEQ ID NO:206)

Hu01G06-107=Full Length Sh01G06 IGHV1-18 M69L K64Q G44S Heavy Chain (Humanized Heavy Chain Variable Region and Human IgG1 Constant Region) (SEQ ID NO:184) plus Full Length Hu01G06 IGKV1-39 V48I Light Chain (Humanized Kappa Chain Variable Region and Human Kappa Constant Region) (SEQ ID NO:210)

Hu01G06-108=Full Length Sh01G06 IGHV1-69 T30S I69L Heavy Chain (Humanized Heavy Chain Variable Region and Human IgG1 Constant Region) (SEQ ID NO:188) plus Full Length Hu01G06 IGKV1-39 V48I Light Chain (Humanized Kappa Chain Variable Region and Human Kappa Constant Region) (SEQ ID NO:210)

Hu01G06-112=Full Length Sh01G06 IGHV1-18 M69L K64Q G44S Heavy Chain (Humanized Heavy Chain Variable Region and Human IgG1 Constant Region) (SEQ ID NO:184) plus Full Length Hu01G06 IGKV1-39 S43A V48I Light Chain (Humanized Kappa Chain Variable Region and Human Kappa Constant Region) (SEQ ID NO:208)

Hu01G06-113=Full Length Sh01G06 IGHV1-69 T30S I69L Heavy Chain (Humanized Heavy Chain Variable Region and Human IgG1 Constant Region) (SEQ ID NO:188) plus Full Length Hu01G06 IGKV1-39 S43A V48I Light Chain (Humanized Kappa Chain Variable Region and Human Kappa Constant Region) (SEQ ID NO:208)

Hu01G06-122=Full Length Hu01G06 IGHV1-18 F1 Heavy Chain (Humanized Heavy Chain Variable Region and Human IgG1 Constant Region) (SEQ ID NO:256) plus Full Length Hu01G06 IGKV1-39 F1 Light Chain (Humanized Kappa Chain Variable Region and Human Kappa Constant Region) (SEQ ID NO:208)

Hu01G06-127=Full Length Hu01G06 IGHV1-18 F2 Heavy Chain (Humanized Heavy Chain Variable Region and Human IgG1 Constant Region) (SEQ ID NO:258) plus Full Length Hu01G06 IGKV1-39 F2 Light Chain (Humanized Kappa Chain Variable Region and Human Kappa Constant Region) (SEQ ID NO:264)

Hu01G06-135=Full Length Hu01G06 IGHV1-69 F1 Heavy Chain (Humanized Heavy Chain Variable Region and Human IgG1 Constant Region) (SEQ ID NO:260) plus Full Length Hu01G06 IGKV1-39 F1 Light Chain (Humanized Kappa Chain Variable Region and Human Kappa Constant Region) (SEQ ID NO:208)

Hu01G06-138=Full Length Hu01G06 IGHV1-69 F2 Heavy Chain (Humanized Heavy Chain Variable Region and Human IgG1 Constant Region) (SEQ ID NO:262) plus Full Length Hu01G06 IGKV1-39 F1 Light Chain (Humanized Kappa Chain Variable Region and Human Kappa Constant Region) (SEQ ID NO:208)

Hu01G06-146=Full Length Hu01G06 IGHV1-69 F2 Heavy Chain (Humanized Heavy Chain Variable Region and Human IgG1 Constant Region) (SEQ ID NO:262) plus Full Length Hu01G06 IGKV1-39 F2 Light Chain (Humanized Kappa Chain Variable Region and Human Kappa Constant Region) (SEQ ID NO:264)

Hu06C11-27=Full Length HE LM 06C11 IGHV2-70 Heavy Chain (Humanized Heavy Chain Variable Region and Human IgG1 Constant Region) (SEQ ID NO:194) plus Full Length Sh06C11 IGKV1-16 Light Chain (Humanized Kappa Chain Variable Region and Human Kappa Constant Region) (SEQ ID NO:214)

Hu06C11-30=Full Length Hu06C11 IGHV2-5 Heavy Chain (Humanized Heavy Chain Variable Region and Human IgG1 Constant Region) (SEQ ID NO:196) plus Full Length Sh06C11 IGKV1-16 Light Chain (Humanized Kappa Chain Variable Region and Human Kappa Constant Region) (SEQ ID NO:214)

Hu14F11-39=Full Length Sh14F11 IGHV2-5 Heavy Chain (Humanized Heavy Chain Variable Region and Human IgG1 Constant Region) (SEQ ID NO:200) plus Full Length Hu14F11 IGKV1-16 Light Chain (Humanized Kappa Chain Variable Region and Human Kappa Constant Region) (SEQ ID NO:218)

Hu14F11-47=Full Length Sh14F11-IGHV2-70 Heavy Chain (Humanized Heavy Chain Variable Region and Human IgG1 Constant Region) (SEQ ID NO:202) plus Full Length Hu14F11 IGKV1-16 Light Chain (Humanized Kappa Chain Variable Region and Human Kappa Constant Region) (SEQ ID NO:218)

Example 15

Binding Affinities of Humanized and Chimeric Anti-GDF15 Monoclonal Antibodies

The binding affinities and kinetics of binding of chimeric and humanized antibodies to mFc-rhGDF15 were measured by surface plasmon resonance, using a BIAcore® T100 instrument (GE Healthcare, Piscataway, N.J.).

Goat anti-human IgGs (Fc fragment specific, Jackson ImmunoResearch, West Grove, Pa.) were immobilized on carboxymethylated dextran CM4 sensor chips by amine coupling, according to a standard protocol. Analyses were performed at 37° C. using PBS containing 0.05% surfactant P20 as running buffer. The antibodies were captured in individual flow cells at a flow rate of 10 µL/minute. Injection time was varied for each antibody to yield an Rmax between 30 and 60 RU. Buffer or mFc-rhGDF15 diluted in running buffer was injected sequentially over a reference surface (no antibody captured) and the active surface (antibody to be tested) for 240 seconds at 60 µL/minute. The dissociation phase was monitored for up to 1200 seconds. The surface was then regenerated with two 60-second injections of 10 mM Glycine-HCl, pH 2.25, at a flow rate of 30 µL/minute. The GDF15 concentration range tested was 20 nM to 0.625 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined Kinetic values of purified monoclonal antibodies on mFc-rhGDF15 are summarized in Table 24.

TABLE 24

| Antibody | $k_a$ (1/Ms) | $k_d$ (1/s) | $K_D$ (M) | n |
|---|---|---|---|---|
| Hu01G06-1 | 4.2E+06 | 6.4E−04 | 1.6E−10 | 8 |
| Hu01G06-46 | 3.6E+06 | 3.8E−04 | 1.1E−10 | 11 |
| Hu01G06-52 | 3.6E+06 | 3.6E−04 | 9.9E−11 | 10 |
| Hu06C11-1 | 5.3E+06 | 8.4E−04 | 1.8E−10 | 2 |
| Hu06C11-27 | 4.7E+06 | 8.2E−04 | 1.8E−10 | 2 |
| Hu06C11-30 | 4.8E+06 | 8.7E−04 | 1.8E−10 | 2 |
| Hu14F11-1 | 3.0E+06 | 4.6E−04 | 1.6E−10 | 2 |
| Hu14F11-39 | 3.0E+06 | 1.9E−04 | 6.6E−11 | 2 |
| Hu14F11-47 | 3.3E+06 | 1.8E−04 | 6.5E−11 | 2 |

The results in Table 24 demonstrate that the chimeric and each of the humanized antibodies, have fast association rates ($k_a$), very slow disassociation rates ($k_d$) and very high affinities ($K_D$). In particular, the antibodies have affinities ranging from about 65 pM to about 200 pM.

Kinetic values of chimeric 01G06 (Hu01G06-1), two initial lead humanized 01G06 monoclonal antibodies (Hu01G06-46 and -52), and sequence optimized humanized 01G06 monoclonal antibody variants Hu01G06-100 through -114 (in supernatant) on mFc-rhGDF15 are summarized in Table 25.

TABLE 25

| Antibody | $k_a$ (1/Ms) | $k_d$ (1/s) | $K_D$ (M) | n |
|---|---|---|---|---|
| Hu01G06-1 | 4.9E+06 | 7.1E−04 | 1.4E−10 | 3 |
| Hu01G06-46 | 4.1E+06 | 4.3E−04 | 1.0E−10 | 3 |
| Hu01G06-52 | 5.0E+06 | 4.4E−04 | 8.9E−11 | 3 |
| Hu01G06-100 | 4.1E+06 | 6.2E−04 | 1.5E−10 | 3 |
| Hu01G06-101 | 4.4E+06 | 6.3E−04 | 1.4E−10 | 3 |
| Hu01G06-102 | 4.4E+06 | 4.6E−04 | 1.1E−10 | 3 |
| Hu01G06-103 | 4.4E+06 | 4.7E−04 | 1.1E−10 | 3 |
| Hu01G06-104 | 4.5E+06 | 5.2E−04 | 1.2E−10 | 3 |
| Hu01G06-105 | 4.3E+06 | 5.6E−04 | 1.3E−10 | 3 |
| Hu01G06-106 | 4.3E+06 | 7.0E−04 | 1.6E−10 | 3 |
| Hu01G06-107 | 4.1E+06 | 4.7E−04 | 1.2E−10 | 3 |
| Hu01G06-108 | 4.2E+06 | 4.6E−04 | 1.2E−10 | 3 |
| Hu01G06-109 | 4.6E+06 | 5.6E−04 | 1.3E−10 | 4 |
| Hu01G06-110 | 4.3E+06 | 5.8E−04 | 1.4E−10 | 4 |
| Hu01G06-111 | 4.3E+06 | 6.6E−04 | 1.6E−10 | 3 |
| Hu01G06-112 | 4.7E+06 | 5.3E−04 | 1.2E−10 | 3 |
| Hu01G06-113 | 4.5E+06 | 4.8E−04 | 1.1E−10 | 3 |
| Hu01G06-114 | 4.5E+06 | 5.4E−04 | 1.3E−10 | 3 |

The results in Table 25 demonstrate that the sequence optimized antibodies, Hu01G06-100 through -114, have binding affinities ranging from about 89 pM to about 160 pM.

Binding affinities and binding kinetics of mFc-rhGDF15 with chimeric 14F11 (Hu14F11-1), chimeric light 14F11 with chimeric heavy 06C11 (Hu14F11-23), and chimeric light 06C11 with chimeric heavy 14F11 (Hu14F11-24) heavy monoclonal antibody variants (in supernatant) were measured using biolayer interferometry (BLI) on an Octet™ QK instrument (ForteBio, Inc., Menlo Park, Calif.). The Octet analysis was performed at 30° C. using 1× Kinetics Buffer (ForteBio, Inc.) as assay buffer. Anti-human IgG Fc Capture (AHC) biosensors (ForteBio, Inc.) were used to capture human antibodies onto the sensors. Sensors were saturated in assay buffer for at 300 seconds before the assay. Antibodies were loaded onto sensors by dipping the sensors into antibody supernatant solution for 220 seconds, which typically resulted in capture levels of 1.5-2 nm. Baseline was established by dipping the sensors into 1× assay buffer for 200 seconds. Next, association was monitored for 220 seconds in 400 nM mFc-rhGDF15 protein, and dissociation was followed for 600 seconds in buffer alone.

Kinetic parameters for Hu14F11-1, Hu14F11-23, and Hu14F11-24 were determined using the kinetic function of the ForteBio Analysis Software Version 7.0. Kinetic parameters of the antibody, $k_a$, $k_d$, and $K_D$ were determined.

Kinetic values of Hu14F11-1, Hu14F11-23, and Hu14F11-24 heavy monoclonal antibody variants (in supernatant) on mFc-rhGDF15 are summarized in Table 26.

TABLE 26

| Antibody | $k_a$ (1/Ms) | $k_d$ (1/s) | $K_D$ (M) | n |
|---|---|---|---|---|
| Hu14F11-1 | 6.3E+05 | 1.9E−05 | 3.2E−11 | 3 |
| Hu14F11-23 | 3.4E+05 | 6.2E−05 | 1.8E−10 | 1 |
| Hu14F11-24 | 7.1E+05 | 2.2E−04 | 3.1E−10 | 1 |

The results in Table 26 demonstrate that Hu14F11-23 and Hu14F11-24, (i.e., antibodies that consist of one chimeric 06C11 chain (heavy or light) mixed with one chimeric 14F11 chain (heavy or light)), retain binding to GDF15. In particular, these antibodies have high affinities ranging from about 180 pM to about 310 pM.

Example 16

Binding Affinities of Affinity Matured Humanized Anti-GDF15 Monoclonal Antibodies The binding affinities and kinetics of binding of chimeric and humanized antibodies to mFc-rhGDF15, cleaved-rhGDF15, rabbit Fc mature recombinant mouse GDF15 (rFc-rmGDF15), and mouse Fc mature recombinant cynomolgus monkey GDF15 (mFc-rcGDF15) were measured by surface plasmon resonance, using a BIAcore® T100 instrument (GE Healthcare, Piscataway, N.J.).

Goat anti-human IgGs (Fc fragment specific, Jackson ImmunoResearch, West Grove, Pa.) were immobilized on carboxymethylated dextran CM4 sensor chips by amine coupling, according to a standard protocol. Analyses were performed at 37° C. using PBS containing 0.05% surfactant P20 as running buffer. The antibodies were captured in individual flow cells at a flow rate of 10 μL/minute. Injection time was varied for each antibody to yield an Rmax between 30 and 60 RU. Buffer, mFc-rhGDF15, cleaved-rhGDF15, rFc-rmGDF15, or mFc-rcGDF15 diluted in running buffer was injected sequentially over a reference surface (no antibody captured) and the active surface (antibody to be tested) for 240 seconds at 60 μL/minute. The dissociation phase was monitored for up to 1500 seconds. The surface was then regenerated with two 60-second injections of 10 mM Glycine-HCl, pH 2.25, at a flow rate of 30 μL/minute. The GDF15 concentration range tested for each GDF15 protein was 5 nM to 0.3125 nM (two-fold dilutions).

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined Kinetic values of purified monoclonal antibodies on mFc-rhGDF15, mature human GDF15, rFc-rmGDF15, and mFc-rcGDF15 are summarized in Table 27.

TABLE 27

| Protein | Antibody | $k_a$ (1/Ms) | $k_d$ (1/s) | $K_D$ (M) | n |
|---|---|---|---|---|---|
| mFc-rhGDF15 | Hu01G06-122 | 5.9E+06 | 2.1E−05 | 6.5E−12 | 5 |
| | Hu01G06-127 | 4.6E+06 | 4.2E−05 | 1.8E−11 | 4 |
| | Hu01G06-135 | 5.3E+06 | 4.4E−05 | 1.4E−11 | 5 |
| | Hu01G06-138 | 5.9E+06 | 4.1E−05 | 1.1E−11 | 5 |
| | Hu01G06-146 | 5.3E+06 | 2.6E−05 | 9.3E−12 | 5 |

TABLE 27-continued

| Protein | Antibody | $k_a$ (1/Ms) | $k_d$ (1/s) | $K_D$ (M) | n |
|---|---|---|---|---|---|
| Cleaved-rhGDF15 | Hu01G06-122 | 7.9E+06 | 3.4E−05 | 7.9E−12 | 4 |
| | Hu01G06-127 | 6.1E+06 | 3.6E−05 | 1.0E−11 | 4 |
| | Hu01G06-135 | 7.3E+06 | 6.2E−05 | 1.0E−11 | 4 |
| | Hu01G06-138 | 7.9E+06 | 2.5E−05 | 4.5E−12 | 4 |
| | Hu01G06-146 | 6.5E+06 | 5.2E−05 | 1.1E−11 | 4 |
| mFc-rcGDF15 | Hu01G06-122 | 2.3E+06 | 2.4E−05 | 1.0E−11 | 4 |
| | Hu01G06-127 | 1.8E+06 | 1.6E−05 | 9.5E−12 | 4 |
| | Hu01G06-135 | 2.2E+06 | 7.9E−05 | 3.8E−11 | 4 |
| | Hu01G06-138 | 2.3E+06 | 5.3E−05 | 2.5E−11 | 4 |
| | Hu01G06-146 | 2.0E+06 | 1.5E−05 | 8.0E−12 | 4 |
| rFc-rmGDF15 | Hu01G06-122 | 2.2E+07 | 1.4E−03 | 6.3E−11 | 2 |
| | Hu01G06-127 | 3.9E+07 | 2.1E−03 | 5.1E−11 | 2 |
| | Hu01G06-135 | 3.7E+07 | 1.9E−03 | 5.5E−11 | 2 |
| | Hu01G06-138 | 1.9E+07 | 8.0E−04 | 4.4E−11 | 2 |
| | Hu01G06-146 | 1.1E+07 | 7.2E−04 | 6.3E−11 | 2 |

The results in Table 27 demonstrate that the chimeric and each of the humanized antibodies, have fast association rates ($k_a$), very slow disassociation rates ($k_d$) and very high affinities ($K_D$). In particular, the antibodies have affinities ranging from less than 5 pM (e.g., about 4.5 pM) to about 65 pM.

Example 17

Reversal of Cachexia in an HT-1080 Fibroscarcoma Xenograft Model

Figure 23:
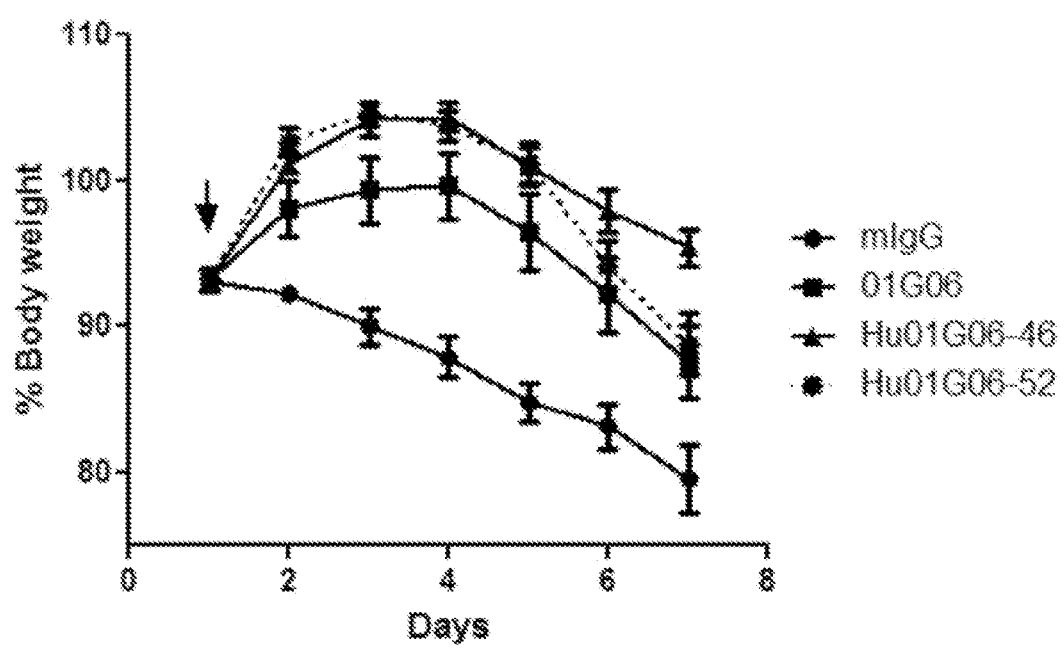
FIG. 23 is a graph summarizing results from an experiment to measure cachectic inhibitory activity of anti-GDF15 antibodies 01G06 (■), Hu01G06-46 (▲), and Hu01G06-52 (*), and a murine IgG control (■) dosed at 2 mg/kg in an HT-1080 fibrosarcoma tumor xenograft model in ICR-SCID mice. The arrow indicates intra-peritoneal injection of antibody.

This Example demonstrates the reversal of cachexia (as indicated by body weight loss) by humanized 01G06, 06C11, 14F11 antibodies in an HT-1080 fibrosarcoma xenograft model. HT-1080 cells were grown in culture at 37° C. and inoculated subcutaneously into the flank of 8-week old female ICR-SCID mice as described above in Example 10. Body weight was measured daily. When body weight reached 93%, the mice were randomly divided into groups of ten mice each. Each group received one of the following treatments: murine IgG control, 01G06, 06C11, 14F11, and their respective humanized versions at 2 mg/kg. Treatment was administered once a day by intra-peritoneal injection. Antibody treatment with 01G06, Hu01G06-46 and Hu01G06-52 resulted in body weight increase to initial weight or 100% (p<0.001) (FIG. 23). Statistical analysis was performed using ANOVA. Results for reversal of body weight on day in the HT-1080 model are shown in FIG. 23 and Table 28, respectively.

TABLE 28

| Gr. | Treatment Agent | mg/kg | % Body weight | ANOVA Analysis (compared to mIgG) |
|---|---|---|---|---|
| 1 | mIgG | 2 | 79.5 | NA |
| 2 | 01G06 | 2 | 87.6 | p < 0.001 |
| 3 | Hu01G06-46 | 2 | 95.4 | p < 0.001 |
| 4 | Hu01G06-52 | 2 | 87.8 | p < 0.001 |

The data in FIG. 23 and Table 28 indicated that antibodies 01G06, Hu01G06-46 and Hu01G06-52 can reverse cachexia in an HT-1080 fibrosarcoma xenograft model.

Figure 24:
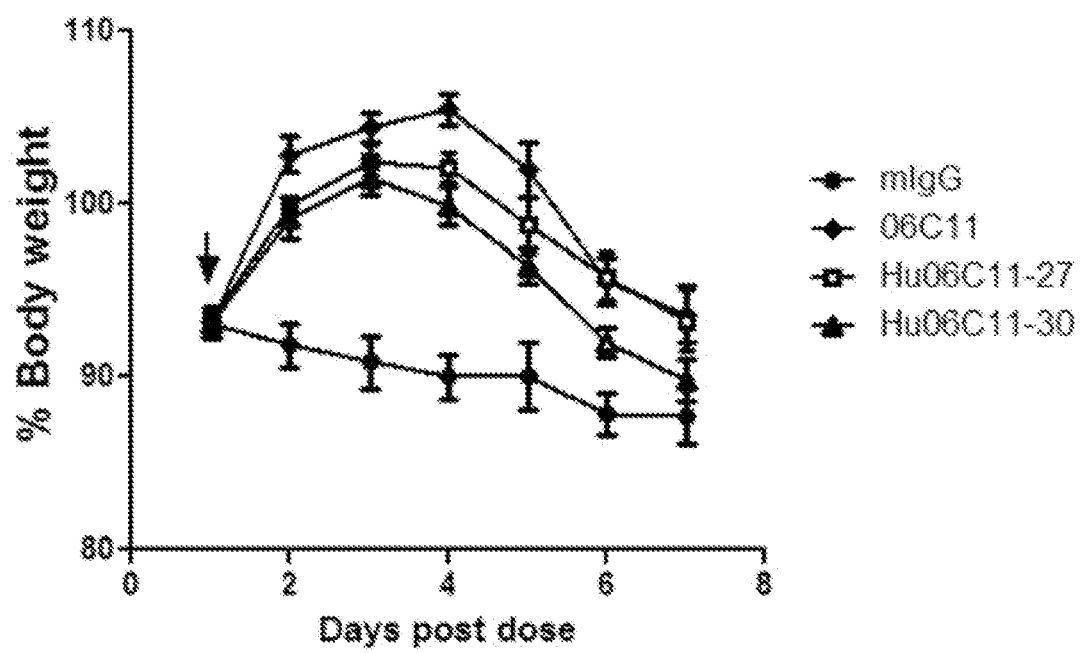
FIG. 24 is a graph summarizing results from an experiment to measure cachectic inhibitory activity of anti-GDF15 antibodies 06C11 (◇), Hu06C11-27 (□), and Hu06C11-30 (▲), and a murine IgG control (●) dosed at 2 mg/kg in an HT-1080 fibrosarcoma tumor xenograft model in ICR-SCID mice. The arrow indicates intra-peritoneal injection of antibody.

Antibody treatment with 06C11, Hu06C11-27, and Hu06C11-30 resulted in body weight increase relative to initial weight or about 100% (p<0.001) (FIG. 24). Statistical analysis was performed using ANOVA. Results for reversal of body weight in the HT-1080 model are shown in FIG. 24 and Table 29.

TABLE 29

| Gr. | Treatment Agent | mg/kg | % Body weight | ANOVA Analysis (compared to mIgG) |
|---|---|---|---|---|
| 1 | mIgG | 2 | 87.7 | NA |
| 2 | 06C11 | 2 | 93.6 | p < 0.001 |
| 3 | Hu06C11-27 | 2 | 93.2 | p < 0.001 |
| 4 | Hu06C11-30 | 2 | 89.8 | p < 0.01 |

The data in FIG. 24 and Table 29 indicate that antibodies 06C11, Hu06C11-27, and Hu06C11-30 can reverse cachexia in an HT-1080 fibrosarcoma xenograft model.

Figure 25:
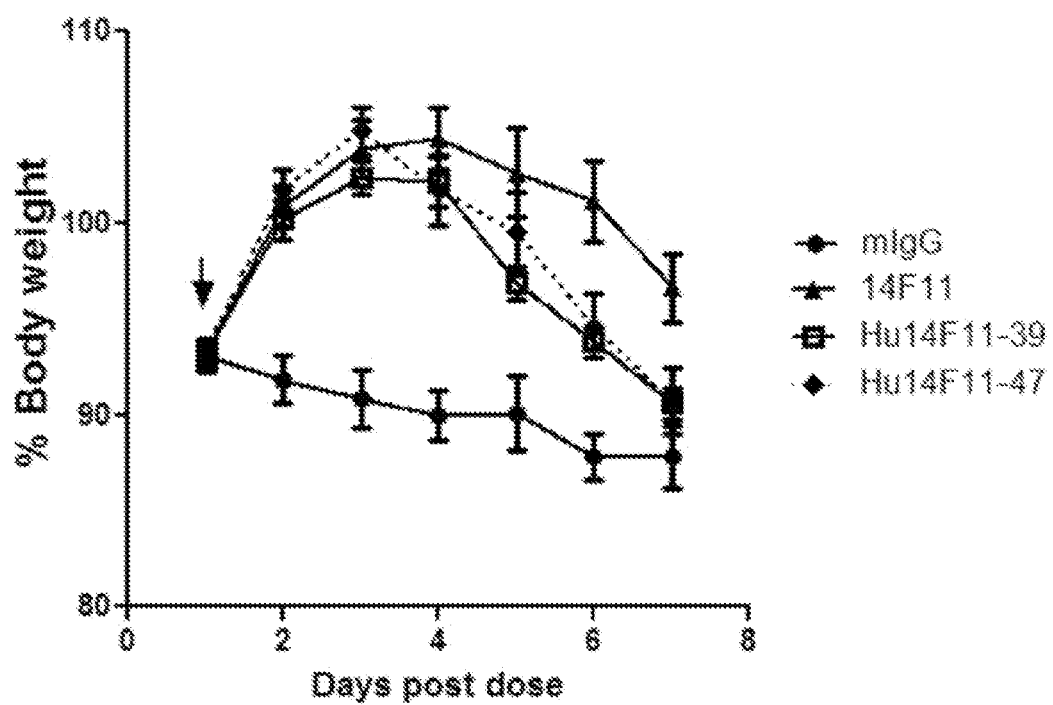
FIG. 25 is a graph summarizing results from an experiment to measure cachectic inhibitory activity of anti-GDF15 antibodies 14F11 (▲), Hu14F11-39 (□), and Hu14F11-47 (◆), and a murine IgG control (●) dosed at 2 mg/kg in an HT-1080 fibrosarcoma tumor xenograft model in ICR-SCID mice. The arrow indicates intra-peritoneal injection of antibody.

Antibody treatment with 14F11, Hu14F11-39, and Hu14F11-47 resulted in body weight increase relative to initial weight or about 100% (p<0.001) (FIG. 25). Statistical analysis was performed using ANOVA. Results for reversal of body weight in the HT-1080 model are shown in FIG. 25 and Table 30.

TABLE 30

| Gr. | Treatment Agent | mg/kg | % Body weight | ANOVA Analysis (compared to mIgG) |
|---|---|---|---|---|
| 1 | mIgG | 2 | 87.7 | NA |
| 2 | 14F11 | 2 | 96.6 | p < 0.001 |
| 3 | Hu14F11-39 | 2 | 90.5 | p < 0.001 |
| 4 | Hu14F11-47 | 2 | 90.7 | p < 0.001 |

The data in FIG. 25 and Table 30 indicated that antibodies 14F11, Hu14F11-39, and Hu14F11-47 can reverse cachexia in an HT-1080 fibrosarcoma xenograft model.

Figure 26:
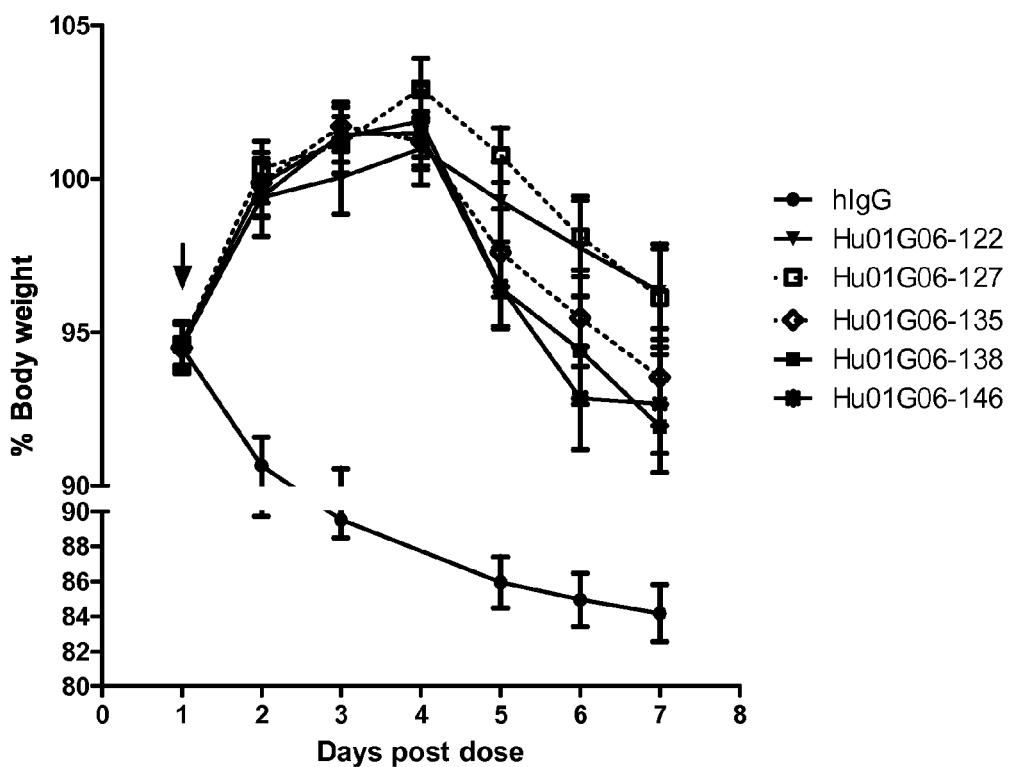
FIG. 26 is a graph summarizing results from an experiment to measure cachectic inhibitory activity of anti-GDF15 antibodies Hu01G06-122 (▼), Hu01G06-127 (□), Hu01G06-135 (◇), Hu01G06-138 (■), and Hu01G06-146 (*), and a human IgG control (●) dosed at 2 mg/kg in an HT-1080 fibrosarcoma tumor xenograft model in ICR-SCID mice. The arrow indicates intra-peritoneal injection of antibody.

Antibody treatment with humanized 01G06 antibodies (i.e., antibodies Hu01G06-122, Hu01G06-127, Hu01G06-135, Hu01G06-138 and Hu01G06-146) resulted in body weight increase relative to initial weight or about 100% (p<0.001) (FIG. 26). Statistical analysis was performed using ANOVA. Treatment with human IgG (hIgG) was used as a control. Results for reversal of body weights in the HT-1080 model are shown in FIG. 26 and Table 31.

TABLE 31

| Gr. | Treatment Agent | mg/kg | % Body weight | ANOVA Analysis (compared to hIgG) |
|---|---|---|---|---|
| 1 | hIgG | 2 | 84.2 | NA |
| 2 | Hu01G06-122 | 2 | 96.3 | p < 0.001 |
| 3 | Hu01G06-127 | 2 | 96.1 | p < 0.001 |
| 4 | Hu01G06-135 | 2 | 93.5 | p < 0.001 |
| 5 | Hu01G06-138 | 2 | 91.9 | p < 0.001 |
| 6 | Hu01G06-146 | 2 | 92.7 | p < 0.001 |

The data in FIG. 26 and Table 31 indicated that humanized anti-GDF15 antibodies Hu01G06-122, Hu01G06-127, Hu01G06-135, Hu01G06-138 and Hu01G06-146 can reverse cachexia in an HT-1080 fibrosarcoma xenograft model.

Example 18

Reversal of Cachexia in an mFc-rhGDF15-Induced Model

This Example demonstrates the reversal of cachexia (as indicated by body weight loss) by humanized 01G06 antibodies (i.e., antibody Hu01G06-122, Hu01G06-127, Hu01G06-

135, Hu01G06-138, or Hu01G06-146) in an mFc-rhGDF15-induced cachexia model. mFc-rhGDF15 (1 µg/g) was administered subcutaneously into the flank of 8-week old female ICR-SCID mice. Body weight was measured daily. When body weight reached 93%, the mice were randomly divided into six groups of ten mice each. Each group received one of the following treatments: human IgG control (hIgG), Hu01G06-122, Hu01G06-127, Hu01G06-135, Hu01G06-138 or Hu01G06-146 at 2 mg/kg. Treatment was administered once by intra-peritoneal injection. Treatment with antibody Hu01G06-122, Hu01G06-127, Hu01G06-135, Hu01G06-138 or Hu01G06-146 resulted in body weight increase relative to initial weight or about 100% (p<0.001) (FIG. 27 and Table 32).

TABLE 32

| Gr. | Treatment Agent | mg/kg | % Body weight | ANOVA Analysis (compared to hIgG) |
|---|---|---|---|---|
| 1 | hIgG | 2 | 70.6 | NA |
| 2 | Hu01G06-122 | 2 | 101.7 | p < 0.001 |
| 3 | Hu01G06-127 | 2 | 103.2 | p < 0.001 |
| 4 | Hu01G06-135 | 2 | 102.5 | p < 0.001 |
| 5 | Hu01G06-138 | 2 | 101.8 | p < 0.001 |
| 6 | Hu01G06-146 | 2 | 102.5 | p < 0.001 |

Figure 27:
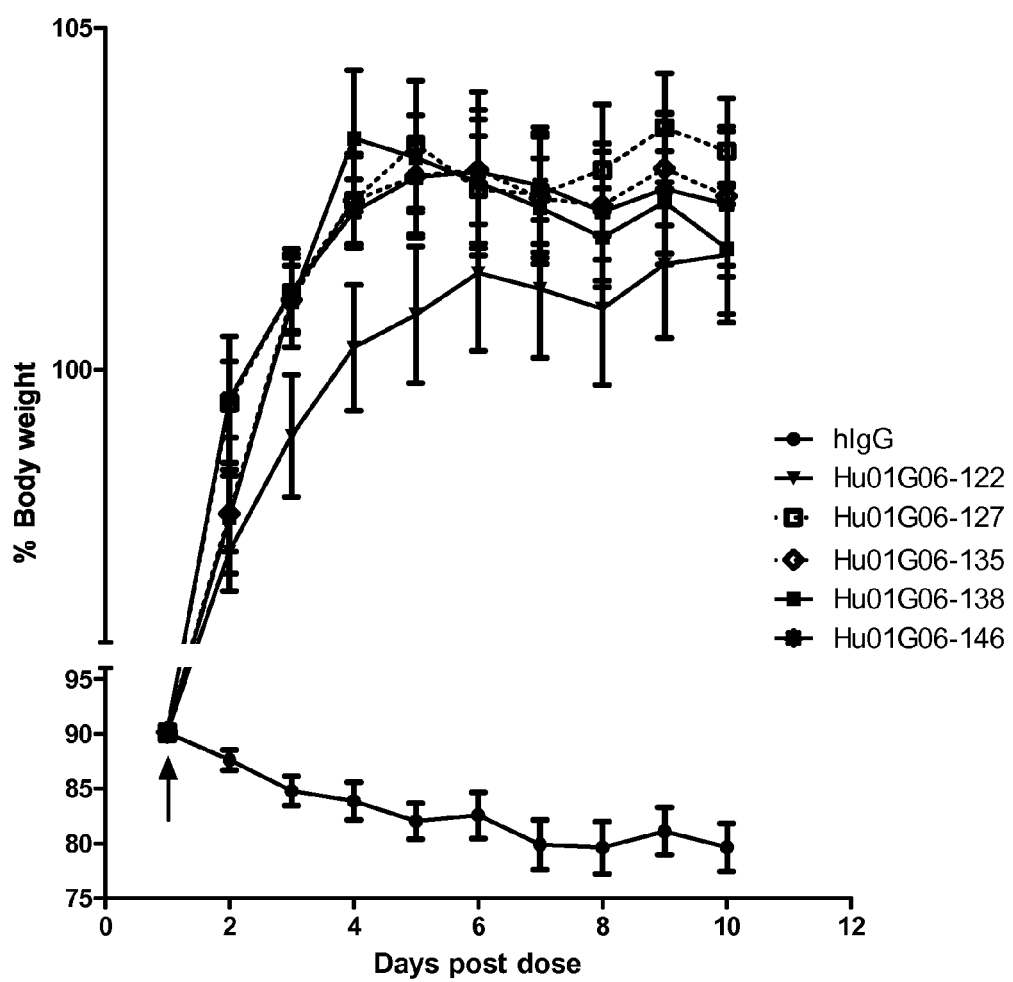
FIG. 27 is a graph summarizing results from an experiment to measure cachectic inhibitory activity of anti-GDF15 antibodies Hu01G06-122 (▼), Hu01G06-127 (□), Hu01G06-135 (◇), Hu01G06-138 (■), and Hu01G06-146 (*), and a human IgG control (●) dosed at 2 mg/kg in an mFc-rhGDF15 cachectic model in ICR-SCID mice. The arrow indicates intra-peritoneal injection of antibody.

The data in FIG. 27 and Table 32 indicate that the disclosed anti-GDF15 antibodies can reverse cachexia in an mFc-rhGDF15-induced mouse model (i.e., a non-tumor bearing mouse model).

These results indicate that humanized anti-GDF15 antibodies can reverse cachexia in an mFc-rhGDF15-induced cachexia model.

Example 19

Dose Response Reversal of Cachexia in an HT-1080 Fibroscarcoma Xenograft Model

Figure 28:
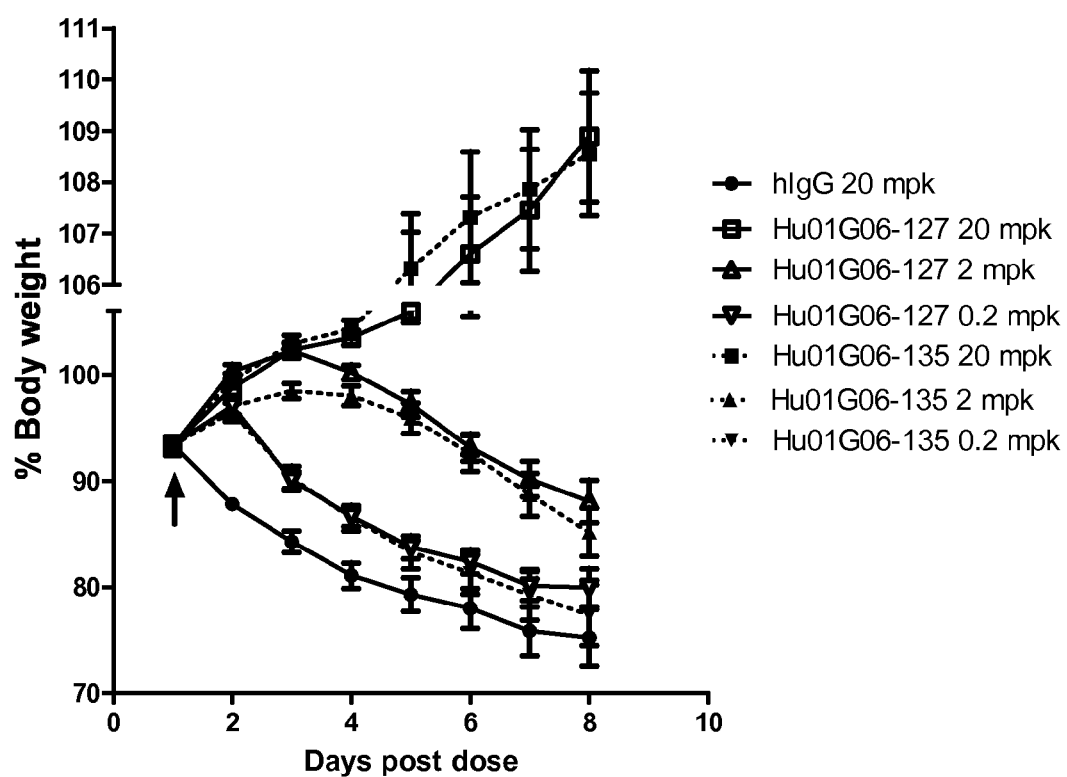
FIG. 28 is a graph summarizing results from an experiment to measure cachectic dose response inhibitory activity of anti-GDF15 antibodies Hu01G06-127 dosed at 20 mg/kg (□), 2 mg/kg (Δ), and 0.2 mg/kg (▽); Hu01G06-135 at 20 mg/kg (■), 2 mg/kg (▲), and 0.2 mg/kg (▼), and a human IgG control at 20 mg/kg (*) in an HT-1080 fibrosarcoma tumor xenograft model in ICR-SCID mice. The arrow indicates intravenous injection of antibody.

This Example demonstrates the dose response reversal of cachexia (as indicated by body weight loss) by humanized Hu01G06-127 and Hu01G06-135 antibodies in an HT-1080 fibrosarcoma xenograft model. HT-1080 cells were grown in culture at 37° C. and inoculated subcutaneously into the flank of 8-week old female ICR-SCID mice as described above in Example 10. Body weight was measured daily. When body weight reached 93%, the mice were randomly divided into groups of ten mice each. Each group received one of the following treatments: human IgG control (hIgG; 20 mg/kg), Hu01G06-127 (20 mg/kg, 2 mg/kg, or 0.2 mg/kg) and Hu01G06-135 (20 mg/kg, 2 mg/kg, or 0.2 mg/kg). Treatment was administered once a day by intravenous injection. Antibody treatment with Hu01G06-127 and Hu01G06-135 at 20 mg/kg resulted in body weight increase above the initial weight or 108% (p<0.001) (FIG. 28). Antibody treatment with Hu01G06-127 and Hu01G06-135 at 2 mg/kg resulted in limited body weight decrease compare to control (hIgG) from the initial weight or 88-85% (p<0.001) (FIG. 28). Statistical analysis was performed using ANOVA. Results for changes of body weight at the end of the study in the HT-1080 model are shown in FIG. 28 and Table 33.

TABLE 33

| Gr. | Treatment Agent | mg/kg | % Body weight | ANOVA Analysis (compared to hIgG) |
|---|---|---|---|---|
| 1 | hIgG | 20 | 75.2 | NA |
| 2 | Hu01G06-127 | 20 | 108.9 | p < 0.001 |
| 3 | Hu01G06-127 | 2.0 | 88.1 | p < 0.001 |
| 4 | Hu01G06-127 | 0.2 | 80.0 | NS |
| 5 | Hu01G06-135 | 20 | 108.6 | p < 0.001 |
| 6 | Hu01G06-135 | 2.0 | 85.2 | p < 0.01 |
| 7 | Hu01G06-135 | 0.2 | 77.3 | NS |

The data in FIG. 28 and Table 33 indicated that antibodies Hu01G06-127 and Hu01G06-135 can reverse cachexia in an HT-1080 fibrosarcoma xenograft model in a dose-dependent manner.

Example 20

Reversal of Muscle and Fat Loss in an HT-1080 Xenograft Tumor Model

This Example demonstrates the reversal of cachexia (as indicated by body weight loss, muscle mass loss and fat mass loss) by antibody 01G06 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. A cohort of ten 8-week old female ICR SCID mice with the same body weight was selected for subcutaneous inoculation into the flank with matrigel, as a non tumor (SHAM) control arm. Body weight was measured daily. When body weight reached 91% in the tumor bearing mice, the mice were randomly divided into two groups of ten mice each. Each group received one of the following treatments: human IgG control (hIgG) or Hu01G06-127 10 mg/kg on day 1, day 3 and day 6. Treatment was administered by intra-peritoneal injection. Treatment with antibody Hu01G06-127 resulted in body weight increase to 105% of initial weight compared to non-tumor bearing control mice (SHAM; p<0.001) (FIG. 29A and Table 34).

TABLE 34

| Gr. | Treatment Agent | mg/kg | % Body weight | ANOVA Analysis (compared to hIgG) |
|---|---|---|---|---|
| 1 | hIgG | 10 | 84.3 | NA |
| 2 | Hu01G06-127 | 10 | 105.4 | p < 0.001 |
| 2 | SHAM no tumor control | none | 101.9 | p < 0.001 |

Figure 29A:
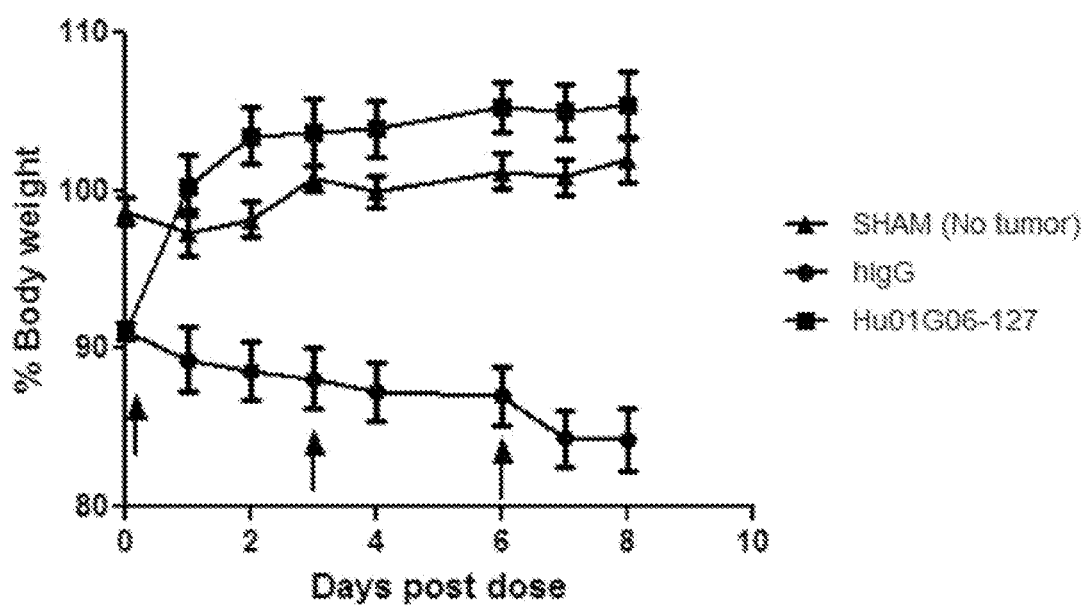
FIGS. 29A-29C are graphs summarizing results from an experiment to demonstrate anti-cachectic activity of anti-GDF15 antibodies Hu01G06-127 (■), dosed at 10 mg/kg, in immune-incompetent mice (ICR-SCID) bearing an HT-1080 fibrosarcoma tumor xenograft model. Treatment with antibody Hu01G06-127 reversed body weight loss (FIG. 29A); induced a gain of gonadal fat mass (FIG. 29B); and induced a gain of muscle mass of gastrocnemius muscle (FIG. 29 C) compared to negative control (hIgG (●)

The data in FIG. 29A and Table 34 indicate that the disclosed anti-GDF15 antibody can completely reverse cachexia in an HT-1080 fibrosarcoma xenograft model.

Figure 29B:
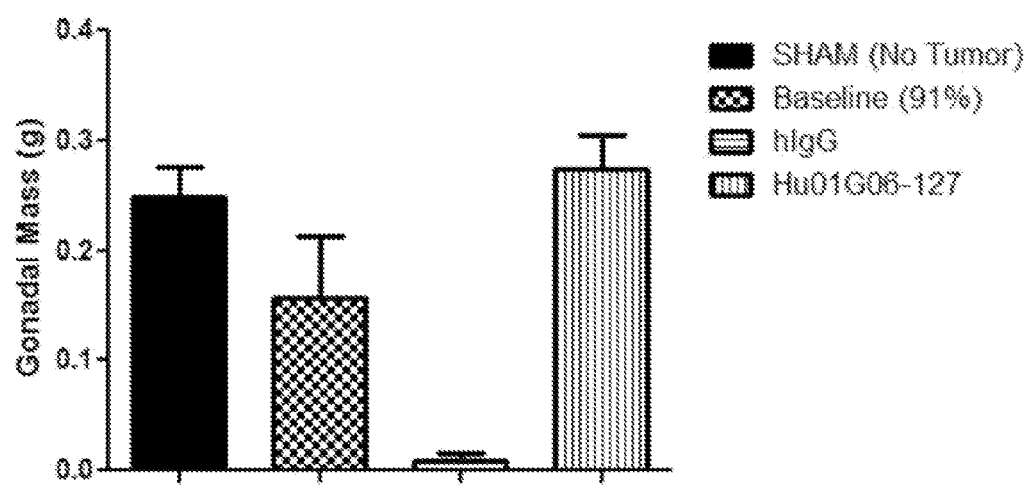
Figure 29C:
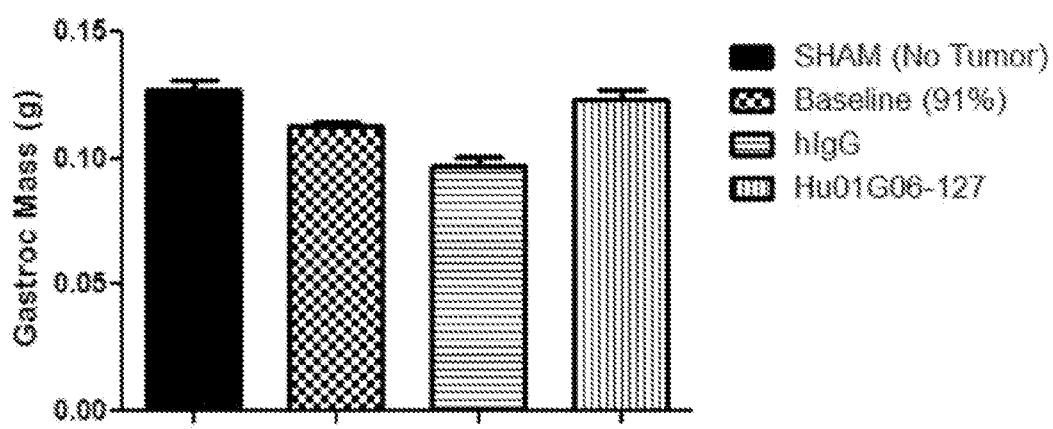

In this experiment, a group of ten mice were sacrificed at the time of dosing (baseline or 91% body weight loss, without treatment) and at the end of the study (eight days post dose, either hIgG or Hu01G06-127 as well SHAM non tumor control mice). Gonadal fat and the gastrocnemius muscles were removed surgically and weighed. As shown in FIG. 29B, significant gonadal fat mass loss was observed seven days post dose with hIgG, but not in the group treated with antibody Hu01G06-127 compared to baseline control (91% body weight loss). Moreover, treatment with Hu01G06-127 not only prevented further fat loss (compared to baseline group), but also, was able to restore the normal levels of gonadal fat (compared to SHAM non-tumor control) (FIG. 29B). In addition, significant gastrocnemius muscle mass loss was observed seven days post dose with hIgG, but not in the group treated with antibody Hu01G06-127 compared to baseline control (91% body weight loss) (FIG. 29C). Treatment with Hu01G06-127 not only prevented further muscle loss (compare to baseline group), but also was able to restore the normal levels of gastrocnemius muscle (compared to SHAM non tumor control) (FIG. 29C).

These results indicate that the disclosed anti-GDF15 antibodies can completely reverse cachexia measured by the loss of muscle mass, loss of fat and involuntary weight loss in an HT-1080 xenograft tumor model.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human GDF15 comprising an immunoglobulin heavy chain variable region and an immunoglobulin light chain variable region selected from the group consisting of:

(a) (i) an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F2), a $CDR_{H2}$ comprising an amino acid sequence selected from the group consisting of SEQ ID NO:237 and SEQ ID NO:241 (Hu01G06 IGHV1-18 F2), and a $CDR_{H3}$ comprising the amino acid sequence of SEQ ID NO:15 (Hu01G06 IGHV1-18 F2); and (ii) an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2);

(b) (i) an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F1), a $CDR_{H2}$ comprising an amino acid sequence selected from the group consisting of SEQ ID NO:238 and SEQ ID NO:241 (Hu01G06 IGHV1-69 F1), and a $CDR_{H3}$ comprising the amino acid sequence of SEQ ID NO:15 (Hu01G06 IGHV1-69 F1); and (ii) an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1);

(c) (i) an immunoglobulin heavy chain variable region comprising a $CDR_{H1}$ comprising the amino acid sequence of SEQ ID NO:1 (01G06, Ch01G06 Chimeric, Hu01G06 IGHV1-18, Hu01G06 IGHV1-69, Sh01G06 IGHV1-18 M69L, Sh01G06 IGHV1-69 T3OS I69L), a $CDR_{H2}$ comprising the amino acid sequence of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), and a $CDR_{H3}$ comprising the amino acid sequence of SEQ ID NO:15 (01G06, Ch01G06 Chimeric, Hu01G06 IGHV1-18, Hu01G06 IGHV1-69, Sh01G06 IGHV1-18 M69L, Sh01G06 IGHV1-69 T30S I69L); and (ii) an immunoglobulin light chain variable region comprising a $CDR_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I), a $CDR_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I), and a $CDR_{L3}$ comprising the amino acid sequence of SEQ ID NO:32 (01G06, Ch01G06 Chimeric, Hu01G06 IGKV1-39, Hu01G06 IGKV1-39 S43A V48I, Hu01G06 IGKV1-39 V48I);

(d) (i) an immunoglobulin heavy chain variable region comprising a $CDR_{H1}$ comprising the amino acid sequence of SEQ ID NO:2 (03G05), a $CDR_{H2}$ comprising the amino acid sequence of SEQ ID NO:8 (03G05), and a CDR$_{H3}$ comprising the amino acid sequence of SEQ ID NO:16 (03G05); and
  (ii) an immunoglobulin light chain variable region comprising a CDR$_{L1}$ comprising the amino acid sequence of SEQ ID NO:22 (03G05), a CDR$_{L2}$ comprising the amino acid sequence of SEQ ID NO:27 (03G05), and a CDR$_{L3}$ comprising the amino acid sequence of SEQ ID NO 33 (03G05);
(e) (i) an immunoglobulin heavy chain variable region comprising a CDR$_{H1}$ comprising the amino acid sequence of SEQ ID NO:3 (04F08), a CDR$_{H2}$ comprising the amino acid sequence of SEQ ID NO:9 (04F08), and a CDR$_{H3}$ comprising the amino acid sequence of SEQ ID NO:17 (04F08); and
  (ii) an immunoglobulin light chain variable region comprising a CDR$_{L1}$ comprising the amino acid sequence of SEQ ID NO:23 (04F08), a CDR$_{L2}$ comprising the amino acid sequence of SEQ ID NO:28 (04F08), and a CDR$_{L3}$ comprising the amino acid sequence of SEQ ID NO:34 (04F08);
(f) (i) an immunoglobulin heavy chain variable region comprising a CDR$_{H1}$ comprising the amino acid sequence of SEQ ID NO:4 (06C11, Ch06C11 Chimeric, Hu06C11 IGHV2-5), a CDR$_{H2}$ comprising the amino acid sequence of SEQ ID NO:9 (06C11, Ch06C11 Chimeric, Hu06C11 IGHV2-5), and a CDR$_{H3}$ comprising the amino acid sequence of SEQ ID NO:18 (06C11, Ch06C11 Chimeric, Hu06C11 IGHV2-5); and
  (ii) an immunoglobulin light chain variable region comprising a CDR$_{L1}$ comprising the amino acid sequence of SEQ ID NO:23 (06C11, Ch06C11 Chimeric, Sh06C11 IGKV1-16), a CDR$_{L2}$ comprising the amino acid sequence of SEQ ID NO:28 (06C11, Ch06C11 Chimeric, Sh06C11 IGKV1-16), and a CDR$_{L3}$ comprising the amino acid sequence of SEQ ID NO:35 (06C11, Ch06C11 Chimeric, Sh06C11 IGKV1-16);
(g) (i) an immunoglobulin heavy chain variable region comprising a CDR$_{H1}$ comprising the amino acid sequence of SEQ ID NO:1 (08G01), a CDR$_{H2}$ comprising the amino acid sequence of SEQ ID NO:10 (08G01), and a CDR$_{H3}$ comprising the amino acid sequence of SEQ ID NO:15 (08G01); and
  (ii) an immunoglobulin light chain variable region comprising a CDR$_{L1}$ comprising the amino acid sequence of SEQ ID NO:24 (08G01), a CDR$_{L2}$ comprising the amino acid sequence of SEQ ID NO:29 (08G01), and a CDR$_{L3}$ comprising the amino acid sequence of SEQ ID NO:32 (08G01);
(h) (i) an immunoglobulin heavy chain variable region comprising a CDR$_{H1}$ comprising the amino acid sequence of SEQ ID NO:5 (14F11, Ch14F11 Chimeric, Sh14F11 IGHV2-5, Sh14F11 IGHV2-70), a CDR$_{H2}$ comprising the amino acid sequence of SEQ ID NO:11 (14F11, Ch14F11 Chimeric, Sh14F11 IGHV2-5, Sh14F11 IGHV2-70), and a CDR$_{H3}$ comprising the amino acid sequence of SEQ ID NO:19 (14F11, Ch14F11 Chimeric, Sh14F11 IGHV2-5, Sh14F11 IGHV2-70); and
  (ii) an immunoglobulin light chain variable region comprising a CDR$_{L1}$ comprising the amino acid sequence of SEQ ID NO:23 (14F11, Ch14F11 Chimeric, Hu14F11 IGKV1-16), a CDR$_{L2}$ comprising the amino acid sequence of SEQ ID NO:30 (14F11, Ch14F11 Chimeric, Hu14F11 IGKV1-16), and a CDR$_{L3}$ comprising the amino acid sequence of SEQ ID NO:36 (14F11, Ch14F11 Chimeric, Hu14F11 IGKV1-16);
(i) (i) an immunoglobulin heavy chain variable region comprising a CDR$_{H1}$ comprising the amino acid sequence of SEQ ID NO:6 (17B11), a CDR$_{H2}$ comprising the amino acid sequence of SEQ ID NO:12 (17B11), and a CDR$_{H3}$ comprising the amino acid sequence of SEQ ID NO:20 (17B11); and
  (ii) an immunoglobulin light chain variable region comprising a CDR$_{L1}$ comprising the amino acid sequence of SEQ ID NO:25 (17B11), a CDR$_{L2}$ comprising the amino acid sequence of SEQ ID NO:31 (17B11), and a CDR$_{L3}$ comprising the amino acid sequence of SEQ ID NO:37 (17B11);
(j) (i) an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L), a CDR$_{H2}$ comprising the amino acid sequence of SEQ ID NO:13 (Sh01G06 IGHV1-18 M69L K64Q G44S, Sh01G06 IGHV1-18 M69L K64Q, Sh01G06 IGHV1-69 T30S K64Q I69L), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L); and
  (ii) an immunoglobulin light chain variable region comprising a CDR$_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I), a CDR$_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I), and a CDR$_{L3}$ comprising the amino acid sequence of SEQ ID NO:32 (01G06, Ch01G06 Chimeric, Hu01G06 IGKV1-39, Hu01G06 IGKV1-39 S43A V48I, Hu01G06 IGKV1-39 V48I);
(k) (i) an immunoglobulin heavy chain variable region comprising a CDR$_{H1}$ comprising an amino acid sequence selected from the group consisting of SEQ ID NO:1 and SEQ ID NO:38 (Hu01G06 IGHV1-18 F1), a CDR$_{H2}$ comprising an amino acid sequence selected from the group consisting of SEQ ID NO:236 and SEQ ID NO:240 (Hu01G06 IGHV1-18 F1), and a CDR$_{H3}$ comprising the amino acid sequence of SEQ ID NO:15 (Hu01G06 IGHV1-18 F1); and
  (ii) an immunoglobulin light chain variable region comprising a CDR$_{L1}$ comprising the amino acid sequence of SEQ ID NO:21 (Hu01G06 IGKV1-39 F1), a CDR$_{L2}$ comprising the amino acid sequence of SEQ ID NO:26 (Hu01G06 IGKV1-39 F1), and a CDR$_{L3}$ comprising the amino acid sequence of SEQ ID NO:32 (Hu01G06 IGKV1-39 F1);
(l) (i) an immunoglobulin heavy chain variable region comprising a CDR$_{H1}$ comprising an amino acid sequence selected from the group consisting of SEQ ID NO:1 and SEQ ID NO:234 (Hu01G06 IGHV1-69 F2), a CDR$_{H2}$ comprising an amino acid sequence selected from the group consisting of SEQ ID NO:239 and SEQ ID NO:240 (Hu01G06 IGHV1-69 F2), and a CDR$_{H3}$ comprising the amino acid sequence of SEQ ID NO:15 (Hu01G06 IGHV1-69 F2); and
  (ii) an immunoglobulin light chain variable region comprising a CDR$_{L1}$ comprising the amino acid sequence of SEQ ID NO:21 (Hu01G06 IGKV1-39 F1), a CDR$_{L2}$ comprising the amino acid sequence of SEQ ID NO:26 (Hu01G06 IGKV1-39 F1), and a CDR$_{L3}$ comprising the amino acid sequence of SEQ ID NO:32 (Hu01G06 IGKV1-39 F1);

(m) (i) an immunoglobulin heavy chain variable region comprising a CDR$_{H1}$ comprising an amino acid sequence selected from the group consisting of SEQ ID NO:1 and SEQ ID NO:234 (Hu01G06 IGHV1-69 F2), a CDR$_{H2}$ comprising an amino acid sequence selected from the group consisting of SEQ ID NO:239 and SEQ ID NO:240 (Hu01G06 IGHV1-69 F2), and a CDR$_{H3}$ comprising the amino acid sequence of SEQ ID NO:15 (Hu01G06 IGHV1-69 F2); and (ii) an immunoglobulin light chain variable region comprising a CDR$_{L1}$ comprising the amino acid sequence of SEQ ID NO:21 (Hu01G06 IGKV1-39 F2), a CDR$_{L2}$ comprising the amino acid sequence of SEQ ID NO:26 (Hu01G06 IGKV1-39 F2), and a CDR$_{L3}$ comprising the amino acid sequence of SEQ ID NO:244 (Hu01G06 IGKV1-39 F2);

(n) (i) an immunoglobulin heavy chain variable region comprising a CDR$_{H1}$ comprising the amino acid sequence of SEQ ID NO:4 (HE LM 06C11 IGHV2-70), a CDR$_{H2}$ comprising the amino acid sequence of SEQ ID NO:14 (HE LM 06C11 IGHV2-70), and a CDR$_{H3}$ comprising the amino acid sequence of SEQ ID NO:18 (HE LM 06C11 IGHV2-70); and (ii) an immunoglobulin light chain variable region comprising a CDR$_{L1}$ comprising the amino acid sequence of SEQ ID NO:23 (Ch06C11 Chimeric, Sh06C11 IGKV1-16), a CDR$_{L2}$ comprising the amino acid sequence of SEQ ID NO:28 (Ch06C11 Chimeric, Sh06C11 IGKV1-16), and a CDR$_{L3}$ comprising the amino acid sequence of SEQ ID NO:35 (Ch06C11 Chimeric, Sh06C11 IGKV1-16);

(o) (i) an immunoglobulin heavy chain variable region comprising a CDR$_{H1}$ comprising the amino acid sequence of SEQ ID NO:4 (Ch06C11 Chimeric), a CDR$_{H2}$ comprising the amino acid sequence of SEQ ID NO:9 (Ch06C11 Chimeric), and a CDR$_{H3}$ comprising the amino acid sequence of SEQ ID NO:18 (Ch06C11 Chimeric); and (ii) an immunoglobulin light chain variable region comprising a CDR$_{L1}$ comprising the amino acid sequence of SEQ ID NO:23 (Ch14F11 Chimeric), a CDR$_{L2}$ comprising the amino acid sequence of SEQ ID NO:30 (Ch14F11 Chimeric), and a CDR$_{L3}$ comprising the amino acid sequence of SEQ ID NO:36 (Ch14F11 Chimeric); and (p) (i) an immunoglobulin heavy chain variable region comprising a CDR$_{H1}$ comprising the amino acid sequence of SEQ ID NO:5 (Ch14F11 Chimeric), a CDR$_{H2}$ comprising the amino acid sequence of SEQ ID NO:11 (Ch14F11 Chimeric), and a CDR$_{H3}$ comprising the amino acid sequence of SEQ ID NO:19 (Ch14F11 Chimeric); and (ii) an immunoglobulin light chain variable region comprising a CDR$_{L1}$ comprising the amino acid sequence of SEQ ID NO:23 (Ch06C11 Chimeric), a CDR$_{L2}$ comprising the amino acid sequence of SEQ ID NO:28 (Ch06C11 Chimeric), and a CDR$_{L3}$ comprising the amino acid sequence of SEQ ID NO:35 (Ch06C11 Chimeric).

2. The antibody of claim 1, wherein the CDR sequences are interposed between human or humanized framework sequences.

3. An isolated nucleic acid comprising a nucleotide sequence encoding an immunoglobulin heavy chain variable region of claim 1.

4. An isolated nucleic acid comprising a nucleotide sequence encoding an immunoglobulin light chain variable region of claim 1.

5. An expression vector comprising the nucleic acid of claim 3.

6. An expression vector comprising the nucleic acid of claim 4.

7. A host cell comprising the expression vector of claim 5.

8. A host cell comprising the expression vector of claim 6.

9. A method of producing a polypeptide comprising an immunoglobulin heavy chain variable region or an immunoglobulin light chain variable region, the method comprising:

(a) growing the host cell of claim 8 under conditions so that the host cell expresses the polypeptide comprising the immunoglobulin heavy chain variable region or the immunoglobulin light chain variable region; and (b) purifying the polypeptide comprising the immunoglobulin heavy chain variable region or the immunoglobulin light chain variable region.

10. An isolated antibody that binds human GDF15, comprising an immunoglobulin heavy chain variable region and an immunoglobulin light chain variable region selected from the group consisting of:

(a) an immunoglobulin heavy chain variable region comprising the amino acid sequence of SEQ ID NO:248 (Hu01G06 IGHV1-18 F2), and an immunoglobulin light chain variable region comprising the amino acid sequence of SEQ ID NO:254 (Hu01G06 IGKV1-39 F2);

(b) an immunoglobulin heavy chain variable region comprising the amino acid sequence of SEQ ID NO:250 (Hu01G06 IGHV1-69 F1), and an immunoglobulin light chain variable region comprising the amino acid sequence of SEQ ID NO:92 (Hu01G06 IGKV1-39 F1);

(c) an immunoglobulin heavy chain variable region comprising the amino acid sequence of SEQ ID NO:40 (01G06, Ch01G06 Chimeric), and an immunoglobulin light chain variable region comprising the amino acid sequence of SEQ ID NO:76 (01G06, Ch01G06 Chimeric);

(d) an immunoglobulin heavy chain variable region comprising the amino acid sequence of SEQ ID NO:42 (03G05), and an immunoglobulin light chain variable region comprising the amino acid sequence of SEQ ID NO:78 (03G05);

(e) an immunoglobulin heavy chain variable region comprising the amino acid sequence of SEQ ID NO:44 (04F08), and an immunoglobulin light chain variable region comprising the amino acid sequence of SEQ ID NO:80 (04F08);

(f) an immunoglobulin heavy chain variable region comprising the amino acid sequence of SEQ ID NO:46 (06C11), and an immunoglobulin light chain variable region comprising the amino acid sequence of SEQ ID NO:82 (06C11);

(g) an immunoglobulin heavy chain variable region comprising the amino acid sequence of SEQ ID NO:48 (08G01), and an immunoglobulin light chain variable region comprising the amino acid sequence of SEQ ID NO:84 (08G01);

(h) an immunoglobulin heavy chain variable region comprising the amino acid sequence of SEQ ID NO:50 (14F11), and an immunoglobulin light chain variable region comprising the amino acid sequence of SEQ ID NO:86 (14F11);

(i) an immunoglobulin heavy chain variable region comprising the amino acid sequence of SEQ ID NO:52 (17B11), and an immunoglobulin light chain variable region comprising the amino acid sequence of SEQ ID NO:88 (17B11);

(j) an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:76 (Ch01G06 Chimeric);

(k) an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:76 (Ch01G06 Chimeric);

(l) an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:76 (Ch01G06 Chimeric);

(m) an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:76 (Ch01G06 Chimeric);

(n) an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:76 (Ch01G06 Chimeric);

(o) an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:76 (Ch01G06 Chimeric);

(p) an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:76 (Ch01G06 Chimeric);

(q) an immunoglobulin heavy chain variable region comprising the amino acid sequence of SEQ ID NO:40 (Ch01G06 Chimeric), and an immunoglobulin light chain variable region comprising the amino acid sequence of SEQ ID NO:90 (Hu01G06 IGKV1-39);

(r) an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:90 (Hu01G06 IGKV1-39);

(s) an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:90 (Hu01G06 IGKV1-39);

(t) an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:90 (Hu01G06 IGKV1-39);

(u) an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:90 (Hu01G06 IGKV1-39);

(v) an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:90 (Hu01G06 IGKV1-39);

(w) an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:90 (Hu01G06 IGKV1-39);

(x) an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:90 (Hu01G06 IGKV1-39);

(y) an immunoglobulin heavy chain variable region comprising the amino acid sequence of SEQ ID NO:40 (Ch01G06 Chimeric), and an immunoglobulin light chain variable region comprising the amino acid sequence of SEQ ID NO:92 (Hu01G06 IGKV1-39 S43A V48I);

(z) an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:92 (Hu01G06 IGKV1-39 S43A V48I);

(aa) an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:92 (Hu01G06 IGKV1-39 S43A V48I);

(bb) an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:92 (Hu01G06 IGKV1-39 S43A V48I);

(cc) an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:92 (Hu01G06 IGKV1-39 S43A V48I);

(dd) an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:92 (Hu01G06 IGKV1-39 S43A V48I);

(ee) an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:92 (Hu01G06 IGKV1-39 S43A V48I);

(ff) an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:92 (Hu01G06 IGKV1-39 S43A V48I);

(gg) an immunoglobulin heavy chain variable region comprising the amino acid sequence of SEQ ID NO:40 (Ch01G06 Chimeric), and an immunoglobulin light chain variable region comprising the amino acid sequence of SEQ ID NO:94 (Hu01G06 IGKV1-39 V48I);

(hh) an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:94 (Hu01G06 IGKV1-39 V48I);

(ii) an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:94 (Hu01G06 IGKV1-39 V48I);

(jj) an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:94 (Hu01G06 IGKV1-39 V48I);

(kk) an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:94 (Hu01G06 IGKV1-39 V48I);

(ll) an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:94 (Hu01G06 IGKV1-39 V48I);

(mm) an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:94 (Hu01G06 IGKV1-39 V48I);

(nn) an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:94 (Hu01G06 IGKV1-39 V48I);

(oo) an immunoglobulin heavy chain variable region comprising the amino acid sequence of SEQ ID NO:246 (Hu01G06 IGHV1-18 F1), and an immunoglobulin light chain variable region comprising the amino acid sequence of SEQ ID NO:92 (Hu01G06 IGKV1-39 F1);

(pp) an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:92 (Hu01G06 IGKV1-39 F1);

(qq) an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:254 (Hu01G06 IGKV1-39 F2);

(rr) an immunoglobulin heavy chain variable region comprising the amino acid sequence of SEQ ID NO:68 (HELM 06C11 IGHV2-70), and an immunoglobulin light chain variable region comprising the amino acid sequence of SEQ ID NO:82 (Ch06C11 Chimeric);

(ss) an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:82 (Ch06C11 Chimeric);

(tt) an immunoglobulin heavy chain variable region comprising the amino acid sequence of SEQ ID NO:46 (Ch06C11 Chimeric), and an immunoglobulin light chain variable region comprising the amino acid sequence of SEQ ID NO:96 (Sh06C11 IGKV1-16);

(uu) an immunoglobulin heavy chain variable region comprising the amino acid sequence of SEQ ID NO:68 (HELM 06C11 IGHV2-70), and an immunoglobulin light chain variable region comprising the amino acid sequence of SEQ ID NO:96 (Sh06C11 IGKV1-16);

(vv) an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:96 (Sh06C11 IGKV1-16);

(ww) an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:86 (Ch14F11 Chimeric);

(xx) an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:86 (Ch14F11 Chimeric);

(yy) an immunoglobulin heavy chain variable region comprising the amino acid sequence of SEQ ID NO:50 (Ch14F11 Chimeric), and an immunoglobulin light chain variable region comprising the amino acid sequence of SEQ ID NO:98 (Hu14F11 IGKV1-16);

(zz) an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:98 (Hu14F11 IGKV1-16); and (aaa) an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:98 (Hu14F11 IGKV1-16).

11. An isolated antibody that binds human GDF15 comprising an immunoglobulin heavy chain and an immunoglobulin light chain selected from the group consisting of:

(a) an immunoglobulin heavy chain comprising the amino acid sequence of SEQ ID NO:258 (Hu01G06 IGHV1-18 F2), and an immunoglobulin light chain comprising the amino acid sequence of SEQ ID NO:264 (Hu01G06 IGKV1-39 F2);

(b) an immunoglobulin heavy chain comprising the amino acid sequence of SEQ ID NO:260 (Hu01G06 IGHV1-69 F1), and an immunoglobulin light chain comprising the amino acid sequence of SEQ ID NO:208 (Hu01G06 IGKV1-39 F1);

(c) an immunoglobulin heavy chain comprising the amino acid sequence of SEQ ID NO:176 (Ch01G06 Chimeric), and an immunoglobulin light chain comprising the amino acid sequence of SEQ ID NO:204 (Ch01G06 Chimeric);

(d) an immunoglobulin heavy chain comprising the amino acid sequence of SEQ ID NO:192 (Ch06C11 Chimeric), and an immunoglobulin light chain comprising the amino acid sequence of SEQ ID NO:212 (Ch06C11 Chimeric);

(e) an immunoglobulin heavy chain comprising the amino acid sequence of SEQ ID NO:198 (Ch14F11 Chimeric), and an immunoglobulin light chain comprising the amino acid sequence of SEQ ID NO:216 (Ch14F11 Chimeric);

(f) an immunoglobulin heavy chain comprising the amino acid sequence of SEQ ID NO:178 (Hu01G06 IGHV1-18), and an immunoglobulin light chain comprising the amino acid sequence of SEQ ID NO:206 (Hu01G06 IGKV1-39);

(g) an immunoglobulin heavy chain comprising the amino acid sequence of SEQ ID NO:180 (Hu01G06 IGHV1-69), and an immunoglobulin light chain comprising the amino acid sequence of SEQ ID NO:206 (Hu01G06 IGKV1-39);

(h) an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:210 (Hu01G06 IGKV1-39 V48I);

(i) an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:210 (Hu01G06 IGKV1-39 V48I);

(j) an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:208 (Hu01G06 IGKV1-39 S43A V48I);

(k) an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:208 (Hu01G06 IGKV1-39 S43A V48I);

(l) an immunoglobulin heavy chain comprising the amino acid sequence of SEQ ID NO:256 (Hu01G06 IGHV1-18 F1), and an immunoglobulin light chain comprising the amino acid sequence of SEQ ID NO:208 (Hu01G06 IGKV1-39 F1);

(m) an immunoglobulin heavy chain comprising the amino acid sequence of SEQ ID NO:262 (Hu01G06 IGHV1-69 F2), and an immunoglobulin light chain comprising the amino acid sequence of SEQ ID NO:208 (Hu01G06 IGKV1-39 F1);

(n) an immunoglobulin heavy chain comprising the amino acid sequence of SEQ ID NO:262 (Hu01G06 IGHV1-69 F2), and an immunoglobulin light chain comprising the amino acid sequence of SEQ ID NO:264 (Hu01G06 IGKV1-39 F2);

(o) an immunoglobulin heavy chain comprising the amino acid sequence of SEQ ID NO:194 (HE LM 06C11 IGHV2-70), and an immunoglobulin light chain comprising the amino acid sequence of SEQ ID NO:214 (Sh06C11 IGKV1-16);

(p) an immunoglobulin heavy chain comprising the amino acid sequence of SEQ ID NO:196 (Hu06C11 IGHV2-5), and an immunoglobulin light chain comprising the amino acid sequence of SEQ ID NO:214 (Sh06C11 IGKV1-16);

(q) an immunoglobulin heavy chain comprising the amino acid sequence of SEQ ID NO:200 (Sh14F11 IGHV2-5), and an immunoglobulin light chain comprising the amino acid sequence of SEQ ID NO:218 (Hu14F11 IGKV1-16); and (r) an immunoglobulin heavy chain comprising the amino acid sequence of SEQ ID NO:202 (Sh14F11 IGHV2-70), and an immunoglobulin light chain comprising the amino acid sequence of SEQ ID NO:218 (Hu14F11 IGKV1-16).

* * * * *

SEQUENCE LISTING

```
<160> NUMBER OF SEQ ID NOS: 266

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Asn Met Asp
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Trp Ile His
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Tyr Gly Met Gly Val Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Thr Tyr Gly Met Gly Val Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Tyr Gly Met Gly Val Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Ser Gly Met Gly Val Ser
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ile Asn Pro Asn Asn Gly Gly Ile Phe Phe Asn Gln Lys Phe Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ile Asn Pro Ser Asn Gly Arg Ser Lys Tyr Asn Glu Lys Phe Lys
1               5                   10                  15

Asn

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Ile Tyr Trp Asp Asp Asp Lys Arg Tyr Asn Pro Ser Leu Lys Ser
1               5                   10                  15

```
<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Ile Asn Pro Asn Asn Gly Gly Thr Phe Tyr Asn Gln Lys Phe Lys
1               5                   10                  15

Gly

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ile Trp Trp Asp Asp Asp Lys Tyr Tyr Asn Pro Ser Leu Lys Ser
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Asn Asp Trp Asp Asp Asp Lys Arg Tyr Lys Ser Ser Leu Lys Ser
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ile Asn Pro Asn Asn Gly Gly Ile Phe Phe Asn Gln Lys Phe Gln
1               5                   10                  15

Gly

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Ile Tyr Trp Asp Asp Asp Lys Arg Tyr Asn Pro Ser Leu Lys Thr
1               5                   10                  15

<210> SEQ ID NO 15
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 15

Glu Ala Ile Thr Thr Val Gly Ala Met Asp Tyr
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Val Leu Asp Gly Ala Met Asp Tyr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Gly Tyr Ser Asn Leu Phe Ala Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Gly Tyr Asp Asp Tyr Trp Gly Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly His Tyr Ser Ala Met Asp Tyr
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Val Gly Gly Leu Glu Gly Tyr Phe Asp Tyr
1               5                   10
```

```
<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Thr Ser Glu Asn Leu His Asn Tyr Leu Ala
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Glu Ser Val Asp Asn Tyr Gly Ile Ser Phe Met Asn
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ala Ser Gln Asn Val Gly Thr Asn Val Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gly Asn Ile His Asn Tyr Leu Ala
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Ser Val Ser Thr Ser Arg Phe Ser Tyr Met His
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Asp Ala Lys Thr Leu Ala Asp
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Ser Asn Gln Gly Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ala Ser Tyr Arg Tyr Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Ala Lys Thr Leu Ala Asp
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Pro Ser Tyr Arg Tyr Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ala Ser Asn Leu Glu Ser
1               5

<210> SEQ ID NO 32
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 32

Gln His Phe Trp Ser Ser Pro Tyr Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Ser Lys Glu Val Pro Trp Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Tyr Asn Ser Tyr Pro Tyr Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Tyr Asn Asn Tyr Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Tyr Asn Ser Tyr Pro His Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln His Ser Trp Glu Ile Pro Tyr Thr
1               5
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Phe Thr Asp Tyr
1               5

<210> SEQ ID NO 39
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaggtcctgc tgcaacagtc tggacctgag ctggtgaagc ctggggcttc agtgaagata      60
ccctgcaagg cttctggata cacattcact gactacaaca tggactgggt gaagcagagc     120
catggaaaga gccttgagtg gattggacaa attaatccta acaatggtgg tatttcttc     180 aaccagaagt tcaagggcaa ggccacattg actgtagaca gtcctccaa tacagccttc     240 atggaggtcc gcagcctgac atctgaggac actgcagtct attactgtgc aagagaggca     300
attactacgg taggcgctat ggactactgg ggtcaaggaa cctcagtcac cgtctcctca     360

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser
        115                 120

<210> SEQ ID NO 41
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
caggtccaac tgcagcagcc tggggctgaa ctggtgaagc ctggggcttc agtgaagctg      60
tcctgcaagg cttctggcta caccttcacc agctactgga ttcactgggt gaaccagagg     120
cctggacaag gccttgagtg gattggagac attaatccta gcaacggccg tagtaagtat     180
aatgagaagt tcaagaacaa ggccacaatg actgcagaca atcctccaa cacagcctac      240
atgcaactca gcagcctgac atctgaggac tctgcggtct attactgtgc aagagaggtt     300
ctggatggtg ctatggacta ctggggtcaa ggaacctcag tcaccgtctc ctca           354
```

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Ile His Trp Val Asn Gln Arg Pro Gly Gln Gly Leu Glu Trp Ile
            35                  40                  45

Gly Asp Ile Asn Pro Ser Asn Gly Arg Ser Lys Tyr Asn Glu Lys Phe
        50                  55                  60

Lys Asn Lys Ala Thr Met Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Leu Asp Gly Ala Met Asp Tyr Trp Gly Gln Gly Thr
            100                 105                 110

Ser Val Thr Val Ser Ser
        115

<210> SEQ ID NO 43
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
caggttactc tgaaagagtc tggccctggg atattgcagc cctcccagac cctcagtctg      60
acttgttctt tctctgggtt ttcactgagc acttatggta tgggtgtgac ctggattcgt     120
cagccttcag gaaagggtct ggagtggctg gcacacattt actgggatga tgacaagcgc     180
tataacccat ccctgaagag ccggctcaca atctccaagg atacctccaa caaccaggta     240
ttcctcaaga tcaccagtgt ggacactgca gatactgcca catactactg tgctcaaacg     300
gggtatagta acttgtttgc ttactggggc caagggactc tggtcactgt ctctgca        357
```

<210> SEQ ID NO 44
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 44

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Thr Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Thr Gly Tyr Ser Asn Leu Phe Ala Tyr Trp Gly Gln Gly
            100                 105                 110

Thr Leu Val Thr Val Ser Ala
        115

<210> SEQ ID NO 45
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
caggttactc tgaaagagtc tggccctggg atattgcagc cctcccagac cctcagtctg      60
acttgttctt tctctgggtt ttcactgaac acttatggta tgggtgtgag ctggattcgt     120
cagccttcag gaaagggtct ggagtggctg gcacacattt actgggatga tgacaagcgc     180
tataacccat ccctgaagag ccggctcaca atctccaagg atgcctccaa caaccgggtc     240
ttcctcaaga tcaccagtgt ggacactgca gatactgcca catactactg tgctcaaaga     300
ggttatgatg attactgggg ttactggggc caagggactc tggtcactat ctctgca       357

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80
```

Phe Leu Lys Ile Thr Ser Val Asp Thr Ala Asp Thr Ala Thr Tyr Tyr
                85                  90                  95

Cys Ala Gln Arg Gly Tyr Asp Tyr Trp Gly Tyr Trp Gly Gln Gly
            100                 105                 110

Thr Leu Val Thr Ile Ser Ala
        115

<210> SEQ ID NO 47
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gaggtcctgc tgcaacagtc tggacctgag gtggtgaagc ctggggcttc agtgaagata      60
ccctgcaagg cttctggata cacattcact gactacaaca tggactgggt gaagcagagc    120
catggaaaga gccttgagtg gattggagag attaatccta acaatggtgg tactttctac    180
aaccagaagt tcaagggcaa ggccacattg actgtagaca gtcctccag cacagcctac     240 atggagctcc gcagcctgac atctgaggac actgcagtct attactgtgc aagagaggca    300
attactacgg taggcgctat ggactactgg ggtcaaggaa cctcagtcac cgtctcctca    360

<210> SEQ ID NO 48
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Leu Leu Gln Gln Ser Gly Pro Glu Val Val Lys Pro Gly Ala
1               5                   10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Glu Ile Asn Pro Asn Asn Gly Gly Thr Phe Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser
        115                 120

<210> SEQ ID NO 49
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
caggttactc tgaaagagtc tggccctgga atattgcagc cctcccagac cctcagtctg      60

```
acttgttctt tctctgggtt ttcactgagc acttatggta tgggtgtagg ctggattcgt    120
cagccttcag gaaagggtct agagtggctg gcagacattt ggtgggatga cgataagtac    180
tataacccat ccctgaagag ccggctcaca atctccaagg atacctccag caatgaggta    240
ttcctcaaga tcgccattgt ggacactgca gatactgcca cttactactg tgctcgaaga    300
ggtcactact ctgctatgga ctactggggt caaggaacct cagtcaccgt ctcctca      357
```

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser
        115

<210> SEQ ID NO 51
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
caggttactc tgaaagagtc tggccctggg atattgcagc cctcccagac cctcagtctg     60
acttgttctt tctctgggtt ttcactgagc acttctggta tgggtgtgag ttggattcgt    120
cagccttcag gaaagggtct ggagtggctg gcacacaatg actgggatga tgacaagcgc    180
tataagtcat ccctgaagag ccggctcaca atatccaagg atacctccag aaaccaggta    240
ttcctcaaga tcaccagtgt ggacactgca gatactgcca catactactg tgctcgaaga    300
gttgggggat tagagggcta ttttgattac tggggccaag caccactctc acagtctcc     360 tca                                                                  363
```

<210> SEQ ID NO 52
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Asn Asp Trp Asp Asp Lys Arg Tyr Lys Ser Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Val Gly Gly Leu Glu Gly Tyr Phe Asp Tyr Trp Gly
                100                 105                 110

Gln Gly Thr Thr Leu Thr Val Ser Ser
            115                 120

<210> SEQ ID NO 53
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caagtgcaac ttgtgcagtc gggtgcggaa gtcaaaaagc cgggagcgtc ggtgaaagta      60
tcgtgtaaag cgtcgggata tacgtttacg gactataaca tggactgggt acgacaggca     120
ccggggaaat cgttggaatg gatcggacag attaatccga caatggggg aattttctttt     180 aatcagaaat tcaaaggacg ggcgacgttg acggtcgata tcgacgaa tacgcgtat       240 atggaattga ggtcgcttcg ctcggacgat acggcggtct attactgcgc caggggaggcg    300 atcacgacgg tagggcgat ggattattgg ggacagggga cgcttgtgac ggtatcgtcg     360

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 55
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
caagtccagc ttgtccagtc gggagcggaa gtgaagaaac cggggtcgtc ggtcaaagta      60
tcgtgtaaag cgtcgggata tacgtttacg gactataaca tggattgggt acgacaggct     120
ccgggaaaat cattggaatg gattggacag attaatccga ataatggggg tatcttcttt     180
aatcaaaagt ttaaagggag gcgacgttg acggtggaca aatcgacaaa tacggcgtat      240
atggaattgt cgtcgcttcg gtcggaggac acggcggtgt attactgcgc gagggaggcg     300
atcacgacgg tcggggcgat ggattattgg ggacagggaa cgcttgtgac ggtatcgtcg     360

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 57
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtccagc ttgtgcaatc gggagcggaa gtgaagaaac cgggagcgtc ggtaaaagtc      60
tcgtgcaaag cgtcggggta tacgtttacg gactataaca tggactgggt cgccaagcg     120 cctggacagg gtcttgaatg gatggggcag attaatccga ataatggagg gatcttcttt      180
aatcagaaat tcaaaggaag ggtaacgctg acgacagaca cgtcaacatc gacggcctat      240
atggaattgc ggtcgttgcg atcagatgat acggcggtct actattgtgc gagggaggcg      300
attacgacgg tgggagcgat ggattattgg ggacagggga cgttggtaac ggtatcgtcg      360

<210> SEQ ID NO 58
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 59
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtccagc ttgtgcaatc gggagcggaa gtgaagaaac cgggagcgtc ggtaaaagtc      60
tcgtgcaaag cgtcggggta tacgtttacg gactataaca tggactgggt gcgccaagcg      120
cctggacaga gccttgaatg gatggggcag attaatccga ataatggagg gatcttcttt      180
aatcagaaat tccagggaag ggtaacgctg acgacagaca cgtcaacatc gacggcctat      240
atggaattgc ggtcgttgcg atcagatgat acggcggtct actattgtgc gagggaggcg      300
attacgacgg tgggagcgat ggattattgg ggacagggga cgttggtaac ggtatcgtcg      360

<210> SEQ ID NO 60
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
            115                 120

<210> SEQ ID NO 61
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caggtccagc ttgtgcaatc gggagcggaa gtgaagaaac cgggagcgtc ggtaaaagtc      60
tcgtgcaaag cgtcgggggta tacgtttacg gactataaca tggactgggt gcgccaagcg    120
cctggacagg gtcttgaatg gatggggcag attaatccga ataatggagg gatcttcttt    180
aatcagaaat tccagggaag ggtaacgctg acgacagaca cgtcaacatc gacggcctat    240
atggaattgc ggtcgttgcg atcagatgat acggcggtct actattgtgc gagggaggcg    300
attacgacgg tgggagcgat ggattattgg ggacagggga cgttggtaac ggtatcgtcg    360

<210> SEQ ID NO 62
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
            115                 120

<210> SEQ ID NO 63
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
caagtacagc ttgtacagtc gggagcggaa gtcaagaaac cgggatcgtc ggtcaaagtg      60
tcgtgtaaag cgtcgggata tacgtttagc gactataaca tggattgggt gcgacaagcg     120
cctgggcagg gacttgaatg gatgggtcag atcaatccga ataatggggg aatcttttc      180 aatcagaagt ttaaagggag ggtaacgctg acggcggata aaagcacgtc aacggcgtat     240
atggagttgt cgtcgttgcg gtcggaggac acggcggtct attactgcgc gagggaagcg     300
attacgacgg tgggagcgat ggattattgg gggcagggaa cgcttgtaac ggtgtcatcg     360

<210> SEQ ID NO 64
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 65
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caagtacagc ttgtacagtc gggagcggaa gtcaagaaac cgggatcgtc ggtcaaagtg      60
tcgtgtaaag cgtcgggata tacgtttagc gactataaca tggattgggt gcgacaagcg     120
cctgggcagg gacttgaatg gatgggtcag atcaatccga ataatggggg aatcttttc      180 aatcagaagt ttcaggggag ggtaacgctg acggcggata aaagcacgtc aacggcgtat     240
atggagttgt cgtcgttgcg gtcggaggac acggcggtct attactgcgc gagggaagcg     300

```
attacgacgg tgggagcgat ggattattgg gggcagggaa cgcttgtaac ggtgtcatcg    360
```

<210> SEQ ID NO 66
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 67
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
caggtgactt tgaaagaatc cggtcccgca ttggtaaagc caacccagac acttacgctc    60
acatgtacat tttccggatt cagcttgaac acttacggga tgggagtgtc gtggattcgg    120
caacctccgg ggaaggctct ggagtggctg gcgcacatct actgggatga tgacaaaagg    180
tataacccct cacttaaaac gagactgacg atctcgaagg acacaagcaa gaatcaggtc    240
gtcctcacga ttcgaatgt agacccggtg gatactgccg tctattactg cgcgcaacgc    300
gggtatgatg actactgggg atattggggt cagggcaccc tcgtgaccat ctcgtca      357
```

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Ala Leu Glu

```
                35                  40                  45
Trp Leu Ala His Ile Tyr Trp Asp Asp Lys Arg Tyr Asn Pro Ser
            50                  55                  60
Leu Lys Thr Arg Leu Thr Ile Ser Lys Asp Thr Ser Lys Asn Gln Val
65                  70                  75                  80
Val Leu Thr Ile Thr Asn Val Asp Pro Val Asp Thr Ala Val Tyr Tyr
                85                  90                  95
Cys Ala Gln Arg Gly Tyr Asp Asp Tyr Trp Gly Tyr Trp Gly Gln Gly
                100                 105                 110
Thr Leu Val Thr Ile Ser Ser
            115

<210> SEQ ID NO 69
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caagtaacgc tcaaggagtc cggacccacc ttggtgaagc cgacgcagac cttgactctt      60
acgtgcactt tctcggggtt ttcactgaat acgtacggga tgggtgtctc atggatcagg     120
caacctccgg ggaaaggatt ggaatggctg gcgcacatct actgggatga cgataagaga     180
tataacccaa gcctcaagtc gcggctcacc attacaaaag atacatcgaa aaatcaggtc     240
gtacttacta tcacgaacat ggaccccgtg gacacagcaa catattactg tgcccagcgc     300
ggctatgacg attattgggg ttactgggga cagggaacac tggtcacggt gtccagc        357

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Asn Thr Tyr
            20                  25                  30
Gly Met Gly Val Ser Trp Ile Arg Gln Pro Pro Gly Lys Gly Leu Glu
        35                  40                  45
Trp Leu Ala His Ile Tyr Trp Asp Asp Lys Arg Tyr Asn Pro Ser
            50                  55                  60
Leu Lys Ser Arg Leu Thr Ile Thr Lys Asp Thr Ser Lys Asn Gln Val
65                  70                  75                  80
Val Leu Thr Ile Thr Asn Met Asp Pro Val Asp Thr Ala Thr Tyr Tyr
                85                  90                  95
Cys Ala Gln Arg Gly Tyr Asp Asp Tyr Trp Gly Tyr Trp Gly Gln Gly
                100                 105                 110
Thr Leu Val Thr Val Ser Ser
            115

<210> SEQ ID NO 71
<211> LENGTH: 357
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 71

```
cagatcactt tgaaagaaag cggaccgacc ttggtcaagc ccacacaaac cctcacgctc    60
acgtgtacat tttcgggggtt ctcgctttca acttacggga tgggagtagg gtggattcgc   120
cagccgcctg gtaaagcgtt ggagtggctt gcagacatct ggtgggacga cgataagtac   180
tataatccct cgctcaagtc cagactgacc atcacgaaag atacgagcaa gaaccaggtc   240
gtgctgacaa tgactaacat ggacccagtg gatacggcta catattactg cgccaggcgg   300
ggtcactact cagcgatgga ttattggggc cagggaacac tggtaacggt gtcgtcc      357
```

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser
        115
```

<210> SEQ ID NO 73
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
caagtgactc tcaaggagtc cggacccgcc ctggtcaaac caacgcagac actgacgctc    60
acatgcacct tcagcggatt tcgttgtca acgtacggca tgggtgtggg gtggattcgc   120
cagcctccgg ggaaagccct tgaatggttg gcggacatct ggtgggatga tgacaagtac   180
tataatccct cacttaagtc acggttgacg atctcgaaag acaccagcaa gaaccaggta   240
gtgctgacaa tgactaacat ggacccggtc gatacagcgg tctactattg tgctagaagg   300
ggacactact ccgcaatgga ttattggggt caggggacgc tcgtaaccgt gtcgtcg     357
```

<210> SEQ ID NO 74

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser
        115

<210> SEQ ID NO 75
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gacatccaga tgactcagtc tccagcctcc ctatctgcat ctgtgggaga aactgtcacc        60
atcacatgtc gaacaagtga gaatcttcac aattatttag catggtatca gcagaaacag       120
ggaaaatctc ctcagctcct ggtctatgat gcaaaaacct tagcagatgg tgtgccatca       180
aggttcagtg gcagtggatc aggaacacaa tattctctca agatcaacag cctgcagcct       240
gaagattttg ggagttatta ctgtcaacat ttttggagta gtccttacac gttcggaggg       300
gggaccaagc tggaaataaa a                                                 321

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys
            100                 105

<210> SEQ ID NO 77
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gacattgtgt tgacccaatc tccagcttct ttggctgtgt ctctagggca gagggccacc      60
atctcctgca gagccagcga aagtgttgat aattatggca ttagttttat gaactggttc     120
caacagaaac caggacagcc acccaaactc ctcatctatg ctgcatccaa ccaaggctcc     180
ggggtccctg ccaggtttag tggcagtggg tctgggacag acttcagcct caacatccat     240
cctatggagg aggatgatac tgcaatgtat ttctgtcagc aaagtaagga ggttccgtgg     300
acgttcggtg aggctccaa gctggaaatc aaa                                    333

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Ser Lys Leu Glu Ile Lys
            100                 105                 110

<210> SEQ ID NO 79
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gacattgtga tgacccagtc tcaaaaattc atgtccacat cagtaggaga cagggtcagc      60
gtcacctgca aggccagtca gaatgtgggt actaatgtag cctggtatca acagaaatta     120

```
ggacaatctc ctaaaacact gatttactcg gcatcctacc ggtacagtgg agtccctgat    180
cgcttcacag gcagtggatc tgggacagat tcactctca ccatcagcaa tgtgcagtct    240
gaagacttgg cagagtattt ctgtcagcaa tataacagct atccgtacac gttcggaggg    300
gggaccaagc tggaaataaa a                                             321
```

<210> SEQ ID NO 80
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Leu Gly Gln Ser Pro Lys Thr Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105
```

<210> SEQ ID NO 81
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
gacattgtga tgacccagtc tcaaaaattc atgtccacat cagtaggaga cagggtcagc    60
gtcacctgca aggccagtca gaatgtgggt actaatgtag cctggtttca acagaaacca    120
ggtcaatctc ctaaagcact gatttactcg gcatcttacc ggtacagtgg agtccctgat    180
cgcttcacag gcagtggatc tgggacagat tcattctca ccatcagcaa tgtgcagtct    240
gaagacctgg cagagtattt ctgtcagcaa tataacaact atcctctcac gttcggtgct    300
gggaccaagc tggagctgaa a                                             321
```

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30
```

Val Ala Trp Phe Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105

<210> SEQ ID NO 83
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
gacatccaga tgactcagtc tccagcctcc ctatctgcat ctgtgggaga aactgtcacc      60
atcacatgtc gagcaagtgg gaatattcac aattatttag catggtatca gcagaaacag     120
ggaaaatctc ctcagctcct ggtctataat gcaaaaacct tagcagatgg tgtgccatca    180
aggttcagtg gcagtggatc aggaacacaa tattctctca agatcaacag cctgcagcct     240
gaagattttg ggagttatta ctgtcaacat ttttggagtt ctccttacac gttcggaggg     300
gggaccaagc tggaaataaa a                                                321

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys
            100                 105

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
gacattgtaa tgacccagtc tcaaaaattc atgtccacat cagtaggaga cagggtcagc      60
gtcacctgca aggccagtca gaatgtgggt actaatgtag cctggtatca acagaaacca    120
gggcaatctc ctaaagcact gatttactcg ccatcctacc ggtacagtgg agtccctgat    180
cgcttcacag gcagtggatc tgggacagat ttcactctca ccatcagcaa tgtgcagtct    240
gaagacttgg cagaatattt ctgtcagcaa tataacagct atcctcacac gttcggaggg    300
gggaccaagc tggaaatgaa a                                              321
```

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Asp Ile Val Met Thr Gln Ser Gln Lys Phe Met Ser Thr Ser Val Gly
1               5                   10                  15
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Ala Leu Ile
        35                  40                  45
Tyr Ser Pro Ser Tyr Arg Tyr Ser Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln Tyr Asn Ser Tyr Pro His
                85                  90                  95
Thr Phe Gly Gly Gly Thr Lys Leu Glu Met Lys
            100                 105
```

<210> SEQ ID NO 87
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
gacattgtgc tgacacagtc tcctgcttcc ttagctgtat ctctggggca gagggccacc     60
atctcatgca gggccagcca aagtgtcagt acatctaggt ttagttatat gcactggttc    120
caacagaaac caggacaggc acccaaactc ctcatcaagt atgcatccaa ctagaatct    180
ggggtccctg ccaggttcag tggcagtggg tctgggacag acttcaccct caacatccat    240
cctgtggagg gggaggatac tgcaacatat tactgtcagc acagttggga gattccgtac    300
acgttcggag gggggaccaa gctggaaata aaa                                 333
```

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

Asp Ile Val Leu Thr Gln Ser Pro Ala Ser Leu Ala Val Ser Leu Gly
1               5                   10                  15
Gln Arg Ala Thr Ile Ser Cys Arg Ala Ser Gln Ser Val Ser Thr Ser
            20                  25                  30
Arg Phe Ser Tyr Met His Trp Phe Gln Gln Lys Pro Gly Gln Ala Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Gly Glu Asp Thr Ala Thr Tyr Tyr Cys Gln His Ser Trp
                85                  90                  95
Glu Ile Pro Tyr Thr Phe Gly Gly Gly Thr Lys Leu Glu Ile Lys
            100                 105                 110

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaagtcac cgaaactcct tgtctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgt cgccctacac atttgggcag     300
gggaccaagt tggaaatcaa g                                               321

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15
Asp Arg Val Thr Ile Thr Cys Arg Thr Ser Glu Asn Leu His Asn Tyr
            20                  25                  30
Leu Ala Trp Tyr Gln Gln Lys Pro Gly Lys Ser Pro Lys Leu Leu Val
        35                  40                  45
Tyr Asp Ala Lys Thr Leu Ala Asp Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln His Phe Trp Ser Ser Pro Tyr
                85                  90                  95
Thr Phe Gly Gln Gly Thr Lys Leu Glu Ile Lys
            100                 105

<210> SEQ ID NO 91
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaaggccc cgaaactcct tatctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgt cgccctacac atttgggcag     300
gggaccaagt tggaaatcaa g                                                321
```

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ala Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys
            100                 105
```

<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaagtcac cgaaactcct tatctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgt cgccctacac atttgggcag     300
gggaccaagt tggaaatcaa g                                                321
```

<210> SEQ ID NO 94

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys
            100                 105

<210> SEQ ID NO 95
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gacatccaaa tgacccaatc gccctcctcc ctctccgcat cagtagggga ccgcgtcaca      60
attacttgca aagcgtcgca gaacgtcgga acgaatgtgg cgtggtttca gcagaagccc     120
ggaaaagctc cgaagagctt gatctactcg gcctcatata ggtattcggg tgtgccgagc     180
cggtttagcg gtcggggtc aggtactgat tcacgctca caatttcatc gttgcagcca      240
gaagatttcg ccacatatta ctgtcagcag tacaacaatt accctctgac gttcggccag     300
ggaaccaaac ttgagatcaa g                                               321

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Asn Asn Tyr Pro Leu
            85                  90                  95

Thr Phe Gly Gln Gly Thr Lys Leu Glu Ile Lys
            100                 105

<210> SEQ ID NO 97
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gatatccaga tgacacagtc accctcgtcg ctctcagctt ccgtaggcga cagggtcact      60
attacgtgta aagcatcaca gaacgtcgga acgaatgtgg cgtggtttca gcagaagccc     120
gggaagagcc ccaaagcgct tatctactcc ccgtcgtatc ggtattccgg tgtgccaagc     180
agattttcgg ggtcaggttc gggaactgac tttaccctga ccatctcgtc cctccaaccg     240
gaagatttcg ccacgtactt ctgccagcag tacaacagct atcctcacac attcggacaa     300
gggacaaagt tggagattaa a                                               321

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Pro Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro His
            85                  90                  95

Thr Phe Gly Gln Gly Thr Lys Leu Glu Ile Lys
            100                 105

<210> SEQ ID NO 99
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gaggtcctgc tgcaacagtc tggacctgag ctggtgaagc ctggggcttc agtgaagata     60
ccctgcaagg cttctggata cacattcact gactacaaca tggactgggt gaagcagagc    120
catggaaaga gccttgagtg gattggacaa attaatccta acaatggtgg tatttttctc    180
aaccagaagt tcaagggcaa ggccacattg actgtagaca gtcctccaa tacagccttc     240
```

```
atggaggtcc gcagcctgac atctgaggac actgcagtct attactgtgc aagagaggca      300
attactacgg taggcgctat ggactactgg ggtcaaggaa cctcagtcac cgtctcctca      360
gccaaaacga cacccccatc tgtctatcca ctggcccctg gatctgctgc ccaaactaac      420
tccatggtga ccctgggatg cctggtcaag ggctatttcc ctgagccagt gacagtgacc      480
tggaactctg gatccctgtc cagcggtgtg cacaccttcc cagctgtcct gcagtctgac      540
ctctacactc tgagcagctc agtgactgtc ccctccagca cctggcccag cgagaccgtc      600
acctgcaacg ttgcccaccc ggccagcagc accaaggtgg acaagaaaat tgtgcccagg      660
gattgtggtt gtaagccttg catatgtaca gtcccagaag tatcatctgt cttcatcttc      720
cccccaaagc ccaaggatgt gctcaccatt actctgactc ctaaggtcac gtgtgttgtg      780
gtagacatca gcaaggatga tcccgaggtc cagttcagct ggtttgtaga tgatgtggag      840
gtgcacacag ctcagacgca accccgggag gagcagttca acagcacttt ccgctcagtc      900
agtgaacttc ccatcatgca ccaggactgg ctcaatggca aggagttcaa atgcagggtc      960
aacagtgcag ctttccctgc ccccatcgag aaaaccatct ccaaaaccaa aggcagaccg     1020
aaggctccac aggtgtacac cattccacct cccaaggagc agatggccaa ggataaagtc     1080
agtctgacct gcatgataac agacttcttc cctgaagaca ttactgtgga gtggcagtgg     1140
aatgggcagc cagcggagaa ctacaagaac actcagccca tcatggacac agatggctct     1200
tacttcgtct acagcaagct caatgtgcag aagagcaact gggaggcagg aaatactttc     1260
acctgctctg tgttacatga gggcctgcac aaccaccata ctgagaagag cctctcccac     1320
tctcctggta aa                                                        1332
```

<210> SEQ ID NO 100
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160
```

```
Trp Asn Ser Gly Ser Leu Ser Ser Gly Val His Thr Phe Pro Ala Val
                165                 170                 175
Leu Gln Ser Asp Leu Tyr Thr Leu Ser Ser Val Thr Val Pro Ser
            180                 185                 190
Ser Thr Trp Pro Ser Glu Thr Val Thr Cys Asn Val Ala His Pro Ala
        195                 200                 205
Ser Ser Thr Lys Val Asp Lys Lys Ile Val Pro Arg Asp Cys Gly Cys
    210                 215                 220
Lys Pro Cys Ile Cys Thr Val Pro Glu Val Ser Ser Val Phe Ile Phe
225                 230                 235                 240
Pro Pro Lys Pro Lys Asp Val Leu Thr Ile Thr Leu Thr Pro Lys Val
                245                 250                 255
Thr Cys Val Val Val Asp Ile Ser Lys Asp Asp Pro Glu Val Gln Phe
            260                 265                 270
Ser Trp Phe Val Asp Asp Val Glu Val His Thr Ala Gln Thr Gln Pro
        275                 280                 285
Arg Glu Glu Gln Phe Asn Ser Thr Phe Arg Ser Val Ser Glu Leu Pro
    290                 295                 300
Ile Met His Gln Asp Trp Leu Asn Gly Lys Glu Phe Lys Cys Arg Val
305                 310                 315                 320
Asn Ser Ala Ala Phe Pro Ala Pro Ile Glu Lys Thr Ile Ser Lys Thr
                325                 330                 335
Lys Gly Arg Pro Lys Ala Pro Gln Val Tyr Thr Ile Pro Pro Pro Lys
            340                 345                 350
Glu Gln Met Ala Lys Asp Lys Val Ser Leu Thr Cys Met Ile Thr Asp
        355                 360                 365
Phe Phe Pro Glu Asp Ile Thr Val Glu Trp Gln Trp Asn Gly Gln Pro
    370                 375                 380
Ala Glu Asn Tyr Lys Asn Thr Gln Pro Ile Met Asp Thr Asp Gly Ser
385                 390                 395                 400
Tyr Phe Val Tyr Ser Lys Leu Asn Val Gln Lys Ser Asn Trp Glu Ala
                405                 410                 415
Gly Asn Thr Phe Thr Cys Ser Val Leu His Glu Gly Leu His Asn His
            420                 425                 430
His Thr Glu Lys Ser Leu Ser His Ser Pro Gly Lys
        435                 440

<210> SEQ ID NO 101
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gacatccaga tgactcagtc tccagcctcc ctatctgcat ctgtgggaga aactgtcacc      60
atcacatgtc gaacaagtga gaatcttcac aattatttag catggtatca gcagaaacag     120
ggaaaatctc ctcagctcct ggtctatgat gcaaaaacct tagcagatgg tgtgccatca     180
aggttcagtg gcagtggatc aggaacacaa tattctctca agatcaacag cctgcagcct     240
gaagattttg ggagttatta ctgtcaacat ttttggagta gtccttacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
```

```
cccaaagaca tcaatgtcaa gtggaagatt gatggcagtg aacgacaaaa tggcgtcctg      480
aacagttgga ctgatcagga cagcaaagac agcacctaca gcatgagcag caccctcacg      540
ttgaccaagg acgagtatga acgacataac agctatacct gtgaggccac tcacaagaca      600
tcaacttcac ccattgtcaa gagcttcaac aggaatgagt gt                          642
```

<210> SEQ ID NO 102
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 103
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
caggtccaac tgcagcagcc tggggctgaa ctggtgaagc ctggggcttc agtgaagctg      60
tcctgcaagg cttctggcta caccttcacc agctactgga ttcactgggt gaaccagagg      120
cctggacaag gccttgagtg gattggagac attaatccta gcaacggccg tagtaagtat      180
```

-continued

```
aatgagaagt tcaagaacaa ggccacaatg actgcagaca atcctccaa cacagcctac      240 atgcaactca gcagcctgac atctgaggac tctgcggtct attactgtgc aagagaggtt     300
ctggatggtg ctatggacta ctggggtcaa ggaacctcag tcaccgtctc ctcagccaaa     360
acgacacccc catctgtcta tccactggcc cctggatctg ctgcccaaac taactccatg     420
gtgaccctgg gatgcctggt caagggctat ttccctgagc cagtgacagt gacctggaac     480
tctggatccc tgtccagcgg tgtgcacacc ttcccagctg tcctgcagtc tgacctctac     540
actctgagca gctcagtgac tgtcccctcc agcacctggc ccagcgagac cgtcacctgc     600
aacgttgccc accggccag cagcaccaag gtggacaaga aaattgtgcc cagggattgt     660
ggttgtaagc cttgcatatg tacagtccca gaagtatcat ctgtcttcat cttccccca     720 aagcccaagg atgtgctcac cattactctg actcctaagg tcacgtgtgt tgtggtagac     780
atcagcaagg atgatcccga ggtccagttc agctggtttg tagatgatgt ggaggtgcac     840
acagctcaga cgcaaccccg ggaggagcag ttcaacagca ctttccgctc agtcagtgaa     900
cttcccatca tgcaccagga ctggctcaat ggcaaggagt tcaaatgcag ggtcaacagt     960 gcagcttttcc ctgcccccat cgagaaaacc atctccaaaa ccaaaggcag accgaaggct     1020
ccacaggtgt acaccattcc acctcccaag gagcagatgg ccaaggataa agtcagtctg     1080
acctgcatga taacagactt cttccctgaa gacattactg tggagtggca gtggaatggg     1140
cagccagcgg agaactacaa gaacactcag cccatcatgg acacagatgg ctcttacttc     1200
gtctacagca agctcaatgt gcagaagagc aactgggagg caggaaatac tttcacctgc     1260
tctgtgttac atgagggcct gcacaaccac catactgaga gagcctctc ccactctcct     1320 ggtaaa                                                                 1326
```

<210> SEQ ID NO 104
<211> LENGTH: 442
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Ile His Trp Val Asn Gln Arg Pro Gly Gln Gly Leu Glu Trp Ile
            35                  40                  45

Gly Asp Ile Asn Pro Ser Asn Gly Arg Ser Lys Tyr Asn Glu Lys Phe
        50                  55                  60

Lys Asn Lys Ala Thr Met Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Leu Asp Gly Ala Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
```

```
                145                 150                 155                 160
        Ser Gly Ser Leu Ser Ser Gly Val His Thr Phe Pro Ala Val Leu Gln
                        165                 170                 175

Ser Asp Leu Tyr Thr Leu Ser Ser Val Thr Val Pro Ser Ser Thr
                        180                 185                 190

Trp Pro Ser Glu Thr Val Thr Cys Asn Val Ala His Pro Ala Ser Ser
                        195                 200                 205

Thr Lys Val Asp Lys Lys Ile Val Pro Arg Asp Cys Gly Cys Lys Pro
                210                 215                 220

Cys Ile Cys Thr Val Pro Glu Val Ser Ser Val Phe Ile Phe Pro Pro
        225                 230                 235                 240

Lys Pro Lys Asp Val Leu Thr Ile Thr Leu Thr Pro Lys Val Thr Cys
                        245                 250                 255

Val Val Val Asp Ile Ser Lys Asp Asp Pro Glu Val Gln Phe Ser Trp
                        260                 265                 270

Phe Val Asp Asp Val Glu Val His Thr Ala Gln Thr Gln Pro Arg Glu
                        275                 280                 285

Glu Gln Phe Asn Ser Thr Phe Arg Ser Val Ser Glu Leu Pro Ile Met
                290                 295                 300

His Gln Asp Trp Leu Asn Gly Lys Glu Phe Lys Cys Arg Val Asn Ser
        305                 310                 315                 320

Ala Ala Phe Pro Ala Pro Ile Glu Lys Thr Ile Ser Lys Thr Lys Gly
                        325                 330                 335

Arg Pro Lys Ala Pro Gln Val Tyr Thr Ile Pro Pro Lys Glu Gln
                        340                 345                 350

Met Ala Lys Asp Lys Val Ser Leu Thr Cys Met Ile Thr Asp Phe Phe
                        355                 360                 365

Pro Glu Asp Ile Thr Val Glu Trp Gln Trp Asn Gly Gln Pro Ala Glu
                370                 375                 380

Asn Tyr Lys Asn Thr Gln Pro Ile Met Asp Thr Asp Gly Ser Tyr Phe
        385                 390                 395                 400

Val Tyr Ser Lys Leu Asn Val Gln Lys Ser Asn Trp Glu Ala Gly Asn
                        405                 410                 415

Thr Phe Thr Cys Ser Val Leu His Glu Gly Leu His Asn His His Thr
                        420                 425                 430

Glu Lys Ser Leu Ser His Ser Pro Gly Lys
                        435                 440

<210> SEQ ID NO 105
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gacattgtgt tgacccaatc tccagcttct ttggctgtgt ctctagggca gagggccacc        60
atctcctgca gagccagcga aagtgtttgat aattatggca ttagttttat gaactggttc      120
caacagaaac aggacagcc  acccaaactc ctcatctatg ctgcatccaa ccaaggctcc       180
ggggtccctg ccaggtttag tggcagtggg tctgggacag acttcagcct caacatccat       240
cctatggagg aggatgatac tgcaatgtat ttctgtcagc aaagtaagga ggttccgtgg       300
acgttcggtg gaggctccaa gctggaaatc aaacgggctg atgctgcacc aactgtatcc       360
```

```
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc     600 actcacaaga catcaacttc acccattgtc aagagcttca acaggaatga gtgt          654
```

```
<210> SEQ ID NO 106
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Ser Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

```
<210> SEQ ID NO 107
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
caggttactc tgaaagagtc tggccctggg atattgcagc cctcccagac cctcagtctg    60
acttgttctt tctctgggtt ttcactgagc acttatggta tgggtgtgac ctggattcgt    120
cagccttcag gaaagggtct ggagtggctg gcacacattt actgggatga tgacaagcgc    180
```

```
tataacccat ccctgaagag ccggctcaca atctccaagg atacctccaa caaccaggta      240
ttcctcaaga tcaccagtgt ggacactgca gatactgcca catactactg tgctcaaacg      300
gggtatagta acttgtttgc ttactggggc caagggactc tggtcactgt ctctgcagcc      360
aaaacgacac ccccatctgt ctatccactg gcccctggat ctgctgccca aactaactcc      420
atggtgaccc tgggatgcct ggtcaagggc tatttccctg agccagtgac agtgacctgg      480
aactctggat ccctgtccag cggtgtgcac accttcccag ctgtcctgca gtctgacctc      540
tacactctga gcagctcagt gactgtcccc tccagcacct ggcccagcga gaccgtcacc      600
tgcaacgttg cccacccggc cagcagcacc aaggtggaca gaaaaattgt gcccagggat      660
tgtggttgta agccttgcat atgtacagtc ccagaagtat catctgtctt catcttcccc      720
ccaaagccca aggatgtgct caccattact ctgactccta aggtcacgtg tgttgtggta      780
gacatcagca aggatgatcc cgaggtccag ttcagctggt ttgtagatga tgtggaggtg      840
cacacagctc agacgcaacc ccgggaggag cagttcaaca gcactttccg ctcagtcagt      900
gaacttccca tcatgcacca ggactggctc aatggcaagg agttcaaatg cagggtcaac      960
agtgcagctt ccctgccccc catcgagaaa accatctcca aaaccaaagg cagaccgaag     1020
gctccacagg tgtacaccat tccacctccc aaggagcaga tggccaagga taaagtcagt     1080
ctgacctgca tgataacaga cttcttccct gaagacatta ctgtggagtg cagtggaat      1140 gggcagccag cggagaacta caagaacact cagcccatca tggacacaga tggctcttac     1200
ttcgtctaca gcaagctcaa tgtgcagaag agcaactggg aggcaggaaa tactttcacc     1260
tgctctgtgt tacatgaggg cctgcacaac caccatactg agaagagcct ctcccactct     1320
cctggtaaa                                                             1329
```

<210> SEQ ID NO 108
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Thr Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Thr Gly Tyr Ser Asn Leu Phe Ala Tyr Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140
```

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
        180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 109
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gacattgtga tgacccagtc tcaaaaattc atgtccacat cagtaggaga cagggtcagc      60
gtcacctgca aggccagtca gaatgtgggt actaatgtag cctggtatca acagaaatta     120
ggacaatctc ctaaaacact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Leu Gly Gln Ser Pro Lys Thr Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 111
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
caggttactc tgaaagagtc tggccctggg atattgcagc cctcccagac cctcagtctg    60
acttgttctt tctctggggtt ttcactgaac acttatggta tgggtgtgag ctggattcgt   120

```
cagccttcag gaaagggtct ggagtggctg gcacacattt actgggatga tgacaagcgc    180
tataacccat ccctgaagag ccggctcaca atctccaagg atgcctccaa caaccgggtc    240
ttcctcaaga tcaccagtgt ggacactgca gatactgcca catactactg tgctcaaaga    300
ggttatgatg attactgggg ttactggggc caagggactc tggtcactat ctctgcagcc    360
aaaacgacac ccccatctgt ctatccactg gcccctggat ctgctgccca aactaactcc    420
atggtgaccc tgggatgcct ggtcaagggc tatttccctg agccagtgac agtgacctgg    480
aactctggat ccctgtccag cggtgtgcac accttcccag ctgtcctgca gtctgacctc    540
tacactctga gcagctcagt gactgtcccc tccagcacct ggcccagcga gaccgtcacc    600
tgcaacgttg cccacccggc cagcagcacc aaggtggaca gaaaaattgt gcccagggat    660
tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgcaacc ccgggaggag cagttcaaca gcactttccg ctcagtcagt    900
gaacttccca tcatgcacca ggactggctc aatggcaagg agttcaaatg cagggtcaac    960
agtgcagctt ccctgccccc catcgagaaa accatctcca aaaccaaagg cagaccgaag   1020
gctccacagg tgtacaccat tccacctccc aaggagcaga tggccaagga taaagtcagt   1080
ctgacctgca tgataacaga cttcttccct gaagacatta ctgtggagtg cagtggaat   1140 gggcagccag cggagaacta caagaacact cagcccatca tggacacaga tggctcttac   1200
ttcgtctaca gcaagctcaa tgtgcagaag agcaactggg aggcaggaaa tactttcacc   1260
tgctctgtgt tacatgaggg cctgcacaac caccatactg agaagagcct ctcccactct   1320
cctggtaaa                                                           1329

<210> SEQ ID NO 112
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140
```

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
        180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
        340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 113
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gacattgtga tgacccagtc tcaaaaattc atgtccacat cagtaggaga cagggtcagc        60
gtcacctgca aggccagtca gaatgtgggt actaatgtag cctggtttca acagaaacca       120
ggtcaatctc ctaaagcact gatttactcg gcatcttacc ggtacagtgg agtccctgat       180
cgcttcacag gcagtggatc tgggacagat ttcattctca ccatcagcaa tgtgcagtct       240
gaagacctgg cagagtattt ctgtcagcaa tataacaact atcctctcac gttcggtgct       300

```
gggaccaagc tggagctgaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642
```

```
<210> SEQ ID NO 114
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114
```

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

```
<210> SEQ ID NO 115
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
gaggtcctgc tgcaacagtc tggacctgag gtggtgaagc ctggggcttc agtgaagata    60
ccctgcaagg cttctggata cacattcact gactacaaca tggactgggt gaagcagagc    120
```

```
catgaaaga gccttgagtg gattggagag attaatccta caatggtgg tactttctac      180 aaccagaagt tcaagggcaa ggccacattg actgtagaca agtcctccag cacagcctac      240
atggagctcc gcagcctgac atctgaggac actgcagtct attactgtgc aagagaggca      300
attactacgg taggcgctat ggactactgg ggtcaaggaa cctcagtcac cgtctcctca      360
gccaaaacaa cacccccatc agtctatcca ctggcccctg gtgtggaga tacaactggt      420 tcctccgtga ctctgggatg cctggtcaag ggctacttcc ctgagtcagt gactgtgact      480
tggaactctg gatccctgtc agcagtgtg cacaccttcc cagctctcct gcagtctgga      540
ctctacacta tgagcagctc agtgactgtc ccctccagca cctggccaag tcagaccgtc      600
acctgcagcg ttgctcaccc agccagcagc accacggtgg acaaaaaact gagcccagc      660 gggcccattt caacaatcaa cccctgtcct ccatgcaagg agtgtcacaa atgcccagct      720
cctaacctcg agggtggacc atccgtcttc atcttccctc aaatatcaa ggatgtactc      780 atgatctccc tgacacccaa ggtcacgtgt gtggtggtgg atgtgagcga ggatgaccca      840
gacgtccaga tcagctggtt tgtgaacaac gtggaagtac acacagctca gacacaaacc      900
catagagagg attacaacag tactatccgg gtggtcagca ccctccccat ccagcaccag      960
gactggatga gtggcaagga gttcaaatgc aaggtcaaca acaaagacct cccatcaccc     1020
atcgagagaa ccatctcaaa aattaaaggg ctagtcagag ctccacaagt atacatcttg     1080
ccgccaccag cagagcagtt gtccaggaaa gatgtcagtc tcacttgcct ggtcgtgggc     1140
ttcaaccctg agacatcag tgtggagtgg accagcaatg ggcatacaga ggagaactac     1200
aaggacaccg caccagtcct agactctgac ggttcttact tcatatatag caagctcaat     1260
atgaaaacaa gcaagtggga gaaaacagat tccttctcat gcaacgtgag acacgagggt     1320
ctgaaaaatt actacctgaa gaagaccatc tcccggtctc cgggtaaa               1368
```

<210> SEQ ID NO 116
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Glu Val Leu Leu Gln Gln Ser Gly Pro Glu Val Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Glu Ile Asn Pro Asn Asn Gly Gly Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Cys Gly Asp Thr Thr Gly Ser Ser Val Thr
```

130                 135                 140
Leu Gly Cys Leu Val Lys Gly Tyr Phe Pro Glu Ser Val Thr Val Thr
145                 150                 155                 160

Trp Asn Ser Gly Ser Leu Ser Ser Val His Thr Phe Pro Ala Leu
            165                 170                 175

Leu Gln Ser Gly Leu Tyr Thr Met Ser Ser Val Thr Val Pro Ser
            180                 185                 190

Ser Thr Trp Pro Ser Gln Thr Val Thr Cys Ser Val Ala His Pro Ala
            195                 200                 205

Ser Ser Thr Thr Val Asp Lys Lys Leu Glu Pro Ser Gly Pro Ile Ser
210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
            245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
            275                 280                 285

Asn Asn Val Glu Val His Thr Ala Gln Thr Gln Thr His Arg Glu Asp
290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Pro Ala Glu Gln Leu Ser
            355                 360                 365

Arg Lys Asp Val Ser Leu Thr Cys Leu Val Val Gly Phe Asn Pro Gly
370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
            405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
            435                 440                 445

Thr Ile Ser Arg Ser Pro Gly Lys
450                 455

<210> SEQ ID NO 117
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctataat gcaaaaacct tagcagatgg tgtgccatca   180

```
aggttcagtg gcagtggatc aggaacacaa tattctctca agatcaacag cctgcagcct      240
gaagattttg ggagttatta ctgtcaacat ttttggagtt ctccttacac gttcggaggg      300
gggaccaagc tggaaataaa acgggctgat gctgcaccaa ctgtatccat cttcccacca      360
tccagtgagc agttaacatc tggaggtgcc tcagtcgtgt gcttcttgaa caacttctac      420
cccaaagaca tcaatgtcaa gtggaagatt gatggcagtg aacgacaaaa tggcgtcctg      480
aacagttgga ctgatcagga cagcaaagac agcacctaca gcatgagcag caccctcacg      540
ttgaccaagg acgagtatga acgacataac agctatacct gtgaggccac tcacaagaca      600
tcaacttcac ccattgtcaa gagcttcaac aggaatgagt gt                          642
```

<210> SEQ ID NO 118
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 119
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
caggttactc tgaaagagtc tggccctgga atattgcagc cctcccagac cctcagtctg      60
acttgttctt tctctgggtt ttcactgagc acttatggta tgggtgtagg ctggattcgt     120
cagccttcag gaaagggtct agagtggctg gcagacattt ggtgggatga cgataagtac     180
tataacccat ccctgaagag ccggctcaca atctccaagg atacctccag caatgaggta     240
ttcctcaaga tcgccattgt ggacactgca gatactgcca cttactactg tgctcgaaga     300
ggtcactact ctgctatgga ctactggggt caaggaacct cagtcaccgt ctcctcagcc     360
aaaacgacac ccccatctgt ctatccactg gcccctggat ctgctgccca aactaactcc     420
atggtgaccc tgggatgcct ggtcaagggc tatttccctg agccagtgac agtgacctgg     480
aactctggat ccctgtccag cggtgtgcac accttccag ctgtcctgca gtctgacctc      540
tacactctga gcagctcagt gactgtcccc tccagcacct ggcccagcga gaccgtcacc     600
tgcaacgttg cccacccggc cagcagcacc aaggtggaca gaaaattgt gcccagggat      660 tgtggttgta agccttgcat atgtacagtc ccagaagtat catctgtctt catcttcccc     720
ccaaagccca aggatgtgct caccattact ctgactccta aggtcacgtg tgttgtggta     780
gacatcagca aggatgatcc cgaggtccag ttcagctggt ttgtagatga tgtggaggtg     840
cacacagctc agacgcaacc ccgggaggag cagttcaaca gcactttccg ctcagtcagt     900
gaacttccca tcatgcacca ggactggctc aatggcaagg agttcaaatg cagggtcaac     960
agtgcagctt ccctgcccc catcgagaaa accatctcca aaccaaagg cagaccgaag      1020 gctccacagg tgtacaccat tccacctccc aaggagcaga tggccaagga taaagtcagt     1080
ctgacctgca tgataacaga cttcttccct gaagacatta ctgtggagtg cagtggaat      1140 gggcagccag cggagaacta caagaacact cagcccatca tggacacaga tggctcttac     1200
ttcgtctaca gcaagctcaa tgtgcagaag agcaactggg aggcaggaaa tactttcacc     1260
tgctctgtgt tacatgaggg cctgcacaac caccatactg agaagagcct ctcccactct     1320
cctggtaaa                                                             1329
```

<210> SEQ ID NO 120
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110
```

```
Thr Ser Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 121
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gacattgtaa tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg ccatcctacc ggtacagtgg agtccctgat   180
```

```
cgcttcacag gcagtggatc tgggacagat ttcactctca ccatcagcaa tgtgcagtct    240
gaagacttgg cagaatattt ctgtcagcaa tataacagct atcctcacac gttcggaggg    300
gggaccaagc tggaaatgaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642
```

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Thr Phe Gly Gly Gly Thr Lys Leu Glu Met Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 123
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
caggttactc tgaaagagtc tggccctggg atattgcagc cctcccagac cctcagtctg      60
acttgttctt tctctgggtt ttcactgagc acttctggta tgggtgtgag ttggattcgt     120
cagccttcag gaaagggtct ggagtggctg gcacacaatg actgggatga tgacaagcgc     180
tataagtcat ccctgaagag ccggctcaca atatccaagg ataccctccag aaaccaggta    240
ttcctcaaga tcaccagtgt ggacactgca gatactgcca catactactg tgctcgaaga    300
gttgggggat tagagggcta ttttgattac tggggccaag gcaccactct cacagtctcc    360
tcagccaaaa cgacaccccc atctgtctat ccactggccc ctggatctgc tgcccaaact    420
aactccatgg tgaccctggg atgcctggtc aagggctatt tccctgagcc agtgacagtg    480
acctggaact ctggatccct gtccagcggt gtgcacacct tcccagctgt cctgcagtct    540
gacctctaca ctctgagcag ctcagtgact gtccccctcc gcacctggcc cagcgagacc    600
gtcacctgca acgttgccca cccggccagc agcaccaagg tggacaagaa aattgtgccc    660
agggattgtg gttgtaagcc ttgcatatgt acagtcccag aagtatcatc tgtcttcatc    720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caatgcagg    960
gtcaacagtg cagctttccc tgcccccatc gagaaaacca tctccaaaac caaaggcaga   1020
ccgaaggctc cacaggtgta caccattcca cctcccaagg agcagatggc caaggataaa   1080
gtcagtctga cctgcatgat aacagacttc ttccctgaag acattactgt ggagtggcag   1140
tggaatgggc agccagcgga gaactacaag aacactcagc ccatcatgga cacagatggc   1200
tcttacttcg tctacagcaa gctcaatgtg cagaagagca ctgggaggc aggaaatact   1260
ttcacctgct ctgtgttaca tgagggcctg cacaaccacc atactgagaa gagcctctcc   1320
cactctcctg gtaaa                                                     1335
```

<210> SEQ ID NO 124
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Asn Asp Trp Asp Asp Asp Lys Arg Tyr Lys Ser Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Val Gly Gly Leu Glu Gly Tyr Phe Asp Tyr Trp Gly
            100                 105                 110
```

Gln Gly Thr Thr Leu Thr Val Ser Ser Ala Lys Thr Thr Pro Pro Ser
            115                 120                 125

Val Tyr Pro Leu Ala Pro Gly Ser Ala Ala Gln Thr Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 125
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gacattgtgc tgacacagtc tcctgcttcc ttagctgtat ctctggggca gagggccacc      60
atctcatgca gggccagcca agtgtcagt acatctaggt ttagttatat gcactggttc     120

```
caacagaaac caggacaggc acccaaactc ctcatcaagt atgcatccaa cctagaatct    180
ggggtccctg ccaggttcag tggcagtggg tctgggacag acttcaccct caacatccat    240
cctgtggagg gggaggatac tgcaacatat tactgtcagc acagttggga gattccgtac    300
acgttcggag gggggaccaa gctggaaata aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc    600 actcacaaga catcaacttc acccattgtc aagagcttca caggaatga gtgt          654
```

<210> SEQ ID NO 126
<211> LENGTH: 218
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 126

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Phe Ser Tyr Met His Trp Phe Gln Gln Lys Pro Gly Gln Ala Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Gly Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 127
<211> LENGTH: 360
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 127

```
gaagtgttgt tgcagcagtc agggccggag ttggtaaaac cgggagcgtc ggtgaaaatc    60
ccgtgcaaag cgtcggggta tacgtttacg gactataaca tggattgggt gaaacagtcg   120
catgggaaat cgcttgaatg gattggtcag atcaatccga ataatggagg aatcttcttt   180
aatcagaagt ttaaaggaaa agcgacgctt acagtcgata agtcgtcgaa cacggcgttc   240
atggaagtac ggtcgcttac gtcggaagat acggcggtct attactgtgc gagggaggcg   300
attacgacgg tgggagcgat ggactattgg ggacaaggga cgtcggtcac ggtatcgtcg   360
```

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Tyr Thr Phe Thr Ser Tyr
1               5

<210> SEQ ID NO 129
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
caggtgacac tcaaagaatc aggacccgga atccttcagc ccagccagac cttgtcgctg    60
acttgttcgt tctccggttt cagcctgaat acttatggga tgggtgtgtc atggatcagg   120
caaccgtccg ggaaaggatt ggagtggctc gcgcacatct actgggacga tgacaaacgc   180
tacaatcctt cgctgaagag ccgattgacg atttccaagg atgcctcgaa caaccgggta   240
tttcttaaga tcacgtcggt cgatacggca gacacggcga cctattactg cgcccaaaga   300
gggtacgatg actattgggg atattggggc caggggacac tcgtcacaat ttcagct     357
```

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Phe Ser Leu Ser Thr Tyr Gly Met
1               5

<210> SEQ ID NO 131
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
caggtcacgc tgaaagagtc aggtcccgga atccttcaac cttcgcagac attgtcactc    60
```

```
acatgttcct tctccggggtt ctcgctctcg acttatggca tgggtgtagg atggattcgg    120
cagcccagcg ggaaggggct tgagtggttg gcggatatct ggtgggacga cgacaaatac    180
tacaatccga gcctgaagtc ccgcctcacc atttcgaaag atacgtcatc aaacgaagtc    240
tttttgaaga tcgccatcgt ggacacggcg gatacagcga cgtattactg cgccagaagg    300
ggacactaca gcgcaatgga ttattgggga caggggacct cggtgactgt gtcgtcc       357
```

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Phe Ser Leu Asn Thr Tyr Gly Met
1               5

<210> SEQ ID NO 133
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
gacatccaaa tgacccagtc acccgcgagc ctttcggcgt cggtcggaga acggtcacg     60 atcacgtgcc ggacatcaga gaatctccat aactacctcg cgtggtatca acagaagcag    120
gggaagtcgc cccagttgct tgtatacgat gcgaaaacgt tggcggatgg ggtgccgtcc    180
agattctcgg gatcgggctc ggggacgcag tactcgctca agatcaattc gctgcagccg    240
gaggactttg ggtcgtacta ttgtcagcat ttttggtcat caccgtatac atttggaggt    300
ggaacgaaac ttgagattaa g                                              321
```

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Phe Ser Leu Ser Thr Ser Gly Met
1               5

<210> SEQ ID NO 135
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
gatatcgtca tgacccagtc ccagaagttc atgtcaactt cagtgggaga cagagtgtcc    60
gtcacatgta aagcctcgca aaatgtggga accaacgtag cgtggttcca gcagaaacct    120
ggccaatcac cgaaggcact gatctactcg gccagctata ggtactcggg agtaccagat    180
cggtttacgg ggtcggggag cgggacggac tttatcctca ctatttccaa tgtccagtcg    240
```

```
gaggaccttg cggaatactt ctgccagcag tataacaact atcccctcac gtttggtgct    300
ggtacaaaat tggagttgaa g                                              321
```

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Tyr Thr Phe Thr Asp Tyr Asn
1               5

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
gacatcgtga tgacacagtc acagaaattc atgtccacat ccgtcggtga tagagtatcc     60
gtcacgtgta aggcctcgca aaacgtagga actaatgtgg cgtggtatca acagaagcca    120
ggacagtcac ccaaagcact catctacagc ccctcatatc ggtacagcgg ggtgccggac    180
aggttcacgg gatcggggag cgggaccgat tttacactga ccatttcgaa tgtccagtcg    240
gaggaccttg cggaatactt ctgccagcag tataactcgt accctcacac gtttggaggt    300
ggcactaagt tggagatgaa a                                              321
```

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Tyr Thr Phe Thr Ser Tyr Trp
1               5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Gly Gly Gly Ser
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 140

Gly Phe Ser Leu Ser Thr Tyr Gly Met Gly
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Phe Ser Leu Asn Thr Tyr Gly Met Gly
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Phe Ser Leu Ser Thr Ser Gly Met Gly
1               5                   10

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asn Pro Asn Asn Gly Gly
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asn Pro Ser Asn Gly Arg
1               5

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Tyr Trp Asp Asp Asp
1               5

<210> SEQ ID NO 146
<211> LENGTH: 5
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 146

Trp Trp Asp Asp Asp
1               5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Trp Asp Asp Asp
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ile Asn Pro Asn Asn Gly Gly Ile
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Asn Pro Ser Asn Gly Arg Ser
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Tyr Trp Asp Asp Asp Lys
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Asn Pro Asn Asn Gly Gly Thr
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ile Trp Trp Asp Asp Asp Lys
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Asp Trp Asp Asp Asp Lys
1               5

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Arg Glu Ala Ile Thr Thr Val Gly Ala Met Asp Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Arg Glu Val Leu Asp Gly Ala Met Asp Tyr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Gln Thr Gly Tyr Ser Asn Leu Phe Ala Tyr
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 157

Ala Gln Arg Gly Tyr Asp Asp Tyr Trp Gly Tyr
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Arg Arg Gly His Tyr Ser Ala Met Asp Tyr
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Arg Arg Val Gly Gly Leu Glu Gly Tyr Phe Asp Tyr
1               5                   10

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Asn Leu His Asn Tyr
1               5

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Ser Val Asp Asn Tyr Gly Ile Ser Phe
1               5                   10

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Asn Val Gly Thr Asn
1               5

<210> SEQ ID NO 163
<211> LENGTH: 6
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Gly Asn Ile His Asn Tyr
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Gln Ser Val Ser Thr Ser Arg Phe Ser Tyr
1               5                   10

<210> SEQ ID NO 165
<211> LENGTH: 972
<212> TYPE: DNA
<213> ORGANISM: Mus sp.

<400> SEQUENCE: 165

```
gccaaaacga caccccatc tgtctatcca ctggccctg atctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag cgagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgca accccgggag gagcagttca cagcactttt ccgctcagtc     540
agtgaacttc ccatcatgca ccaggactgg ctcaatggca aggagttcaa atgcagggtc     600
aacagtgcag ctttccctgc ccccatcgag aaaaccatct ccaaaccaa aggcagaccg     660
aaggctccac aggtgtacac cattccacct cccaaggagc agatggccaa ggataaagtc     720
agtctgacct gcatgataac agacttcttc cctgaagaca ttactgtgga gtggcagtgg     780
aatgggcagc cagcggagaa ctacaagaac actcagccca tcatggacac agatggctct     840
tacttcgtct acagcaagct caatgtgcag aagagcaact gggaggcagg aaatactttc     900
acctgctctg tgttacatga gggcctgcac aaccaccata ctgagaagag cctctcccac     960
tctcctggta aa                                                         972
```

<210> SEQ ID NO 166
<211> LENGTH: 324
<212> TYPE: PRT
<213> ORGANISM: Mus sp.

<400> SEQUENCE: 166

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr

```
            20                  25                  30
Phe Pro Glu Pro Val Thr Val Thr Trp Asn Ser Gly Ser Leu Ser Ser
         35                  40                  45

Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 167
<211> LENGTH: 1008
<212> TYPE: DNA
<213> ORGANISM: Mus sp.

<400> SEQUENCE: 167
gccaaaacaa caccccatc  agtctatcca ctggccctg  ggtgtggaga tacaactggt      60
tcctccgtga ctctgggatg cctggtcaag ggctacttcc ctgagtcagt gactgtgact     120
tggaactctg gatccctgtc cagcagtgtg cacaccttcc cagctctcct gcagtctgga     180
ctctacacta tgagcagctc agtgactgtc cctccagca  cctggccaag tcagaccgtc     240
acctgcagcg ttgctcaccc agccagcagc accacggtgg acaaaaaact tgagcccagc     300
gggcccattt caacaatcaa ccctgtcct  ccatgcaagg agtgtcacaa atgcccagct     360
cctaacctcg agggtggacc atccgtcttc atcttccctc caaatatcaa ggatgtactc     420
```

```
atgatctccc tgacacccaa ggtcacgtgt gtggtggtgg atgtgagcga ggatgaccca      480
gacgtccaga tcagctggtt tgtgaacaac gtggaagtac acacagctca gacacaaacc      540
catagagagg attacaacag tactatccgg gtggtcagca ccctcccat  ccagcaccag      600 gactggatga gtggcaagga gttcaaatgc aaggtcaaca acaaagacct cccatcaccc      660
atcgagagaa ccatctcaaa aattaaaggg ctagtcagag ctccacaagt atacatcttg      720
ccgccaccag cagagcagtt gtccaggaaa gatgtcagtc tcacttgcct ggtcgtgggc      780
ttcaaccctg gagacatcag tgtggagtgg accagcaatg ggcatacaga ggagaactac      840
aaggacaccg caccagtcct agactctgac ggttcttact tcatatatag caagctcaat      900
atgaaaacaa gcaagtggga gaaaacagat tccttctcat gcaacgtgag acacgagggt      960
ctgaaaaatt actacctgaa gaagaccatc tcccggtctc cgggtaaa              1008
```

<210> SEQ ID NO 168
<211> LENGTH: 336
<212> TYPE: PRT
<213> ORGANISM: Mus sp.

<400> SEQUENCE: 168

```
Ala Lys Thr Thr Pro Ser Val Tyr Pro Leu Ala Pro Gly Cys Gly
 1               5                  10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270
```

```
Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
        290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 169
<211> LENGTH: 321
<212> TYPE: DNA
<213> ORGANISM: Mus sp.

<400> SEQUENCE: 169
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga cagttggact gatcaggac      180 agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg t                                                321

<210> SEQ ID NO 170
<211> LENGTH: 107
<212> TYPE: PRT
<213> ORGANISM: Mus sp.

<400> SEQUENCE: 170

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 171
<211> LENGTH: 990
<212> TYPE: DNA
<213> ORGANISM: Homo sapiens

<400> SEQUENCE: 171
gcctcaacaa aaggaccaag tgtgttccca ctcgccccta gcagcaagag tacatccggg      60
ggcactgcag cactcggctg cctcgtcaag gattattttc cagagccagt aaccgtgagc     120
tggaacagtg gagcactcac ttctggtgtc catacttttc ctgctgtcct gcaaagctct     180
ggcctgtact cactcagctc cgtcgtgacc gtgccatctt catctctggg cactcagacc     240
tacatctgta atgtaaacca caagcctagc aatactaagg tcgataagcg ggtggaaccc     300
```

-continued

```
aagagctgcg acaagactca cacttgtccc ccatgccctg cccctgaact tctgggcggt    360
cccagcgtct ttttgttccc accaaagcct aaagatactc tgatgataag tagaacaccc    420
gaggtgacat gtgttgttgt agacgtttcc cacgaggacc cagaggttaa gttcaactgg    480
tacgttgatg gagtcgaagt acataatgct aagaccaagc ctagagagga gcagtataat    540
agtacatacc gtgtagtcag tgttctcaca gtgctgcacc aagactggct caacggcaaa    600
gaatacaaat gcaaagtgtc caacaaagca ctcccagccc ctatcgagaa gactattagt    660
aaggcaaagg ggcagcctcg tgaaccacag gtgtacactc tgccacccag tagagaggaa    720
atgacaaaga accaagtctc attgacctgc ctggtgaaag gcttctaccc cagcgacatc    780
gccgttgagt gggagagtaa cggtcagcct gagaacaatt acaagacaac ccccccagtg    840
ctggatagtg acgggtcttt ctttctgtac agtaagctga ctgtggacaa gtcccgctgg    900
cagcagggta acgtcttcag ctgttccgtg atgcacgagg cattgcacaa ccactacacc    960
cagaagtcac tgagcctgag cccagggaag                                     990
```

<210> SEQ ID NO 172
<211> LENGTH: 330
<212> TYPE: PRT
<213> ORGANISM: Homo sapiens

<400> SEQUENCE: 172

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
            245                 250                 255
Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 173
<211> LENGTH: 321
<212> TYPE: DNA
<213> ORGANISM: Homo sapiens

<400> SEQUENCE: 173
cgcacagttg ctgcccccag cgtgttcatt ttcccaccta gcgatgagca gctgaaaagc      60
ggtactgcct ctgtcgtatg cttgctcaac aactttttacc cacgtgaggc taaggtgcag    120
tggaaagtgg ataatgcact tcaatctgga aacagtcaag agtccgtgac agaacaggac    180
agcaaagact caacttattc actctcttcc accctgactc tgtccaaggc agactatgaa    240
aaacacaagg tatacgcctg cgaggttaca caccagggtt tgtctagtcc tgtcaccaag    300
tccttcaata ggggcgaatg t                                              321

<210> SEQ ID NO 174
<211> LENGTH: 107
<212> TYPE: PRT
<213> ORGANISM: Homo sapiens

<400> SEQUENCE: 174

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 175
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175 gaagtgtttgt tgcagcagtc agggccggag ttggtaaaac cgggagcgtc ggtgaaaatc      60
```

```
ccgtgcaaag cgtcgggta tacgtttacg gactataaca tggattgggt gaaacagtcg    120
catgggaaat cgcttgaatg gattggtcag atcaatccga ataatggagg aatcttcttt    180
aatcagaagt ttaaaggaaa agcgacgctt acagtcgata agtcgtcgaa cacggcgttc    240
atggaagtac ggtcgcttac gtcggaagat acggcggtct attactgtgc gagggaggcg    300
attacgacgg tgggagcgat ggactattgg ggacaaggga cgtcggtcac ggtatcgtcg    360
gcctcaacaa aaggaccaag tgtgttccca ctcgcccta gcagcaagag tacatccggg     420
ggcactgcag cactcggctg cctcgtcaag gattattttc cagagccagt aaccgtgagc    480
tggaacagtg gagcactcac ttctggtgtc catactttc ctgctgtcct gcaaagctct     540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt      720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt    1020
aaggcaaagg ggcagcctcg tgaaccacag gtgtacactc tgccacccag tagagaggaa    1080
atgacaaaga accaagtctc attgacctgc ctggtgaaag gcttctaccc cagcgacatc    1140
gccgttgagt gggagagtaa cggtcagcct gagaacaatt acaagacaac cccccagtg     1200
ctggatagtg acgggtcttt ctttctgtac agtaagctga ctgtggacaa gtcccgctgg    1260
cagcagggta acgtcttcag ctgttccgtg atgcacgagg cattgcacaa ccactacacc    1320
cagaagtcac tgagcctgag cccagggaag                                     1350
```

<210> SEQ ID NO 176
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 177
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
caagtgcaac ttgtgcagtc gggtgcggaa gtcaaaaagc cgggagcgtc ggtgaaagta      60
tcgtgtaaag cgtcgggata tacgtttacg gactataaca tggactgggt acgacaggca     120
ccggggaaat cgttggaatg gatcggacag attaatccga acaatggggg aattttcttt     180

```
aatcagaaat tcaaaggacg ggcgacgttg acggtcgata catcgacgaa tacggcgtat    240
atggaattga ggtcgcttcg ctcggacgat acggcggtct attactgcgc cagggaggcg    300
atcacgacgg tagggcgat ggattattgg ggacagggga cgcttgtgac ggtatcgtcg     360
gcctcaacaa aaggaccaag tgtgttccca ctcgcccta gcagcaagag tacatccggg     420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt     720 cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt    1020
aaggcaaagg ggcagcctcg tgaaccacag gtgtacactc tgccacccag tagagaggaa    1080
atgacaaaga accaagtctc attgacctgc ctggtgaaag gcttctaccc cagcgacatc    1140
gccgttgagt gggagagtaa cggtcagcct gagaacaatt acaagacaac ccccccagtg    1200
ctggatagtg acgggtcttt ctttctgtac agtaagctga ctgtggacaa gtcccgctgg    1260
cagcagggta acgtcttcag ctgttccgtg atgcacgagg cattgcacaa ccactacacc    1320
cagaagtcac tgagcctgag cccagggaag                                     1350
```

<210> SEQ ID NO 178
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 179
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
caagtccagc ttgtccagtc gggagcggaa gtgaagaaac cggggtcgtc ggtcaaagta    60
tcgtgtaaag cgtcgggata tacgtttacg gactataaca tggattgggt acgacaggct   120
ccgggaaaat cattggaatg gattggacag attaatccga ataatggggg tatcttcttt   180
aatcaaaagt ttaaagggag ggcgacgttg acggtggaca atcgacaaa tacggcgtat   240
```

```
atggaattgt cgtcgcttcg gtcggaggac acggcggtgt attactgcgc gagggaggcg    300
atcacgacgg tcggggcgat ggattattgg ggacagggaa cgcttgtgac ggtatcgtcg    360
gcctcaacaa aaggaccaag tgtgttccca ctcgcccctg cagcaagag tacatccggg     420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 180
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Lys Ser Leu Glu Trp Ile
            35                  40                  45

Gly Gln Ile Asn Pro Asn Asn Gly Gly Ile Phe Phe Asn Gln Lys Phe
        50                  55                  60

Lys Gly Arg Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 181
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
caggtccagc ttgtgcaatc gggagcggaa gtgaagaaac cgggagcgtc ggtaaaagtc     60
tcgtgcaaag cgtcgggta tacgtttacg gactataaca tggactgggt gcgccaagcg    120
cctggacagg gtcttgaatg gatggggcag attaatccga ataatggagg gatcttcttt    180
aatcagaaat tcaaaggaag ggtaacgctg acgacagaca cgtcaacatc gacggcctat    240
atggaattgc ggtcgttgcg atcagatgat acgcgggtct actattgtgc gagggaggcg    300
attacgacgg tgggagcgat ggattattgg ggacagggga cgttggtaac ggtatcgtcg    360
```

```
gcctcaacaa aaggaccaag tgtgttccca ctcgccccta gcagcaagag tacatccggg    420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct tttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

```
<210> SEQ ID NO 182
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 183
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
caggtccagc ttgtgcaatc gggagcggaa gtgaagaaac cgggagcgtc ggtaaaagtc     60
tcgtgcaaag cgtcggggta tacgtttacg gactataaca tggactgggt gcgccaagcg    120
cctggacaga gccttgaatg gatggggcag attaatccga ataatggagg gatcttcttt    180
aatcagaaat tccagggaag ggtaacgctg acgacagaca cgtcaacatc gacggcctat    240
atggaattgc ggtcgttgcg atcagatgat acggcggtct actattgtgc gagggaggcg    300
attacgacgg tgggagcgat ggattattgg ggacagggga cgttggtaac ggtatcgtcg    360
gcctcaacaa aaggaccaag tgtgttccca ctcgccccta gcagcaagag tacatccggg    420
```

```
ggcactgcag cactcggctg cctcgtcaag gattattttc cagagccagt aaccgtgagc    480
tggaacagtg gagcactcac ttctggtgtc catactttc ctgctgtcct gcaaagctct     540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgta atgcacgagg cattgcacaa ccactacacc   1320
cagaagtcac tgagcctgag cccagggaag                                    1350
```

<210> SEQ ID NO 184
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 185
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
caggtccagc ttgtgcaatc gggagcggaa gtgaagaaac cgggagcgtc ggtaaaagtc      60
tcgtgcaaag cgtcggggta tacgtttacg gactataaca tggactgggt gcgccaagcg     120
cctggacagg gtcttgaatg gatggggcag attaatccga ataatggagg gatcttcttt     180
aatcagaaat tccagggaag ggtaacgctg acgacagaca cgtcaacatc gacggcctat     240
atggaattgc ggtcgttgcg atcagatgat acggcggtct actattgtgc gagggaggcg     300
attacgacgg tgggagcgat ggattattgg ggacagggga cgttggtaac ggtatcgtcg     360
gcctcaacaa aggaccaagt gtgttcccca ctcgccccta gcagcaagag tacatccggg     420
ggcactgcag cactcggctg cctcgtcaag gattattttc cagagccagt aaccgtgagc     480
tggaacagtg gagcactcac ttctggtgtc catacttttc ctgctgtcct gcaaagctct     540
```

-continued

```
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt    720 cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 186
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

| Pro | Ser | Asn | Thr | Lys | Val | Asp | Lys | Arg | Val | Glu | Pro | Lys | Ser | Cys | Asp |
|-----|-----|-----|-----|-----|-----|-----|-----|-----|-----|-----|-----|-----|-----|-----|-----|
| | 210 | | | | 215 | | | | | 220 | | | | | |

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 187
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
caagtacagc ttgtacagtc gggagcggaa gtcaagaaac cgggatcgtc ggtcaaagtg        60
tcgtgtaaag cgtcgggata tacgtttagc gactataaca tggattgggt gcgacaagcg       120
cctgggcagg gacttgaatg gatgggtcag atcaatccga ataatggggg aatcttttc        180 aatcagaagt ttaagggag gtaacgctg acgcggata aaagcacgtc aacggcgtat         240
atggagttgt cgtcgttgcg gtcggaggac acggcggtct attactgcgc gagggaagcg       300
attacgacgg tgggagcgat ggattattgg gggcagggaa cgcttgtaac ggtgtcatcg       360
gcctcaacaa aaggaccaag tgtgttccca ctcgccccta gcagcaagag tacatccggg       420
ggcactgcag cactcggctg cctcgtcaag gattattttc cagagccagt aaccgtgagc       480
tggaacagtg gagcactcac ttctggtgtc catactttc ctgctgtcct gcaaagctct       540
ggcctgtact cactcagctc cgtcgtgacc gtgccatctt catctctggg cactcagacc       600

```
tacatctgta atgtaaacca caagcctagc aatactaagg tcgataagcg ggtggaaccc    660
aagagctgcg acaagactca cacttgtccc ccatgccctg ccctgaact tctgggcggt    720 cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 188
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 189
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189
caagtacagc ttgtacagtc gggagcggaa gtcaagaaac cgggatcgtc ggtcaaagtg      60
tcgtgtaaag cgtcgggata tacgtttagc gactataaca tggattgggt gcgacaagcg     120
cctgggcagg gacttgaatg gatgggtcag atcaatccga ataatggggg aatctttttc     180
aatcagaagt ttcaggggag ggtaacgctg acggcggata aaagcacgtc aacggcgtat     240
atggagttgt cgtcgttgcg gtcggaggac acggcggtct attactgcgc gagggaagcg     300
attacgacgg tgggagcgat ggattattgg gggcagggaa cgcttgtaac ggtgtcatcg     360
gcctcaacaa aggaccaagt gtgttcccca ctcgccccta gcagcaagag tacatccggg     420
ggcactgcag cactcggctg cctcgtcaag gattatttc cagagccagt aaccgtgagc      480
tggaacagtg agcactcac ttctggtgtc catactttc ctgctgtcct gcaaagctct       540
ggcctgtact cactcagctc cgtcgtgacc gtgccatctt catctctggg cactcagacc     600
tacatctgta atgtaaacca caagcctagc aatactaagg tcgataagcg ggtggaaccc     660
aagagctgcg acaagactca cacttgtccc ccatgccctg cccctgaact tctgggcggt     720

```
cccagcgtct ttttgttccc accaaagcct aaagatactc tgatgataag tagaacaccc      780
gaggtgacat gtgttgttgt agacgtttcc cacgaggacc cagaggttaa gttcaactgg      840
tacgttgatg gagtcgaagt acataatgct aagaccaagc ctagagagga gcagtataat      900
agtacatacc gtgtagtcag tgttctcaca gtgctgcacc aagactggct caacggcaaa      960
gaatacaaat gcaaagtgtc caacaaagca ctcccagccc ctatcgagaa gactattagt     1020
aaggcaaagg ggcagcctcg tgaaccacag gtgtacactc tgccacccag tagagaggaa     1080
atgacaaaga accaagtctc attgacctgc ctggtgaaag gcttctaccc cagcgacatc     1140
gccgttgagt gggagagtaa cggtcagcct gagaacaatt acaagacaac cccccccagtg     1200 ctggatagtg acgggtcttt ctttctgtac agtaagctga ctgtggacaa gtcccgctgg     1260
cagcagggta acgtcttcag ctgttccgtg atgcacgagg cattgcacaa ccactacacc     1320
cagaagtcac tgagcctgag cccagggaag                                       1350
```

<210> SEQ ID NO 190
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

| | | | | | | | | | | | |
|---|---|---|---|---|---|---|---|---|---|---|---|
|Pro|Ser|Val|Phe|Leu|Phe|Pro|Pro|Lys|Pro|Lys|Asp|Thr|Leu|Met|Ile|
| | | | |245| | | |250| | | |  |  |255|  |

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 191
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
caggtgacac tcaaagaatc aggacccgga atccttcagc ccagccagac cttgtcgctg      60
acttgttcgt tctccggttt cagcctgaat acttatggga tgggtgtgtc atggatcagg     120
caaccgtccg ggaaaggatt ggagtggctc gcgcacatct actgggacga tgacaaacgc     180
tacaatcctt cgctgaagag ccgattgacg atttccaagg atgcctcgaa caaccgggta     240
tttcttaaga tcacgtcggt cgatacggca gacacggcga cctattactg cgcccaaaga     300
gggtacgatg actattgggg atattggggc caggggacac tcgtcacaat ttcagctgcc     360
tcaacaaaag gaccaagtgt gttcccactc gcccctagca gcaagagtac atccgggggc     420
actgcagcac tcggctgcct cgtcaaggat tattttccag agccagtaac cgtgagctgg     480
aacagtggag cactcacttc tggtgtccat acttttcctg ctgtcctgca aagtctggc     540 ctgtactcac tcagctccgt cgtgaccgtg ccatcttcat ctctgggcac tcagacctac     600
atctgtaatg taaaccacaa gcctagcaat actaaggtcg ataagcgggt ggaacccaag     660
agctgcgaca agactcacac ttgtccccca tgccctgccc ctgaacttct gggcggtccc     720
agcgtctttt tgttcccacc aaagcctaaa gatactctga tgataagtag aacacccgag     780

```
gtgacatgtg ttgttgtaga cgtttcccac gaggacccag aggttaagtt caactggtac    840
gttgatggag tcgaagtaca taatgctaag accaagccta gagaggagca gtataatagt    900
acataccgtg tagtcagtgt tctcacagtg ctgcaccaag actggctcaa cggcaaagaa    960
tacaaatgca aagtgtccaa caaagcactc ccagccccta tcgagaagac tattagtaag   1020 gcaaagggc agcctcgtga accacaggtg tacactctgc cacccagtag agaggaaatg   1080
acaaagaacc aagtctcatt gacctgcctg gtgaaaggct tctacccag cgacatcgcc    1140 gttgagtggg agagtaacgg tcagcctgag aacaattaca agacaacccc cccagtgctg   1200
gatagtgacg ggtctttctt tctgtacagt aagctgactg tggacaagtc cgctggcag   1260 cagggtaacg tcttcagctg ttccgtgatg cacgaggcat tgcacaacca ctacacccag   1320
aagtcactga gcctgagccc agggaag                                      1347
```

<210> SEQ ID NO 192
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 193
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
caggtgactt tgaaagaatc cggtcccgca ttggtaaagc caacccagac acttacgctc    60
acatgtacat tttccggatt cagcttgaac acttacggga tgggagtgtc gtggattcgg   120
caacctccgg ggaaggctct ggagtggctg gcgcacatct actgggatga tgacaaaagg   180
tataacccct cacttaaaac gagactgacg atctcgaagg acacaagcaa gaatcaggtc   240
gtcctcacga ttacgaatgt agacccggtg gatactgccg tctattactg cgcgcaacgc   300
gggtatgatg actactgggg atattggggt cagggcaccc tcgtgaccat ctcgtcagcc   360
tcaacaaaag gaccaagtgt gttcccactc gccccctagca gcaagagtac atccgggggc   420
actgcagcac tcggctgcct cgtcaaggat tattttccag agccagtaac cgtgagctgg   480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaccacaa gcctagcaat actaaggtcg ataagcgggt ggaacccaag   660
agctgcgaca agactcacac ttgtccccca tgccctgccc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900

```
acataccgtg tagtcagtgt ctctcacagtg ctgcaccaag actggctcaa cggcaaagaa    960
tacaaatgca aagtgtccaa caaagcactc ccagccccta tcgagaagac tattagtaag   1020
gcaaaggggc agcctcgtga accacaggtg tacactctgc cacccagtag agaggaaatg   1080
acaaagaacc aagtctcatt gacctgcctg gtgaaaggct tctacccag cgacatcgcc    1140 gttgagtggg agagtaacgg tcagcctgag aacaattaca agacaacccc cccagtgctg   1200
gatagtgacg ggtctttctt tctgtacagt aagctgactg tggacaagtc cgctggcag    1260 cagggtaacg tcttcagctg ttccgtgatg cacgaggcat tgcacaacca ctacacccag   1320
aagtcactga gcctgagccc agggaag                                        1347
```

<210> SEQ ID NO 194
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Thr Arg Leu Thr Ile Ser Lys Asp Thr Ser Lys Asn Gln Val
65                  70                  75                  80

Val Leu Thr Ile Thr Asn Val Asp Pro Val Asp Thr Ala Val Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
           275                 280                 285
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 195
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
caagtaacgc tcaaggagtc cggacccacc ttggtgaagc cgacgcagac cttgactctt      60
acgtgcactt tctcggggtt ttcactgaat acgtacggga tgggtgtctc atggatcagg    120
caacctccgg ggaaaggatt ggaatggctg gcgcacatct actgggatga cgataagaga    180
tataacccaa gcctcaagtc gcggctcacc attacaaaag atacatcgaa aaatcaggtc    240
gtacttacta tcacgaacat ggaccccgtg acacagcaa catattactg tgcccagcgc    300
ggctatgacg attattgggg ttactgggga cagggaacac tggtcacggt gtccagcgcc    360
tcaacaaaag gaccaagtgt gttcccactc gcccctagca gcaagagtac atccgggggc    420
actgcagcac tcggctgcct cgtcaaggat tatttccag agccagtaac cgtgagctgg    480
aacagtggag cactcacttc tggtgtccat acttttcctg ctgtcctgca agctctggc    540 ctgtactcac tcagctccgt cgtgaccgtg ccatcttcat ctctgggcac tcagacctac    600
atctgtaatg taaaccacaa gcctagcaat actaaggtcg ataagcgggt ggaacccaag    660
agctgcgaca agactcacac ttgtccccca tgccctgccc ctgaacttct gggcggtccc    720
agcgtctttt tgttcccacc aaagcctaaa gatactctga tgataagtag aacacccgag    780
gtgacatgtg ttgttgtaga cgtttccac gaggacccag aggttaagtt caactggtac    840
gttgatggag tcgaagtaca taatgctaag accaagccta gagaggagca gtataatagt    900
acataccgtg tagtcagtgt tctcacagtg ctgcaccaag actggctcaa cggcaaagaa    960
tacaaatgca aagtgtccaa caaagcactc ccagccccta tcgagaagac tattagtaag   1020
```

```
gcaaaggggc agcctcgtga accacaggtg tacactctgc cacccagtag agaggaaatg    1080
acaaagaacc aagtctcatt gacctgcctg gtgaaaggct tctacccag cgacatcgcc    1140 gttgagtggg agagtaacgg tcagcctgag aacaattaca agacaacccc cccagtgctg    1200
gatagtgacg ggtctttctt tctgtacagt aagctgactg tggacaagtc ccgctggcag    1260
cagggtaacg tcttcagctg ttccgtgatg cacgaggcat tgcacaacca ctacacccag    1320
aagtcactga gcctgagccc agggaag                                        1347
```

<210> SEQ ID NO 196
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 197
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
caggtcacgc tgaaagagtc aggtcccgga atccttcaac cttcgcagac attgtcactc      60
acatgttcct tctccgggtt ctcgctctcg acttatggca tgggtgtagg atggattcgg     120
cagcccagcg ggaaggggct tgagtggttg gcggatatct ggtgggacga cgacaaatac     180
tacaatccga gcctgaagtc ccgcctcacc atttcgaaag atacgtcatc aaacgaagtc     240 ttttttgaaga tcgccatcgt ggacacggcg gatacagcga cgtattactg cgccagaagg     300
ggacactaca gcgcaatgga ttattgggga caggggacct cggtgactgt gtcgtccgcc     360
tcaacaaaag gaccaagtgt gttcccactc gcccctagca gcaagagtac atccgggggc     420
actgcagcac tcggctgcct cgtcaaggat tattttccag agccagtaac cgtgagctgg     480
aacagtggag cactcacttc tggtgtccat acttttcctg ctgtcctgca agctctggc      540 ctgtactcac tcagctccgt cgtgaccgtg ccatcttcat ctctgggcac tcagacctac     600
atctgtaatg taaaccacaa gcctagcaat actaaggtcg ataagcgggt ggaacccaag     660
agctgcgaca agactcacac ttgtccccca tgccctgccc ctgaacttct gggcggtccc     720
agcgtctttt tgttcccacc aaagcctaaa gatactctga tgataagtag aacacccgag     780
gtgacatgtg ttgttgtaga cgtttcccac gaggacccag aggttaagtt caactggtac     840
gttgatggag tcgaagtaca taatgctaag accaagccta gagaggagca gtataatagt     900
acataccgtg tagtcagtgt tctcacagtg ctgcaccaag actggctcaa cggcaaagaa     960
tacaaatgca agtgtccaa caaagcactc ccagccccta tcgagaagac tattagtaag    1020 gcaaggggc agcctcgtga accacaggtg tacactctgc cacccagtag agaggaaatg    1080
acaaagaacc aagtctcatt gacctgcctg gtgaaaggct tctaccccag cgacatcgcc    1140
```

```
gttgagtggg agagtaacgg tcagcctgag aacaattaca agacaacccc cccagtgctg    1200
gatagtgacg ggtctttctt tctgtacagt aagctgactg tggacaagtc ccgctggcag    1260
cagggtaacg tcttcagctg ttccgtgatg cacgaggcat tgcacaacca ctacacccag    1320
aagtcactga gcctgagccc agggaag                                        1347
```

<210> SEQ ID NO 198
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Ser Lys Asp Thr Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 199
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199
cagatcactt tgaaagaaag cggaccgacc ttggtcaagc ccacacaaac cctcacgctc      60
acgtgtacat tttcggggtt ctcgctttca acttacggga tgggagtagg gtggattcgc     120
cagccgcctg gtaaagcgtt ggagtggctt gcagacatct ggtgggacga cgataagtac     180
tataatccct cgctcaagtc cagactgacc atcacgaaag atacgagcaa gaaccaggtc     240
gtgctgacaa tgactaacat ggacccagtg gatacggcta catattactg cgccaggcgg     300
ggtcactact cagcgatgga ttattggggc cagggaacac tggtaacggt gtcgtccgcc     360
tcaacaaaag gaccaagtgt gttcccactc gccctagca gcaagagtac atccgggggc      420
actgcagcac tcggctgcct cgtcaaggat tattttccag agccagtaac cgtgagctgg     480
aacagtggag cactcacttc tggtgtccat acttttcctg ctgtcctgca aagctctggc     540
ctgtactcac tcagctccgt cgtgaccgtg ccatcttcat ctctgggcac tcagacctac     600
atctgtaatg taaaccacaa gcctagcaat actaaggtcg ataagcgggt ggaacccaag     660
agctgcgaca agactcacac ttgtccccca tgccctgccc ctgaacttct gggcggtccc     720
agcgtctttt tgttcccacc aaagcctaaa gatactctga tgataagtag aacacccgag     780
gtgacatgtg ttgttgtaga cgtttcccac gaggacccag aggttaagtt caactggtac     840
gttgatggag tcgaagtaca taatgctaag accaagccta gagaggagca gtataatagt     900
acataccgtg tagtcagtgt tctcacagtg ctgcaccaag actggctcaa cggcaaagaa     960
tacaaatgca aagtgtccaa caaagcactc ccagccccta tcgagaagac tattagtaag    1020
gcaagggggc agcctcgtga accacaggtg tacactctgc cacccagtag agaggaaatg    1080
acaaagaacc aagtctcatt gacctgcctg gtgaaaggct ctaccccag cgacatcgcc     1140 gttgagtggg agagtaacgg tcagcctgag aacaattaca agacaacccc cccagtgctg    1200
gatagtgacg ggtctttctt tctgtacagt aagctgactg tggacaagtc ccgctggcag    1260
```

```
caggttaacg tcttcagctg ttccgtgatg cacgaggcat tgcacaacca ctacacccag   1320
aagtcactga gcctgagccc agggaag                                        1347
```

<210> SEQ ID NO 200
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
              340                 345                 350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 201
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

```
caagtgactc tcaaggagtc cggacccgcc ctggtcaaac caacgcagac actgacgctc      60
acatgcacct tcagcggatt ttcgttgtca acgtacggca tgggtgtggg gtggattcgc     120
cagcctccgg ggaaagccct tgaatggttg gcggacatct ggtgggatga tgacaagtac     180
tataatccct cacttaagtc acggttgacg atctcgaaag acaccagcaa gaaccaggta     240
gtgctgacaa tgactaacat ggacccggtc gatacagcgg tctactattg tgctagaagg     300
ggacactact ccgcaatgga ttattggggt caggggacgc tcgtaaccgt gtcgtcggcc     360
tcaacaaaag gaccaagtgt gttcccactc gcccctagca gcaagagtac atccgggggc     420
actgcagcac tcggctgcct cgtcaaggat tattttccag agccagtaac cgtgagctgg     480
aacagtggag cactcacttc tggtgtccat acttttcctg ctgtcctgca aagctctggc     540
ctgtactcac tcagctccgt cgtgaccgtg ccatcttcat ctctgggcac tcagacctac     600
atctgtaatg taaaccacaa gcctagcaat actaaggtcg ataagcgggt ggaacccaag     660
agctgcgaca agactcacac ttgtccccca tgccctgccc ctgaacttct gggcggtccc     720
agcgtctttt tgttcccacc aaagcctaaa gatactctga tgataagtag aacacccgag     780
gtgacatgtg ttgttgtaga cgtttcccac gaggacccag aggttaagtt caactggtac     840
gttgatggag tcgaagtaca taatgctaag accaagccta gagaggagca gtataatagt     900
acataccgtg tagtcagtgt tctcacagtg ctgcaccaag actggctcaa cggcaaagaa     960
tacaaatgca agtgtccaa caaagcactc ccagccccta tcgagaagac tattagtaag    1020
gcaaaggggc agcctcgtga accacaggtg tacactctgc acccagtag agaggaaatg    1080
acaaagaacc aagtctcatt gacctgcctg gtgaaaggct tctacccag cgacatcgcc    1140
gttgagtggg agagtaacgg tcagcctgag aacaattaca gacaaccccc ccagtgctg    1200
gatagtgacg ggtctttctt tctgtacagt aagctgactg tggacaagtc ccgctggcag    1260
cagggtaacg tcttcagctg ttccgtgatg cacgaggcat tgcacaacca ctacacccag    1320
aagtcactga gcctgagccc agggaag                                         1347
```

<210> SEQ ID NO 202
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 203
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
gacatccaaa tgacccagtc acccgcgagc ctttcggcgt cggtcggaga acggtcacg      60 atcacgtgcc ggacatcaga gaatctccat aactacctcg cgtggtatca acagaagcag    120
gggaagtcgc cccagttgct tgtatacgat gcgaaaacgt tggcggatgg ggtgccgtcc    180
agattctcgg gatcgggctc ggggacgcag tactcgctca agatcaattc gctgcagccg    240
gaggactttg gtcgtacta ttgtcagcat ttttggtcat caccgtatac atttggaggt     300
ggaacgaaac ttgagattaa gcgcacagtt gctgccccca gcgtgttcat tttcccacct    360
agcgatgagc agctgaaaag cggtactgcc tctgtcgtat gcttgctcaa caacttttac    420
ccacgtgagg ctaaggtgca gtggaaagtg gataatgcac ttcaatctgg aaacagtcaa    480
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat agggggcgaat gt                       642

<210> SEQ ID NO 204
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

```
Thr Phe Gly Gly Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 205
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 205

```
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaagtcac cgaaactcct tgtctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgt cgcctacac atttgggcag     300
gggaccaagt tggaaatcaa gcgcacagtt gctgccccca gcgtgttcat tttcccacct     360
agcgatgagc agctgaaaag cggtactgcc tctgtcgtat gcttgctcaa caacttttac     420
ccacgtgagg ctaaggtgca gtggaaagtg gataatgcac tcaatctgg aaacagtcaa      480
gagtccgtga cagaacagga cagcaaagac tcaacttatt cactctcttc caccctgact     540
ctgtccaagg cagactatga aaaacacaag gtatacgcct gcgaggttac acaccagggt     600
ttgtctagtc ctgtcaccaa gtccttcaat agggcgaat gt                        642
```

<210> SEQ ID NO 206
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

```
Asp Ile Gln Met Thr Gln Ser Pro Ser Ser Leu Ser Ala Ser Val Gly
1               5                   10                  15
Asp Arg Val Thr Ile Thr Cys Arg Thr Ser Glu Asn Leu His Asn Tyr
                20                  25                  30
Leu Ala Trp Tyr Gln Gln Lys Pro Gly Lys Ser Pro Lys Leu Leu Val
            35                  40                  45
Tyr Asp Ala Lys Thr Leu Ala Asp Gly Val Pro Ser Arg Phe Ser Gly
```

```
                    50                  55                  60
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Ser Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 207
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207

```
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaaggccc cgaaactcct tatctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgt cgccctacac atttgggcag     300
gggaccaagt tggaaatcaa agcacagtt gctgccccca gcgtgttcat tttcccacct     360
agcgatgagc agctgaaaag cggtactgcc tctgtcgtat gcttgctcaa caactttttac    420 ccacgtgagg ctaaggtgca gtggaaagtg ataatgcac ttcaatctgg aaacagtcaa     480
gagtccgtga cagaacagga cagcaaagac tcaacttatt cactctcttc caccctgact    540
ctgtccaagg cagactatga aaacacaag gtatacgcct gcgaggttac acaccagggt    600
ttgtctagtc ctgtcaccaa gtccttcaat aggggcgaat gt                      642
```

<210> SEQ ID NO 208
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Asp Ile Gln Met Thr Gln Ser Pro Ser Ser Leu Ser Ala Ser Val Gly
  1               5                  10                  15
```

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ala Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 209
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaagtcac cgaaactcct tatctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgt cgccctacac atttgggcag     300
gggaccaagt tggaaatcaa gcgcacagtt gctgccccca gcgtgttcat ttttcccacct     360 agcgatgagc agctgaaaag cggtactgcc tctgtcgtat gcttgctcaa caacttttac     420
ccacgtgagg ctaaggtgca gtggaaagtg gataatgcac ttcaatctgg aaacagtcaa     480
gagtccgtga cagaacagga cagcaaagac tcaacttatt cactctcttc caccctgact     540
ctgtccaagg cagactatga aaaacacaag gtatacgcct gcgaggttac acaccagggt     600
ttgtctagtc ctgtcaccaa gtccttcaat agggcgaat gt                         642

<210> SEQ ID NO 210
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 211
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
gatatcgtca tgacccagtc ccagaagttc atgtcaactt cagtgggaga cagagtgtcc      60
gtcacatgta agcctcgca aaatgtggga accaacgtag cgtggttcca gcagaaacct     120
ggccaatcac cgaaggcact gatctactcg gccagctata ggtactcggg agtaccagat     180
cggtttacgg ggtcggggag cgggacggac tttatcctca ctatttccaa tgtccagtcg     240
gaggaccttg cggaatactt ctgccagcag tataacaact atcccctcac gtttggtgct     300
ggtacaaaat tggagttgaa gcgcacagtt gctgccccca gcgtgttcat tttcccacct     360
agcgatgagc agctgaaaag cggtactgcc tctgtcgtat gcttgctcaa caacttttac     420
ccacgtgagg ctaaggtgca gtggaaagtg gataatgcac ttcaatctgg aaacagtcaa     480
gagtccgtga cagaacagga cagcaaagac tcaacttatt cactctcttc caccctgact     540
ctgtccaagg cagactatga aaaacacaag gtatacgcct gcgaggttac acaccagggt     600
ttgtctagtc ctgtcaccaa gtccttcaat agggcgaat gt                        642

<210> SEQ ID NO 212
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 213
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213
gacatccaaa tgacccaatc gccctcctcc ctctccgcat cagtagggga ccgcgtcaca     60
attacttgca aagcgtcgca gaacgtcgga acgaatgtgg cgtggtttca gcagaagccc    120
ggaaaagctc cgaagagctt gatctactcg gcctcatata ggtattcggg tgtgccgagc    180
cggtttagcg gtcggggtc aggtactgat ttcacgctca aatttcatc gttgcagcca     240 gaagatttcg ccacatatta ctgtcagcag tacaacaatt accctctgac gttcggccag    300
ggaaccaaac ttgagatcaa gcgcacagtt gctgccccca gcgtgttcat tttcccacct    360
agcgatgagc agctgaaaag cggtactgcc tctgtcgtat gcttgctcaa caactttta    420 ccacgtgagg ctaaggtgca gtggaaagtg gataatgcac ttcaatctgg aaacagtcaa    480

```
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat aggggcgaat gt                      642
```

```
<210> SEQ ID NO 214
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 215
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
gacatcgtga tgacacagtc acagaaattc atgtccacat ccgtcggtga tagagtatcc    60
gtcacgtgta aggcctcgca aaacgtagga actaatgtgg cgtggtatca acagaagcca   120
ggacagtcac ccaaagcact catctacagc ccctcatatc ggtacagcgg ggtgccggac   180
aggttcacgg gatcggggag cgggaccgat tttacactga ccatttcgaa tgtccagtcg   240
```

```
gaggaccttg cggaatactt ctgccagcag tataactcgt accctcacac gtttggaggt    300
ggcactaagt tggagatgaa acgcacagtt gctgccccca gcgtgttcat tttcccacct    360
agcgatgagc agctgaaaag cggtactgcc tctgtcgtat gcttgctcaa caactttttac   420 ccacgtgagg ctaaggtgca gtggaaagtg gataatgcac ttcaatctgg aaacagtcaa    480
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat aggggcgaat gt                       642
```

<210> SEQ ID NO 216
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Thr Phe Gly Gly Gly Thr Lys Leu Glu Met Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 217
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217

```
gatatccaga tgacacagtc accctcgtcg ctctcagctt ccgtaggcga cagggtcact    60
```

```
attacgtgta aagcatcaca gaacgtcgga acgaatgtgg cgtggtttca gcagaagccc    120
gggaagagcc ccaaagcgct tatctactcc ccgtcgtatc ggtattccgg tgtgccaagc    180
agattttcgg ggtcaggttc gggaactgac tttaccctga ccatctcgtc cctccaaccg    240
gaagatttcg ccacgtactt ctgccagcag tacaacagct atcctcacac attcggacaa    300
gggacaaagt tggagattaa acgcacagtt gctgccccca gcgtgttcat tttcccacct    360
agcgatgagc agctgaaaag cggtactgcc tctgtcgtat gcttgctcaa caacttttac    420
ccacgtgagg ctaaggtgca gtggaaagtg gataatgcac ttcaatctgg aaacagtcaa    480
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat aggggcgaat gt                       642
```

<210> SEQ ID NO 218
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Pro Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 219
<211> LENGTH: 1035
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 219

```
gggtgtaaac cctgcatctg cacggtgccg gaggtgtcct ccgtctttat cttccctccc      60
aaacccaagg atgtgctgac aatcactttg actccaaaag tcacatgcgt agtcgtggac     120
atctcgaaag acgacccgga agtgcagttc tcgtggtttg ttgatgatgt agaagtgcat     180
accgctcaaa cccagccgag ggaagaacag tttaacagca cgtttaggag tgtgtcggaa     240
ctgcccatta tgcaccagga ttggcttaat gggaaggagt tcaaatgtcg cgtgaatagt     300
gcggcgttcc cagcccctat tgaaaagact atttccaaaa cgaagggtcg gcccaaagct     360
ccccaagtat acacaatccc tccgccgaaa gaacaaatgg caaaagacaa agtgagtttg     420
acgtgcatga tcacggactt ttttcccggag gatatcaccg tcgaatggca atggaatggg     480
caacctgccg aaaactacaa gaatacacaa cccattatgg ataccgatgg atcgtatttc     540
gtctactcaa agttgaacgt acagaagtca aattgggagg cagggaatac gttcacttgc     600
agtgttttgc acgaaggcct ccataaccac catacggaaa agtcactgtc gcactccccg     660
ggaaaaatcg agggcagaat ggatggtgga ggagggtcgg cgcgcaacgg ggaccactgt     720
ccgctcgggc cgggcgttg ctgccgtctg cacacggtcc gcgcgtcgct ggaagacctg     780
ggctgggcca ttgggtgct gtcgccacgg gaggtgcaag tgaccatgtg catcggcgcg     840
tgcccgagcc agttccgggc ggcaaacatg cacgcgcaga tcaagacgag cctgcaccgc     900
ctgaagcccg acacggtgcc agcgccctgc tgcgtgcccg ccagctacaa tcccatggtg     960
ctcattcaaa agaccgacac cggggtgtcg ctccagacct atgatgactt gttagccaaa    1020
gactgccact gcata                                                    1035
```

<210> SEQ ID NO 220
<211> LENGTH: 345
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 220

```
Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
    50                  55                  60

Gln Pro Arg Glu Glu Gln Phe Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140
```

```
Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
            165                 170                 175

Gly Ser Tyr Phe Val Tyr Ser Lys Leu Asn Val Gln Lys Ser Asn Trp
        180                 185                 190

Glu Ala Gly Asn Thr Phe Thr Cys Ser Val Leu His Glu Gly Leu His
    195                 200                 205

Asn His His Thr Glu Lys Ser Leu Ser His Ser Pro Gly Lys Ile Glu
210                 215                 220

Gly Arg Met Asp Gly Gly Gly Ser Ala Arg Asn Gly Asp His Cys
225                 230                 235                 240

Pro Leu Gly Pro Gly Arg Cys Cys Arg Leu His Thr Val Arg Ala Ser
                245                 250                 255

Leu Glu Asp Leu Gly Trp Ala Asp Trp Val Leu Ser Pro Arg Glu Val
            260                 265                 270

Gln Val Thr Met Cys Ile Gly Ala Cys Pro Ser Gln Phe Arg Ala Ala
        275                 280                 285

Asn Met His Ala Gln Ile Lys Thr Ser Leu His Arg Leu Lys Pro Asp
    290                 295                 300

Thr Val Pro Ala Pro Cys Cys Val Pro Ala Ser Tyr Asn Pro Met Val
305                 310                 315                 320

Leu Ile Gln Lys Thr Asp Thr Gly Val Ser Leu Gln Thr Tyr Asp Asp
                325                 330                 335

Leu Leu Ala Lys Asp Cys His Cys Ile
            340                 345

<210> SEQ ID NO 221
<211> LENGTH: 1026
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
tcgaaaccca cttgccctcc tccggagctg ttgggcggac cctccgtgtt tatctttccc    60
ccgaagccga aagataccct tatgatctca cggacgccgg aggtcacttg cgtagtagtg   120
gatgtgtcgg aggatgaccc cgaagtccag ttcacctggt atatcaataa cgagcaagtg   180
aggacagcga ggcccccact tagggagcag cagttcaact ccacaattcg ggtcgtcagc   240
actttgccca tcgctcatga ggactggctc cgcggaaaag agttcaagtg taaggtgcat   300
aacaaggcat tgccagcgcc tattgaaaag acaatctcga aggcgcgagg gcagccgctc   360
gagcccaaag tgtatacgat gggaccccg agggaagaat tgtcgtcgcg ctcagtaagc   420
cttacgtgca tgattaacgg tttctaccct agcgacatca gcgtagagtg gaaaagaat   480 ggaaaggcgg aggataacta caagacgact cccgcggtgc tggattcgga tgggtcgtac   540
tttctgtata gcaaattgtc agtcccgacc tcagaatggc agaggggtga cgtgttcacg   600
tgctccgtga tgcacgaagc acttcacaat cactacaccc agaaatcaat ctcgcggtcc   660
ccaggcaaag gtggaggagg gtcggctcac gcccacctc gcgattcgtg tccgctgggg   720
cctggtagat gctgtcatct cgagacagtc caggccacgc tggaggacct cgggtggtca   780
gactgggtcc tgtccccacg acaactgcag ctttcgatgt gcgtggggga atgtccgcac   840
```

```
ttgtacagat cggcgaatac ccacgctcag attaaggcac gactccatgg tttgcagcca    900
gataaagtcc ccgcaccttg ctgtgtcccc agctcatata ctcctgtcgt actcatgcat    960
cggacagaca gcggcgtgtc gcttcaaacg tatgacgacc tcgtagcgag aggatgtcat   1020
tgcgcc                                                              1026
```

<210> SEQ ID NO 222
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Ser Lys Pro Thr Cys Pro Pro Glu Leu Leu Gly Gly Pro Ser Val
1               5                   10                  15

Phe Ile Phe Pro Pro Lys Pro Lys Asp Thr Leu Met Ile Ser Arg Thr
                20                  25                  30

Pro Glu Val Thr Cys Val Val Val Asp Val Ser Glu Asp Asp Pro Glu
            35                  40                  45

Val Gln Phe Thr Trp Tyr Ile Asn Asn Glu Gln Val Arg Thr Ala Arg
    50                  55                  60

Pro Pro Leu Arg Glu Gln Gln Phe Asn Ser Thr Ile Arg Val Val Ser
65                  70                  75                  80

Thr Leu Pro Ile Ala His Glu Asp Trp Leu Arg Gly Lys Glu Phe Lys
                85                  90                  95

Cys Lys Val His Asn Lys Ala Leu Pro Ala Pro Ile Glu Lys Thr Ile
                100                 105                 110

Ser Lys Ala Arg Gly Gln Pro Leu Glu Pro Lys Val Tyr Thr Met Gly
            115                 120                 125

Pro Pro Arg Glu Glu Leu Ser Ser Arg Ser Val Ser Leu Thr Cys Met
130                 135                 140

Ile Asn Gly Phe Tyr Pro Ser Asp Ile Ser Val Glu Trp Glu Lys Asn
145                 150                 155                 160

Gly Lys Ala Glu Asp Asn Tyr Lys Thr Thr Pro Ala Val Leu Asp Ser
                165                 170                 175

Asp Gly Ser Tyr Phe Leu Tyr Ser Lys Leu Ser Val Pro Thr Ser Glu
            180                 185                 190

Trp Gln Arg Gly Asp Val Phe Thr Cys Ser Val Met His Glu Ala Leu
        195                 200                 205

His Asn His Tyr Thr Gln Lys Ser Ile Ser Arg Ser Pro Gly Lys Gly
    210                 215                 220

Gly Gly Gly Ser Ala His Ala His Pro Arg Asp Ser Cys Pro Leu Gly
225                 230                 235                 240

Pro Gly Arg Cys Cys His Leu Glu Thr Val Gln Ala Thr Leu Glu Asp
                245                 250                 255

Leu Gly Trp Ser Asp Trp Val Leu Ser Pro Arg Gln Leu Gln Leu Ser
            260                 265                 270

Met Cys Val Gly Glu Cys Pro His Leu Tyr Arg Ser Ala Asn Thr His
        275                 280                 285

Ala Gln Ile Lys Ala Arg Leu His Gly Leu Gln Pro Asp Lys Val Pro
    290                 295                 300

Ala Pro Cys Cys Val Pro Ser Ser Tyr Thr Pro Val Val Leu Met His
305                 310                 315                 320
```

```
Arg Thr Asp Ser Gly Val Ser Leu Gln Thr Tyr Asp Asp Leu Val Ala
            325                 330                 335

Arg Gly Cys His Cys Ala
            340

<210> SEQ ID NO 223
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ile Glu Gly Arg Met Asp Gly Gly Gly Ser Ala Arg
225                 230                 235                 240

Asn Gly Asp His Cys Pro Leu Gly Pro Gly Arg Cys Cys Arg Leu His
                245                 250                 255

Thr Val Arg Ala Ser Leu Glu Asp Leu Gly Trp Ala Asp Trp Val Leu
            260                 265                 270

Ser Pro Arg Glu Val Gln Val Thr Met Cys Ile Gly Ala Cys Pro Ser
        275                 280                 285

Gln Phe Arg Ala Ala Asn Met His Ala Gln Ile Lys Thr Ser Leu His
    290                 295                 300

Arg Leu Lys Pro Asp Thr Val Pro Ala Pro Cys Cys Val Pro Ala Ser
305                 310                 315                 320

Tyr Asn Pro Met Val Leu Ile Gln Lys Thr Asp Thr Gly Val Ser Leu
                325                 330                 335
```

-continued

Gln Thr Tyr Asp Asp Leu Leu Ala Lys Asp Cys His Cys Ile
                340                 345                 350

<210> SEQ ID NO 224
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Ala Arg Asn Gly Asp His Cys Pro
225                 230                 235                 240

Leu Gly Pro Gly Arg Cys Cys Arg Leu His Thr Val Arg Ala Ser Leu
                245                 250                 255

Glu Asp Leu Gly Trp Ala Asp Trp Val Leu Ser Pro Arg Glu Val Gln
            260                 265                 270

Val Thr Met Cys Ile Gly Ala Cys Pro Ser Gln Phe Arg Ala Ala Asn
        275                 280                 285

Met His Ala Gln Ile Lys Thr Ser Leu His Arg Leu Lys Pro Asp Thr
    290                 295                 300

Val Pro Ala Pro Cys Cys Val Pro Ala Ser Tyr Asn Pro Met Val Leu
305                 310                 315                 320

Ile Gln Lys Thr Asp Thr Gly Val Ser Leu Gln Thr Tyr Asp Leu
                325                 330                 335

Leu Ala Lys Asp Cys His Cys Ile

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ctaatacgac tcactatagg gc                                              22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
tatgcaaggc ttacaaccac a                                               21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
aggacagggg ttgattgttg a                                               21

<210> SEQ ID NO 228
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ctcattcctg ttgaagctct tgacaat                                         27

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
aagcagtggt atcaacgcag agt                                             23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
cgactgaggc acctccagat gtt                                             23

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gtaaaacgac ggccagt                                                  17

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
caggaaacag ctatgacc                                                 18

<210> SEQ ID NO 233
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ctaatacgac tcactatagg gcaagcagtg gtatcaacgc agagt                   45

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Tyr Thr Phe Ser Asp Tyr
1               5

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Tyr Thr Phe Ser Asp Tyr Asn
1               5

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gln Ile Asn Pro Tyr Asn His Leu Ile Phe Phe Asn Gln Lys Phe Gln
1               5                   10                  15

Gly

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gln Ile Asn Pro Asn Asn Gly Leu Ile Phe Phe Asn Gln Lys Phe Gln
1               5                   10                  15

Gly

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Ile Asn Pro Asn Asn Gly Leu Ile Phe Phe Asn Gln Lys Phe Lys
1               5                   10                  15

Gly

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gln Ile Asn Pro Tyr Asn His Leu Ile Phe Phe Asn Gln Lys Phe Lys
1               5                   10                  15

Gly

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asn Pro Tyr Asn His Leu
1               5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asn Pro Asn Asn Gly Leu

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Ile Asn Pro Tyr Asn His Leu Ile
1               5

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Ile Asn Pro Asn Asn Gly Leu Ile
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Gln His Phe Trp Ser Asp Pro Tyr Thr
1               5

<210> SEQ ID NO 245
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245
caggtccagc ttgtgcaatc gggagcggaa gtgaagaaac cgggagcgtc ggtaaaagtc      60
tcgtgcaaag cgtcgggta tacgtttacg gactataaca tggactgggt gcgccaagcg     120
cctggacaga gccttgaatg gatggggcag attaatccgt acaatcacct gatcttcttt     180
aatcagaaat tccagggaag ggtaacgctg acgacagaca cgtcaacatc gacggcctat     240
atggaattgc ggtcgttgcg atcagatgat acggcggtct actattgtgc gagggaggcg     300
attacgacgg tgggagcgat ggattattgg ggacagggga cgttggtaac ggtatcgtcg     360

<210> SEQ ID NO 246
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 246

Gln Val Gln Leu Val Gln Ser Gly Ala Glu Val Lys Lys Pro Gly Ala

```
  1               5                   10                  15
Ser Val Lys Val Ser Cys Lys Ala Ser Gly Tyr Thr Phe Thr Asp Tyr
             20                  25                  30

Asn Met Asp Trp Val Arg Gln Ala Pro Gly Gln Ser Leu Glu Trp Met
             35                  40                  45

Gly Gln Ile Asn Pro Tyr Asn His Leu Ile Phe Phe Asn Gln Lys Phe
 50                  55                  60

Gln Gly Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg Glu Ala Ile Thr Thr Val Gly Ala Met Asp Tyr Trp Gly Gln
            100                 105                 110

Gly Thr Leu Val Thr Val Ser Ser
            115                 120

<210> SEQ ID NO 247
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
caggtccagc ttgtgcaatc gggagcggaa gtgaagaaac cgggagcgtc ggtaaaagtc    60
tcgtgcaaag cgtcggggta tacgtttacg gactataaca tggactgggt gcgccaagcg   120
cctggacaga gccttgaatg gatggggcag attaatccga ataatggact gatcttcttt   180
aatcagaaat tccagggaag ggtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360

<210> SEQ ID NO 248
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Asn Met Asp Trp Val Arg Gln Ala Pro Gly Gln Ser Leu Glu Trp Met
             35                  40                  45

Gly Gln Ile Asn Pro Asn Asn Gly Leu Ile Phe Phe Asn Gln Lys Phe
 50                  55                  60

Gln Gly Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg Glu Ala Ile Thr Thr Val Gly Ala Met Asp Tyr Trp Gly Gln
            100                 105                 110

Gly Thr Leu Val Thr Val Ser Ser
```

<210> SEQ ID NO 249
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249

```
caagtacagc ttgtacagtc gggagcggaa gtcaagaaac cgggatcgtc ggtcaaagtg    60
tcgtgtaaag cgtcgggata tacgtttagc gactataaca tggattgggt gcgacaagcg   120
cctgggcagg gacttgaatg gatgggtcag atcaatccga ataatgggct gatcttttc   180
aatcagaagt ttaaagggag ggtaacgctg acggcggata aaagcacgtc aacggcgtat   240
atggagttgt cgtcgttgcg gtcggaggac acggcggtct attactgcgc gagggaagcg   300
attacgacgg tgggagcgat ggattattgg gggcagggaa cgcttgtaac ggtgtcatcg   360
```

<210> SEQ ID NO 250
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

```
Gln Val Gln Leu Val Gln Ser Gly Ala Glu Val Lys Lys Pro Gly Ser
1               5                  10                  15
Ser Val Lys Val Ser Cys Lys Ala Ser Gly Tyr Thr Phe Ser Asp Tyr
            20                  25                  30
Asn Met Asp Trp Val Arg Gln Ala Pro Gly Gln Gly Leu Glu Trp Met
        35                  40                  45
Gly Gln Ile Asn Pro Asn Asn Gly Leu Ile Phe Phe Asn Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Ala Ile Thr Thr Val Gly Ala Met Asp Tyr Trp Gly Gln
            100                 105                 110
Gly Thr Leu Val Thr Val Ser Ser
        115                 120
```

<210> SEQ ID NO 251
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 251

```
caagtacagc ttgtacagtc gggagcggaa gtcaagaaac cgggatcgtc ggtcaaagtg    60
tcgtgtaaag cgtcgggata tacgtttagc gactataaca tggattgggt gcgacaagcg   120
cctgggcagg gacttgaatg gatgggtcag atcaatccgt acaatcacct gatcttttc   180
aatcagaagt ttaaagggag ggtaacgctg acggcggata aaagcacgtc aacggcgtat   240
```

```
atggagttgt cgtcgttgcg gtcggaggac acggcggtct attactgcgc gagggaagcg    300
attacgacgg tgggagcgat ggattattgg gggcagggaa cgcttgtaac ggtgtcatcg    360
```

<210> SEQ ID NO 252
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Tyr Asn His Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 253
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

```
gacatccaaa tgacccagtc gccgtcgtcg ctttcagcgt cggtagggga tcgggtcaca    60
attacgtgcc gaacgtcaga gaatttgcat aactacctcg cgtggtatca gcagaagccc   120
gggaagtcac cgaaactcct tatctacgat gcgaaaacgc tggcggatgg agtgccgtcg   180
agattctcgg gaagcggatc cggtacggac tatacgctta cgatctcatc gctccagccc   240
gaggactttg cgacgtacta ttgtcagcat ttttggtcgg acccctacac atttgggcag   300
gggaccaagt tggaaatcaa g                                              321
```

<210> SEQ ID NO 254
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30
```

| | | | | | | | | | | |
|---|---|---|---|---|---|---|---|---|---|---|
| Leu | Ala | Trp | Tyr | Gln | Gln | Lys | Pro | Gly | Lys | Ser | Pro | Lys | Leu | Leu | Ile |
| | | | 35 | | | | 40 | | | | 45 | | | | |

Tyr Asp Ala Lys Thr Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Asp Pro Tyr
            85                  90                  95

Thr Phe Gly Gln Gly Thr Lys Leu Glu Ile Lys
            100                 105

<210> SEQ ID NO 255
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255

```
caggtccagc ttgtgcaatc gggagcggaa gtgaagaaac cgggagcgtc ggtaaaagtc     60
tcgtgcaaag cgtcgggta tacgtttacg gactataaca tggactgggt gcgccaagcg   120
cctggacaga gccttgaatg gatggggcag attaatccgt acaatcacct gatcttcttt   180
aatcagaaat ccaggggaag ggtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360
gcctcaacaa aaggaccaag tgtgttccca ctcgccccta gcagcaagag tacatccggg   420
ggcactgcag cactcggctg cctcgtcaag gattattttc cagagccagt aaccgtgagc   480
tggaacagtg gagcactcac ttctggtgtc catacttttc ctgctgtcct gcaaagctct   540
ggcctgtact cactcagctc cgtcgtgacc gtgccatctt catctctggg cactcagacc   600
tacatctgta atgtaaacca caagcctagc aatactaagg tcgataagcg ggtggaaccc   660
aagagctgcg acaagactca cacttgtccc ccatgccctg cccctgaact tctgggcggt   720
cccagcgtct tttgttccc accaaagcct aaagatactc tgatgataag tagaacaccc   780
gaggtgacat gtgttgttgt agacgtttcc cacgaggacc cagaggttaa gttcaactgg   840
tacgttgatg gagtcgaagt acataatgct aagaccaagc ctagagagga gcagtataat   900
agtacatacc gtgtagtcag tgttctcaca gtgctgcacc aagactggct caacggcaaa   960
gaatacaaat gcaaagtgtc caacaaagca ctcccagccc ctatcgagaa gactattagt  1020
aaggcaaagg gcagcctcg tgaaccacag gtgtacactc tgccacccag tagagaggaa  1080
atgacaaaga accaagtctc attgacctgc ctggtgaaag gcttctaccc cagcgacatc  1140
gccgttgagt gggagagtaa cggtcagcct gagaacaatt acaagacaac ccccccagtg  1200
ctggatagtg acgggtcttt ctttctgtac agtaagctga ctgtggacaa gtcccgctgg  1260
cagcagggta acgtcttcag ctgttccgtg atgcacgagg cattgcacaa ccactacacc  1320
cagaagtcac tgagcctgag cccagggaag                                   1350
```

<210> SEQ ID NO 256
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Tyr Asn His Leu Ile Phe Phe Asn Gln Lys Phe
 50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Lys Leu Thr Val Asp
        405                 410                 415

Lys Ser Arg Trp Gln Gln Gly Asn Val Phe Ser Cys Ser Val Met His
    420                 425                 430

Glu Ala Leu His Asn His Tyr Thr Gln Lys Ser Leu Ser Leu Ser Pro
        435                 440                 445

Gly Lys
    450

<210> SEQ ID NO 257
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
caggtccagc ttgtgcaatc gggagcggaa gtgaagaaac cgggagcgtc ggtaaaagtc      60
tcgtgcaaag cgtcggggta tacgtttacg gactataaca tggactgggt gcgccaagcg     120
cctggacaga gccttgaatg gatggggcag attaatccga ataatggact gatcttcttt     180
aatcagaaat tccagggaag ggtaacgctg acgacagaca cgtcaacatc gacggcctat     240
atggaattgc ggtcgttgcg atcagatgat acggcggtct actattgtgc gagggaggcg     300
attacgacgg tgggagcgat ggattattgg ggacagggga cgttggtaac ggtatcgtcg     360
gcctcaacaa aaggaccaag tgtgttccca ctcgccccta gcagcaagag tacatccggg     420
ggcactgcag cactcggctg cctcgtcaag gattattttc cagagccagt aaccgtgagc     480
tggaacagtg gagcactcac ttctggtgtc catacttttc ctgctgtcct gcaaagctct     540
ggcctgtact cactcagctc cgtcgtgacc gtgccatctt catctctggg cactcagacc     600
tacatctgta atgtaaacca caagcctagc aatactaagg tcgataagcg ggtggaaccc     660
aagagctgcg acaagactca cacttgtccc ccatgccctg cccctgaact tctgggcggt     720
cccagcgtct ttttgttccc accaaagcct aaagatactc tgatgataag tagaacaccc     780
gaggtgacat gtgttgttgt agacgtttcc cacgaggacc cagaggttaa gttcaactgg     840
tacgttgatg gagtcgaagt acataatgct aagaccaagc ctagagagga gcagtataat     900
agtacatacc gtgtagtcag tgttctcaca gtgctgcacc aagactggct caacggcaaa     960
gaatacaaat gcaaagtgtc caacaaagca ctcccagccc tatcgagaa gactattagt    1020 aaggcaaagg ggcagcctcg tgaaccacag gtgtacactc tgccacccag tagagaggaa    1080
atgacaaaga accaagtctc attgacctgc ctggtgaaag gcttctaccc cagcgacatc    1140
gccgttgagt gggagagtaa cggtcagcct gagaacaatt acaagacaac ccccccagtg    1200
ctggatagtg acgggtcttt ctttctgtac agtaagctga ctgtggacaa gtcccgctgg    1260
cagcagggta cgtcttcag ctgttccgtg atgcacgagg cattgcacaa ccactacacc    1320
cagaagtcac tgagcctgag cccagggaag                                     1350

<210> SEQ ID NO 258
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

-continued

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
            35                  40                  45

Gly Gln Ile Asn Pro Asn Asn Gly Leu Ile Phe Phe Asn Gln Lys Phe
        50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 259
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
caagtacagc ttgtacagtc gggagcggaa gtcaagaaac cgggatcgtc ggtcaaagtg      60
tcgtgtaaag cgtcgggata tacgtttagc gactataaca tggattgggt gcgacaagcg     120
cctgggcagg gacttgaatg gatgggtcag atcaatccga ataatgggct gatctttttc     180
aatcagaagt ttaaagggag ggtaacgctg acggcggata aaagcacgtc aacggcgtat     240
atggagttgt cgtcgttgcg gtcggaggac acggcggtct attactgcgc gagggaagcg     300
attacgacgg tgggagcgat ggattattgg gggcagggaa cgcttgtaac ggtgtcatcg     360
gcctcaacaa aaggaccaag tgtgttccca ctcgccccta gcagcaagag tacatccggg     420
ggcactgcag cactcggctg cctcgtcaag gattattttc cagagccagt aaccgtgagc     480
tggaacagtg agcactcac ttctggtgtc catactttc ctgctgtcct gcaaagctct      540
ggcctgtact cactcagctc cgtcgtgacc gtgccatctt catctctggg cactcagacc     600
tacatctgta atgtaaacca caagcctagc aatactaagg tcgataagcg ggtggaaccc     660
aagagctgcg acaagactca cacttgtccc ccatgccctg cccctgaact tctgggcggt     720
cccagcgtct ttttgttccc accaaagcct aaagatactc tgatgataag tagaacaccc     780
gaggtgacat gtgttgttgt agacgtttcc cacgaggacc cagaggttaa gttcaactgg     840
tacgttgatg gagtcgaagt acataatgct aagaccaagc ctagaggaga gcagtataat     900
agtacatacc gtgtagtcag tgttctcaca gtgctgcacc aagactggct caacggcaaa     960
gaatacaaat gcaaagtgtc caacaaagca ctcccagccc ctatcgagaa gactattagt    1020
aaggcaaagg ggcagcctcg tgaaccacag gtgtacactc tgccacccag tagagaggaa    1080
atgacaaaga accaagtctc attgacctgc ctggtgaaag cttctaccc cagcgacatc    1140 gccgttgagt gggagagtaa cggtcagcct gagaacaatt acaagacaac ccccccagtg    1200
ctggatagtg acgggtcttt ctttctgtac agtaagctga ctgtggacaa gtcccgctgg    1260
cagcagggta acgtcttcag ctgttccgtg atgcacgagg cattgcacaa ccactacacc    1320
cagaagtcac tgagcctgag cccagggaag                                    1350

<210> SEQ ID NO 260
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Val Gln Leu Val Gln Ser Gly Ala Glu Val Lys Lys Pro Gly Ser
1               5                  10                  15

```
Ser Val Lys Val Ser Cys Lys Ala Ser Gly Tyr Thr Phe Ser Asp Tyr
             20                  25                  30

Asn Met Asp Trp Val Arg Gln Ala Pro Gly Gln Gly Leu Glu Trp Met
         35                  40                  45

Gly Gln Ile Asn Pro Asn Asn Gly Leu Ile Phe Phe Asn Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
            435                 440                 445

Gly Lys
    450

<210> SEQ ID NO 261
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
caagtacagc ttgtacagtc gggagcggaa gtcaagaaac cgggatcgtc ggtcaaagtg      60
tcgtgtaaag cgtcgggata tacgtttagc gactataaca tggattgggt gcgacaagcg     120
cctgggcagg gacttgaatg gatgggtcag atcaatccgt acaatcacct gatcttttc     180 aatcagaagt ttaaagggag ggtaacgctg acggcggata aaagcacgtc aacggcgtat     240
atggagttgt cgtcgttgcg gtcggaggac acggcggtct attactgcgc gagggaagcg     300
attacgacgt gggagcgat ggattattgg gggcagggaa cgcttgtaac ggtgtcatcg     360
gcctcaacaa aaggaccaag tgtgttccca ctcgccccta gcagcaagag tacatccggg     420
ggcactgcag cactcggctg cctcgtcaag gattattttc cagagccagt aaccgtgagc     480
tggaacagtg gagcactcac ttctggtgtc catactttc ctgctgtcct gcaaagctct     540
ggcctgtact cactcagctc cgtcgtgacc gtgccatctt catctctggg cactcagacc     600
tacatctgta atgtaaacca caagcctagc aatactaagg tcgataagcg ggtggaaccc     660
aagagctgcg acaagactca cacttgtccc ccatgccctg ccctgaact tctgggcggt     720 cccagcgtct ttttgttccc accaaagcct aaagatactc tgatgataag tagaacaccc     780
gaggtgacat gtgttgttgt agacgtttcc cacgaggacc cagaggttaa gttcaactgg     840
tacgttgatg gagtcgaagt acataatgct aagaccaagc ctagagagga gcagtataat     900
agtacatacc gtgtagtcag tgttctcaca gtgctgcacc aagactggct caacggcaaa     960
gaatacaaat gcaaagtgtc caacaaagca ctcccagccc ctatcgagaa gactattagt    1020
aaggcaaagg ggcagcctcg tgaaccacag gtgtacactc tgccacccag tagagggaa    1080 atgacaaaga accaagtctc attgacctgc ctggtgaaag gcttctaccc cagcgacatc    1140
gccgttgagt gggagagtaa cggtcagcct gagaacaatt acaagacaac cccccagtg    1200 ctggatagtg acgggtcttt cttctgtac agtaagctga ctgtggacaa gtcccgctgg    1260
cagcagggta acgtcttcag ctgttccgtg atgcacgagg cattgcacaa ccactacacc    1320
cagaagtcac tgagcctgag cccagggaag                                     1350

<210> SEQ ID NO 262
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

-continued

```
Asn Met Asp Trp Val Arg Gln Ala Pro Gly Gln Gly Leu Glu Trp Met
    35                  40                  45
Gly Gln Ile Asn Pro Tyr Asn His Leu Ile Phe Phe Asn Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Ala Ile Thr Thr Val Gly Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 263
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
gacatccaaa tgacccagtc gccgtcgtcg ctttcagcgt cggtagggga tcgggtcaca      60
attacgtgcc gaacgtcaga gaatttgcat aactacctcg cgtggtatca gcagaagccc     120
gggaagtcac cgaaactcct tatctacgat gcgaaaacgc tggcggatgg agtgccgtcg     180
agattctcgg gaagcggatc cggtacggac tatacgctta cgatctcatc gctccagccc     240
gaggactttg cgacgtacta ttgtcagcat ttttggtcgg accccta cac atttgggcag     300 gggaccaagt tggaaatcaa agcgcacagtt gctgccccca gcgtgttcat tttcccacct     360
agcgatgagc agctgaaaag cggtactgcc tctgtcgtat gcttgctcaa caactttt ac     420 ccacgtgagg ctaaggtgca gtggaaagtg gataatgcac ttcaatctgg aaacagtcaa     480
gagtccgtga cagaacagga cagcaaagac tcaacttatt cactctcttc caccctgact     540
ctgtccaagg cagactatga aaacacaag gtatacgcct cgaggttac acaccagggt       600 ttgtctagtc ctgtcaccaa gtccttcaat aggggcgaat gt                       642

<210> SEQ ID NO 264
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Asp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Gly Gly Gly
1

<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 266

His His His His His His
1               5
```